US008426449B2

(12) United States Patent
Hutchinson et al.

(10) Patent No.: US 8,426,449 B2
(45) Date of Patent: Apr. 23, 2013

(54) AMINOALKYLPHENYL ANTAGONISTS OF PROSTAGLANDIN D2 RECEPTORS

(75) Inventors: John Howard Hutchinson, San Diego, CA (US); Brian Andrew Stearns, Encinitas, CA (US); Yen Pham Truong, San Diego, CA (US); Thomas Jon Seiders, San Diego, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 163 days.

(21) Appl. No.: 12/935,253

(22) PCT Filed: Mar. 25, 2009

(86) PCT No.: PCT/US2009/038291
§ 371 (c)(1),
(2), (4) Date: Feb. 3, 2011

(87) PCT Pub. No.: WO2009/145989
PCT Pub. Date: Dec. 3, 2009

(65) Prior Publication Data
US 2011/0130453 A1    Jun. 2, 2011

Related U.S. Application Data

(60) Provisional application No. 61/041,869, filed on Apr. 2, 2008.

(51) Int. Cl.
*A01N 43/40* (2006.01)
*C07D 213/62* (2006.01)
*C07D 229/00* (2006.01)

(52) U.S. Cl.
USPC ............................ 514/351; 546/300; 562/442

(58) Field of Classification Search .................. 514/351; 546/300; 562/442
See application file for complete search history.

(56) References Cited

U.S. PATENT DOCUMENTS

| | | |
|---|---|---|
| 5,191,086 A | 3/1993 | Poss |
| 5,219,856 A | 6/1993 | Olson |
| 5,239,084 A | 8/1993 | Guerry et al. |
| 5,250,548 A | 10/1993 | Winn et al. |
| 5,326,776 A | 7/1994 | Winn et al. |
| 5,334,598 A | 8/1994 | Bagley et al. |
| 5,668,176 A | 9/1997 | Bagley et al. |
| 5,827,868 A | 10/1998 | Misra et al. |
| 5,977,117 A | 11/1999 | Chan et al. |
| 6,028,080 A | 2/2000 | Ackermann et al. |
| 6,429,213 B1 | 8/2002 | Xue et al. |
| 6,617,351 B1 | 9/2003 | Arnold et al. |
| 6,858,626 B2 | 2/2005 | Xue et al. |
| 6,884,593 B1 | 4/2005 | Hirai et al. |
| 7,005,440 B1 | 2/2006 | Jayyosi et al. |
| 7,144,913 B2 | 12/2006 | Wang et al. |
| 7,205,329 B2 | 4/2007 | Chien et al. |
| 7,321,001 B2 | 1/2008 | Fu et al. |
| 8,242,145 B2 * | 8/2012 | Hutchinson et al. .......... 514/351 |
| 2001/0047027 A1 | 11/2001 | Labelle et al. |
| 2002/0198251 A1 | 12/2002 | Sundermann et al. |
| 2004/0214888 A1 | 10/2004 | Matsuura et al. |
| 2004/0220237 A1 | 11/2004 | Fu et al. |
| 2005/0154044 A1 | 7/2005 | Beaulieu et al. |
| 2005/0272756 A1 | 12/2005 | Leblanc et al. |
| 2006/0100425 A1 | 5/2006 | Bennani et al. |
| 2006/0106081 A1 | 5/2006 | Bennani et al. |
| 2006/0148830 A1 | 7/2006 | Terakado et al. |
| 2007/0155726 A1 | 7/2007 | Arzaiz et al. |
| 2008/0045508 A1 | 2/2008 | Allison et al. |
| 2008/0085891 A1 | 4/2008 | Fu et al. |
| 2008/0167378 A1 | 7/2008 | Fukatsu et al. |
| 2008/0306109 A1 | 12/2008 | Hynd et al. |
| 2009/0048238 A1 | 2/2009 | Aebi et al. |
| 2009/0186923 A1 | 7/2009 | Armer et al. |
| 2009/0197959 A1 | 8/2009 | Hutchinson et al. |
| 2010/0004331 A1 | 1/2010 | Hutchinson et al. |
| 2010/0081673 A1 | 4/2010 | Hutchinson et al. |
| 2010/0113503 A1 | 5/2010 | Hutchinson et al. |
| 2010/0173313 A1 | 7/2010 | Bain et al. |
| 2010/0280049 A1 | 11/2010 | Stearns et al. |
| 2010/0298368 A1 | 11/2010 | Stearns et al. |
| 2011/0021573 A1 | 1/2011 | Hutchinson et al. |
| 2011/0039852 A1 | 2/2011 | Hutchinson et al. |
| 2011/0098302 A1 | 4/2011 | Hutchinson et al. |

(Continued)

FOREIGN PATENT DOCUMENTS

| | | |
|---|---|---|
| EP | 0276064 | 7/1988 |
| EP | 0300688 | 1/1989 |

(Continued)

OTHER PUBLICATIONS

Arima and Fukuda, "Prostaglandin D2 Receptors DP and CRTH2 in the Pathogenesis of Asthma," Curr. Mol. Med. 8:365-375 (2008).
Brannan et al. "Inhibition of mast cell $PGD_2$, release protects against mannitol-induced airway narrowing." *European Respiratory Journal*, 2006 27:944-950, ERS Journals Ltd.
Crosignani et al., "Discovery of a new class of potent, selective, and orally bioavailable CRTH2(DP2) receptor antagonists for the treatment of allergic inflammatory diseases" J Med Chem 51:2227-2243 (2008).
Evans et al., "Seeing the future of bioactive lipid drug targets," Nature Chem Biol 6:476-479 (2010).
Hata and Breyer, "Pharmacology and signaling of prostaglandin receptors: Multiple roles in inflammation and immune modulation," Pharmacol. Ther. 103:147-166 (2004).
Jatakanon et al. "Neutrophilic Inflammation in Severe Persistent Asthma." *Am J Respir Crit Care Med*, 1999, 160: 1532-1539.
Johnston et al. "Prostaglandin $D_2$-induced bronchoconstriction is mediated only in part by the thromboxane prostanoid receptor." *Eur Respir J.*, 1995, 8: 411-415. ERS Journals Ltd.

(Continued)

*Primary Examiner* — Blessing Fubara
*Assistant Examiner* — Kauser M Akhoon
(74) *Attorney, Agent, or Firm* — Wilson, Sonsini, Goodrich & Rosati

(57) ABSTRACT

Described herein are compounds that are antagonists of $PGD_2$ receptors. Also described are pharmaceutical compositions and medicaments that include the compounds described herein that are antagonists of $PGD_2$ receptors. Also described herein are methods of using such antagonists of $PGD_2$ receptors, alone and in combination with other compounds, for treating respiratory, cardiovascular, and other $PGD_2$-dependent or $PGD_2$-mediated conditions or diseases.

17 Claims, No Drawings

U.S. PATENT DOCUMENTS

| | | |
|---|---|---|
| 2011/0098352 A1 | 4/2011 | Hutchinson et al. |
| 2011/0130453 A1 | 6/2011 | Hutchinson et al. |
| 2011/0144160 A1 | 6/2011 | Hutchinson et al. |
| 2011/0190227 A1 | 8/2011 | Hutchinson et al. |
| 2011/0245303 A1 | 10/2011 | Hutchinson et al. |

FOREIGN PATENT DOCUMENTS

| | | |
|---|---|---|
| EP | 0480659 | 4/1992 |
| EP | 1170594 A2 | 1/2002 |
| JP | 2004-182657 A | 7/2004 |
| WO | WO-95-03044 | 2/1995 |
| WO | WO-95-04277 A1 | 2/1995 |
| WO | WO-95-26188 A1 | 10/1995 |
| WO | WO 97-25321 A2 | 7/1997 |
| WO | WO 98-05637 A1 | 2/1998 |
| WO | WO-99-11605 A1 | 3/1999 |
| WO | WO-99-47497 A2 | 9/1999 |
| WO | WO-99-65867 A1 | 12/1999 |
| WO | WO-2006-056854 A1 | 6/2001 |
| WO | WO-01-72714 A2 | 10/2001 |
| WO | WO-2004-058164 A2 | 7/2004 |
| WO | WO-2004-096777 A1 | 11/2004 |
| WO | WO-2005-040144 A1 | 5/2005 |
| WO | WO-2005-044260 A1 | 5/2005 |
| WO | WO-2005-051373 A1 | 6/2005 |
| WO | WO-2005-054176 A1 | 6/2005 |
| WO | WO-2005-073234 A2 | 8/2005 |
| WO | WO-2005-086836 A2 | 9/2005 |
| WO | WO-2005-100298 A1 | 10/2005 |
| WO | WO-2005-105727 A1 | 10/2005 |
| WO | WO-2006-005909 A1 | 1/2006 |
| WO | WO-2006-001825 | 2/2006 |
| WO | WO-2006-014357 A1 | 2/2006 |
| WO | WO-2006-014413 A1 | 2/2006 |
| WO | WO-2006-037982 A2 | 4/2006 |
| WO | WO-2006-052798 A2 | 5/2006 |
| WO | WO-2006-052798 A2 | 6/2006 |
| WO | WO-2006-125596 A1 | 11/2006 |
| WO | WO-2006-133926 A1 | 12/2006 |
| WO | WO-2007-024922 A1 | 3/2007 |
| WO | WO-2007-037187 A1 | 4/2007 |
| WO | WO-2007-039736 A1 | 4/2007 |
| WO | WO-2007-068894 A2 | 6/2007 |
| WO | WO-2007-081570 A2 | 7/2007 |
| WO | WO-2008-004096 A1 | 1/2008 |
| WO | WO-2008-004100 A2 | 1/2008 |
| WO | WO-2008-017932 A2 | 2/2008 |
| WO | WO-2008-024746 A1 | 2/2008 |
| WO | WO-2008-074982 A1 | 6/2008 |
| WO | WO-2008-137027 A2 | 11/2008 |
| WO | WO 2008-154642 A2 | 12/2008 |
| WO | WO-2009-003861 A1 | 1/2009 |
| WO | WO-2009-044147 A1 | 4/2009 |
| WO | WO-2009-063202 A2 | 5/2009 |
| WO | WO-2009-063215 A2 | 5/2009 |
| WO | WO-2009-089192 A1 | 7/2009 |
| WO | WO-2009-099901 | 8/2009 |
| WO | WO-2009-099902 | 8/2009 |
| WO | WO 2009-102893 A2 | 8/2009 |
| WO | WO-2009-108720 | 9/2009 |
| WO | WO-2009-145989 A2 | 12/2009 |
| WO | WO-2010-003120 A2 | 1/2010 |
| WO | WO-2010-003127 A2 | 1/2010 |
| WO | WO-2010-037054 | 4/2010 |
| WO | WO-2010-037059 | 4/2010 |
| WO | WO-2010-039977 A2 | 4/2010 |
| WO | WO 2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |

OTHER PUBLICATIONS

Kim et al., "Regulation of Immune Cells by Eicosanoid Receptors" TheScientificWorld Journal 7:1307-1328 (2007).

Kostenis and Ulven, "Emerging roles of DP and CRTH2 in allergic inflammation," Trends Mol. Med. 12(4):148-158 (2006).

Ly and Bacon, "Small-molecule CRTH2 antagonists for the treatment of allergic inflammation: an overview," Exp Opin Invest Drugs 14:769 (2005).

Medina and Liu. "PGD2 Antagonists," Annual Reports Med. Chem. 41:221-235 (2006).

Pettipher et al., "Antagonism of the prostaglandin D2 receptors DP1 and CRTH2 as an approach to treat allergic diseases," Nature Reviews/Drug Discovery 6:313-325 (2007).

Pettipher et al., "The roles of the prostaglandin D(2) receptors DP(1) and CRTH2 in promoting allergic responses," Br J Pharmacol 153:S191 (2008).

Pettipher et al., "Antagonists of the prostaglandin D2 receptor CRTH2," Drug News Perspect 21:317-322 (2008).

Sagel et al. "Sputum Biomarkers of Inflammation in Cystic Fibrosis Lung Disease." *Proc. Am Thorac Soc.*, 2007, 4: 406-417.

Sandig et al., "Contrary prostaglandins: the opposing roles of PGD2 and its metabolites in leukocyte function," J Leukocyte Biology 81:372-382 (2007).

Scott et al., "Discovery and optimization of a biphenylacetic acid series of prostaglandin D2 receptor DP2 antagonists with efficacy in a murine model of allergic rhinitis," Bioorg Med Chem Ltrs (2011), doi: 10.1016fj.bmcl.2011.01.024.

Srinivas et al., "Biaryl amino acid templates in place of D-Pro-L-Pro in cyclic beta-hairpin cationic antimicrobial peptidornimetics," Organic & Biomolecular Chemistry 5(19):3100-3105 (2007).

Stearns et al., "Novel tricyclic antagonists of the prostaglandin D2 receptor DP2 with efficacy in a murine model of allergic rhinitis," Bioorg Med Chem Ltrs 19:4647-4651 (2009).

Stebbins et al., "DP2 Receptor Antagonists: Novel Therapeutic Target for COPD," Mol Cell Pharmacol 2(3):89-96 (2010).

Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Ther 332(3):764-775 (2010).

Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).

Stock et al., "Sodium [2'-[(cyclopropanecarbonyl-ethyl-amino)-methyl]-4'-(6-ethoxy-pyridin-3-y1)-6-methoxy-biphenyl-3-yl]-acetate (AM432): A potent, selective prostaglandin D2 receptor antagonist," Bioorg Med Chem Ltrs 21:1036-1040 (2011).

Sugimoto et al. "An Orally Bioavailable Small Molecule Antagonist of CRTH2, Ramatroban (BAY u3405), Inhibits Prostaglandim $D_2$-Induced Eosinophil Migration in Vitro." *The Journal of Pharmacology and Experimental Therapeutics*, 2003, 305:347-352, The American Society for Pharmacology and Experimental Therapeutics.

Takeshita et al., "CRTH2 is a prominent effector in contact hypersensitivity-induced neutrophil inflammation," Intl Immunol 16(7):947,959 (2004).

Tirouvanziam et al., "Profound functional and signaling changes in viable inflammatory neutrophils homing to cystic fibrosis airways," PNAS 105(11):4335-4339 (2008).

Torisu et al. "Discovery or new chemical leads for prostaglandin $D_2$ receptor antagonists." *Bioorganic & Medicinal Chemistry Letters*, 2004, 14: 4557-4562, Elsevier.

Ulven and Kostenis, "Targeting the Prostaglandin D2 Receptors DP and CRTH2 for Treatment of Inflammation," Curr. Topics Med. Chem. 6:1427-1444 (2006).

Ulven et al., "Minor Structural Modifications Convert the Dual TP/CRTH2 Antagonist Ramatroban into a Highly Selective and Potent CRTH2Antogonist," J Med Chem 48(4):897-900 (2005).

Wardlaw et al. "New insights into the relationship between airway inflammation and asthma." (Abstract) *Clinical Science*, 2002, 103: 201-211. The Biochemical Society and the Medical Research Society.

EP09709954.3 Search Report mailed Feb. 21, 2011.

PCT/US09/38291 Search Report and Written Opinion mailed Nov. 27, 2009.

Science IP Structure Search, Part 1. dated Sep. 5, 2008.

Science IP Structure Search, Part 2, dated Sep. 5, 2008.

\* cited by examiner

AMINOALKYLPHENYL ANTAGONISTS OF PROSTAGLANDIN D2 RECEPTORS

RELATED APPLICATIONS

This application is filed pursuant to 35 U.S.C. §371 as a United States National Phase Application of International Application No. PCT/US2009/038291, entitled "AMINOALKYLPHENYL ANTAGONISTS OF PROSTAGLANDIN $D_2$ RECEPTORS" filed Mar. 25, 2009, which claims the benefit of U.S provisional patent application no. 61/041,869 entitled "AMINOALKYLPHENYL ANTAGONISTS OF PROSTAGLANDIN $D_2$ RECEPTORS" filed on Apr. 2, 2008, all of which are incorporated herein by reference in their entirety.

BACKGROUND OF THE INVENTION

Prostaglandins are acidic lipids derived from the metabolism of arachidonic acid by the action of cyclooxygenase enzymes and downstream synthases. Prostaglandins have a diverse range of activities and have a well recognized role in pain and inflammation. Prostaglandin $D_2$ ($PGD_2$) is an acidic lipid mediator derived from the metabolism of arachidonic acid by cyclooxygenases and $PGD_2$ synthases. $PGD_2$ is produced by mast cells, macrophages and $T_H2$ lymphocytes in response to local tissue damage as well as allergic inflammation in diseases such as asthma, rhinitis, and atopic dermatitis. Exogenous $PGD_2$ applied to bronchial airways elucidates many characteristics of an asthmatic response suggesting that $PGD_2$ plays an important pro-inflammatory role in allergic diseases.

$PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$). $DP_2$ is associated with promoting chemotaxis and activation of $T_H2$ lymphocytes, eosinophils and basophils. In particular, $PGD_2$ binds to $DP_2$, and mediates its effects through a $G_i$-dependant elevation in calcium levels and reduction of intracellular cyclic AMP. In $T_H2$ lymphocytes, IL4, IL5 and IL13 cytokine production is stimulated. These cytokines have been implicated in numerous biological actions including, by way of example only, immunoglobulin E production, airway response, mucous secretion, and eosinophil recruitment.

SUMMARY OF THE INVENTION

Presented herein are compounds, pharmaceutical compositions and medicaments, methods, for (a) diagnosing, preventing, or treating allergic and non-allergic inflammation, (b) mitigating adverse signs and symptoms that are associated with inflammation, and/or (c) controlling immunological, proliferative or metabolic disorders. These disorders may arise from one or more of a genetic, iatrogenic, immunological, infectious, metabolic, oncological, toxic, surgical, and/or traumatic etiology. In one aspect, the methods, compounds, pharmaceutical compositions, and medicaments described herein comprise antagonists of $PGD_2$ receptors. In one aspect, the methods, compounds, pharmaceutical compositions, and medicaments described herein comprise antagonists of $DP_2$.

In one aspect provided herein are compounds of Formula (I), Formula (II), Formula (III), Formula (IV), Formula (V), Formula (VI) and Formula (VII), pharmaceutically acceptable salts, pharmaceutically acceptable prodrugs, and pharmaceutically acceptable solvates thereof, which are anatgonists of $DP_2$, and are used to treat patients suffering from one or more $PGD_2$-dependent conditions or diseases, including, but not limited to, asthma, rhinitis, allergic conjunctivitis, atopic dermatitis, chronic obstructive pulmonary disease (COPD), pulmonary hypertension, interstitial lung fibrosis, cystic fibrosis, arthritis, allergy, psoriasis, inflammatory bowel disease, adult respiratory distress syndrome, myocardial infarction, aneurysm, stroke, cancer, wound healing, endotoxic shock, pain, inflammatory conditions, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, angioedema, anaphylaxia, chronic cough and Churg Strauss syndrome. In some embodiments, $PGD_2$-dependent conditions or diseases include those wherein an absolute or relative excess of $PGD_2$ is present and/or observed.

In one aspect is a compound having the structure of Formula (I), pharmaceutically acceptable salts, pharmaceutically acceptable solvates, or pharmaceutically acceptable prodrugs thereof:

A compound having the structure of Formula (I), or pharmaceutically acceptable salt, pharmaceutically acceptable solvate, or pharmaceutically acceptable prodrug thereof:

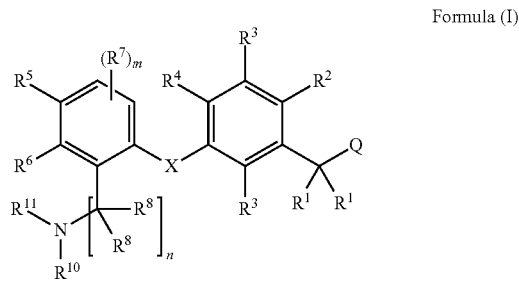

Formula (I)

wherein,

Q is tetrazolyl or —C(=O)-$Q^1$;
  $Q^1$ is —OH, or —O($C_1$-$C_6$alkyl);
X is —O—, —S—, —S(=O)—, —S(=O)$_2$—, —$NR^{13}$—, —$CH_2$—, or —C(=O)—;
each $R^1$ is independently selected from H, F, and $C_1$-$C_4$alkyl;
each of $R^2$, $R^3$, $R^4$, $R^5$, $R^6$, and $R^7$ is independently H, halogen, —CN, —$NO_2$, —OH, —$OR^{13}$, —$SR^{12}$, —S(=O)$R^{12}$, —S(=O)$_2R^{12}$, —C(=O)$R^{12}$, —OC(=O)$R^{12}$, —$CO_2R^{13}$, —$OCO_2R^{13}$, —CH($R^{13}$)$_2$, —N($R^{13}$)$_2$, —$NHCH_2CO_2R^{13}$, —$OCH_2CO_2R^{13}$, —$SCH_2CO_2R^{13}$, —C(=O)N($R^{13}$)$_2$, —OC(=O)N($R^{13}$)$_2$, —$NR^{13}$C(=O)N($R^{13}$)$_2$, —$NR^{13}$C(=O)$R^{12}$, —$NR^{13}$C(=O)O$R^{12}$, —$NR^{13}$S(=O)$_2R^{12}$, —C(OH)($R^{13}$)$_2$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted $C_2$-$C_{10}$heterocycloalkyl, optionally substituted phenyl, or optionally substituted monocyclic heteroaryl;
each $R^8$ is H;
$R^{10}$ is H, $C_1$-$C_6$alkyl, —C(=O)$R^{14}$, —C(=O)O$R^{15}$, —C(=O)N($R^{16}$)$_2$, —S(=O)$_2$N($R^{16}$)$_2$ or —S(=O)$_2R^{14}$;
$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted aryl), —C$_1$-C$_4$alkyl-(optionally substituted heteroaryl), or -L$^3$-X$^3$-Q$^3$;

L$^3$ is a C$_1$-C$_4$alkylene or arylene;

X$^3$ is a bond, —O—, —S—, —S(=O)—, —S(=O)$_2$—, —C(=O)—, —NR$^{13}$S(=O)$_2$—, or —NR$^{13}$—;

Q$^3$ is C$_1$-C$_6$alkyl, C$_1$-C$_6$fluoroalkyl, an optionally substituted C$_3$-C$_{10}$cycloalkyl, an optionally substituted C$_2$-C$_{10}$heterocycloalkyl, an optionally substituted aryl, an optionally substituted heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted aryl), or —C$_1$-C$_4$alkyl-(optionally substituted heteroaryl);

R$^{15}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted C$_2$-C$_{10}$heterocycloalkyl, an optionally substituted aryl, an optionally substituted heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted aryl) or —C$_1$-C$_4$alkyl-(optionally substituted heteroaryl);

each R$^{16}$ is independently H, —CN, C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted C$_2$-C$_{10}$heterocycloalkyl, an optionally substituted aryl, an optionally substituted heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted aryl) or —C$_1$-C$_4$alkyl-(optionally substituted heteroaryl); or two R$^{16}$ groups attached to the same N atom are taken together with the N atom to which they are attached to form an optionally substituted C$_2$-C$_{10}$heterocycloalkyl;

R$^{11}$ is H, C$_1$-C$_6$alkyl, C$_1$-C$_6$heteroalkyl, C$_1$-C$_6$haloalkyl, an optionally substituted monocyclic or bicyclic C$_3$-C$_{10}$cycloalkyl, an optionally substituted monocyclic or bicyclic C$_2$-C$_{10}$heterocycloalkyl, an optionally substituted aryl, an optionally substituted heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted aryl), —C$_1$-C$_4$alkyl-(optionally substituted heteroaryl), —C$_1$-C$_6$alkylene-O—R$^{17}$, —C$_1$-C$_6$alkylene-S—R$^{17}$, —C$_1$-C$_6$alkylene-S(=O)—R$^{17}$, —C$_1$-C$_6$alkylene-S(=O)$_2$—R$^{17}$, —C$_1$-C$_6$alkylene-NR$^{13}$R$^{17}$, —C$_1$-C$_6$alkylene-C(=O)—R$^{17}$, —C$_1$-C$_6$alkylene-C(=O)O—R$^{17}$, —C$_1$-C$_6$alkylene-OC(=O)—R$^{17}$, —C$_1$-C$_6$alkylene-NR$^{13}$C(=O)—R$^{17}$ or —C$_1$-C$_6$alkylene-C(=O)NR$^{13}$—R$^{17}$;

R$^{17}$ is H, C$_1$-C$_4$alkyl, C$_1$-C$_4$heteroalkyl, C$_1$-C$_4$haloalkyl, an optionally substituted C$_3$-C$_{10}$cycloalkyl, an optionally substituted C$_2$-C$_{10}$heterocycloalkyl, an optionally substituted aryl, an optionally substituted benzyl, or an optionally substituted heteroaryl;

R$^{12}$ is C$_1$-C$_6$alkyl, C$_1$-C$_6$heteroalkyl, C$_1$-C$_6$fluoroalkyl, optionally substituted C$_3$-C$_{10}$cycloalkyl, optionally substituted C$_2$-C$_{10}$heterocycloalkyl, optionally substituted aryl, —C$_1$-C$_4$alkyl-(optionally substituted aryl) or optionally substituted heteroaryl; and each R$^{13}$ is independently selected from H, C$_1$-C$_6$heteroalkyl, C$_1$-C$_6$fluoroalkyl, an optionally substituted C$_3$-C$_{10}$cycloalkyl, an optionally substituted C$_2$-C$_{10}$heterocycloalkyl, an optionally substituted aryl, —C$_1$-C$_4$alkyl-(optionally substituted aryl), and an optionally substituted heteroaryl; or two R$^{13}$ groups attached to the same N atom are taken together with the N atom to which they are attached to form an optionally substituted C$_2$-C$_{10}$heterocycloalkyl;

m is 0, 1, or 2; n is 1, 2, 3, or 4.

For any and all of the embodiments, substituents can be selected from among from a subset of the listed alternatives. For example, in some embodiments, n is 1 or 2. In other embodiments, n is 2, 3, or 4. In yet other embodiments, n is 3 or 4. In yet other embodiments, n is 1.

In one aspect, Q is —C(=O)-Q$^1$; Q$^1$ is —OH, or —O(C$_1$-C$_4$alkyl). In another aspect, Q$^1$ is —OH, —OCH$_3$, or —OCH$_2$CH$_3$. In yet another aspect, Q is —C(=O)OH, —C(=O)OCH$_3$, —C(=O)OCH$_2$CH$_3$.

In some embodiments, each R$^1$ is independently selected from H, F, and —CH$_3$. In other embodiments, one R$^1$ is H and the other R$^1$ is selected from H, F, and —CH$_3$.

In some embodiments, X is —O—, —S—, —S(=O)—, —S(=O)$_2$—, or —CH$_2$—. In other embodiments, X is —O—, —S—, or —CH$_2$—. In some embodiments, X is —S—, —S(=O)—, or —S(=O)$_2$—. In one aspect, X is —O—.

In one aspect, m is 0 or 1; and n is 1.

In one aspect, the compound of Formula (I) has the structure of Formula (II):

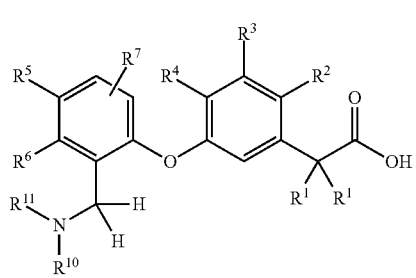

Formula (II)

In some embodiments, each R$^1$ is H.

In some embodiments, at least one of R$^2$, R$^3$, and R$^4$, is hydrogen. In some embodiments, at least two of R$^2$, R$^3$, and R$^4$, are hydrogen. In some embodiments, R$^2$, and R$^3$ are hydrogen.

In some embodiments, at least one of R$^5$, R$^6$, and R$^7$, is hydrogen. In some embodiments, at least two of R$^5$, R$^6$, and R$^7$, are hydrogen. In some embodiments, R$^6$, and R$^7$ are hydrogen.

In some embodiments, each of R$^2$, R$^3$, R$^6$, and R$^7$ is independently H, halogen, —CN, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —OCO$_2$R$^{13}$, —N(R$^{13}$)$_2$, —C$_1$-C$_4$alkyl, C$_1$-C$_4$fluoroalkyl, an optionally substituted C$_3$-C$_6$cycloalkyl, an optionally substituted C$_2$-C$_6$heterocycloalkyl, C$_1$-C$_4$fluoroalkoxy, C$_1$-C$_4$alkoxy, C$_1$-C$_4$heteroalkyl, optionally substituted phenyl, or an optionally substituted monocyclic heteroaryl.

In some embodiments, $R^4$ is H, halogen, —CN, —NO$_2$, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, C$_1$-C$_4$alkyl, C$_1$-C$_4$fluoroalkyl, C$_1$-C$_4$fluoroalkoxy, C$_1$-C$_4$alkoxy, C$_1$-C$_4$heteroalkyl, an optionally substituted C$_3$-C$_6$cycloalkyl, an optionally substituted C$_2$-C$_6$heterocycloalkyl, optionally substituted phenyl, or an optionally substituted monocyclic heteroaryl.

In some embodiments, $R^5$ is H, halogen, —CN, —NO$_2$, —OH, —OR$^{13}$, —SR$^{12}$, —S(=O)R$^{12}$, —S(=O)$_2$R$^{12}$, —C(=O)R$^{12}$, —OC(=O)R$^{12}$, —CO$_2$R$^{13}$, —OCO$_2$R$^{13}$, —N(R$^{13}$)$_2$, —NHCH$_2$CO$_2$R$^{13}$, —OCH$_2$CO$_2$R$^{13}$, —SCH$_2$CO$_2$R$^{13}$, —C(=O)N(R$^{13}$)$_2$, —OC(=O)N(R$^{13}$)$_2$, —NR$^{13}$C(=O)N(R$^{13}$)$_2$, —NR$^{13}$C(=O)R$^{12}$, —NR$^{13}$C(=O)OR$^{12}$, —NR$^{13}$S(=O)$_2$R$^{12}$, C$_1$-C$_6$alkyl, C$_1$-C$_6$fluoroalkyl, C$_1$-C$_6$fluoroalkoxy, C$_1$-C$_6$alkoxy, C$_1$-C$_6$heteroalkyl, an optionally substituted C$_3$-C$_{10}$cycloalkyl, an optionally substituted C$_2$-C$_{10}$heterocycloalkyl, optionally substituted phenyl, or an optionally substituted monocyclic heteroaryl.

In one aspect, each of $R^2$, $R^3$, $R^6$, and $R^7$ is independently H, halogen, —CN, —OH, —OR$^{13}$, —SR$^{12}$, —S(=O)R$^{12}$, —S(=O)$_2$R$^{12}$, —N(R$^{13}$)$_2$, —C$_1$-C$_4$alkyl, C$_1$-C$_4$fluoroalkyl, C$_1$-C$_4$fluoroalkoxy, C$_1$-C$_4$alkoxy, or C$_1$-C$_4$heteroalkyl.

In another aspect, $R^4$ is H, halogen, —OH, —OR$^{13}$, C$_1$-C$_4$alkyl, C$_1$-C$_4$fluoroalkyl, C$_1$-C$_4$fluoroalkoxy, C$_1$-C$_4$alkoxy, or C$_1$-C$_4$heteroalkyl.

In some embodiments, each of $R^2$, $R^3$, $R^6$ and $R^7$ is independently H, halogen, —OH, C$_1$-C$_4$alkyl, C$_1$-C$_4$alkoxy, C$_1$-C$_4$fluoroalkyl, C$_1$-C$_4$fluoroalkoxy, or C$_1$-C$_3$heteroalkyl.

In some embodiments, $R^5$ is H, F, Cl, Br, I, —CN, —NO$_2$, —OH—CH$_3$, —CH$_2$CH$_3$, —CH$_2$CH$_2$CH$_3$, —CH(CH$_3$)$_2$, —C(CH$_3$)$_3$, —CF$_3$, —CH$_2$CF$_3$, —OCH$_3$, —OCH$_2$CH$_3$, —OCF$_3$, —S(=O)$_2$CH$_3$, —S(=O)$_2$ (optionally substituted phenyl), —C(=O)-(optionally substituted phenyl), —C(=O)(C$_1$-C$_4$alkyl), —CO$_2$H, —CO$_2$CH$_3$, —CO$_2$CH$_2$CH$_3$, —NH$_2$, —C(=O)NH$_2$, —C(=O)NH(CH$_3$), —C(=O)NH(CH$_2$CH$_3$), —C(=O)NH—C(CH$_3$)$_3$, —C(=O)NH—CH(CH$_3$)$_2$, —C(=O)NH(CH$_2$CF$_3$), —C(=O)NH(CH$_2$CH$_2$OCH$_3$), —C(=O)NH (optionally substituted phenyl), —C(=O)NH (optionally substituted benzyl), —C(=O)NH (optionally substituted monocyclic heteroaryl), —C(=O)NH (optionally substituted C$_2$-C$_8$heterocycloalkyl), —NHC(=O)(C$_1$-C$_6$alkyl), —NHC(=O) (optionally substituted phenyl), —N(C$_1$-C$_2$alkyl)C(=O)(C$_1$-C$_6$alkyl), —N(C$_1$-C$_2$alkyl)C(=O) (optionally substituted phenyl), —NHS(=O)$_2$(C$_1$-C$_6$alkyl), —NHS(=O)$_2$ (optionally substituted phenyl), —N(C$_1$-C$_2$alkyl)S(=O)$_2$(C$_1$-C$_6$alkyl), —N(C$_1$-C$_2$alkyl)S(=O)$_2$ (optionally substituted phenyl), —NHC(=O)NH$_2$, —NHC(=O)NH (optionally substituted phenyl), —NHC(=O)NH (optionally substituted benzyl), or an optionally substituted group selected from cyclopropyl, cyclobutyl, cyclopentyl, cyclohexyl, pyrrolidinyl, piperidinyl, morpholinyl, piperazinyl, thiomorpholinyl, phenyl, naphthyl, furanyl, thienyl, pyrrolyl, oxazolyl, thiazolyl, imidazolyl, pyrazolyl, isoxazolyl, isothiazolyl, oxadiazolyl, triazolyl, tetrazolyl, pyridinyl, pyridazinyl, pyrazinyl, pyrimidinyl, and triazinyl.

In one aspect, $R^4$ is H, F, Cl, Br, I, —CN, —OH, —OCH$_3$, —OCH$_2$CH$_3$, —SCH$_3$, —NH$_2$, —NHCH$_3$, —N(CH$_3$)$_2$, —CH$_3$, —CH$_2$CH$_3$, —CF$_3$, —CH$_2$CF$_3$, —OCF$_3$, —CH$_2$OH, or —CH$_2$OCH$_3$.

In another aspect, $R^5$ is H, F, Cl, Br, I, —CN, —NO$_2$, —OH—CH$_3$, —CH$_2$CH$_3$, —CH$_2$CH$_2$CH$_3$, —CH(CH$_3$)$_2$, —C(CH$_3$)$_3$, —CF$_3$, —CH$_2$CF$_3$, —OCH$_3$, —OCH$_2$CH$_3$, —OCF$_3$, —S(=O)$_2$CH$_3$, —S(=O)$_2$ (optionally substituted phenyl), —C(=O)-(optionally substituted phenyl), —C(=O)CH$_3$, —CO$_2$H, —CO$_2$CH$_3$, —CO$_2$CH$_2$CH$_3$, —NH$_2$, —C(=O)NH$_2$, —C(=O)NH(CH$_3$), —C(=O)NH(CH$_2$CH$_3$), —C(=O)NH—C(CH$_3$)$_3$, —C(=O)NH—CH(CH$_3$)$_2$, —C(=O)NH(CH$_2$CF$_3$), —C(=O)NH(CH$_2$CH$_2$OCH$_3$), —C(=O)NH (optionally substituted phenyl), —C(=O)NH (optionally substituted monocyclic heteroaryl), —C(=O)NH (optionally substituted heterocycloalkyl), —NHC(=O)(C$_1$-C$_6$alkyl), —NHC(=O) (optionally substituted phenyl), —N(CH$_3$)C(=O)(C$_1$-C$_6$alkyl), —N(CH$_3$)C(=O) (optionally substituted phenyl), —NHS(=O)$_2$(C$_1$-C$_6$alkyl), —NHS(=O)$_2$ (optionally substituted phenyl), —N(CH$_3$)S(=O)$_2$(C$_1$-C$_6$alkyl), or —N(CH$_3$)S(=O)$_2$ (optionally substituted phenyl).

In some embodiments, each of $R^2$, $R^3$, $R^6$ and $R^7$ is independently H, F, Cl, Br, —OH, —OCH$_3$, —OCH$_2$CH$_3$, —CH$_3$, —CH$_2$CH$_3$, —CF$_3$, —CH$_2$CF$_3$, —OCF$_3$, —CH$_2$OH, or —CH$_2$OCH$_3$.

In some embodiments, $R^{11}$ is H, C$_1$-C$_6$alkyl, C$_1$-C$_6$heteroalkyl, C$_1$-C$_6$haloalkyl, an optionally substituted monocyclic or bicyclic C$_3$-C$_{10}$cycloalkyl, an optionally substituted monocyclic or bicyclic C$_2$-C$_{10}$heterocycloalkyl, an optionally substituted phenyl, or an optionally substituted monocyclic heteroaryl, —C$_1$-C$_4$alkyl-(optionally substituted C$_3$-C$_{10}$cycloalkyl), —C$_1$-C$_4$alkyl-(optionally substituted C$_2$-C$_{10}$heterocycloalkyl), —C$_1$-C$_4$alkyl-(optionally substituted phenyl), —C$_1$-C$_4$alkyl-(optionally substituted monocyclic heteroaryl), —C$_1$-C$_6$alkylene-O—R$^{17}$, —C$_1$-C$_6$alkylene-S—R$^{17}$, —C$_1$-C$_6$alkylene-S(=O)—R$^{17}$, —C$_1$-C$_6$alkylene-S(=O)$_2$—R$^{17}$, —C$_1$-C$_6$alkylene-NR$^{13}$R$^{17}$, —C$_1$-C$_6$alkylene-C(=O)—R$^{17}$, —C$_1$-C$_6$alkylene-C(=O)O—R$^{17}$, or —C$_1$-C$_6$alkylene-C(=O)NR$^{13}$—R$^{17}$; $R^{17}$ is H, C$_1$-C$_4$alkyl, C$_1$-C$_4$heteroalkyl, C$_1$-C$_4$haloalkyl, an optionally substituted C$_3$-C$_{10}$cycloalkyl, an optionally substituted phenyl, an optionally substituted benzyl, or an optionally substituted heteroaryl.

In one aspect, $R^{10}$ is —C(=O)R$^{14}$, —C(=O)OR$^{13}$, —C(=O)N(R$^{16}$)$_2$, or —S(=O)$_2$R$^{14}$; $R^{14}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted aryl, an optionally substituted heteroaryl, —C$_1$-C$_4$alkyl-(an optionally substituted cycloalkyl), —C$_1$-C$_4$alkyl-(an optionally substituted aryl) or —C$_1$-C$_4$alkyl-(an optionally substituted heteroaryl); or $R^{14}$ is L$^3$-X$^3$-Q$^3$; L$^3$ is a C$_1$-C$_4$alkylene or arylene; X$^3$ is a bond, —O—, —S—, —S(=O)—, —S(=O)$_2$—, —C(=O)—, —NR$^{13}$S(=O)$_2$—, or —NR$^{13}$—; Q$^3$ is an optionally substituted C$_1$-C$_6$alkyl, C$_1$-C$_6$fluoroalkyl an optionally substituted C$_3$-C$_{10}$cycloalkyl, an optionally substituted aryl, an optionally substituted heteroaryl, —C$_1$-C$_4$alkyl-(an optionally substituted C$_3$-C$_{10}$cycloalkyl), —C$_1$-C$_4$alkyl-(an optionally substituted aryl), or —C$_1$-C$_4$alkyl-(an optionally substituted heteroaryl); $R^{15}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted aryl, an optionally substituted heteroaryl, —C$_1$-C$_4$alkyl-(an optionally substituted C$_3$-C$_6$cycloalkyl), —C$_1$-C$_4$alkyl-(an optionally substituted aryl) or —C$_1$-C$_4$alkyl-(an optionally substituted heteroaryl); each $R^{16}$ is independently H, —CN, C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted aryl, an optionally substituted heteroaryl, —C$_1$-C$_4$alkyl-(an optionally substituted C$_3$-C$_6$cycloalkyl), —C$_1$-C$_4$alkyl-(an optionally substituted aryl) or —C$_1$-C$_4$alkyl-(an optionally substituted heteroaryl); or two $R^{16}$ groups attached to the same N atom are taken together with the N atom to which they are attached to form an optionally substituted C$_2$-C$_{10}$heterocycloalkyl.

In some embodiments, R$^{14}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted phenyl, an optionally substituted naphthyl, an optionally substituted monocyclic heteroaryl, an optionally substituted bicyclic heteroaryl, —C$_1$-C$_4$alkyl-(an optionally substituted C$_3$-C$_{10}$cycloalkyl), —C$_1$-C$_4$alkyl-(an optionally substituted phenyl) or —C$_1$-C$_4$alkyl-(an optionally substituted monocyclic heteroaryl); or R$^{14}$ is L$^3$-X$^3$-Q$^3$; L$^3$ is a C$_1$-C$_4$alkylene or phenylene; X$^3$ is a bond, —O—, —S—, —S(=O)—, —S(=O)$_2$—, —NR$^{13}$S(=O)$_2$—, or —NR$^{13}$—; Q$^3$ is an optionally substituted C$_1$-C$_6$alkyl, C$_1$-C$_6$fluoroalkyl, an optionally substituted C$_3$-C$_{10}$cycloalkyl, an optionally substituted phenyl, an optionally substituted monocyclic heteroaryl, —C$_1$-C$_4$alkyl-(an optionally substituted C$_3$-C$_{10}$cycloalkyl), —C$_1$-C$_4$alkyl-(an optionally substituted phenyl), or —C$_1$-C$_4$alkyl-(an optionally substituted monocyclic heteroaryl).

In some embodiments, R$^{14}$ is C$_1$-C$_6$alkyl, C$_1$-C$_6$-fluoroalkyl, C$_1$-C$_6$heteroalkyl, an optionally substituted C$_3$-C$_{10}$cycloalkyl, an optionally substituted phenyl, an optionally substituted naphthyl, an optionally substituted monocycle heteroaryl, an optionally substituted bicyclic heteroaryl, —C$_1$-C$_4$alkyl-(an optionally substituted C$_3$-C$_{10}$cycloalkyl), —C$_1$-C$_4$alkyl-(an optionally substituted phenyl) or —C$_1$-C$_4$alkyl-(an optionally substituted monocycle heteroaryl); or R$^{14}$ is L$^3$-X$^3$-Q$^3$; L$^3$ is a C$_1$-C$_4$alkylene or phenylene; X$^3$ is a bond, —O—, —S—, —S(=O)—, —S(=O)$_2$—, —C(=O)—, —NR$^{13}$S(=O)$_2$—, or —NR$^{13}$—; Q$^3$ is an optionally substituted C$_1$-C$_4$alkyl, C$_3$-C$_6$cycloalkyl, an optionally substituted phenyl, —C$_1$-C$_4$alkyl-(C$_3$-C$_6$cycloalkyl), or —C$_1$-C$_4$alkyl-(an optionally substituted phenyl). In some other embodiments, R$^{14}$ is C$_1$-C$_6$alkyl, C$_1$-C$_6$fluoroalkyl, C$_1$-C$_6$heteroalkyl, C$_3$-C$_6$cycloalkyl, an optionally substituted phenyl, an optionally substituted naphthyl, an optionally substituted monocyclic heteroaryl, an optionally substituted bicyclic heteroaryl, —C$_1$-C$_4$alkyl-(C$_3$-C$_6$cycloalkyl), —C$_1$-C$_4$alkyl-(an optionally substituted phenyl) or —C$_1$-C$_4$alkyl-(an optionally substituted monocycle heteroaryl); or R$^{14}$ is L$^3$-X$^3$-Q$^3$; L$^3$ is a C$_1$-C$_4$alkylene or phenylene; X$^3$ is a —O—; Q$^3$ is C$_1$-C$_4$alkyl, C$_3$-C$_6$cycloalkyl, an optionally substituted phenyl, —C$_1$-C$_4$alkyl-(C$_3$-C$_6$cycloalkyl), or —C$_1$-C$_4$alkyl-(an optionally substituted phenyl). In some embodiments, L$^3$ is a C$_1$-C$_4$alkylene. In some embodiments, L$^3$ is phenylene.

In some embodiments, R$^{14}$ is C$_1$-C$_4$alkyl, C$_1$-C$_4$fluoroalkyl, C$_1$-C$_4$heteroalkyl, C$_3$-C$_6$cycloalkyl, an optionally substituted phenyl, an optionally substituted napthyl, an optionally substituted monocyclic heteroaryl, —C$_1$-C$_4$alkyl-(an optionally substituted phenyl) or —C$_1$-C$_4$alkyl-(an optionally substituted monocycle heteroaryl). In some embodiments, R$^{14}$ is C$_1$-C$_4$alkyl, C$_1$-C$_4$fluoroalkyl, C$_1$-C$_4$heteroalkyl, C$_3$-C$_6$cycloalkyl, an optionally substituted phenyl, an optionally substituted napthyl, an optionally substituted monocycle heteroaryl, —C$_1$-C$_2$alkyl-(an optionally substituted phenyl) or —C$_1$-C$_2$alkyl-(an optionally substituted monocyclic heteroaryl).

In some embodiments, R$^{14}$ is C$_1$-C$_4$alkyl, C$_1$-C$_4$fluoroalkyl, C$_3$-C$_6$cycloalkyl, an optionally substituted phenyl, an optionally substituted napthyl, or an optionally substituted monocyclic heteroaryl. In some embodiments, R$^{14}$ is C$_1$-C$_4$alkyl, C$_1$-C$_4$fluoroalkyl, C$_3$-C$_6$cycloalkyl, an optionally substituted phenyl, or an optionally substituted napthyl. In some embodiments, R$^{14}$ is C$_1$-C$_4$alkyl, C$_1$-C$_4$fluoroalkyl, C$_3$-C$_6$cycloalkyl, or an optionally substituted phenyl. In some embodiments, R$^{14}$ is C$_1$-C$_4$alkyl, or C$_3$-C$_6$cycloalkyl. In some embodiments, R$^{14}$ is C$_1$-C$_4$alkyl.

In some embodiments, R$^{10}$ is —C(=O)R$^{14}$.

In one aspect, the compound of Formula (I) has the structure of Formula (III):

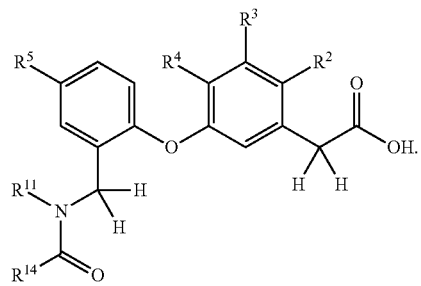

Formula (III)

In some embodiments, R$^{10}$ —S(=O)$_2$R$^{14}$.

In one aspect, the compound of Formula (I) has the structure of Formula (VI):

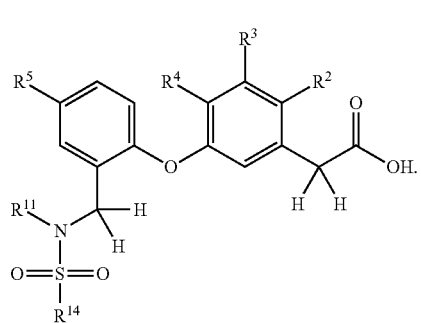

Formula (VI)

In some embodiments, R$^{15}$ is C$_1$-C$_6$alkyl, C$_1$-C$_6$fluoroalkyl, C$_1$-C$_6$heteroalkyl, an optionally substituted C$_3$-C$_{10}$cycloalkyl, an optionally substituted phenyl, an optionally substituted monocyclic heteroaryl, —C$_1$-C$_2$alkyl-(an optionally substituted C$_3$-C$_6$cycloalkyl), —C$_1$-C$_2$alkyl-(an optionally substituted phenyl) or —C$_1$-C$_2$alkyl-(an optionally substituted monocyclic heteroaryl).

In other embodiments, R$^{15}$ is C$_1$-C$_4$alkyl, C$_3$-C$_6$cycloalkyl, an optionally substituted phenyl, an optionally substituted monocyclic heteroaryl, —C$_1$-C$_2$alkyl-(C$_3$-C$_6$cycloalkyl), —C$_1$-C$_2$alkyl-(an optionally substituted phenyl) or —C$_1$-C$_2$alkyl-(an optionally substituted monocyclic heteroaryl).

In some other embodiments, R$^{15}$ is C$_1$-C$_4$alkyl, —C$_1$-C$_2$alkyl-(an optionally substituted phenyl) or —C$_1$-C$_2$alkyl-(an optionally substituted monocyclic heteroaryl).

In one aspect, R$^{10}$ is —C(=O)OR$^{15}$.

In one aspect, the compound of Formula (I) has the structure of Formula (IV):

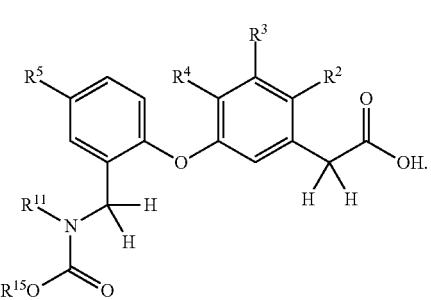

Formula (IV)

In some embodiments, each $R^{16}$ is independently H, —CN, $C_1$-$C_6$alkyl, $C_1$-$C_6$-fluoroalkyl, $C_1$-$C_6$heteroalkyl, an optionally substituted $C_3$-$C_6$cycloalkyl, an optionally substituted phenyl, an optionally substituted monocyclic heteroaryl, —$C_1$-$C_2$alkyl-(an optionally substituted $C_3$-$C_6$cycloalkyl), —$C_1$-$C_2$alkyl-(an optionally substituted phenyl) or —$C_1$-$C_2$alkyl-(an optionally substituted monocyclic heteroaryl).

In some embodiments, each $R^{16}$ is independently H, —CN, $C_1$-$C_4$alkyl, an optionally substituted $C_3$-$C_6$cycloalkyl, an optionally substituted phenyl, an optionally substituted monocyclic heteroaryl, —$C_1$-$C_1$alkyl-(an optionally substituted $C_3$-$C_6$cycloalkyl), —$C_1$-$C_2$alkyl-(an optionally substituted phenyl) or —$C_1$-$C_2$alkyl-(an optionally substituted monocyclic heteroaryl).

In other embodiments, one $R^{16}$ is H or $C_1$-$C_4$alkyl and the other $R^{16}$ is H, $C_1$-$C_4$alkyl, an optionally substituted $C_3$-$C_6$cycloalkyl, an optionally substituted phenyl, an optionally substituted monocyclic heteroaryl, —$C_1$-$C_2$alkyl-(an optionally substituted $C_3$-$C_6$cycloalkyl), —$C_1$-$C_2$alkyl-(an optionally substituted phenyl) or —$C_1$-$C_2$alkyl-(an optionally substituted monocycle heteroaryl). In other embodiments, one $R^{16}$ is H or $C_1$-$C_4$alkyl and the other $R^{16}$ is H, $C_1$-$C_4$alkyl, $C_3$-$C_6$cycloalkyl, an optionally substituted phenyl, an optionally substituted monocycle heteroaryl, —$C_1$-$C_2$alkyl-($C_3$-$C_6$cycloalkyl), —$C_1$-$C_2$alkyl-(an optionally substituted phenyl) or —$C_1$-$C_2$alkyl-(an optionally substituted monocyclic heteroaryl).

In one aspect, $R^{10}$ is —C(=O)N($R^{16}$)$_2$.

In one aspect, the compound of Formula (I) has the structure of Formula (V):

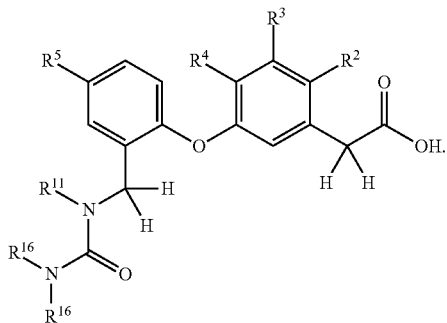

Formula (V)

In some embodiments, $R^{11}$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$C(CH$_3$)$_3$, —CH$_2$CF$_3$, —CH$_2$CH$_2$OH, —CH$_2$CH$_2$OCH$_3$, —CH$_2$CH$_2$N(CH$_3$)$_2$, —CH$_2$COOH, —CH$_2$C(O)NH$_2$, —CH$_2$-(optionally substituted phenyl), —CH$_2$CH$_2$-(optionally substituted phenyl), —CH(CH$_3$)CH$_2$-(optionally substituted phenyl), —C(CH$_3$)$_2$CH$_2$-(optionally substituted phenyl), optionally substituted phenyl, o-tolyl, cyclopropyl, cyclobutyl, cyclopentyl, cyclohexyl, indan-1-yl, indan-2-yl, 2-hydroxy-indan-1-yl, or 2-methoxy-indan-1-yl.

In some embodiments, $R^4$ is H, F, Cl, Br, —OCH$_3$, —CH$_3$, —CF$_3$, or —OCF$_3$.

In some embodiments, $R^{11}$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$C(CH$_3$)$_3$, —CH$_2$CF$_3$, —CH$_2$-(optionally substituted phenyl), —CH$_2$CH$_2$-(optionally substituted phenyl), —CH(CH$_3$)CH$_2$-(optionally substituted phenyl), —C(CH$_3$)$_2$CH$_2$-(optionally substituted phenyl), optionally substituted phenyl, o-tolyl, cyclopropyl, cyclobutyl, cyclopentyl, cyclohexyl, indan-1-yl, indan-2-yl, 2-hydroxy-indan-1-yl, or 2-methoxy-indan-1-yl.

In some embodiments, $R^5$ is H, F, Cl, Br, —OH—CH$_3$, —CH$_2$CH$_3$, CH$_2$CH$_2$CH$_3$, —CH(CH$_3$)$_2$, —C(CH$_3$)$_3$, —CF$_3$, —CH$_2$CF$_3$, —OCH$_3$, —OCH$_2$CH$_3$, —OCF$_3$, —S(=O)$_2$CH$_3$, —NHC(=O)($C_1$-$C_6$alkyl), —NHC(=O) (optionally substituted phenyl), —N(CH$_3$)C(=O)($C_1$-$C_6$alkyl), —N(CH$_3$)C(=O) (optionally substituted phenyl), —NHS(=O)$_2$($C_1$-$C_6$alkyl), —NHS(=O)$_2$ (optionally substituted phenyl), —N(CH$_3$)S(=O)$_2$($C_1$-$C_6$alkyl), or —N(CH$_3$)S(=O)$_2$ (optionally substituted phenyl). In some embodiments, $R^5$ is H, F, Cl, Br, —CH$_3$, —CF$_3$, —OCH$_3$, —OCF$_3$, —S(=O)$_2$CH$_3$, —NHC(=O)($C_1$-$C_6$alkyl), —NHC(=O) (optionally substituted phenyl), —N(CH$_3$)C(=O)($C_1$-$C_6$alkyl), —N(CH$_3$)C(=O) (optionally substituted phenyl), —NHS(=O)$_2$($C_1$-$C_6$alkyl), —NHS(=O)$_2$ (optionally substituted phenyl), —N(CH$_3$)S(=O)$_2$($C_1$-$C_6$alkyl), or —N(CH$_3$)S(=O)$_2$ (optionally substituted phenyl). In some embodiments, $R^5$ is H, F, Cl, Br, —CH$_3$, —CF$_3$, —OCH$_3$, or —OCF$_3$.

In some embodiments, $R^{11}$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$C(CH$_3$)$_3$, —CH$_2$CF$_3$, —CH$_2$-(optionally substituted phenyl), —CH$_2$CH$_2$-(optionally substituted phenyl), —CH(CH$_3$)CH$_2$-(optionally substituted phenyl), —C(CH$_3$)$_2$CH$_2$-(optionally substituted phenyl), optionally substituted phenyl, o-tolyl, cyclopropyl, cyclobutyl, cyclopentyl, or cyclohexyl. In some embodiments, $R^{11}$ is H, —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$C(CH$_3$)$_3$, —CH$_2$CF$_3$, —CH$_2$-(optionally substituted phenyl), —CH$_2$CH$_2$-(optionally substituted phenyl), —CH(CH$_3$)CH$_2$-(optionally substituted phenyl), or —C(CH$_3$)$_2$CH$_2$-(optionally substituted phenyl). In some embodiments, $R^{11}$ is optionally substituted phenyl, o-tolyl, cyclopropyl, cyclobutyl, cyclopentyl, or cyclohexyl. In some embodiments, $R^{11}$ is cyclopropyl, cyclobutyl, cyclopentyl, or cyclohexyl. In some embodiments, $R^{11}$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$C(CH$_3$)$_3$, or —CH$_2$CF$_3$.

In one aspect, described herein is a compound having the structure of Formula (VII), pharmaceutically acceptable salt, pharmaceutically acceptable solvate, or pharmaceutically acceptable prodrug thereof:

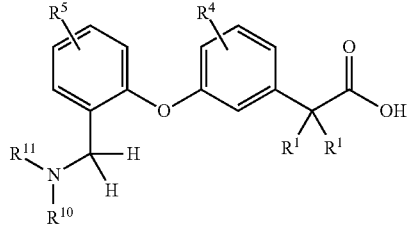

Formula (VII)

wherein,
each $R^1$ is independently selected from H, F, and —CH$_3$;
$R^4$ is H, halogen, —OH, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, or $C_3$-$C_6$cycloalkyl;
$R^5$ is H, halogen, —CN, —NO$_2$, —OH, —OR$^{13}$, —SR$^{12}$, —S(=O)R$^{12}$, —S(=O)$_2$R$^{12}$, —C(=O)R$^{12}$, —OC(=O)$^{12}$, —CO$_2$R$^{13}$, —OCO$_2$R$^{13}$, —N(R$^{13}$)$_2$, —C(=O)N(R$^{13}$)$_2$, —OC(=O)N(R$^{13}$)$_2$, —NR$^{13}$C (=O)N(R¹³)₂, —NR¹³C(=O)R¹², —NR¹³C(=O)OR¹², —NR¹³S(=O)₂R¹², —C(OH)(R¹³)₂, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, $C_3$-$C_6$cycloalkyl, an optionally substituted $C_2$-$C_{10}$heterocycloalkyl, optionally substituted phenyl, or optionally substituted monocycle heteroaryl;

$R^{10}$ is —C(=O)OR¹⁴, —C(=O)OR¹⁵, —C(=O)N(R¹⁶)₂, or —S(=O)₂R¹⁴;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted napthyl, an optionally substituted monocyclic or bicyclic heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted phenyl), —$C_1$-$C_4$alkyl-(optionally substituted napthyl), —$C_1$-$C_4$alkyl-(optionally substituted monocyclic or bicyclic heteroaryl), or -L³-X³-Q³;

L³ is a $C_1$-$C_4$alkylene or phenylene;

X³ is a bond, —O—, —S—, —S(=O)—, —S(=O)₂—, —C(=O)—, —NR¹³S(=O)₂—, or —NR¹³—;

Q³ is $C_1$-$C_4$alkyl, $C_1$-$C_4$fluoroalkyl, $C_3$-$C_6$cycloalkyl, an optionally substituted phenyl, an optionally substituted monocyclic heteroaryl, —$C_1$-$C_4$alkyl-(optionally substituted phenyl), or —$C_1$-$C_4$alkyl-(optionally substituted monocyclic heteroaryl);

$R^{15}$ is $C_1$-$C_6$alkyl, $C_1$-$C_6$fluoroalkyl, $C_3$-$C_6$cycloalkyl, an optionally substituted phenyl, —$C_1$-$C_4$alkyl-($C_3$-$C_6$cycloalkyl), —$C_1$-$C_4$alkyl-(optionally substituted phenyl) or —$C_1$-$C_4$alkyl-(optionally substituted monocyclic heteroaryl);

each $R^{16}$ is independently H, —CN, $C_1$-$C_6$alkyl, $C_1$-$C_6$fluoroalkyl, $C_1$-$C_6$heteroalkyl, $C_3$-$C_6$cycloalkyl, an optionally substituted $C_2$-$C_8$heterocycloalkyl, an optionally substituted phenyl, an optionally substituted monocyclic heteroaryl, —$C_1$-$C_4$alkyl-($C_3$-$C_6$cycloalkyl), —$C_1$-$C_4$alkyl-(optionally substituted $C_2$-$C_8$heterocycloalkyl), —$C_1$-$C_4$alkyl-(optionally substituted phenyl) or —$C_1$-$C_4$alkyl-(optionally substituted monocycle heteroaryl); or two $R^{16}$ groups attached to the same N atom are taken together with the N atom to which they are attached to form an optionally substituted $C_2$-$C_8$heterocycloalkyl;

$R^{11}$ is H, $C_1$-$C_6$alkyl, $C_1$-$C_6$heteroalkyl, $C_1$-$C_6$haloalkyl, an optionally substituted monocyclic or bicyclic $C_3$-$C_{10}$cycloalkyl, an optionally substituted phenyl, an optionally substituted monocyclic heteroaryl, —$C_1$-$C_4$alkyl-($C_3$-$C_6$cycloalkyl), —$C_1$-$C_4$alkyl-(optionally substituted phenyl), or —$C_1$-$C_4$alkyl-(optionally substituted monocyclic heteroaryl);

$R^{12}$ is $C_1$-$C_6$alkyl, $C_1$-$C_6$heteroalkyl, $C_1$-$C_6$fluoroalkyl, optionally substituted $C_3$-$C_{10}$cycloalkyl, optionally substituted $C_2$-$C_{10}$heterocycloalkyl, optionally substituted aryl, —$C_1$-$C_4$alkyl-(optionally substituted aryl) or optionally substituted heteroaryl; and each $R^{13}$ is independently selected from H, $C_1$-$C_6$heteroalkyl, $C_1$-$C_6$fluoroalkyl, an optionally substituted $C_3$-$C_{10}$cycloalkyl, an optionally substituted $C_2$-$C_{10}$heterocycloalkyl, an optionally substituted aryl, —$C_1$-$C_4$alkyl-(optionally substituted aryl), and an optionally substituted heteroaryl; or two $R^{13}$ groups attached to the same N atom are taken together with the N atom to which they are attached to form an optionally substituted $C_2$-$C_{10}$heterocycloalkyl.

In one aspect, the compound of Formula (VII) has the following structure:

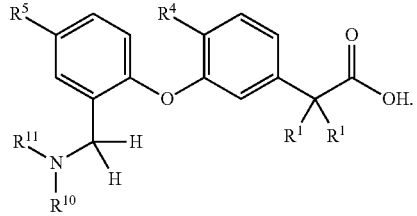

In one aspect, each $R^1$ is H.

In some embodiments, $R^4$ is H, halogen, —OH, $C_1$-$C_4$alkyl, $C_1$-$C_4$fluoroalkyl, $C_1$-$C_4$fluoroalkoxy, or $C_1$-$C_4$alkoxy.

In some embodiments, $R^{11}$ is H, $C_1$-$C_6$alkyl, $C_1$-$C_6$heteroalkyl, $C_1$-$C_6$haloalkyl, —$C_1$-$C_4$alkyl-($C_3$-$C_6$cycloalkyl), —$C_1$-$C_4$alkyl-(optionally substituted phenyl), or —$C_1$-$C_4$alkyl-(optionally substituted monocyclic heteroaryl).

In some embodiments, $R^5$ is H, halogen, —OH, —OR¹³, —S(=O)₂($C_1$-$C_4$alkyl), —NHC(=O)($C_1$-$C_6$alkyl), —NHC(=O) (optionally substituted phenyl), —N(CH₃)C(=O)$C_1$-$C_6$alkyl), —N(CH₃)C(=O) optionally substituted phenyl), —NHS(=O)₂($C_1$-$C_6$alkyl), —NHS(=O)₂ (optionally substituted phenyl), —N(CH₃)S(=O)₂($C_1$-$C_6$alkyl), —N(CH₃)S(=O)₂ (optionally substituted phenyl), —C(OH)($C_1$-$C_4$fluoroalkyl, $C_1$-$C_4$-fluoroalkoxy, $C_1$-$C_4$alkoxy, $C_1$-$C_4$heteroalkyl, $C_3$-$C_6$cycloalkyl, an optionally substituted $C_2$-$C_{10}$heterocycloalkyl, optionally substituted phenyl, or optionally substituted monocyclic heteroaryl. In some embodiments, $R^5$ is $C_3$-$C_6$cycloalkyl, an optionally substituted $C_2$-$C_{10}$heterocycloalkyl, optionally substituted phenyl, or optionally substituted monocyclic heteroaryl. In some embodiments, $R^5$ is optionally substituted phenyl, or optionally substituted monocyclic heteroaryl.

In some embodiments, $R^{14}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, an optionally substituted naphthyl, or an optionally substituted monocyclic or bicyclic heteroaryl. In some embodiments, $R^{14}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, or an optionally substituted naphthyl.

In some embodiments, $R^{15}$ is $C_1$-$C_6$alkyl, $C_1$-$C_6$fluoroalkyl, $C_3$-$C_6$cycloalkyl, —$C_1$-$C_2$alkyl-($C_3$-$C_6$cycloalkyl), or —$C_1$-$C_2$alkyl)-optionally substituted phenyl).

In some embodiments, one $R^{16}$ is H or $C_1$-$C_4$alkyl and the other $R^{16}$ is H, —CN, $C_1$-$C_6$alkyl, $C_1$-$C_6$fluoroalkyl, $C_1$-$C_6$heteroalkyl, $C_3$-$C_6$cycloalkyl, an optionally substituted $C_2$-$C_{10}$heterocycloalkyl, an optionally substituted phenyl, an optionally substituted monocyclic heteroaryl, —$C_1$-$C_2$alkyl-($C_3$-$C_6$cycloalkyl), —$C_1$-$C_2$alkyl-(optionally substituted $C_2$-$C_{10}$heterocycloalkyl), —$C_1$-$C_2$alkyl-(optionally substituted phenyl) or —$C_1$-$C_4$alkyl-(optionally substituted monocyclic heteroaryl).

In some embodiments, one $R^{16}$ is H or $C_1$-$C_4$alkyl and the other $R^{16}$ is H, $C_1$-$C_4$alkyl, or —$C_1$-$C_2$alkyl-(optionally substituted phenyl).

In some embodiments, $R^5$ is H, halogen, —OH, —OR¹³, —S(=O)₂($C_1$-$C_4$alkyl), —NHC(=O)($C_1$-$C_6$alkyl), —NHC (=O) (optionally substituted phenyl), —N(CH$_3$)C(=O)C$_1$-C$_6$alkyl), —N(CH$_3$)C(=O) (optionally substituted phenyl), —NHS(=O)$_2$(C$_1$-C$_6$alkyl), —NHS(=O)$_2$ (optionally substituted phenyl), —N(CH$_3$)S(=O)$_2$(C$_1$-C$_6$alkyl), —N(CH$_3$)S(=O)$_2$ (optionally substituted phenyl), C$_1$-C$_4$alkyl, C$_1$-C$_4$fluoroalkyl, C$_1$-C$_4$fluoroalkoxy, C$_1$-C$_4$alkoxy, C$_1$-C$_4$heteroalkyl, or C$_3$-C$_6$cycloalkyl.

In some embodiments, R$^5$ is H, halogen, —S(=O)$_2$(C$_1$-C$_4$alkyl), —NHC(=O)(C$_1$-C$_6$alkyl), —NHC(=O) (optionally substituted phenyl), —N(CH$_3$)C(=O)(C$_1$-C$_6$alkyl), —N(CH$_3$)C(=O) (optionally substituted phenyl), —NHS(=O)$_2$(C$_1$-C$_6$alkyl), —NHS(=O)$_2$ (optionally substituted phenyl), —N(CH$_3$)S(=O)$_2$(C$_1$-C$_6$alkyl), —N(CH$_3$)S(=O)$_2$ (optionally substituted phenyl), C$_1$-C$_4$alkyl, C$_1$-C$_4$fluoroalkyl, C$_1$-C$_4$fluoroalkoxy, C$_1$-C$_4$alkoxy, C$_1$-C$_4$heteroalkyl, or C$_3$-C$_6$cycloalkyl. In some embodiments, R$^5$ is H, halogen, C$_1$-C$_4$alkyl, C$_1$-C$_4$fluoroalkyl, C$_1$-C$_4$fluoroalkoxy, C$_1$-C$_4$alkoxy, or C$_3$-C$_6$cycloalkyl Any combination of the groups described above for the various variables is contemplated herein.

Compounds of Formula (I), Formula (II), Formula (III), Formula (IV), Formula (V), Formula (VI) and Formula (VII), are antagonists of DP$_2$. In a specific aspect, the antagonist of DP$_2$ is selective for DP$_2$. In some embodiments, the antagonist of DP$_2$ is also an antagonist of DP$_2$. In some embodiments, the antagonist of DP$_2$ is also an antagonist of TP (thromboxane receptor).

In some embodiments, presented herein are compounds selected from active metabolites, solvates, pharmaceutically acceptable salts or pharmaceutically acceptable prodrugs of a compound of any of Formula (I), Formula (II), Formula (III), Formula (IV), Formula (V), Formula (VI) or Formula (VII).

In one aspect, provided herein is a pharmaceutical composition comprising a therapeutically effective amount of a compound provided herein. In some embodiments, the pharmaceutical composition also includes at least one pharmaceutically acceptable excipient.

In certain embodiments, presented herein are methods for treating a PGD$_2$-dependent condition or disease in a patient comprising administering to the patient a therapeutically effective amount of an antagonist of DP$_2$ having the structure of any of Formula (I), Formula (II), Formula (III), Formula (IV), Formula (V), Formula (VI) or Formula (VII). In certain aspects, provided herein is a method for treating inflammation in a mammal comprising administering a therapeutically effective amount of a compound provided herein to the mammal in need.

In a specific aspect, provided herein is a method for treating asthma in a mammal comprising administering a therapeutically effective amount of a compound provided herein to the mammal in need. In a further or alternative embodiment, provided herein is a method for treating asthma in a mammal comprising administering a therapeutically effective amount of a compound provided herein, such as, for example, a compound of any of Formula (I), Formula (II), Formula (III), Formula (IV), Formula (V), Formula (VI) or Formula (VII), to the mammal in need.

In a specific aspect, presented herein are compounds in Table 1, or pharmaceutically acceptable salts, solvates or prodrugs thereof. Also presented herein are compounds in Table 2, or pharmaceutically acceptable salts, solvates or prodrugs thereof.

In one aspect, the compounds of Formula (I), Formula (II), Formula (III), Formula (IV), Formula (V), Formula (VI) or Formula (VII), are antagonists of DP$_2$. In some embodiments such antagonists of DP$_2$ also antagonize other related PGD$_2$ receptors. Related PGD$_2$ receptors include, but are not limited to, DP$_1$ and TP.

In further or alternative embodiments, the compounds of Formula (I), Formula (II), Formula (III), Formula (IV), Formula (V), Formula (VI) or Formula (VII), are included into pharmaceutical compositions or medicaments used for treating a PGD$_2$-dependent or PGD$_2$ mediated condition or disease in a patient.

In another aspect, compounds of any of Formula (I), Formula (II), Formula (III), Formula (IV), Formula (V), Formula (VI) or Formula (VII), are used to treat or prevent inflammatory conditions. Inflammatory conditions include, but are not limited to, asthma, rhinitis, chronic obstructive pulmonary disease, pulmonary hypertension, interstitial lung fibrosis, atherosclerosis, aortic aneurysm, myocardial infarction, and stroke.

In another aspect, compounds of any of Formula (I), Formula (II), Formula (III), Formula (IV), Formula (V), Formula (VI) or Formula (VII), are used to treat or prevent immunological disorders. In one aspect the immunological disorders include, but are not limited to, allergy or to excessive or inappropriate response to an endogenous or exogenous antigen. In certain embodiments, the immunological disorder that is characterized by immune dysregulation that is not accompanied by inflammation.

In another aspect, compounds of any of Formula (I), Formula (II), Formula (III), Formula (IV), Formula (V), Formula (VI) or Formula (VII), are used to treat or prevent proliferative disorders. In one aspect the proliferative disorders include, but are not limited to, cancer and noncancerous disorders, including, but not limited to, those involving the skin or lymphatic tissues.

In another aspect, compounds of any of Formula (I), Formula (II), Formula (III), Formula (IV), Formula (V), Formula (VI) or Formula (VII), are used to treat or prevent metabolic disorders. In one aspect the metabolic disorders include, but are not limited to, bone remodeling, loss or gain.

In additional aspects, such conditions are iatrogenic and increases in, or abnormal localization of, PGD$_2$ is induced by other therapies or medical or surgical procedures. In other embodiments, the PGD$_2$-dependent or PGD$_2$ mediated condition or disease is caused by surgery.

In other aspects, the methods, compounds, pharmaceutical compositions, and medicaments described herein are used to prevent the cellular activity of PGD$_2$. In other aspects, such methods, compounds, pharmaceutical compositions, and medicaments comprise DP$_2$ antagonists disclosed herein for the treatment of asthma by modulating the activity of enzymes or proteins in a patient wherein such enzymes or proteins are involved in the PGD$_2$ pathway such as, by way of example, DP$_2$. In yet other aspects, the methods, compounds, pharmaceutical compositions, and medicaments described herein are used in combination with other medical treatments or surgical modalities.

In one aspect are methods for reducing/antagonizing the PGD$_2$ activation of DP$_2$ in a mammal comprising administering to the mammal at least once an effective amount of a compound having the structure of any of Formula (I), Formula (II), Formula (III), Formula (IV), Formula (V), Formula (VI) or Formula (VII).

In another aspect are methods for modulating, including reducing and/or antagonizing the activation of DP$_2$, directly or indirectly, in a mammal comprising administering to the mammal at least once an effective amount of at least one compound having the structure of any of Formula (I), Formula (II), Formula (III), Formula (IV), Formula (V), Formula (VI) or Formula (VII).

In another aspect, presented herein are methods for modulating, including reducing and/or antagonizing the activity of $PGD_2$ in a mammal, directly or indirectly, comprising administering to the mammal at least once an effective amount of at least one compound having the structure of any of Formula (I), Formula (II), Formula (III), Formula (IV), Formula (V), Formula (VI) or Formula (VII).

In another aspect are methods for treating $PGD_2$-dependent or $PGD_2$ mediated conditions or diseases, comprising administering to the mammal at least once an effective amount of at least one compound having the structure of any of Formula (I), Formula (II), Formula (III), Formula (IV), Formula (V), Formula (VI) or Formula (VII).

In another aspect are methods for treating inflammation comprising administering to the mammal at least once an effective amount of at least one compound having the structure of any of Formula (I), Formula (II), Formula (III), Formula (IV), Formula (V), Formula (VI) or Formula (VII).

In another aspect are methods for treating immunological abnormalities comprising administering to the mammal at least once an effective amount of at least one compound having the structure of any of Formula (I), Formula (II), Formula (III), Formula (IV), Formula (V), Formula (VI) or Formula (VII).

In another aspect are methods for treating respiratory diseases comprising administering to the mammal at least once an effective amount of at least one compound having the structure of any of Formula (I), Formula (II), Formula (III), Formula (IV), Formula (V), Formula (VI) or Formula (VII). In a further embodiment of this aspect, the respiratory disease is asthma. In a further embodiment of this aspect, the respiratory disease includes, but is not limited to, adult respiratory distress syndrome and allergic (extrinsic) asthma, non-allergic (intrinsic) asthma, acute severe asthma, chronic asthma, clinical asthma, nocturnal asthma, neutrophilic asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma.

In another aspect are methods for treating respiratory diseases comprising administering to the mammal at least once an effective amount of at least one compound having the structure of any of Formula (I), Formula (II), Formula (III), Formula (IV), Formula (V), Formula (VI) or Formula (VII). In a further embodiment of this aspect, the respiratory disease is rhinitis. In a further embodiment of this aspect, the respiratory disease includes, but is not limited to, allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In another aspect are methods for treating chronic obstructive pulmonary disease comprising administering to the mammal at least once an effective amount of at least one compound having the structure of any of Formula (I), Formula (II), Formula (III), Formula (IV), Formula (V), Formula (VI) or Formula (VII). In a further embodiment of this aspect, chronic obstructive pulmonary disease includes, but is not limited to, chronic bronchitis and/or emphysema, pulmonary hypertension, interstitial lung fibrosis and/or airway inflammation and cystic fibrosis.

In another aspect are methods for preventing increased mucosal secretion and/or edema in a disease or condition comprising administering to the mammal at least once an effective amount of at least one compound having the structure of any of Formula (I), Formula (II), Formula (III), Formula (IV), Formula (V), Formula (VI) or Formula (VII).

In another aspect are methods for treating vasoconstriction, atherosclerosis and its sequelae myocardial ischemia, myocardial infarction, aortic aneurysm, vasculitis, cardiac arrhythmia, and stroke comprising administering to the mammal an effective amount of a compound having the structure of any of Formula (I), Formula (II), Formula (III), Formula (IV), Formula (V), Formula (VI) or Formula (VII).

In another aspect are methods for treating organ reperfusion injury following organ ischemia and/or endotoxic shock comprising administering to the mammal at least once an effective amount of at least one compound having the structure of any of Formula (I), Formula (II), Formula (III), Formula (IV), Formula (V), Formula (VI) or Formula (VII).

In another aspect are methods for reducing the constriction of blood vessels in a mammal comprising administering to the mammal at least once an effective amount of at least one compound having the structure of any of Formula (I), Formula (II), Formula (III), Formula (IV), Formula (V), Formula (VI) or Formula (VII).

In another aspect are methods for lowering or preventing an increase in blood pressure of a mammal comprising administering to the mammal at least once an effective amount of at least one compound having the structure of any of Formula (I), Formula (II), Formula (III), Formula (IV), Formula (V), Formula (VI) or Formula (VII).

In another aspect are methods for preventing eosinophil and/or basophil and/or dendritic cell and/or neutrophil and/or monocyte or TH2 cell recruitment comprising administering to the mammal at least once an effective amount of at least one compound having the structure of any of Formula (I), Formula (II), Formula (III), Formula (IV), Formula (V), Formula (VI) or Formula (VII).

A further aspect are methods for the prevention or treatment of abnormal bone remodeling, loss or gain, including diseases or conditions as, by way of example, osteopenia, osteoporosis, Paget's disease, cancer, trauma, surgery, and other diseases comprising administering to the mammal at least once an effective amount of at least one compound having the structure of any of Formula (I), Formula (II), Formula (III), Formula (IV), Formula (V), Formula (VI) or Formula (VII).

In another aspect are methods for preventing ocular inflammation and allergic conjunctivitis, vernal keratoconjunctivitis, and papillary conjunctivitis comprising administering to the mammal at least once an effective amount of at least one having the structure of any of Formula (I), Formula (II), Formula (III), Formula (IV), Formula (V), Formula (VI) or Formula (VII).

In another aspect are methods for treating CNS disorders comprising administering to the mammal at least once an effective amount of at least one compound having the structure of any of Formula (I), Formula (II), Formula (III), Formula (IV), Formula (V), Formula (VI) or Formula (VII). CNS disorders include, but are not limited to, multiple sclerosis, Parkinson's disease, Alzheimer's or other degenerative disease, stroke, cerebral ischemia, retinal ischemia, post-surgical cognitive dysfunction, migraine, peripheral neuropathy/neuropathic pain, spinal cord injury, cerebral edema and head injury.

A further aspect are methods for the treatment of cancer comprising administering to the mammal at least once an effective amount of at least one compound having the structure of any of Formula (I), Formula (II), Formula (M), Formula (IV), Formula (V), Formula (VI) or Formula (VII). The type of cancer includes, but is not limited to, pancreatic cancer and other solid or hematological tumors.

In another aspect are methods for treating endotoxic shock and septic shock comprising administering to the mammal at least once an effective amount of at least one compound having the structure of any of Formula (I), Formula (II), Formula (III), Formula (IV), Formula (V), Formula (VI) or Formula (VII).

In another aspect are methods for treating rheumatoid arthritis and osteoarthritis comprising administering to the mammal at least once an effective amount of at least one compound having the structure of any of Formula (I), Formula (II), Formula (III), Formula (IV), Formula (V), Formula (VI) or Formula (VII).

In another aspect are methods for treating or preventing increased gastrointestinal diseases comprising administering to the mammal at least once an effective amount of at least one compound having the structure of any of Formula (I), Formula (II), Formula (III), Formula (IV), Formula (V), Formula (VI) or Formula (VII). Such diseases include, by way of example only, chronic gastritis, eosinophilic gastroenteritis, and gastric motor dysfunction.

A further aspect are methods for treating kidney diseases comprising administering to the mammal at least once an effective amount of at least one compound having the structure of any of Formula (I), Formula (II), Formula (III), Formula (IV), Formula (V), Formula (VI) or Formula (VII). Such diseases include, by way of example only, acute tubular necrosis, glomerulonephritis, cyclosporine nephrotoxicity, renal ischemia, and reperfusion injury.

In another aspect are methods for preventing or treating acute or chronic renal insufficiency comprising administering to the mammal at least once an effective amount of at least one compound having the structure of any of Formula (I), Formula (II), Formula (III), Formula (IV), Formula (V), Formula (VI) or Formula (VII).

In another aspect are methods to diminish the inflammatory aspects of acute infections within one or more solid organs or tissues such as the kidney with acute pyelonephritis.

In another aspect are methods for preventing or treating acute or chronic disorders involving recruitment or activation of eosinophils comprising administering to the mammal at least once an effective amount of at least one compound having the structure of any of Formula (I), Formula (II), Formula (III), Formula (IV), Formula (V), Formula (VI) or Formula (VII).

In another aspect are methods for preventing or treating acute or chronic erosive disease or motor dysfunction of the gastrointestinal tract caused by non-steroidal anti-inflammatory drugs (including selective or non-selective cyclooxygenase-1 or -2 inhibitors) comprising administering to the mammal at least once an effective amount of at least one compound having the structure of any of Formula (I), Formula (II), Formula (III), Formula (IV), Formula (V), Formula (VI) or Formula (VII).

A further aspect are methods for the prevention or treatment of rejection or dysfunction in a transplanted organ or tissue comprising administering to the mammal at least once an effective amount of at least one compound having the structure of any of Formula (I), Formula (II), Formula (III), Formula (IV), Formula (V), Formula (VI) or Formula (VII).

In another aspect are methods for treating inflammatory responses of the skin comprising administering to the mammal at least once an effective amount of at least one compound having the structure of any of Formula (I), Formula (II), Formula (III), Formula (IV), Formula (V), Formula (VI) or Formula (VII). Such inflammatory responses of the skin include, by way of example, dermatitis, contact dermatitis, eczema, urticaria, rosacea, and scarring. In another aspect are methods for reducing psoriatic lesions in the skin, joints, or other tissues or organs, comprising administering to the mammal an effective amount of a first compound having the structure of any of Formula (I), Formula (II), Formula (III), Formula (IV), Formula (V), Formula (VI) or Formula (VII).

A further aspect are methods for the treatment of cystitis, including, by way of example only, interstitial cystitis, comprising administering to the mammal at least once an effective amount of at least one compound having the structure of any of Formula (I), Formula (II), Formula (III), Formula (IV), Formula (V), Formula (VI) or Formula (VII).

A further aspect are methods for the treatment of metabolic syndromes such as Familial Mediterranean Fever comprising administering to the mammal at least once an effective amount of at least one compound having the structure of any of Formula (I), Formula (II), Formula (III), Formula (IV), Formula (V), Formula (VI) or Formula (VII).

In a further aspect are methods to treat hepatorenal syndrome comprising administering to the mammal at least once an effective amount of at least one compound having the structure of any of Formula (I), Formula (II), Formula (III), Formula (IV), Formula (V), Formula (VI) or Formula (VII).

In a further aspect are methods to modulate the immune response to endogenous or exogenous antigens.

In a further aspect are methods to treat acute or chronic allergic responses to exogenous substances that have been ingested such as foods (e.g., peanuts) or drugs (e.g., penicillin, non-steroidal anti-inflammatory drugs or the like).

In another aspect is the use of a compound of any of Formula (I), Formula (II), Formula (III), Formula (IV), Formula (V), Formula (VI) or Formula (VII), in the manufacture of a medicament for treating an inflammatory disease or condition in an animal in which the activity of at least one $PGD_2$-associated protein contributes to the pathology and/or symptoms of the disease or condition. In one embodiment of this aspect, the $PGD_2$ pathway protein is CRTH2. In another or further embodiment of this aspect, the inflammatory disease or conditions are respiratory, cardiovascular, or proliferative diseases.

In any of the aforementioned aspects are further embodiments in which: (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal; and/or (h) the effective amount of the compound is administered by ophthalmic administration; and/or (i) the effective amount of the compound is administered rectally to the mammal.

In any of the aforementioned aspects are further embodiments in which the mammal is a human, including embodiments wherein the human has an asthmatic condition or one or more other condition(s) selected from the group consisting of allergic (extrinsic) asthma, non-allergic (intrinsic) asthma, acute severe asthma, chronic asthma, clinical asthma, nocturnal asthma, neutrophilic asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, or seasonal asthma, or chronic obstructive pulmonary disease, or pulmonary hypertension or interstitial lung fibrosis. In any of the aforementioned aspects are further embodiments in which the mammal is an animal model for pulmonary inflammation, examples of which are provided herein.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the treatment of $PGD_2$ dependent diseases or conditions are further embodiments comprising administering at least one additional agent in addition to the administration of a compound having the structure of any of Formula (I), Formula (II), Formula (III), Formula (IV), Formula (V), Formula (VI) or Formula (VII). In various embodiments, each agent is administered in any order, including simultaneously. In certain embodiments, the at least one additional agent is, by way of example only, an anti-inflammatory agent, a different compound having the structure of any of Formula (I), Formula (II), Formula (III), Formula (IV), Formula (V), Formula (VI) or Formula (VII), a $DP_1$ receptor antagonist, a TP receptor antagonist, or a different $DP_2$ receptor antagonist.

In other embodiments, a compound of any of Formula (I), Formula (II), Formula (III), Formula (IV), Formula (V), Formula (VI) or Formula (VII), is combined with an additional agent that is a respiratory agent, including, but not limited to antihistamines (e.g., Zyrtec®), bronchodilators, LABAs (e.g., salmeterol), theophylline, IgE modulators (e.g., Xolair® and omalizumab), steroids (e.g., fluticasone).

In further or alternative embodiments, the anti-inflammatory agent is, by way of example only, a leukotriene pathway modulator such as a CysLT1 receptor antagonists (e.g., montelukast), a CysLT2 receptor antagonist, a 5-lipoxygenase inhibitor (e.g., zileuton), a 5-lipoxygenase-activating protein inhibitor (e.g., MK-0591, MK-886, DG-031 (BAY X1005), 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid), a LTA4 hydrolase inhibitor, a $LTC_4$ synthase inhibitor, a BLT1 receptor antagonist or a BLT2 receptor antagonist.

In any of the aforementioned aspects involving the treatment of proliferative disorders, including cancer, are further embodiments comprising administering at least one additional agent, including by way of example only alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In any of the aforementioned aspects involving the therapy of an immunogical disorder requiring immunosuppression or involving the therapy of transplanted organs or tissues or cells are further embodiments comprising administering at least one additional agent, including by way of example only azathioprine, a corticosteroid, cyclophosphamide, cyclosporin, dacluzimab, mycophenolate mofetil, OKT3, rapamycin, tacrolimus, or thymoglobulin.

In any of the aforementioned aspects involving the therapy of interstitial cystitis are further embodiments comprising administering at least one additional agent selected from, e.g., dimethylsulfoxide, omalizumab, and pentosan polysulfate.

In any of the aforementioned aspects involving the therapy of disorders of bone are further embodiments comprising administering at least one additional agent such as, by way of example only, minerals, vitamins, bisphosphonates, anabolic steroids, parathyroid hormone or analogs, and cathepsin K inhibitors dronabinol.

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal.

In any of the aforementioned aspects the $PGD_2$-dependent or $PGD_2$ mediated diseases or conditions include, but are not limited to, asthma, rhinitis, chronic obstructive pulmonary disease, pulmonary hypertension, interstitial lung fibrosis, arthritis, allergy, inflammatory bowel disease, adult respiratory distress syndrome, myocardial infarction, aneurysm, stroke, cancer, and endotoxic shock.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and $T_H2$ lymphocytes in response to local tissue damage as well as in response allergic inflammation observed in diseases such as asthma, rhinitis, and atopic dermatitis. More specifically, exogenous $PGD_2$ applied to bronchial airways elicits many responses that are characteristic of acute asthma.

$PGD_2$ is a major mast cell product that acts via two receptors, the D-type prostanoid (DP, also known as $DP_1$) and the chemoattractant receptor-homologous molecule expressed on Th2 cells (CRTH2, also known as $DP_2$) receptors. $DP_2$ mediates the chemotaxis of eosinophils, basophils, and Th2 lymphocytes, and $DP_1$ receptor plays an important role in eosinophil trafficking. $DP_1$ antagonists do not inhibit the release of eosinophils when induced by the $DP_2$-selective agonists. However, eosinophils in human bone marrow specimens express $DP_1$ and $DP_2$ receptors at similar levels and human peripheral blood expresses both $DP_1$ and $DP_2$, but the $DP_1$ receptor is expressed at lower levels. In agreement with this, the chemotaxis of human peripheral blood eosinophils is inhibited by both $DP_1$ and $DP_2$ antagonists. Accordingly, $DP_1$, $DP_2$ and dual $DP_1/DP_2$ antagonists are useful in the treatment of allergic inflammation.

Activation of $DP_2$ is associated with chemotaxis and activation of $T_H2$ lymphocytes, eosinophils and basophils. In particular, $PGD_2$ binds to $DP_2$ and mediates many of its effects through a $G_i$-dependent elevation of intracellular calcium levels and reduction of cyclic AMP. In $T_H2$ lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

The terms CRTH2 and $DP_2$, refer to the same receptor and are used interchangeably herein. Likewise, another common name for DP is $DP_1$, and the two terms are used interchangeably herein.

Illustrative Biological Activity

Prostaglandins (PGs) are recognized physiological lipid acid mediators produced by the release of arachidonic acid from cell membrane phospholipids and converted to prostaglandins by the action of $COX_1$ and $COX_2$ cyclooxygenases and PG synthases. The cyclooxygenases sequentially convert arachidonic acid to cyclic endoperoxide prostaglandin $G_2$ ($PGG_2$) and subsequently, prostaglandin $H_2$ ($PGH_2$). Depending on the tissue, physiological signal, and/or synthase type, $PGH_2$ can be converted to numerous different prostaglandins, such as $PGE_2$, $PGD_2$, $PGF_2\alpha$, and $PGI_2$ as well as thromboxane $A_2$, another eicosanoid signaling molecule. These mediators then elicit a wide variety of physiological responses including vasoconstriction or dilation, platelet aggregation, calcium transport, pain sensitization, hormone release, inflammatory and immune response, and cellular growth.

Prostaglandin $D_2$ is a major metabolite produced from the $PGH_2$ intermediate via hematopoietic $PGD_2$ synthase or lipocalin $PGD_2$ synthase. In the brain and central nervous system, $PGD_2$ is produced and thought to function in pain perception and sleep regulation. In other tissues, $PGD_2$ is produced primarily in immunoglobulin E (IgE) activated mast cells and to a lesser extent, in macrophages, dendritic cells, T helper 2 ($T_H2$) lymphocytes and other leukocytes. In the cell, $PGD_2$ is rapidly metabolized and converted to other downstream effectors including $\Delta^{12}PGJ_2$, $9\alpha11\beta PGF_2$, 13,14-dihydro-15-keto-$PGD_2$, and 15-deoxy-$\Delta^{12,14}PGD_2$.

Mast-cell-derived $PGD_2$ is produced in high concentrations in response to an allergen challenge. Studies in preclinical species have observed the following features when $PGD_2$ is applied to in vivo preparations, or its overproduction is engineered by genetic manipulation:

Vasodilatation leading to erythema (flare) and -potentiation of oedema (wheal).
Recruitment of eosinophils and TH2 lymphocytes.
Modulation of TH2-cytokine production.
Bronchoconstriction.
Injection of $PGD_2$ into human skin has been shown to produce a long lasting erythema, to potentiate the effects of other mediators on induration and leukocyte infiltration in human skin and to enhance oedema formation in rat skin. It is most likely that these effects of $PGD_2$, like those of other vasodilator prostaglandins, are due to an increased blood flow to the inflamed lesion and are, therefore, most likely to be mediated predominantly by the $DP_1$ receptor. Although these observations make it clear that $DP_1$ mediates the vascular effects of $PGD_2$, the capacity of $PGD_2$ to promote the cellular changes associated with inflammation is not due to an action on $DP_1$.

The main receptors that are activated by $PGD_2$ or its metabolites and mediate its effects are $DP_1$, CRTH2 (or $DP_2$) and TP.

$DP_1$ (or DP) is a O-protein coupled seven-transmembrane receptor that, upon activation by $PGD_2$ binding, leads to an increase in intracellular cAMP levels. $DP_1$ is expressed in the brain, bronchial smooth muscle, vascular and airway smooth muscle, dendritic cells, and platelets and induces $PGD_2$ dependent bronchodilation, vasodilation, platelet aggregation inhibition, and suppression of cytokine production. Genetic analysis of $DP_1$ function using knock-out mice has shown that mice lacking DP do not develop asthmatic responses in an ovalbumin-induced asthma model. Analysis of selective DP anatgonists in guinea pig allergic rhinitis models demonstrated dramatic inhibition of early nasal responses, as assessed by sneezing, mucosal plasma exudation and eosinophil infiltration. DP antagonism alleviates allergen-induced plasma exudation in the conjunctiva in a guinea pig allergic conjunctivitis model and antigen-induced esinophil infiltration into the lung in a guinea pig asthma model.

Much of the pro-inflammatory activity of $PGD_2$ is through interaction with $DP_2$ (or CRTH2). $DP_2$ is a G-protein coupled receptor and is typically highly expressed in $T_H2$ lymphocytes, eosinophils and basophils. $DP_2$ activation functions to directly activate and recruit $T_H2$ lymphocytes and eosinophils. Activated $T_H2$ lymphocytes produce and secrete inflammatory cytokines including IL4, IL5, and IL13. Despite binding $PGD_2$ with a similar affinity as $DP_1$, $DP_2$ is not structurally related to $DP_1$ and signals through a different mechanism—the effects of $DP_2$ are mediated through Gi-dependent elevation in intracellular calcium levels and reduction in intracellular levels of cyclic AMP. $DP_2$ activation is important in eosinophil recruitment in response to allergic challenge in such tissues as nasal mucosa, bronchial airways, and skin. The application of either $PGD_2$ or selective $DP_2$ agonists both exacerbate and enhance allergic responses in lung and skin. $DP_2$ activation appears to have a crucial role in mediating allergic responses, and thus the use of antagonists of $PGD_2$ activation of the $DP_2$ receptor are an attractive approach to treat the inflammatory component of allergic diseases such as asthma, rhinitis, and dermatitis.

TP receptors primarily function to antagonize $DP_1$ receptor's effects such as promoting bronchoconstriction, vasoconstriction, and platelet aggregation. While TP receptor's main ligand is thromboxane $A_2$, it also binds and is activated by the $PGD_2$ derivative, $9\alpha11\beta PGF_2$. TP is a Gq-coupled prostanoid receptor that binds thromboxane with high affinity, promoting platelet aggregation and constriction of both vascular and airway smooth muscle. $PGD_2$ activates the TP receptor in human bronchial muscle, probably through the formation of the 11-ketoreductase metabolite $9\alpha11\beta PGF2$. The bronchoconstrictor effects of TP dominate over the bronchodilator effects of $DP_1$ in the airways.

$DP_1$ and $DP_2$ have crucial, and complementary, roles in the physiological response of animals to $PGD_2$ and bloackade of either one or both of these receptors may prove beneficial in alleviating allergic diseases or conditions triggered by $PGD_2$, such as, but not limited to, allergic rhinitis, asthma, dermatitis, and allergic conjunctivitis.

Compounds

Compounds of any one of Formula (I), Formula (II), Formula (III), Formula (IV, Formula (V), Formula (VI) or Formula (VII), including pharmaceutically acceptable salts, pharmaceutically acceptable prodrugs, and solvates thereof, antagonize or modulate $DP_2$ and are used to treat patients suffering from $PGD_2$-dependent or $PGD_2$ mediated conditions or diseases, including, but not limited to, asthma, rhinitis, dermatitis, and inflammatory conditions.

In one aspect is a compound having the structure of Formula (I), pharmaceutically acceptable salts, pharmaceutically acceptable solvates, or pharmaceutically acceptable prodrugs thereof:

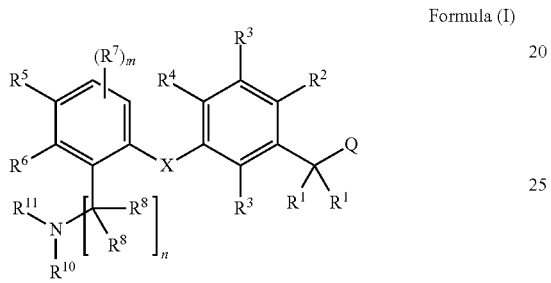

Formula (I)

wherein,

Q is tetrazolyl or —C(=O)-$Q^1$;

$Q^1$ is —OH, —$OR^{13}$, —$NHSO_2R^{12}$, —$N(R^{13})_2$, —NH—OH, or —NH—CN;

X is —O—, —S—, —S(=O)—, —$S(=O)_2$—, —$NR^{13}$—, —$CH_2$—, or —C(=O)—;

each $R^1$ is independently selected from H, halogen, $C_1$-$C_4$alkyl, and $C_1$-$C_4$haloalkyl; or both $R^1$ groups taken together with the carbon atom to which they are attached form a $C_3$-$C_6$cycloalkyl;

each of $R^2$, $R^3$, $R^4$, $R^5$, $R^6$, and $R^7$ is independently H, halogen, —CN, —$NO_2$, —OH, —$OR^{13}$, —$SR^{12}$, —$S(=O)R^{12}$, —$S(=O)_2R^{12}$, —C(=O)$R^{12}$, —OC(=O)$R^{12}$, —$CO_2R^{13}$, —$OCO_2R^{13}$, —CH($R^{13}$)$_2$, —$N(R^{13})_2$, —$NHCH_2CO_2R^{13}$, —$OCH_2CO_2R^{13}$, —$SCH_2CO_2R^{13}$, —C(=O)$N(R^{13})_2$, —OC(=O)$(R^{13})_2$, —$NR^{13}C(=O)N(R^{13})_2$, —$NR^{13}C(=O)R^{12}$, —$NR^{13}C(=O)R^{12}$, —$NR^{13}S(=O)_2R^{12}$, —C(OH)$(R^{13})_2$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted heterocycloalkyl, optionally substituted phenyl, optionally substituted monocyclic heteroaryl, or an optionally substituted group selected from among —$C_1$-$C_4$alkyl-$C_3$-$C_{10}$cycloalkyl, —$C_1$-$C_4$alkyl-heterocycloalkyl, —$C_1$-$C_4$alkyl-aryl, and —$C_1$-$C_4$alkyl-heteroaryl; or each of $R^2$, $R^3$, $R^4$, $R^5$, $R^6$, and $R^7$ is independently —$X^1$-$L^1$-$Q^2$, where, $X^1$ is a bond, —O—, —S—, —$S(=O)_2$—, or —$NR^{13}$—;

$L^1$ is a bond or a $C_1$-$C_4$alkylene;

$Q^2$ is —$CO_2R^{13}$, —C(=O)$R^{12}$, —C(=O)$N(R^{13})_2$, —C(=O)$NHSO_2R^{12}$, an optionally substituted $C_3$-$C_{10}$cycloalkyl, an optionally substituted heterocycloalkyl, an optionally substituted aryl, or an optionally substituted heteroaryl;

each $R^8$ is each independently selected from H, halogen, $C_1$-$C_4$alkyl, and $C_1$-$C_4$haloalkyl; or both $R^8$ groups are taken together with the carbon atom to which they are attached to form a $C_3$-$C_6$cycloalkyl;

$R^{10}$ is H, —C(=O)$R^{14}$, —C(=O)$OR^{15}$, —C(=O)$N(R^{16})_2$, —$S(=O)_2N(R^{16})_2$, or —$S(=O)_2R^{14}$;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl; or $R^{14}$ is $L^3$-$X^3$-$Q^3$;

$L^3$ is a $C_1$-$C_6$alkylene or an optionally substituted aryl;

$X^3$ is a bond, —O—, —S—, —$S(=O)_2$—, —$NR^{13}S(=O)_2$—, or —$NR^{13}$—;

$Q^3$ is an optionally substituted $C_1$-$C_6$alkyl, $C_1$-$C_6$fluoroalkyl an optionally substituted $C_3$-$C_{10}$cycloalkyl, an optionally substituted heterocycloalkyl, an optionally substituted aryl, an optionally substituted heteroaryl, an optionally substituted $C_1$-$C_4$alkyl-$C_3$-$C_{10}$cycloalkyl, an optionally substituted $C_1$-$C_4$alkyl-heterocycloalkyl, an optionally substituted $C_1$-$C_4$alkyl-aryl, or an optionally substituted $C_1$-$C_4$alkyl-heteroaryl;

$R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl;

each $R^{16}$ is independently H, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted heterocycloalkyl, an optionally substituted aryl, an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl or an optionally substituted —$C_1$-$C_4$alkyl-heteroaryl; or two $R^{16}$ groups attached to the same N atom are taken together with the N atom to which they are attached to form an optionally substituted heterocycloalkyl;

$R^{11}$ is H, $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted aryl, or an optionally substituted heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-aryl, an optionally substituted —$C_1$-$C_4$alkyl-heteroaryl, or an optionally substituted group selected from —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-$S(=O)_2$—$R^{17}$, —$C_1$-$C_6$alkylene-$NR^{13}R^{17}$, —$C_1$-$C_6$alkylene-C(=O)—$R^{17}$, —$C_1$-$C_6$alkylene-C(=O)O—$R^{17}$, —$C_1$-$C_6$alkylene-OC(=O)—$R^{17}$, —$C_1$-$C_6$alkylene-$NR^{13}C(=O)$—$R^{17}$ or —$C_1$-$C_6$alkylene-C(=O)$NR^{13}$—$R^{17}$;

$R^{17}$ is H, $C_1$-$C_6$alkyl, $C_1$-$C_6$heteroalkyl, $C_1$-$C_6$haloalkyl, an optionally substituted cycloalkyl, an optionally substituted heterocycloalkyl, an optionally substituted aryl, an optionally substituted benzyl, or an optionally substituted heteroaryl;

$R^{12}$ is $C_1$-$C_6$alkyl, $C_1$-$C_6$heteroalkyl, $C_1$-$C_6$fluoroalkyl, optionally substituted $C_3$-$C_{10}$cycloalkyl, optionally substituted heterocycloalkyl, optionally substituted aryl, optionally substituted —$C_1$-$C_4$alkyl-aryl or optionally substituted heteroaryl; and each $R^{13}$ is independently selected from H, $C_1$-$C_6$heteroalkyl, $C_1$-$C_6$fluoroalkyl, an optionally substituted $C_3$-$C_{10}$cycloalkyl, an optionally substituted heterocycloalkyl, an optionally substituted aryl, an optionally substituted —$C_1$-$C_4$alkyl-aryl, and an optionally substituted heteroaryl; or two $R^{13}$ groups attached to the same N atom are taken together with the N atom to which they are attached to form an optionally substituted heterocycloalkyl;

m is 0, 1, or 2; n is 1, 2, 3, or 4.

For any and all of the embodiments, substituents can be selected from among from a subset of the listed alternatives. For example, in some embodiments, n is 1 or 2. In other embodiments, n is 2, 3, or 4. In yet other embodiments, n is 3 or 4. In yet other embodiments, n is 1.

In some embodiments, Q is —C(=O)-$Q^1$, —SO$_2$NHC(=O)$R^{12}$, or tetrazolyl. In other embodiments, Q is —C(=O)-$Q^1$, or tetrazolyl. In other embodiments, Q is selected from —CO$_2$H, —CO$_2$Me, —CO$_2$Et, —C(=O)NH$_2$, —C(=O)NHOH, —C(=O)NH—CN, tetrazolyl, —C(=O)—NHSO$_2R^{12}$, or

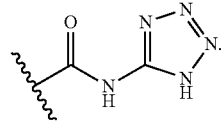

In some other embodiments, Q is selected from —CO$_2$H, —CO$_2$Me, —CO$_2$Et, —C(=O)NH$_2$, —C(=O)—NHSO$_2$CH$_3$, —C(=O)—NHSO$_2$CH$_2$CH$_3$. In other embodiments, Q is —C(=O)-$Q^1$. In yet some other embodiments, Q is —CO$_2$H.

In some embodiments, $Q^1$ is —OH, —$OR^{13}$, —NHSO$_2R^{12}$, or —N($R^{13}$)$_2$. In some other embodiments, $Q^1$ is —OH, —OCH$_3$, —OCH$_2$CH$_3$, or —NHSO$_2$CH$_3$. In some other embodiments, $Q^1$ is —OH, —OCH$_3$, or —OCH$_2$CH$_3$.

In alternative embodiments, each $R^1$ is independently selected from H, F, $C_1$-$C_4$alkyl, and $C_1$-$C_4$haloalkyl; or both $R^1$ groups taken together with the carbon atom to which they are attached form a cyclopropyl, cyclobutyl or cyclohexyl.

In some embodiments, each $R^8$ is each independently selected from H, F, $C_1$-$C_4$alkyl, and $C_1$-$C_4$haloalkyl.

In one aspect, each $R^1$ is independently selected from H, F, and $C_1$-$C_4$alkyl; and each $R^8$ is each independently selected from H, F, and $C_1$-$C_4$alkyl. In one aspect, each $R^1$ is independently selected from H, F, and —CH$_3$. In one aspect, each $R^1$ is H. In some other embodiments, each $R^8$ is each independently selected from H, F, and —CH$_3$. In one aspect, each $R^8$ is H.

In one aspect, Q is —C(=O)-$Q^1$; $Q^1$ is —OH, —$OR^{13}$, —NHSO$_2R^{12}$, or —N($R^{13}$)$_2$; each $R^1$ is independently selected from H, F, $C_1$-$C_4$alkyl, and $C_1$-$C_4$haloalkyl; or both $R^1$ groups taken together with the carbon atom to which they are attached form a cyclopropyl, cyclobutyl or cyclohexyl; each $R^8$ is independently selected from H, F, $C_1$-$C_4$alkyl, and $C_1$-$C_4$haloalkyl.

In some embodiments, X is —O—, —S—, —S(=O)$_2$—, or —CH$_2$—; m is 0 or 1; and n is 1.

In other embodiments, $Q^1$ is —OH, —OCH$_3$, —OCH$_2$CH$_3$, or —NHSO$_2$CH$_3$; each $R^1$ is independently selected from H, F, and $C_1$-$C_4$alkyl; each $R^8$ is independently selected from H, F, and $C_1$-$C_4$alkyl.

In some embodiments, Q is —C(=O)OH, —C(=O)OCH$_3$, —C(=O)OCH$_2$CH$_3$; n=1; and each $R^8$ is H.

In some embodiments, X is —O—, —S—, —S(=O)—, or —S(=O)$_2$—.

In other embodiments, X is —O—. In yet other embodiments, X is —S—, —S(=O)—, or —S(=O)$_2$—. In some other embodiments, X is —CH$_2$—.

In one aspect, the compound of Formula (I) has the structure of Formula (II):

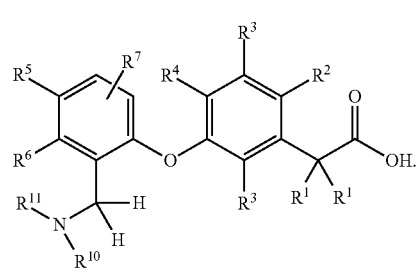

Formula (II)

In some embodiments, each $R^1$ is independently selected from H, F, and —CH$_3$.

In some embodiments, each of $R^2$, $R^3$, $R^6$, and $R^7$ is independently H, halogen, —CN, —OH, —$OR^{13}$, $SR^{12}$, —S(=O)$R^{12}$, —S(=O)$_2R^{12}$, —C(=O)$R^{12}$, —OC(=O)$R^{12}$, —CO$_2R^{13}$, —OCO$_2R^{13}$, —N($R^{13}$)$_2$, —$C_1$-$C_6$alkyl, $C_1$-$C_6$fluoroalkyl, an optionally substituted $C_3$-$C_{10}$cycloalkyl, an optionally substituted heterocycloalkyl, $C_1$-$C_6$fluoroalkoxy, $C_1$-$C_6$alkoxy, $C_1$-$C_6$heteroalkyl, optionally substituted phenyl, or an optionally substituted monocyclic heteroaryl.

In some embodiments, $R^4$ is H, halogen, —CN, —NO$_2$, —OH, —$OR^{13}$, —$SR^{12}$, —S(=O)$R^{12}$, —S(=O)$_2R^{12}$, —C(=O)$R^{12}$, —OC(=O)$R^{12}$, —CO$_2R^{13}$, —N($R^{13}$)$_2$, —NHCH$_2$CO$_2R^{13}$, —OCH$_2$CO$_2R^{13}$, —SCH$_2$CO$_2R^{13}$, —C(=O)N($R^{13}$)$_2$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted heterocycloalkyl, optionally substituted phenyl, or an optionally substituted monocyclic heteroaryl; or $R^4$ is —$X^1$-$L^1$-$Q^2$, where, $X^1$ is a bond, or —O—; $L^1$ is a bond or a $C_1$-$C_4$alkylene; $Q^2$ is —CO$_2R^{12}$, —C(=O)($R^{13}$)$_2$, an optionally substituted $C_3$-$C_{10}$cycloalkyl, an optionally substituted aryl, or an optionally substituted heteroaryl.

In some other embodiments, $R^4$ is H, F, Cl, Br, I, —CN, —OH, —OCH$_3$, —OCH$_2$CH$_3$, —SCH$_3$, —NH$_2$, —NHCH$_3$, —N(CH$_3$)$_2$, —CH$_3$, —CH$_2$CH$_3$, —CF$_3$, —OCF$_3$, —CH$_2$OH, or —CH$_2$OCH$_3$.

In some embodiments, $R^5$ is H, halogen, —CN, —NO$_2$, —OH, —$OR^{13}$, —$SR^{12}$, —S(=O)$R^{12}$, —S(=O)$_2R^{12}$, —C(=O)$R^{12}$, —OC(=O)$R^{12}$, —CO$_2R^{13}$, —OCO$_2R^{13}$, —N($R^{13}$)$_2$, —NHCH$_2$CO$_2R^{13}$, —OCH$_2$CO$_2R^{13}$, —SCH$_2$CO$_2R^{13}$, —C(=O)N($R^{13}$)$_2$, —OC(=O)N($R^{13}$)$_2$, —$NR^{13}$C(=O)N($R^{13}$)$_2$, —$NR^{13}$C(=O)$R^{12}$, —$NR^{13}$C(=O)$OR^{12}$, —$NR^{13}$S(=O)$_2R^{12}$, —$C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted heterocycloalkyl, optionally substituted phenyl, optionally substituted monocyclic heteroaryl; or $R^5$ is —$X^1$-$L^1$-$Q^2$, where, $X^1$ is a bond, —O—, —S—, —S(=O)—, —S(=O)$_2$—, or —$NR^{13}$—; $L^1$ is a bond or a $C_1$-$C_4$alkylene; $Q^2$ is —$CO_2R^{13}$, —C(=O)$R^{12}$, —C(=O)N($R^{13}$)$_2$, —C(=O)NHSO$_2R^{12}$, an optionally substituted $C_3$-$C_{10}$cycloalkyl, an optionally substituted heterocycloalkyl, an optionally substituted aryl, or an optionally substituted heteroaryl.

In some embodiments, each of $R^2$, $R^3$, $R^6$, and $R^7$ is independently H, F, Cl, Br, I, —CN, —OH, —$OR^{13}$, —$SR^{12}$, —S(=O)$R^{12}$, —S(=O)$_2R^{12}$, —N($R^{13}$)$_2$, —$C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl.

In other embodiments, $R^4$ is H, halogen, —CN, —OH, —$OR^{13}$, —$SR^{12}$, —N($R^{13}$)$_2$, $C_1$-$C_6$alkyl, $C_1$-$C_6$fluoroalkyl, $C_1$-$C_6$fluoroalkoxy, $C_1$-$C_6$alkoxy, or $C_1$-$C_6$heteroalkyl; or $R^4$ is —$X^1$-$L^1$-$Q^2$, where, $X^1$ is a bond, or —O—; $L^1$ is a bond or a $C_1$-$C_4$alkylene; $Q^2$ is —$CO_2R^{13}$, —C(=O)N($R^{13}$)$_2$, an optionally substituted $C_3$-$C_{10}$cycloalkyl, an optionally substituted aryl, or an optionally substituted heteroaryl.

In some embodiments, each of $R^2$, $R^3$, $R^6$ and $R^7$ is independently H, halogen, —CN, —OH, —$OR^{13}$, $C_1$-$C_6$alkoxy, $C_1$-$C_6$fluoroalkyl, $C_1$-$C_6$fluoroalkoxy, or $C_1$-$C_6$heteroalkyl.

In some embodiments, each of $R^2$, $R^3$, $R^6$ and $R^7$ is independently H, F, Cl, Br, —CN, —OH, —OCH$_3$, —OCH$_2$CH$_3$, —CH$_3$, —CH$_2$CH$_3$, —CF$_3$, —CH$_2$CF$_3$, —OCF$_3$, —CH$_2$OH, or —CH$_2$OCH$_3$. In some other embodiments, each of $R^6$ and $R^7$ is H.

In some other embodiments, $R^5$ is H, F, Cl, Br, I, —CN, —NO$_2$, —OH—CH$_3$, —CH$_2$CH$_3$, —CH$_2$CH$_2$CH$_3$, i-propyl, -tBu, —CF$_3$, —CH$_2$CF$_3$, —OCH$_3$, —OCH$_2$CH$_3$, —OCF$_3$, —S(=O)$_2$CH$_3$, —S(=O)$_2$ (optionally substituted phenyl), —C(=O)-(optionally substituted phenyl), —C(=O)CH$_3$, —CO$_2$H, —CO$_2$CH$_3$, —CO$_2$CH$_2$CH$_3$, —NH$_2$, —C(=O)NH$_2$, —C(=O)NH(CH$_3$), —C(=O)NH(CH$_2$CH$_3$), —C(=O)NH(tBu), —C(=O)NH(iPr), —C(=O)NH(CH$_2$CF$_3$), —C(=O)NH(CH$_2$CH$_2$OCH$_3$), —C(=O)NH (optionally substituted phenyl), —C(=O)NH (optionally substituted monocyclic heteroaryl), —C(=O) NH (optionally substituted heterocycloalkyl), —NHC(=O)(C$_1$-$C_6$alkyl), —NHC(=O) (optionally substituted phenyl), —N(C$_1$-$C_6$alkyl)C(=O)(C$_1$-$C_6$alkyl), —N(C$_1$-$C_6$alkyl)C(=O) (optionally substituted phenyl), —NHS(=O)$_2$(C$_1$-$C_6$alkyl), —NHS(=O)$_2$ (optionally substituted phenyl), —N(C$_1$-$C_6$alkyl)S(=O)$_2$(C$_1$-$C_6$alkyl), —N(C$_1$-$C_6$alkyl)S(=O)$_2$ (optionally substituted phenyl), —NHC(=O)NH$_2$, —NHC(=O)NH (optionally substituted phenyl), or an optionally substituted group selected from benzyl, cyclopentyl, cyclohexyl, pyrrolidinyl, piperidinyl, morpholinyl, piperazinyl, thiomorpholinyl, phenyl, pyridinyl, pyrazinyl, imidazolyl, pyrazolyl, 1-methylpyrazol-4-yl, isoxazolyl, oxazolyl, thiazolyl, imidazolyl and isoxazolyl.

In one aspect, $R^5$ is H, F, Cl, Br, I, —CN, —NO$_2$, —OH—CH$_3$, —CH$_2$CH$_3$, —CH$_2$CH$_2$CH$_3$, i-propyl, -tBu, —CF$_3$, —CH$_2$CF$_3$, —OCH$_3$, —OCH$_2$CH$_3$, —OCF$_3$, —S(=O)$_2$CH$_3$, —S(=O)$_2$ (optionally substituted phenyl), —C(=O)-(optionally substituted phenyl), —C(=O)CH$_3$, —CO$_2$H, —CO$_2$CH$_3$, —CO$_2$CH$_2$CH$_3$, —NH$_2$, —C(=O)NH$_2$, —C(=O)NH(CH$_3$), —C(=O)NH(CH$_2$CH$_3$), —C(=O)NH(tBu), —C(=O)NH(iPr), —C(=O)NH(CH$_2$CF$_3$), —C(=O)NH(CH$_2$CH$_2$OCH$_3$), —C(=O)NH (optionally substituted phenyl), —C(=O)NH (optionally substituted monocyclic heteroaryl), —C(=O)NH (optionally substituted heterocycloalkyl), —NHC(=O)(C$_1$-$C_6$alkyl), —NHC(=O) (optionally substituted phenyl), —N(CH$_3$)C(=O)(C$_1$-$C_6$alkyl), —N(CH$_3$)C(=O) (optionally substituted phenyl), —NHS(=O)$_2$(C$_1$-$C_6$alkyl), —NHS(=O)$_2$ (optionally substituted phenyl), —N(CH$_3$)S(=O)$_2$(C$_1$-$C_6$alkyl), —N(CH$_3$)S(=O)$_2$ (optionally substituted phenyl), —NHC(=O)NH$_2$, —NHC(=O)NH (optionally substituted phenyl), or an optionally substituted group selected from benzyl, cyclopentyl, cyclohexyl, pyrrolidinyl, piperidinyl, morpholinyl, piperazinyl, thiomorpholinyl, phenyl, pyridinyl, pyrazinyl, imidazolyl, pyrazolyl, 1-methylpyrazol-4-yl, isoxazolyl, oxazolyl, thiazolyl, imidazolyl and isoxazolyl.

In one aspect, $R^{11}$ is H, $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted phenyl, or an optionally substituted monocyclic heteroaryl, an optionally substituted —$C_1$-$C_4$alkyl-cycloalkyl, an optionally substituted —$C_1$-$C_4$alkyl-phenyl, an optionally substituted —$C_1$-$C_4$alkyl-(monocyclic heteroaryl), or an optionally substituted group selected from —$C_1$-$C_6$alkylene-O—$R^{17}$, —$C_1$-$C_6$alkylene-S—$R^{17}$, —$C_1$-$C_6$alkylene-N$R^{13}R^{17}$, —$C_1$-$C_6$alkylene-C(=O)O—$R^{17}$—, —$C_1$-$C_6$alkylene-OC(=O)—$R^{17}$, or —$C_1$-$C_6$alkylene-C(=O)N$R^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted phenyl, an optionally substituted benzyl, or an optionally substituted heteroaryl.

In some embodiments, $R^{11}$ is $C_1$-$C_6$alkyl, $C_1$-$C_6$heteroalkyl, $C_1$-$C_6$haloalkyl, (an optionally substituted monocyclic or bicyclic cycloalkyl), (an optionally substituted monocyclic or bicyclic heterocycloalkyl), an optionally substituted phenyl, or an optionally substituted monocyclic heteroaryl, an optionally substituted —$C_1$-$C_4$alkyl-cycloalkyl, an optionally substituted —$C_1$-$C_4$alkyl-heterocycloalkyl, an optionally substituted —$C_1$-$C_4$alkyl-phenyl, an optionally substituted —$C_1$-$C_4$alkyl-(monocyclic heteroaryl), or an optionally substituted group selected from —$C_1$-$C_6$alkylene-O—$R^{17}$, —$C_1$-$C_6$alkylene-S—$R^{17}$, —$C_1$-$C_6$alkylene-N$R^{13}R^{17}$, —$C_1$-$C_6$alkylene-C(=O)O—$R^{17}$—, —$C_1$-$C_6$alkylene-OC(=O)—$R^{17}$, or —$C_1$-$C_6$alkylene-C(=O)N$R^{13}$—$R^{17}$; $R^{17}$ is H, $C_1$-$C_6$alkyl, $C_1$-$C_6$heteroalkyl, $C_1$-$C_6$haloalkyl, an optionally substituted cycloalkyl, an optionally substituted phenyl, an optionally substituted benzyl, or an optionally substituted heteroaryl.

In some other embodiments, $R^{11}$ is H, —CH$_3$, —CH$_2$CH$_3$, —CH$_2$CH$_2$CH$_3$, —CH$_2$CH$_2$CH$_2$CH$_3$, —CH$_2$C(CH$_3$)$_3$, —CH$_2$CF$_3$, —CH$_2$CH$_2$OH, —CH$_2$CH$_2$OCH$_3$, —CH$_2$CH$_2$N(CH$_3$)$_2$, —CH$_2$COOH, —CH$_2$C(O)NH$_2$, —CH$_2$Ph, —CH$_2$CH$_2$Ph, —CH(CH$_3$)CH$_2$Ph, —CH(CH$_3$)CH(OH)Ph, —C(CH$_3$)$_2$CH$_2$Ph, —C(CH$_3$)$_2$CH$_2$(4-fluorophenyl), phenyl, o-tolyl, cyclopropyl, cyclobutyl, cyclopentyl, cyclohexyl, indan-1-yl, indan-2-yl, 2-hydroxy-indan-1-yl, 2-methoxy-indan-1-yl, thiazol-2-yl, or 2-methyl-pyrimidin-4-yl.

In yet other embodiments, $R^{11}$ is —CH$_3$, —CH$_2$CH$_3$, —CH$_2$CH$_2$CH$_3$, —CH$_2$CH$_2$CH$_2$CH$_3$, —CH$_2$C(CH$_3$)$_3$, —CH$_2$CF$_3$, —CH$_2$CH$_2$OH, —CH$_2$CH$_2$OCH$_3$, —CH$_2$CH$_2$N(CH$_3$)$_2$, —CH$_2$COOH, —CH$_2$C(O)NH$_2$, —CH$_2$Ph, —CH$_2$CH$_2$Ph, —CH(CH$_3$)CH$_2$Ph, —CH(CH$_3$)CH(OH)Ph, —C(CH$_3$)$_2$CH$_2$Ph, —C(CH$_3$)$_2$CH$_2$(4-fluorophenyl), phenyl, o-tolyl, cyclopropyl, cyclobutyl, cyclopentyl, cyclohexyl, indan-1-yl, indan-2-yl, 2-hydroxy-indan-1-yl, 2-methoxy-indan-1-yl, thiazol-2-yl, or 2-methyl-pyrimidin-4-yl.

In some other embodiments, $R^{11}$ is H, —CH$_3$, —CH$_2$CH$_3$, —CH$_2$CH$_2$CH$_3$, —CH$_2$CH$_2$CH$_2$CH$_3$, —CH$_2$C(CH$_3$)$_3$, —CH$_2$CF$_3$, —CH$_2$CH$_2$OH, —CH$_2$CH$_2$OCH$_3$, —CH$_2$CH$_2$N(CH$_3$)$_2$, —CH$_2$COOH, —CH$_2$C(O)NH$_2$, —CH$_2$Ph, —CH$_2$CH$_2$Ph, —CH(CH$_3$)CH$_2$Pb, —CH(CH$_3$)CH(OH)Ph, —C(CH$_3$)$_2$CH$_2$Ph, or —C(CH$_3$)$_2$CH$_2$(4-fluorophenyl).

In some embodiments, $R^{10}$ is H, —C(=O)$R^{14}$, —C(=O) O$R^{15}$, —C(=O)N($R^{16}$)$_2$, or —S(=O)$_2R^{14}$.

In some embodiments, $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; or $R^{14}$ is $L^3$-$X^3$-$Q^3$; $L^3$ is a $C_1$-$C_6$alkylene or an optionally substituted aryl; $X^3$ is a bond, —O—, —S—, —S(=O)$_2$—, —N$R^{13}$S(=O)$_2$—, or —N$R^{13}$—; $Q^3$ is an optionally substituted $C_1$-$C_6$alkyl, $C_1$-$C_6$fluoroalkyl an optionally substituted $C_3$-$C_{10}$cycloalkyl, an optionally substituted aryl, an optionally substituted heteroaryl, an optionally substituted $C_1$-$C_4$alkyl-$C_3$-$C_{10}$cycloalkyl, an optionally substituted $C_1$-$C_4$alkyl-aryl, or an optionally substituted $C_1$-$C_4$alkyl-heteroaryl; $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; each $R^{16}$ is independently H, —CN, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, an optionally substituted —$C_1$-$C_4$alkyl-cycloalkyl, an optionally substituted —$C_1$-$C_4$alkyl-aryl or an optionally substituted —$C_1$-$C_4$alkyl-heteroaryl; or two $R^{16}$ groups attached to the same N atom are taken together with the N atom to which they are attached to form an optionally substituted heterocycloalkyl.

In some embodiments, $R^{10}$ is —C(=O)$R^{14}$, —C(=O)O$R^{15}$, —C(=O)N($R^{16}$)$_2$, or —S(=O)$_2$$R^{14}$.

In some cases, $R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted naphthyl, an optionally substituted monocyclic heteroaryl, an optionally substituted —$C_1$-$C_4$alkyl-cycloalkyl, an optionally substituted —$C_1$-$C_4$alkyl-phenyl or an optionally substituted —$C_1$-$C_4$alkyl-(monocyclic heteroaryl); or $R^{14}$ is $L^3$-$X^3$-$Q^3$; $L^3$ is a $C_1$-$C_6$alkylene or an optionally substituted phenyl; $X^3$ is a bond, —O—, —S—, —S(=O)—, —S(=O)$_2$—, —NR$^{13}$S(=O)$_2$—, or —NR$^{13}$—; $Q^3$ is an optionally substituted $C_1$-$C_6$alkyl, $C_1$-$C_6$fluoroalkyl an optionally substituted $C_3$-$C_{10}$cycloalkyl, an optionally substituted phenyl, an optionally substituted monocyclic heteroaryl, an optionally substituted $C_1$-$C_4$alkyl-$C_3$-$C_{10}$cycloalkyl, an optionally substituted $C_1$-$C_4$alkyl-phenyl, or an optionally substituted $C_1$-$C_4$alkyl-(monocyclic heteroaryl).

In some other cases, $R^{14}$ is $C_1$-$C_6$alkyl, $C_1$-$C_6$fluoroalkyl, $C_1$-$C_6$heteroalkyl, an optionally substituted —$C_1$-$C_4$alkyl-cycloalkyl, an optionally substituted —$C_1$-$C_4$alkyl-phenyl or an optionally substituted —$C_1$-$C_4$alkyl-(monocyclic heteroaryl); or $R^{14}$ is $L^3$-$X^3$-$Q^3$; $L^3$ is a $C_1$-$C_6$alkylene; $X^3$ is a bond, —O—, —S—, —S(=O)—, —S(=O)$_2$—, —NR$^{13}$S(=O)$_2$—, or —NR$^{13}$—; $Q^3$ is an optionally substituted $C_1$-$C_6$alkyl, $C_1$-$C_6$fluoroalkyl an optionally substituted $C_3$-$C_{10}$cycloalkyl, an optionally substituted phenyl, an optionally substituted monocyclic heteroaryl, an optionally substituted $C_1$-$C_4$alkyl-$C_3$-$C_{10}$cycloalkyl, an optionally substituted $C_1$-$C_4$alkyl-phenyl, or an optionally substituted $C_1$-$C_4$alkyl-(monocyclic heteroaryl).

In one aspect, $R^{10}$ is —C(=O)$R^{14}$.
In other aspects, $R^{10}$ is —S(=O)$_2$$R^{14}$.
In yet other aspects, $R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted monocyclic heteroaryl, an optionally substituted —$C_1$-$C_4$alkyl-cycloalkyl, an optionally substituted —$C_1$-$C_4$alkyl-phenyl or an optionally substituted —$C_1$-$C_4$alkyl-(monocyclic heteroaryl).

In yet other aspects, $R^{15}$ is $C_1$-$C_6$alkyl, $C_1$-$C_6$fluoroalkyl, $C_1$-$C_6$heteroalkyl, an optionally substituted —$C_1$-$C_4$alkyl-cycloalkyl, an optionally substituted —$C_1$-$C_4$alkyl-phenyl or an optionally substituted —$C_1$-$C_4$alkyl-(monocyclic heteroaryl).

In some embodiments, $R^{10}$ is —C(=O)O$R^{15}$.
In one aspect, each $R^{16}$ is independently H, —CN, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted monocyclic heteroaryl, an optionally substituted —$C_1$-$C_4$alkyl-cycloalkyl, an optionally substituted —$C_1$-$C_4$alkyl-phenyl or an optionally substituted —$C_1$-$C_4$alkyl-(monocyclic heteroaryl).

In some embodiments, $R^{10}$ is —C(=O)N($R^{16}$)$_2$.

In one aspect, the compound of Formula (I) or Formula (II) has the structure of Formula (III), Formula (IV), Formula (V), Formula (VI) or Formula (VII):

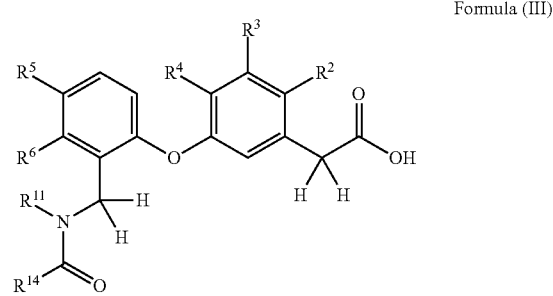

Formula (III)

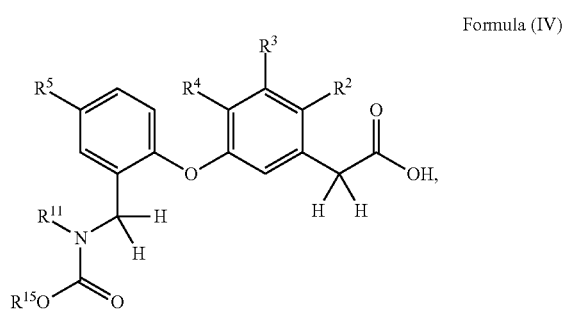

Formula (IV)

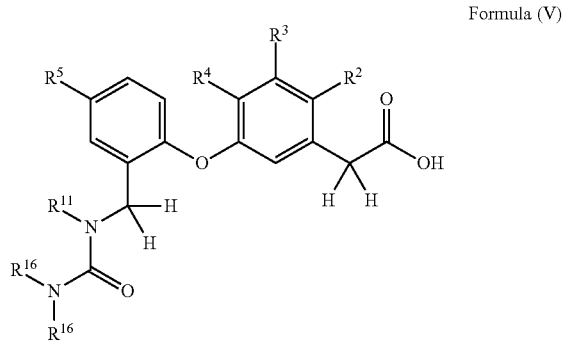

Formula (V)

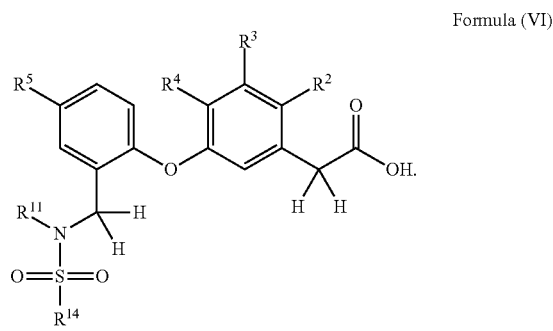

Formula (VI)

In another aspect, described herein is a compound of Formula (VII):

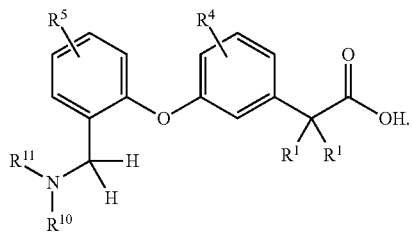

Formula (VII)

In one aspect, the compound of Formula (VII) has the following structure:

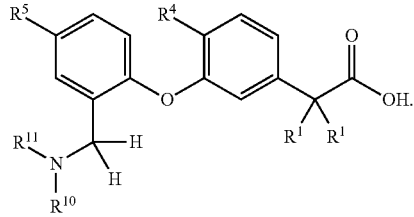

Any combination of the groups described above for the various variables is contemplated herein.

In one aspect, compounds of any one of Formula (I), Formula (II), Formula (III), Formula (IV), Formula (V), Formula (VI) or Formula (VII), include, but are not limited to, those described in Table 1 and Table 2:

TABLE 1

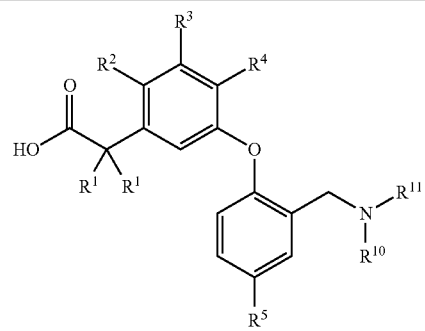

| Cmpd # | $R^1, R^1$ | $R^2$ | $R^3$ | $R^4$ | $R^5$ | $R^{10}$ | $R^{11}$ |
|---|---|---|---|---|---|---|---|
| 1-1 | H, H | H | H | H | —Br | —C(=O)CH$_3$ | —CH$_2$CH$_2$Ph |
| 1-2 | H, H | H | H | H | —Br | —C(=O)CH$_3$ | 2-(4-Fluorophenyl)-1,1,-dimethylethyl |
| 1-3 | H, H | H | H | H | —Br | —C(=O)OCH$_3$ | —CH$_2$Ph |
| 1-4 | H, H | H | H | H | —Br | —C(=O)OCH$_3$ | —CH$_2$CH$_2$Ph |
| 1-5 | H, H | H | H | H | —Br | —C(=O)OCH$_3$ | (S)-1-Methyl-2-phenylethyl |
| 1-6 | H, H | H | H | H | —Br | —C(=O)OBn | (R)-Indan-1-yl |
| 1-7 | H, H | H | H | OCH$_3$ | —Br | H | (1S,2R)-2-Hydroxy-indan-1-yl |
| 1-8 | H, H | H | H | OCH$_3$ | —Br | —C(=O)CH$_3$ | —CH$_2$CH$_3$ |
| 1-9 | H, H | H | H | OCH$_3$ | —Br | —C(=O)CH$_3$ | —CH$_2$Ph |
| 1-10 | H, H | H | H | OCH$_3$ | —Br | —C(=O)OCH$_3$ | —CH$_2$CH$_3$ |
| 1-11 | H, H | H | H | OCH$_3$ | —Br | —C(=O)OCH$_3$ | —CH$_2$Ph |
| 1-12 | H, H | H | H | H | —CF$_3$ | H | (1S,2R)-2-Hydroxy-1-methyl-2-phenylethyl |
| 1-13 | H, H | H | H | H | —CF$_3$ | —C(=O)CH$_3$ | (R)-Indan-1-yl |
| 1-14 | H, H | H | H | H | —CF$_3$ | —C(=O)CH$_3$ | (S)-Indan-1-yl |
| 1-15 | H, H | H | H | H | —CF$_3$ | 4-Chlorobenzoyl | H |
| 1-16 | H, H | H | H | H | —CF$_3$ | —C(=O)Bn | —CH$_3$ |
| 1-17 | H, H | H | H | H | —CF$_3$ | —C(=O)Ph | —CH$_2$CH$_3$ |
| 1-18 | H, H | H | H | H | —CF$_3$ | —C(=O)Bn | —CH$_2$CH$_3$ |
| 1-19 | H, H | H | H | H | —CF$_3$ | —C(=O)OCH$_3$ | (R)-Indan-1-yl |
| 1-20 | H, H | H | H | H | —CF$_3$ | —C(=O)OCH$_3$ | Indan-2-yl |
| 1-21 | H, H | H | H | H | —CF$_3$ | —C(=O)OBn | —CH$_3$ |
| 1-22 | H, H | H | H | H | —CF$_3$ | 4-Chlorobenzenesulfonyl | H |
| 1-23 | H, H | H | H | H | —CF$_3$ | 4-Chlorobenzenesulfonyl | —CH$_3$ |
| 1-24 | H, H | H | H | H | —CF$_3$ | 2-Trifluoromethylbenzenesulfonyl | —CH$_3$ |
| 1-25 | H, H | H | H | H | —CF$_3$ | 4-Methoxylbenzenesulfonyl | —CH$_3$ |
| 1-26 | H, H | H | H | H | —CF$_3$ | 4-Methoxylbenzenesulfonyl | —CH$_2$CH$_3$ |
| 1-27 | H, H | H | H | H | —CF$_3$ | Toluene-4-sulfonyl | —CH$_2$CH$_3$ |
| 1-28 | H, H | H | H | H | —CF$_3$ | 4-Methanesulfonylbenzenesulfonyl | —CH$_2$CH$_3$ |

TABLE 1-continued

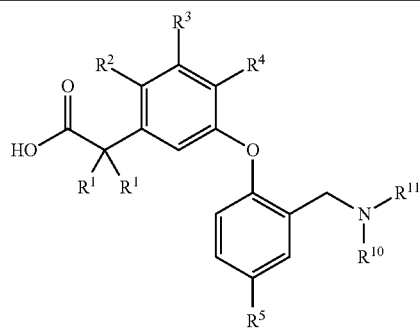

| Cmpd # | R¹, R¹ | R² | R³ | R⁴ | R⁵ | R¹⁰ | R¹¹ |
|---|---|---|---|---|---|---|---|
| 1-29 | H, H | H | H | H | —CF₃ | 4-Acetylbenzene-sulfonyl | —CH₂CH₃ |
| 1-30 | H, H | H | H | H | —CF₃ | Naphthalene-2-sulfonyl | —CH₂CH₃ |
| 1-31 | H, H | H | H | H | —CF₃ | 4-Bromobenzene-sulfonyl | —CH₂CH₃ |
| 1-32 | H, H | H | H | H | —CF₃ | 4-m-Tolylamino-benzenesulfonyl | —CH₂CH₃ |
| 1-33 | H, H | H | H | H | —CF₃ | 4-(Methyl-m-tolylamino)-benzenesulfonyl | —CH₂CH₃ |
| 1-34 | H, H | H | H | OCH₃ | —CF₃ | —C(=O)CH₃ | —CH₂CH₃ |
| 1-35 | H, H | H | H | OCH₃ | —CF₃ | —C(=O)CH₃ | —CH₂Ph |
| 1-36 | H, H | H | H | OCH₃ | —CF₃ | —C(=O)OCH₃ | —CH₂CH₃ |
| 1-37 | H, H | H | H | OCH₃ | —CF₃ | —C(=O)OCH₃ | —CH₂Ph |
| 1-38 | H, H | H | H | H | —NH—C(=O)CH₃ | —C(=O)OCH₃ | (S)-1-Methyl-2-phenylethyl |
| 1-39 | H, H | H | H | H | —N(CH₃)—C(=O)CH₃ | —C(=O)OCH₃ | (S)-1-Methyl-2-phenylethyl |
| 1-40 | CH₃, H | H | H | H | —N(CH₃)—C(=O)CH₃ | —C(=O)OCH₃ | (S)-1-Methyl-2-phenylethyl |
| 1-41 | H, H | H | H | H | —NHSO₂CH₃ | —C(=O)OCH₃ | (S)-1-Methyl-2-phenylethyl |
| 1-42 | H, H | H | H | H | —N(CH₃)—SO₂CH₃ | —C(=O)OCH₃ | (S)-1-Methyl-2-phenylethyl |
| 1-43 | CH₃, H | H | H | H | —N(CH₃)—SO₂CH₃ | —C(=O)OCH₃ | (S)-1-Methyl-2-phenylethyl |
| 1-44 | H, H | H | H | OCH₃ | —NHC(=O)-(4-Chlorophenyl) | —C(=O)OBn | —CH₂CH₃ |
| 1-45 | H, H | H | H | OCH₃ | —NHC(=O)—C(CH₃)₃ | —C(=O)CH₃ | —CH₂CH₃ |
| 1-46 | H, H | H | H | OCH₃ | —NHC(=O)-(4-chlorophenyl) | —C(=O)CH₃ | —CH₂CH₃ |
| 1-47 | H, H | H | H | OCH₃ | —NHC(=O)—C(CH₃)₃ | —C(=O)—(cyclopropyl) | —CH₂CH₃ |
| 1-48 | H, H | H | h | OCH₃ | —NHC(=O)-(4-chlorophenyl) | —C(=O)—(cyclopropyl) | —CH₂CH₃ |

Compounds in Table 1 are named:
(3-{2-[(Acetyl-phenethyl-amino)-methyl]-4-bromo-phenoxy}-phenyl)-acetic acid (Compound 1-1); {3-[2-({Acetyl-[2-(4-fluoro-phenyl)-1,1-dimethyl-ethyl]-amino}-methyl)-4-bromo-phenoxy]-phenyl}-acetic acid (Compound 1-2); (3-{2-[(Benzyl-methoxycarbonyl-amino)-methyl]-4-bromo-phenoxy}-phenyl)-acetic acid (Compound 1-3); (3-{4-Bromo-2-[(methoxycarbonyl-phenethyl-amino)-methyl]-phenoxy}-phenyl)-acetic acid (Compound 1-4); [3-(4-Bromo-2-{[methoxycarbonyl-((S)-1-methyl-2-phenyl-ethyl)-amino]-methyl}-phenoxy)-phenyl]-acetic acid (Compound 1-5); (3-{2-[((R)-Benzyloxycarbonyl-indan-1-yl-amino)-methyl]-4-bromo-phenoxy}-phenyl)-acetic acid (Compound 1-6); (3-{4-Bromo-2-[((1S,2R)-2-hydroxy-indan-1-ylamino)-methyl]-phenoxy}-4-methoxy-phenyl)-acetic acid (Compound 1-7); (3-{2-[(Acetyl-ethyl-amino)-methyl]-4-bromo-phenoxy}-4-methoxy-phenyl)-acetic acid (Compound 1-8); (3-{2-[(Acetyl-benzyl-amino)-methyl]-4-bromo-phenoxy}-4-methoxy-phenyl)-acetic acid (Compound 1-9); (3-{4-Bromo-2-[(ethyl-methoxycarbonyl-amino)-methyl]-phenoxy}-4-methoxy-phenyl)-acetic acid (Compound 1-10); (3-{2-[(Benzyl-methoxycarbonyl-amino)-methyl]-4-bromo-phenoxy}-4-methoxy-phenyl)-acetic acid (Compound 1-11); (3-{2-[((1S,2R)-2-Hydroxy-1-methyl-2-phenyl-ethylamino)-methyl]-4-trifluoromethyl-phenoxy}-phenyl)-acetic acid (Compound 1-12); (3-{2-[((R)-Acetyl-indan-1-yl-amino)-methyl]-4-trifluoromethyl-phenoxy}-phenyl)-acetic acid (Compound 1-13); (3-{2-[((S)-Acetyl-indan-1-yl-amino)-methyl]-4-trifluoromethyl-phenoxy}-phenyl)-acetic acid (Compound 1-14); (3-{2-[(4-Chloro-benzoylamino)-methyl]-4-trifluoromethyl-phenoxy}-phenyl)-acetic acid (Compound 1-15); (3-{2-[(Methyl-phenylacetyl-amino)-methyl]-4-trifluoromethyl-phenoxy}-phenyl)-acetic acid (Compound 1-16); (3-{2-[(Benzoyl-ethyl-amino)-methyl]-4-trifluoromethyl-phenoxy}-phenyl)-acetic acid (Compound 1-17); (3-{2-[(Ethyl-phenylacetyl-amino)-methyl]-4-trifluoromethyl-phenoxy}-phenyl)-acetic acid (Compound 1-18); (3-{2-[((R)-Indan-1-yl-methoxycarbonyl-amino)-methyl]-4-trifluoromethyl-phenoxy}-phenyl)-acetic acid (Compound 1-19); (3-{2-[(Indan-2-yl-methoxycarbonyl-amino)-methyl]-4-trifluoromethyl-phenoxy}-phenyl)-acetic acid (Compound 1-20); (3-{2-[(Benzyloxycarbonyl-methyl-amino)-methyl]-4-trifluoromethyl-phenoxy}-phenyl)-acetic acid (Compound 1-21); (3-{2-[(4-Chloro-benzenesulfonylamino)-methyl]-4-trifluoromethyl-phenoxy}-phenyl)-acetic acid (Compound 1-22); [3-(2-{[(4-Chloro-benzenesulfonyl)-methyl-amino]-methyl}-4-trifluoromethyl-phenoxy)-phenyl]-acetic acid (Compound 1-23); [3-(2-{[Methyl-(2-trifluoromethyl-benzenesulfonyl)-amino]-methyl}-4-trifluoromethyl-phenoxy)-phenyl]-acetic acid (Compound 1-24); [3-(2-{[(4-Methoxy-benzenesulfonyl)-methyl-amino]-methyl}-4-trifluoromethyl-phenoxy)-phenyl]-acetic acid (Compound 1-25); [3-(2-{[Ethyl-(4-methoxy-benzenesulfonyl)-amino]-methyl}-4-trifluoromethyl-phenoxy)-phenyl]-acetic acid (Compound 1-26); [3-(2-{[Ethyl-(toluene-4-sulfonyl)-amino]-methyl}-4-trifluoromethyl-phenoxy)-phenyl]-acetic acid (Compound 1-27); [3-(2-{[Ethyl-(4-methanesulfonyl-benzenesulfonyl)-amino]-methyl}-4-trifluoromethyl-phenoxy)-phenyl]-acetic acid (Compound 1-28); [3-(2-{[(4-Acetyl-benzenesulfonyl)-ethyl-amino]-methyl}-4-trifluoromethyl-phenoxy)-phenyl]-acetic acid (Compound 1-29); [3-(2-{[Ethyl-(naphthalene-2-sulfonyl)-amino]-methyl}-4-trifluoromethyl-phenoxy)-phenyl]-acetic acid (Compound 1-30); [3-(2-{[(4-Bromo-benzenesulfonyl)-ethyl-amino]-methyl}-4-trifluoromethyl-phenoxy)-phenyl]-acetic acid (Compound 1-31); [3-(2-{[Ethyl-(4-m-tolylamino-benzenesulfonyl)-amino]-methyl}-4-trifluoromethyl-phenoxy)-phenyl]-acetic acid (Compound 1-32); {3-[2-({Ethyl-[4-(methyl-m-tolyl-amino)-benzenesulfonyl]-amino}-methyl)-4-trifluoromethyl-phenoxy]-phenyl}-acetic acid (Compound 1-33); (3-{2-[(Acetyl-ethyl-amino)-methyl]-4-trifluoromethyl-phenoxy}-4-methoxy-phenyl)-acetic acid (Compound 1-34); (3-{2-[(Acetyl-benzyl-amino)-methyl]-4-trifluoromethyl-phenoxy}-4-methoxy-phenyl)-acetic acid (Compound 1-35); (3-{2-[(Ethyl-methoxycarbonyl-amino)-methyl]-4-trifluoromethyl-phenoxy}-4-methoxy-phenyl)-acetic acid (Compound 1-36); (3-{2-[(Benzyl-methoxycarbonyl-amino)-methyl]-4-trifluoromethyl-phenoxy}-4-methoxy-phenyl)-acetic acid (Compound 1-37); [3-(4-Acetylamino-2-{[methoxycarbonyl-((S)-1-methyl-2-phenyl-ethyl)-amino]-methyl}-phenoxy)-phenyl]-acetic acid (Compound 1-38); [3-(4-(Acetyl-methyl-amino)-2-{[methoxycarbonyl-((S)-1-methyl-2-phenyl-ethyl)-amino]-methyl}-phenoxy)-phenyl]-acetic acid (Compound 1-39); 2-[3-(4-(Acetyl-methyl-amino)-2-{[methoxycarbonyl-((S)-1-methyl-2-phenyl-ethyl)-amino]-methyl}-phenoxy)-phenyl]-propionic acid (Compound 1-40); [3-(4-Methanesulfonylamino-2-{[methoxycarbonyl-((S)-1-methyl-2-phenyl-ethyl)-amino]-methyl}-phenoxy)-phenyl]-acetic acid (Compound 1-41); [3-(4-(Methanesulfonyl-methyl-amino)-2-{[methoxycarbonyl-((S)-1-methyl-2-phenyl-ethyl)-amino]-methyl}-phenoxy)-phenyl]acetic acid (Compound 1-42); 2-[3-(4-(Methanesulfonyl-methyl-amino)-2-{[methoxycarbonyl-((S)-1-methyl-2-phenyl-ethyl)-amino]-methyl}-phenoxy)-phenyl]-propionic acid (Compound 1-43); {3-[2-[(Benzyloxycarbonyl-ethyl-amino)-methyl]-4-(4-chloro-benzoylamino)-phenoxy]-4-methoxy-phenyl}-acetic acid (Compound 1-44); {3-[2-[(Acetyl-ethyl-amino)-methyl]-4-(2,2-dimethyl-propionylamino)-phenoxy]-4-methoxy-phenyl}-acetic acid (Compound 1-45); {3-[2-[(Acetyl-ethyl-amino)-methyl]-4-(4-chloro-benzoylamino)-phenoxy]-4-methoxy-phenyl}-acetic acid (Compound 1-46); {3-[2-[(Cyclopropanecarbonyl-ethyl-amino)-methyl]-4-(2,2-dimethyl-propionylamino)-phenoxy]-4-methoxy-phenyl}-acetic acid (Compound 1-47); and (3-{4-(4-Chloro-benzoylamino)-2-[(cyclopropanecarbonyl-ethyl-amino)-methyl]-phenoxy}-4-methoxy-phenyl)-acetic acid (Compound 1-48).

TABLE 2

| $R^1, R^1$ | $R^3$ | $R^4$ | $R^5$ | $R^6$ | $R^7$ | $R^{10}$ | $R^{11}$ |
|---|---|---|---|---|---|---|---|
| H, H | H | $OCH_3$ | $CF_3$ | H | H | $-C(=O)CH_3$ | $CH_3$ |
| H, H | H | $OCH_3$ | $CF_3$ | H | H | $-C(=O)CH_3$ | $CH_2C(CH_3)_3$ |
| H, H | H | $OCH_3$ | $CF_3$ | H | H | $-C(=O)CH_3$ | $CH_2CF_3$ |
| H, H | H | $OCH_3$ | $CF_3$ | H | H | $-C(=O)CH_3$ | $CH_2CH_2OH$ |
| H, H | H | $OCH_3$ | $CF_3$ | H | H | $-C(=O)CH_3$ | $CH_2CH_2OCH_3$ |
| H, H | H | $OCH_3$ | $CF_3$ | H | H | $-C(=O)CH_3$ | $CH_2CH_2N(CH_3)_2$ |
| H, H | H | $OCH_3$ | $CF_3$ | H | H | $-C(=O)CH_3$ | $CH_2COOH$ |
| H, H | H | $OCH_3$ | $CF_3$ | H | H | $-C(=O)CH_3$ | $CH_2C(O)NH_2$ |
| H, H | H | F | $CF_3$ | H | H | $-C(=O)CH_3$ | $CH_2CH_3$ |
| H, H | H | F | $CF_3$ | H | H | $-C(=O)CH_3$ | $CH_2CF_3$ |
| H, H | H | $OCH_3$ | $CF_3$ | H | H | $-C(=O)CH_3$ | Cyclopropyl |
| H, H | H | $OCH_3$ | $CF_3$ | H | H | $-C(=O)CH_3$ | (S)-Indan-1-yl |

TABLE 2-continued

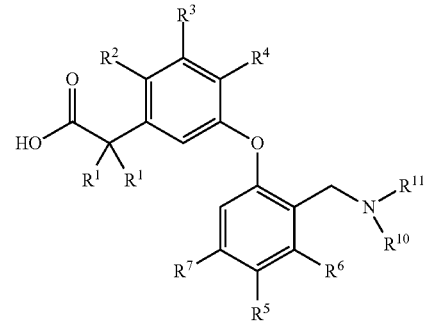

| R¹, R¹ | R³ | R⁴ | R⁵ | R⁶ | R⁷ | R¹⁰ | R¹¹ |
|---|---|---|---|---|---|---|---|
| H, H | H | OCH₃ | CF₃ | H | H | —C(=O)CH₃ | (R)-Indan-1-yl |
| H, H | H | OCH₃ | CF₃ | H | H | —C(=O)CH₃ | (1R,2S)-2-Hydroxy-indan-1-yl |
| H, H | H | OCH₃ | CF₃ | H | H | —C(=O)CH₃ | (1R,2S)-2-Methoxy-indan-1-yl |
| H, H | H | OCH₃ | CF₃ | H | H | —C(=O)CH₃ | Indan-2-yl |
| H, H | H | OCH₃ | CF₃ | H | H | —C(=O)CH₃ | Phenyl |
| H, H | H | OCH₃ | CF₃ | H | H | —C(=O)CH₃ | Phenethyl |
| H, —CH₃ | H | OCH₃ | CF₃ | H | H | —C(=O)CH₃ | CH₂CH₃ |
| H, H | H | OCH₃ | CF₃ | H | H | —C(=O)CH₃ | CH₂CH₃ |
| H, H | H | OCH₃ | CF₃ | H | H | —C(=O)OCH₃ | CH₂CH₃ |
| H, H | H | OCH₃ | CF₃ | H | H | —C(=O)OCH₃ | Phenethyl |
| H, H | H | OCH₃ | CF₃ | H | H | —C(=O)OCH₃ | Indan-2-yl |
| H, H | H | OCH₃ | CF₃ | H | H | —C(=O)OBn | CH₃ |
| H, H | H | OCH₃ | CF₃ | H | H | —C(=O)OBn | CH₂CH₃ |
| H, H | H | F | CF₃ | H | H | —C(=O)OBn | CH₃ |
| H, H | H | OCH₃ | CF₃ | H | H | —C(=O)CH₃ | Cyclobutyl |
| H, H | H | OCH₃ | CF₃ | H | H | —C(=O)CH₃ | Cyclopentyl |
| H, H | H | OCH₃ | CF₃ | H | H | —C(=O)CF₃ | CH₂CH₃ |
| H, H | H | OCH₃ | CF₃ | H | H | —C(=O)—Cyclopropyl | CH₂CH₃ |
| H, H | H | OCH₃ | CF₃ | H | H | —C(=O)OBn | Cyclobutyl |
| H, H | H | OCH₃ | CF₃ | H | H | —C(=O)OBn | Cyclopentyl |
| H, H | H | OCH₃ | CF₃ | H | H | —C(=O)OBn | Cyclopropyl |
| H, H | H | OCH₃ | CO₂H | H | H | —C(=O)CH₃ | CH₂CF₃ |
| H, H | H | OCH₃ | CF₃ | H | H | —C(=O)O-(3,5-Dichloro-benzyl) | CH₂CH₃ |
| H, H | H | OCH₃ | CF₃ | H | H | —C(=O)O-(2-Chlorobenzyl) | CH₂CH₃ |
| H, H | H | OCH₃ | CF₃ | H | H | —C(=O)O-(2,5-Difluoro-benzyl) | CH₂CH₃ |
| H, H | H | OCH₃ | CF₃ | H | H | —C(=O)O-(4-Fluorobenzyl) | CH₂CH₃ |
| H, H | H | OCH₃ | CF₃ | H | H | —C(=O)O-(4-Chlorobenzyl) | CH₂CH₃ |
| H, H | H | OCH₃ | CF₃ | H | H | —C(=O)O-(3-Chlorobenzyl) | CH₂CH₃ |
| H, H | H | OCH₃ | CF₃ | H | H | —C(=O)O—CH(CH₃)—(4-Chloro-phenyl) | CH₂CH₃ |
| H, H | H | OCH₃ | CF₃ | H | H | —C(=O)—CH(CH₃)OPh | CH₂CH₃ |
| H, H | H | OCH₃ | CF₃ | H | H | —C(=O)—CH₂OCH₃ | CH₂CH₃ |
| H, H | H | OCH₃ | CF₃ | H | H | —C(=O)NH-(2-Bromophenyl) | CH₂CH₃ |
| H, H | H | OCH₃ | CF₃ | H | H | —C(=O)CH₂OPh | CH₂CH₃ |
| H, H | H | F | CF₃ | H | H | —C(=O)OBn | CH₂CF₃ |
| H, H | H | OCH₃ | —NHC(=O)CH₃ | H | H | —C(=O)CH₃ | CH₂CH₃ |
| H, H | H | OCH₃ | Pyrazol-1-yl | H | H | —C(=O)CH₃ | CH₂CH₃ |
| H, H | H | OCH₃ | CF₃ | H | H | —C(=O)CH₃ | o-Tolyl |
| H, H | H | OCH₃ | CF₃ | H | H | —C(=O)CH₃ | Thiazol-2-yl |
| H, H | H | OCH₃ | CF₃ | H | H | —C(=O)CH₃ | 2-Methyl-pyrimidin-4-yl |
| H, H | H | CH₃ | CF₃ | H | H | —C(=O)CH₃ | CH₂CH₃ |
| H, H | Cl | H | CF₃ | H | H | —C(=O)OBn | CH₂CH₃ |
| H, H | H | OCH₃ | CF₃ | H | H | —C(=O)CH₃ | CH₂CH₃ |
| H, H | H | CH₃ | CF₃ | H | H | —C(=O)CH₃ | CH₂CH₃ |
| H, H | H | Cyclo-propyl | CF₃ | H | H | —C(=O)CH₃ | CH₂CH₃ |
| H, H | H | CF₃ | CF₃ | H | H | —C(=O)CH₃ | CH₂CH₃ |
| H, H | CF₃ | H | CF₃ | H | H | —C(=O)OBn | CH₂CH₃ |
| H, H | H | OCH₃ | NHC(=O)CH₃ | H | H | —C(=O)CH₃ | CH₂CH₃ |
| H, H | H | OCH₃ | NHC(=O)OCH₃ | H | H | —C(=O)CH₃ | CH₂CH₃ |
| H, H | H | OCH₃ | NHSO₂CH₃ | H | H | —C(=O)CH₃ | CH₂CH₃ |

TABLE 2-continued

| $R^1, R^1$ | $R^3$ | $R^4$ | $R^5$ | $R^6$ | $R^7$ | $R^{10}$ | $R^{11}$ |
|---|---|---|---|---|---|---|---|
| H, H | H | OCH$_3$ | SO$_2$CH$_3$ | H | H | —C(=O)CH$_3$ | CH$_2$CH$_3$ |
| H, H | H | OCH$_3$ | Pyrrolidin-1-yl | H | H | —C(=O)CH$_3$ | CH$_2$CH$_3$ |
| H, H | H | OCH$_3$ | Pyrazol-1-yl | H | H | —C(=O)CH$_3$ | CH$_2$CH$_3$ |
| H, H | H | OCH$_3$ | Cyclopropyl | H | H | —C(=O)CH$_3$ | CH$_2$CH$_3$ |
| H, H | H | OCH$_3$ | Phenyl | H | H | —C(=O)CH$_3$ | CH$_2$CH$_3$ |
| H, H | H | OCH$_3$ | Ozazol-2-yl | H | H | —C(=O)CH$_3$ | CH$_2$CH$_3$ |
| H, H | H | OCH$_3$ | 1H-Pyrazol-4-yl | H | H | —C(=O)CH$_3$ | CH$_2$CH$_3$ |
| H, H | H | OCH$_3$ | Pyridin-2-yl | H | H | —C(=O)CH$_3$ | CH$_2$CH$_3$ |
| H, H | H | OCH$_3$ | CF$_3$ | H | H | —C(=O)O—Cyclopropyl | CH$_2$CH$_3$ |
| H, H | H | OCH$_3$ | CF$_3$ | H | H | —C(=O)NHCH$_3$ | CH$_2$CH$_3$ |
| H, H | H | OCH$_3$ | CF$_3$ | H | H | —C(=O)Cyclopropyl | CH$_2$CH$_3$ |
| H, H | H | OCH$_3$ | CF$_3$ | H | H | —C(=O)Cyclopentyl | CH$_2$CH$_3$ |
| H, H | H | OCH$_3$ | CF$_3$ | H | H | —C(=O)CH$_3$ | CH$_2$CH$_3$ |
| H, H | H | OCH$_3$ | CF$_3$ | H | H | —C(=O)Phenyl | CH$_2$CH$_3$ |
| H, H | H | OCH$_3$ | CF$_3$ | H | H | —C(=O)-(Pyridin-2-yl) | CH$_2$CH$_3$ |
| H, H | H | OCH$_3$ | CF$_3$ | H | H | —C(=O)-(Pyrazin-2-yl) | CH$_2$CH$_3$ |
| H, H | H | OCH$_3$ | CF$_3$ | H | H | —C(=O)-(1-Methyl-1H-pyrazol-3-yl) | CH$_2$CH$_3$ |
| H, H | H | OCH$_3$ | H | H | Br | —C(=O)CH$_3$ | CH$_2$CH$_3$ |
| H, H | H | OCH$_3$ | H | H | —NHC(=O)—CH$_3$ | —C(=O)CH$_3$ | CH$_2$CH$_3$ |
| H, H | H | OCH$_3$ | H | H | —NHC(=O)—OCH$_3$ | —C(=O)CH$_3$ | CH$_2$CH$_3$ |
| H, H | H | OCH$_3$ | H | H | —NHSO$_2$CH$_3$ | —C(=O)CH$_3$ | CH$_2$CH$_3$ |
| H, H | H | OCH$_3$ | H | H | Pyrrolidin-1-yl | —C(=O)CH$_3$ | CH$_2$CH$_3$ |
| H, H | H | OCH$_3$ | H | H | 5' Pyrazol-1-yl | —C(=O)CH$_3$ | CH$_2$CH$_3$ |
| H, H | H | OCH$_3$ | H | SO$_2$CH$_3$ | H | —C(=O)CH$_3$ | CH$_2$CH$_3$ |
| F, F | H | OCH$_3$ | CF$_3$ | H | H | —C(=O)CH$_3$ | CH$_2$CH$_3$ |
| H, H | H | OCH$_3$ | CF$_3$ | H | H | —C(=O)CH$_2$OBn | CH$_2$CH$_3$ |
| H, H | H | OCH$_3$ | CF$_3$ | H | H | —C(=O)(4-Chlorophenoxymethyl) | CH$_2$CH$_3$ |
| H, H | H | OCH$_3$ | CF$_3$ | H | H | C(=O)N(CH$_2$CH$_3$)Bn | CH$_2$CH$_3$ |
| H, H | H | OCH$_3$ | CF$_3$ | H | H | —C(=O)N(H)Bn | CH$_2$CH$_3$ |
| H, H | H | OCH$_3$ | CF$_3$ | H | H | —C(=O)(Pyrrolidin-1-yl) | CH$_2$CH$_3$ |
| H, —CH$_3$ | H | OCH$_3$ | CF$_3$ | H | H | —C(=O)OBn | CH$_2$CH$_3$ |
| H, H | H | OCH$_3$ | CF$_3$ | H | H | —C(=O)N(H)CN | CH$_2$CH$_3$ |
| H, H | H | OCH$_3$ | CF$_3$ | H | H | 4-Chlorobenzenesulfonyl | CH$_2$CH$_3$ |
| H, H | H | OCH$_3$ | CF$_3$ | H | H | Methanesulfonyl | Phenethyl |

Synthesis of Compounds

Compounds of Formula (I), Formula (II), Formula (III), Formula (IV, Formula (V), Formula (VI) and Formula (VII), described in the prior section are synthesized using standard synthetic techniques or using methods known in the art in combination with methods described herein. In additions, solvents, temperatures and other reaction conditions presented herein may vary.

The starting material used for the synthesis of the compounds of Formula (I), Formula (II), Formula (III), Formula (IV, Formula (V), Formula (VI) and Formula (VII), described in the prior section are either synthesized or obtained from commercial sources, such as, but not limited to, Aldrich Chemical Co. (Milwaukee, Wis.), or Sigma Chemical Co. (St. Louis, Mo.). The compounds described herein, and other related compounds having different substituents are synthesized using known techniques and materials, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In certain embodiments, compounds described herein are prepared according to Scheme 1.

Scheme 1:

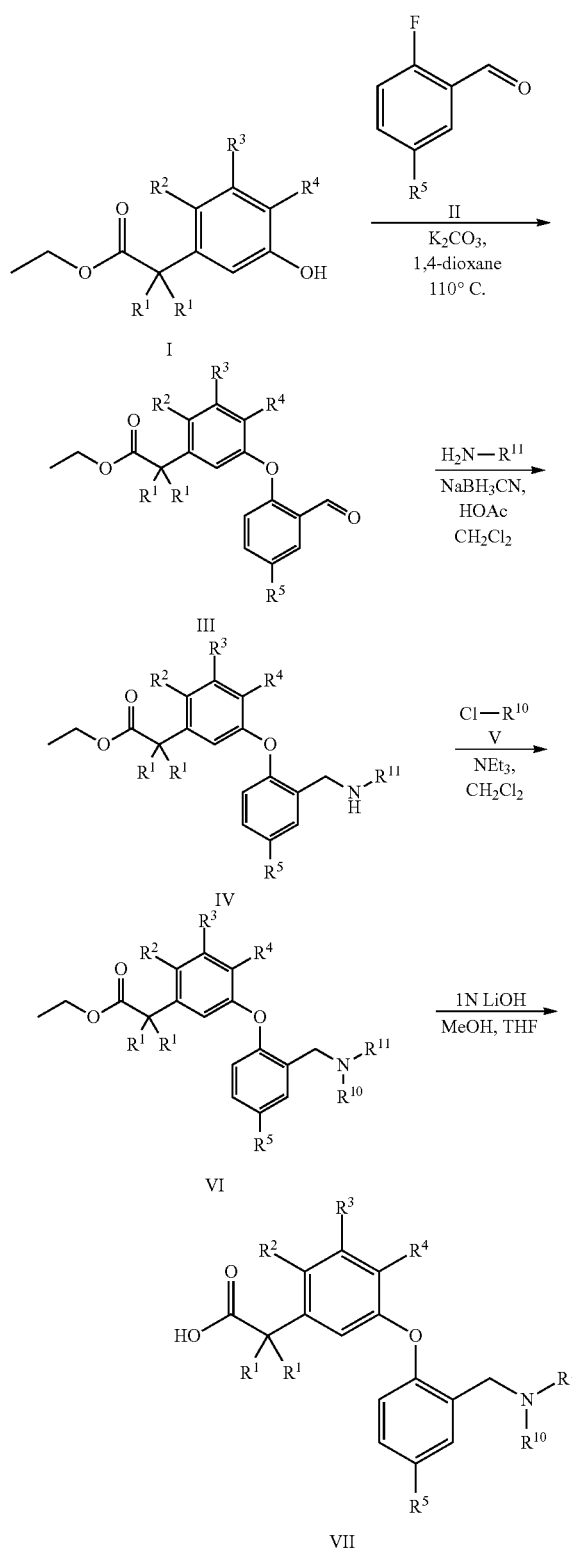

Phenols of structure I are reacted with fluorobenzaldehydes of structure II under $SN_{AR}$ conditions to provide diarylethers of structure III. Other methods of forming diaryl ethers are optionally used, such as metal mediated reactions, including but not limited to the Ulman Ether synthesis, Chan-Lam coupling, and Buchwald-Hartwig synthesis (D. Ma, Q. Cai, Org. Lett., 2003, 5, 3799-3802; C. G. Bates, et al., Org. Lett., 2002, 4, 2803-2806; C. H. Burgos, et al., Angew. Chem. Int. Ed., 2006, 45, 4321-4326; C. H. Burgos, et al., Angew. Chem. Int. Ed., 2006, 45, 4321-4326; D. M. T. Chan, et al., Tetrahedron Lett., 1998, 39, 2933-2936; Z. Liu, R. C. Larock, J. Org. Chem., 2006, 71, 3198-3209; Y.-J. Chen, H.-H. Chen, Org. Lett., 2006, 8, 5609-5612; F. Li, Q. et al., Org. Lett., 2003, 5, 2169-2171; D. A. Evans, et al., Tetrahedron Letters, 1998, 39, 2937-2940; C.-E. Yeom, et al., Synlett, 2007, 146-150). The aldehyde moiety of diaryl ethers of structure III is treated with various amines ($R^{11}$—$NH_2$) under reductive amination conditions to provide amines of structure IV. Amines of structure IV are reacted with a variety of agents, such as, but not limited to alkyl halides, benzyl halides, acyl halides, chloroformates, sulfonyl halides, and the like, to provide compounds of structure VI. In one embodiment, amines of structure IV are treated with acyl halides to provide amides of structure VI (i.e. $R^{10}$ is —C(=O)$R^{14}$).

In some embodiments, amines of structure IV are reacted with, but not limited to, a carboxylic acid and coupling reagent such as EDC, DCC, BOP, HATU or the like, or a carboxylic acid activated ester or an acid halide, alkylchloroformate, arylchloroformate, benzylchloroformate, alkylisocyanate, benzylisocyanate, arylisocyanate, alkylsulfonyl chloride, arylsulfonyl chloride, heteroarylsulfonyl chloride, or the like in dichloromethane, dichloroethane, tetrahydrofuran, dimethoxyethane or the like in the presence of a hindered base such as triethylamine, diisopropylethylamine, N-methylmorpholine, pyridine or the like, to afford compounds of Formula (I).

The ester moiety of diaryl ethers of structure VII is then hydrolyzed to the carboxylic acid to provide carboxylic acids of structure VIII.

In cases where $R^5$ is a halide or other leaving group, metal mediated coupling reactions may be used to introduce other groups at $R^5$. Metal mediated coupling reactions include, but are not limited to Suzuki reactions, Stile cross couplings, Negishi couplings, Kumada couplings, Ullmann reactions, Hiyama Coupling, and variants thereof (Metal-Catalyzed Cross-Coupling Reactions, Armin de Meijere (Editor), François Diederich (Editor), John Wiley & Sons; 2nd edition, 2004; Özdemir, et al., Tetrahedron, 2005, 61, 9791-9798; Ackermann, et al., Org. Lett., 2006, 8, 3457-3460; Blakey, et al., J. Am. Chem. Soc., 2003, 125, 6046-6047; Dai, et al., Org. Lett., 2004, 6, 221-224; Yoshikai, et al, J. Am. Chem. Soc., 2005, 127, 17978-17979; Tang, et al, J. Org. Chem., 2006, 71, 2167-2169; Murata, et al., Synthesis, 2001, 2231-2233).

Carbamates of structure XI are prepared as outlined in Scheme 2:

Scheme 2:

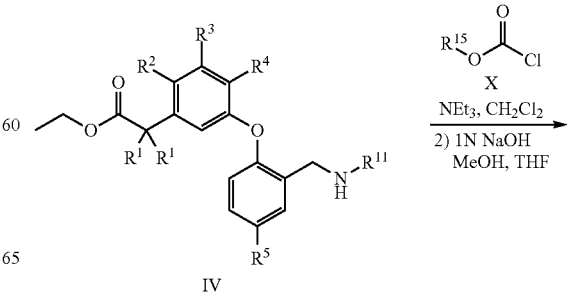

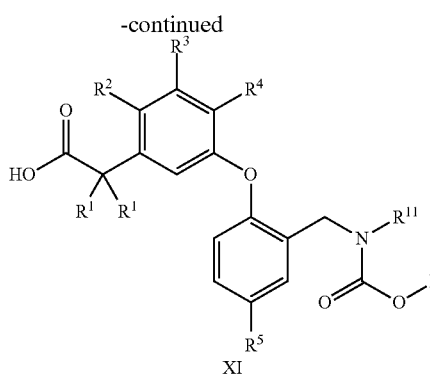

XI

Reaction of amines of structure IV with chloroformates of structure X provide carbamates, which after hydrolysis of the ester moiety, provide carbamates of structure XI. Methods for the preparation of carbamates are known, such as described herein or in reference texts such as, but not limited to, Greene, T. W. and Wuts, P. G. M "Protective Groups in Organic Synthesis", 3rd Edition, p. 549, New York: Wiley, 1999. In one aspect, alkylamines (compounds of structure IV) are treated with phosgene or a phosgene equivalent, such as, for example, trichloromethyl chloroformate or carbonyldiimidazole, to yield an intermediate, which is then treated with a hydroxy containing compound $R^{15}$—OH to provide carbamates of structure XI (i.e. compound of structure VII where $R^{10}$ is —$CO_2R^{15}$).

The synthesis of sulfonamides of structure XIII is depicted in Scheme 3:

Scheme 3:

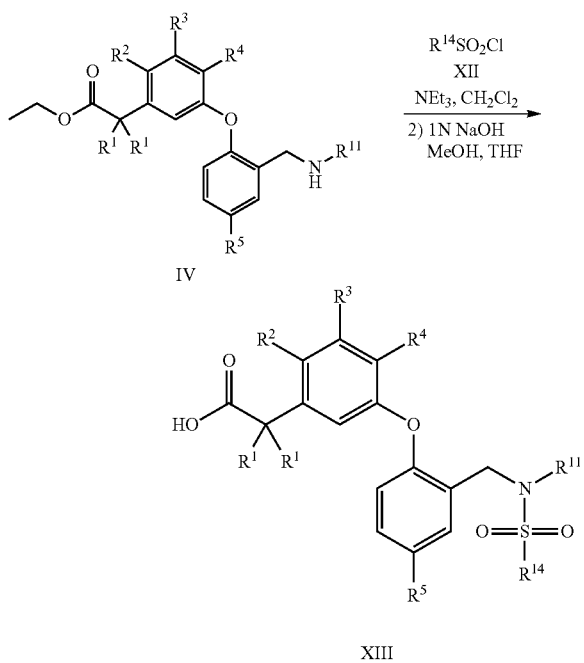

XIII

Reaction of amines of structure IV with sulfonyl chlorides of structure XII provides sulfonamides, which are then treated with base, such as NaOH, to provide sulfonamides of structure XIII (i.e. compound of structure VII where $R^{10}$ is —$SO_2R^{14}$).

The synthesis of ureas of structure XIV is depicted in Scheme 4:

Scheme 4:

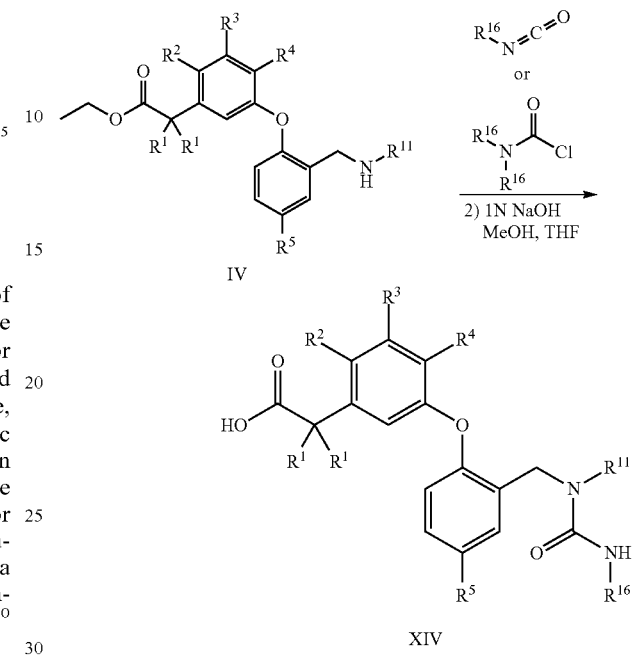

XIV

Reaction of benzylamines of structure IV with isocyanates or carbamoyl chlorides provides ureas of structure XIV after hydrolysis of the ester group. Common methods for the synthesis of isocyanates include the Curtius rearrangement of acyl azides and the Lossen rearrangement of hydroxamic acids.

Formation of Covalent Linkages by Reaction of an Electrophile with a Nucleophile In certain embodiments, the compounds described herein are modified using various electrophiles or nucleophiles to form new functional groups or substituents. Table 3 entitled "Examples of Covalent Linkages and Precursors Thereof" lists selected, non-limiting examples of covalent linkages and precursor functional groups that are used to prepare the modified compounds. Precursor functional groups are shown as electrophilic groups and nucleophilic groups.

TABLE 3

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |

TABLE 3-continued

Examples of Covalent Linkages and Precursors Thereof

| Covalent Linkage Product | Electrophile | Nucleophile |
| --- | --- | --- |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. A detailed description of protecting groups and techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In certain embodiments, compounds of any of Formula (I), Formula (II), Formula (III), Formula (IV), Formula (V), Formula (VI) or Formula (VII), are prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of any of Formula (I), Formula (II), Formula (III), Formula (IV), Formula (V), Formula (VI) or Formula (VII), with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts are also obtained by reacting a compound of any of Formula (I), Formula (II), Formula (III), Formula (IV), Formula (V), Formula (VI) or Formula (VII), with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In other embodiments, compounds of any of Formula (I), Formula (II), Formula (III), Formula (IV), Formula (V), Formula (VI) or Formula (VII), are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds of any of Formula (I), Formula (II), Formula (III), Formula (IV), Formula (V), Formula (VI) or Formula (VII), are conveniently prepared or formed during the processes described herein. By way of example only, hydrates of compounds of any of Formula (I), Formula (II), Formula (III), Formula (IV), Formula (V), Formula (VI) or Formula (VII), are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In yet other embodiments, the compounds of any of Formula (I), Formula (II), Formula (III), Formula (IV), Formula (V), Formula (VI) or Formula (VII), are prepared in various forms, including but not limited to, amorphous forms, milled forms and nano-particulate forms. In addition, compounds of any of Formula (I), Formula (II), Formula (III), Formula (IV), Formula (V), Formula (VI) or Formula (VII), include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

In some embodiments, compounds of any of Formula (I), Formula (II), Formula (III), Formula (IV), Formula (V), Formula (VI) or Formula (VII), are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of any of Formula (I), Formula (II), Formula (III), Formula (IV), Formula (V), Formula (VI) or Formula (VII), which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of a compound described herein is bioavailable by oral administration whereas the parent is not. Furthermore, in some embodiments, the prodrug of a compound described herein has improved solubility in pharmaceutical compositions over the parent drug.

In other embodiments, prodrugs are designed as reversible drug derivatives, for use as modifiers to enhance drug transport to site-specific tissues. In specific embodiments, the design of prodrugs is to increase the effective water solubility of the therapeutic compound for targeting to regions where water is the principal solvent. See, e.g., Fedorak et al., *Am. J. Physiol.*, 269:G210-218 (1995); MeLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Prodrugs as Novel Delivery Systems*, Vol. 14 of the A.C.S. Symposium Series; and Edward B. Roche, *Bioreversible Carriers in Drug Design*, American Pharmaceutical Association and Pergamon Press, 1987.

Additionally, prodrug derivatives of compounds of any of Formula (I), Formula (II), Formula (III), Formula (IV), Formula (V), Formula (VI) or Formula (VII), are prepared, if desired (e.g., for further details see Saulnier et al., (1994), *Bioorganic and Medicinal Chemistry Letters*, Vol. 4, p. 1985). By way of example only, in one aspect appropriate prodrugs are prepared by reacting a non-derivatized compound of any of Formula (I), Formula (II), Formula (III), Formula (IV), Formula (V), Formula (VI) or Formula (VII), with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, some of the herein-described compounds are a prodrug for another derivative or active compound.

In some embodiments, sites on the aromatic ring portion of compounds of any of Formula (I), Formula (II), Formula (III), Formula (IV), Formula (V), Formula (VI) or Formula (VII), are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

In yet another embodiment, the compounds of any of Formula (I), Formula (II), Formula (III), Formula (IV), Formula (V), Formula (VI) or Formula (VII), possess one or more stereocenters and each center exists independently in either the R or S configuration. The compounds presented herein include all diastereomeric, enantiomeric, and epimeric forms as well as the appropriate mixtures thereof. In certain embodiments, compounds of any of Formula (I), Formula (II), Formula (III), Formula (IV), Formula (V), Formula (VI) or Formula (VII), are prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of the compounds described herein. In other embodiments, dissociable complexes are utilized (e.g., crystalline diastereomeric salts). Diastereomers have distinct physical properties (e.g., melting points, boiling points, solubilities, reactivity, etc.) and are, in specific embodiments, separated by taking advantage of these dissimilarities. In these embodiments, the diastereomers are separated by chiral chromatography or by separation/resolution techniques based upon differences in solubility. The optically pure enantiomer is then recovered, along with the resolving agent, by any practical means that does not result in racemization. Jean Jacques, Andre Collet, Samuel H. Wilen, "Enantiomers, Racemates and Resolutions", John Wiley And Sons, Inc., 1981.

Additionally, in certain embodiments, the compounds provided herein exist as geometric isomers. The compounds and methods provided herein include all cis, trans, syn, anti, entgegen (E), and zusammen (Z) isomers as well as the appropriate mixtures thereof. In some embodiments, the compounds described herein exist as tautomers. All tautomers are intended to be within the scope of the molecular formulas described herein. In additional embodiments of the compounds and methods provided herein, mixtures of enantiomers and/or diastereoisomers, resulting from a single preparative step, combination, or interconversion are envisioned.
Certain Terminology Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes," and "included," is not limiting.

An "alkyl" group refers to an aliphatic hydrocarbon group. The alkyl moiety may be a saturated alkyl or an unsaturated alkyl. The alkyl moiety, whether saturated or unsaturated, may be branched, or straight chain. The "alkyl" moiety may have 1 to 10 carbon atoms (whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_4$alkyl" indicates that there are one, two, three, or four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, allyl, but-2-enyl, but-3-enyl, and the like. In one aspect, an alkyl is a $C_1$-$C_6$alkyl.

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0. In some embodiments, when x=2 and y=0, the alkyl groups taken together with the nitrogen atom to which they are attached form a cyclic ring system.

An "amide" is a chemical moiety with formula —C(=O)NHR or —NHC(=O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (I), Formula (II), Formula (III), Formula (IV), Formula (V), Formula (VI) or Formula (VII), thereby forming a prodrug. Any amine, or carboxyl side chain on the compounds described herein is optionally amidified, as desired. See, e.g., Greene and Wuts, Protective Groups in Organic Synthesis, 3$^{rd}$ Ed., John Wiley & Sons, New York, N.Y., 1999, is incorporated herein by reference for such disclosure.

The term "aromatic" refers to a planar ring having a delocalized π-electron system containing 4n+2π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl rings are formed by five, six, seven, eight, nine, or more than nine carbon atoms. In one aspect, an aryl is a $C_5$-$C_{10}$aryl. Aryl groups are optionally substituted. Examples of aryl groups include, but are not limited to phenyl, and naphthalenyl. Depending on the structure, an aryl group can be a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. Illustrative examples of cycloalkyl groups include, but are not limited to, the following moieties:

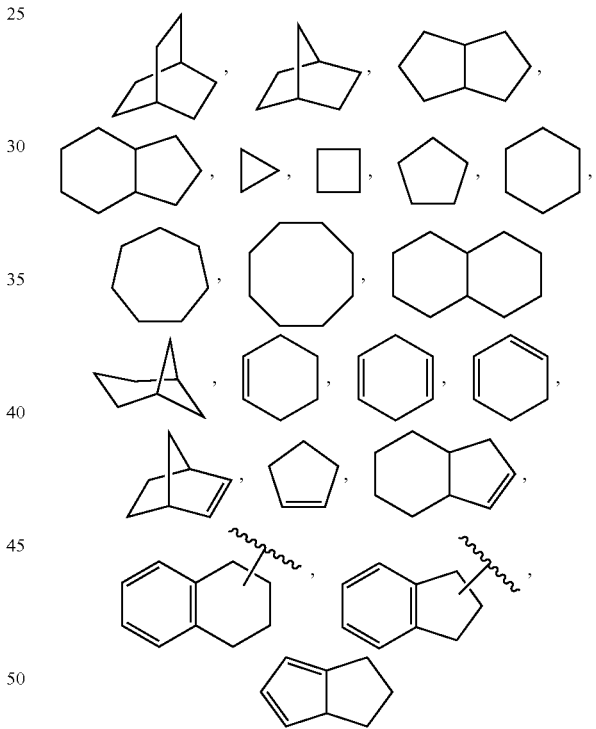

and the like. In some embodiments, cycloalkyl groups are selected from among cyclopropyl, cyclobutyl, cyclopentyl, cyclohexyl, cycloheptyl, and cyclooctyl. In some embodiments, bicyclic cycloalkyl groups are selected from among indanyl, indenyl, and 1,2,3,4-tetrahydronaphthalenyl. Cycloalkyl groups may be substituted or unsubstituted. Depending on the structure, a cycloalkyl group can be a monoradical or a diradical (i.e., an cycloalkylene group, such as, but not limited to, cyclopropan-1,1-diyl, cyclobutan-1,1-diyl, cyclopentan-1,1-diyl, cyclohexan-1,1-diyl, cycloheptan-1,1-diyl, and the like).

The term "ester" refers to a chemical moiety with formula —CO$_2$R, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein is esterified, if desired. Examples of procedures and specific groups to make such esters are found in sources such as Greene and Wuts, Protective Groups in Organic Synthesis, 3$^{rd}$ Ed., John Wiley & Sons, New York, N.Y., 1999.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_4$haloalkyl.

The term "fluoroalkyl" refers to a alkyl in which one or more hydrogen atoms are replaced by a fluorine atom. In one aspect, a fluoroalkyl is a $C_1$-$C_4$fluoroalkyl. Examples of fluoroalkyls include, —$CF_3$, —$CHF_2$, —$CH_2F$, —$CH_2CF_3$ and —$CF_2CF_3$.

The term "heteroalkyl" refers to an alkyl group in which one or more skeletal atoms of the alkyl are selected from an atom other than carbon, e.g., oxygen, nitrogen, sulfur, phosphorus or combinations thereof. In one aspect, heteroalkyl refers to an alkyl group in which one of the skeletal atoms of the alkyl is oxygen, nitrogen, or sulfur. In another aspect, heteroalkyl refers to an alkyl group in which one of the skeletal atoms of the alkyl is oxygen. In one aspect, a heteroalkyl is a $C_2$-$C_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyr-rol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aromatic group that includes one or more ring heteroatoms selected from nitrogen, oxygen and sulfur. Illustrative examples of heteroaryl groups include the following moieties:

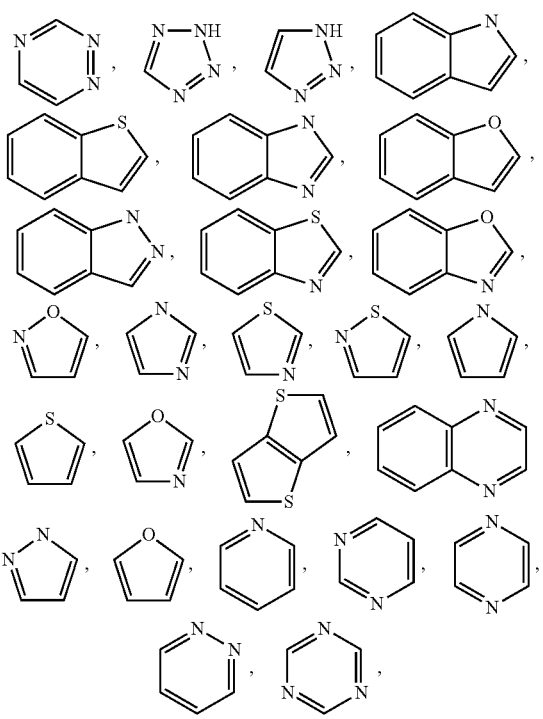

and the like. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In one aspect, the heteroaryl is a $C_1$-$C_{10}$heteroaryl. In another aspect, the heteroaryl is a $C_2$-$C_9$heteroaryl. In some cases, the heteroaryl includes at least one N atom in the ring. In one aspect, monocyclic heteroaryl is a $C_1$-$C_9$heteroaryl. In one aspect, bicyclic heteroaryl is a $C_5$-$C_{10}$heteroaryl.

A "heterocycloalkyl" or "heteroalicyclic" group refers to a cycloalkyl group that includes at least one heteroatom selected from nitrogen, oxygen and sulfur. The radicals may be fused with an aryl or heteroaryl. Illustrative examples of heterocycloalkyl groups, also referred to as non-aromatic heterocycles, include:

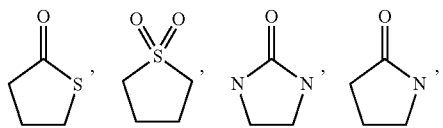

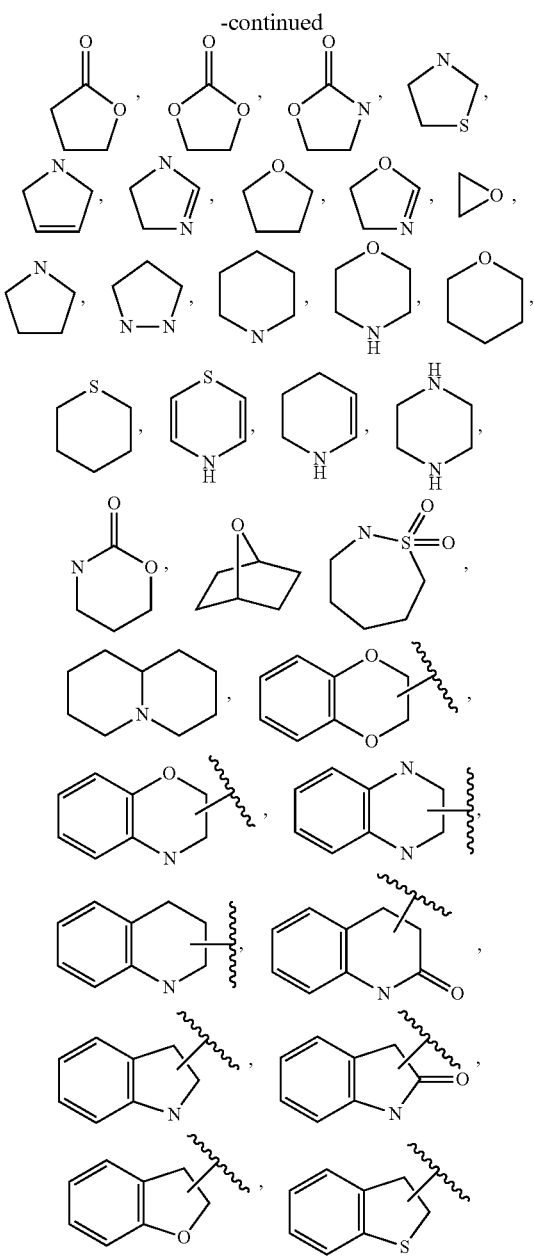

and the like. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "membered ring" includes any cyclic structure. The term "membered" is meant to denote the number of skeletal atoms that constitute the ring. Thus, for example, cyclohexyl, pyridinyl, pyranyl and thiopyranyl are 6-membered rings and cyclopentyl, pyrrolyl, furanyl, and thiophenyl are 5-membered rings.

The term "moiety" refers to a specific segment or functional group of a molecule. Chemical moieties are often recognized chemical entities embedded in or appended to a molecule.

The term "acyclic" refers to a moiety wherein the point of attachment of the moiety to the rest of the molecule is at an atom that is not part of a ring. Non-limiting examples of acyclic groups include alkyl, haloalkyls, heteroalkyl, alkoxy, benzyl, and the like.

The term "cyclic" refers to a moiety wherein the point of attachment to the rest of the molecule is at an atom that is part of a ring. Non-limiting examples of cyclic groups include cycloalkyl, heterocycloalkyl, aryl, heteroaryl, and the like.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, carbonyl, thiocarbonyl, nitro, haloalkyl, fluoroalkyl, and amino, including mono- and di-substituted amino groups, and the protected derivatives thereof. By way of example an optional substituents may be halide, —CN, —NO$_2$, or L$_s$R$_s$, wherein each L$_s$ is independently selected from a bond, —O—, —C(=O)—, —C(=O)—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$ alkyl)-; and each R$_s$ is selected from H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. In one aspect, optional substituents are selected from halogen, —CN, —NH$_2$, —OH, —N(CH$_3$)$_2$, alkyl, fluoroalkyl, heteroalkyl, cycloalkyl, heterocycloalkyl, aryl, heteroaryl, alkoxy, aryloxy, alkylthio, arylthio, alkylsulfoxide, arylsulfoxide, alkylsulfone, and arylsulfone. In one aspect, substituted groups are substituted with one or more substituents selected from halogen, —OH, —OC$_1$-C$_4$alkyl, C$_1$-C$_4$alkyl, C$_1$-C$_4$heteroalkyl, C$_1$-C$_4$fluoroalkyl and —OC$_1$-C$_4$fluoroalkyl. In yet other aspect, substituted groups are substituted with one or more substituents selected from F, Cl, Br, —OH, —OCH$_3$, —CH$_3$, and —CF$_3$. In yet other embodiments, substituted groups are substituted with one or more substituents selected from F, Cl, and Br. In one aspect, substituted groups are substituted with one of the preceding groups.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, the separation of stereoisomers by chiral chromatographic columns.

The methods and formulations described herein include the use of N-oxides (if appropriate), crystalline forms (also known as polymorphs), or pharmaceutically acceptable salts of compounds having the structure of any of Formula (I), Formula (II), Formula (III), Formula (IV), Formula (V), Formula (VI) or Formula (VII), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

Certain Pharmaceutical and Medical Terminology

The term "acceptable" with respect to a formulation, composition or ingredient, as used herein, means having no persistent detrimental effect on the general health of the subject being treated.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist, partial agonist, an inverse agonist and antagonist. In one embodiment, a modulator is an antagonist.

The term "agonist," as used herein, refers to a molecule such as a compound, a drug, an enzyme activator or a hormone modulator that binds to a specific receptor and triggers a response in the cell. An agonist mimics the action of an endogenous ligand (such as prostaglandin, hormone or neurotransmitter) that binds to the same receptor.

The term "antagonist," as used herein, refers to a molecule such as a compound, which diminishes, inhibits, or prevents the action of another molecule or the activity of a receptor site. Antagonists include, but are not limited to, competitive antagonists, non-competitive antagonists, uncompetitive antagonists, partial agonists and inverse agonists.

Competitive antagonists reversibly bind to receptors at the same binding site (active site) as the endogenous ligand or agonist, but without activating the receptor.

Non-competitive antagonists (also known as allosteric antagonists) bind to a distinctly separate binding site from the agonist, exerting their action to that receptor via the other binding site. Non-competitive antagonists do not compete with agonists for binding. The bound antagonists may result in a decreased affinity of an agonist for that receptor, or alternatively may prevent conformational changes in the receptor required for receptor activation after the agonist binds.

Uncompetitive antagonists differ from non-competitive antagonists in that they require receptor activation by an agonist before they can bind to a separate allosteric binding site.

Partial agonists are defined as drugs which, at a given receptor, might differ in the amplitude of the functional response that they elicit after maximal receptor occupancy. Although they are agonists, partial agonists can act as a competitive antagonist if co-administered with a full agonist, as it competes with the full agonist for receptor occupancy and producing a net decrease in the receptor activation observed with the full agonist alone.

An inverse agonist can have effects similar to an antagonist, but causes a distinct set of downstream biological responses. Constitutively active receptors which exhibit intrinsic or basal activity can have inverse agonists, which not only block the effects of binding agonists like a classical antagonist, but inhibit the basal activity of the receptor.

The term "$PGD_2$-dependent", as used herein, refers to conditions or disorders that would not occur, or would not occur to the same extent, in the absence of $PGD_2$.

The term "$PGD_2$-mediated", as used herein, refers to refers to conditions or disorders that might occur in the absence of $PGD_2$ but can occur in the presence of $PGD_2$.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "rhinitis" as used herein refers to any disorder of the nose in which there is inflammation of the mucous lining of the nose by whatever cause (intrinsic, extrinsic or both; allergic or non-allergic).

The term "bone disease," as used herein, refers to a disease or condition of the bone, including, but not limited to, inappropriate bone remodeling, loss or gain, osteopenia, osteomalacia, osteofibrosis, and Paget's disease.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumaticshock; hypertension, valvular heart disease, heart failure, abnormal blood pressure; shock; vasoconstriction (including that associated with migraines); vascular abnormality, inflammation, insufficiency limited to a single organ or tissue.

The term "cancer," as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The term "carrier," as used herein, refers to relatively non-toxic chemical compounds or agents that facilitate the incorporation of a compound into cells or tissues.

The terms "co-administration" or the like, as used herein, are meant to encompass administration of the selected therapeutic agents to a single patient, and are intended to include treatment regimens in which the agents are administered by the same or different mute of administration or at the same or different time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, urticaria.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The terms "fibrosis" or "fibrosing disorder," as used herein, refers to conditions that follow acute or chronic inflammation and are associated with the abnormal accumulation of cells and/or collagen and include but are not limited to fibrosis of individual organs or tissues such as the heart, kidney, joints, lung, or skin, and includes such disorders as idiopathic pulmonary fibrosis and cryptogenic fibrosing alveolitis.

The term "iatrogenic" means a $PGD_2$-dependent or $PGD_2$-mediated condition, disorder, or disease created or worsened by medical or surgical therapy.

The term "inflammatory disorders" refers to those diseases or conditions that are characterized by one or more of the signs of pain, heat, redness, swelling, and loss of function (temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (colitis); skin (dermatitis); or multiple organs and tissues (systemic lupus erythematosus).

The term "immunological disorders" refers to those diseases or conditions that are characterized by inappropriate or deleterious response to an endogenous or exogenous antigen that may result in cellular dysfunction or destruction and consequently dysfunction or destruction of an organ or tissue and which may or may not be accompanied by signs or symptoms of inflammation.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system, i.e., brain and spinal cord.

The terms "ocular disease" or "ophthalmic disease," as used herein, refer to diseases which affect the eye or eyes and potentially the surrounding tissues as well. Ocular or ophthalmic diseases include, but are not limited to, conjunctivitis, retinitis, scleritis, uveitis, allergic conjunctivitis, vernal conjunctivitis, papillary conjunctivitis.

The term "interstitial cystitis" refers to a disorder characterized by lower abdominal discomfort, frequent and sometimes painful urination that is not caused by anatomical abnormalities, infection, toxins, trauma or tumors.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of any of Formula (I), Formula (II), Formula (III), Formula (IV), Formula (V), Formula (VI) or Formula (VII), and a co-agent, are both administered to a patient simultaneously in the form of a single entity or dosage. The term "non-fixed combination" means that the active ingredients, e.g. a compound of any of Formula (I), Formula (II), Formula (III), Formula (IV), Formula (V), Formula (VI) or Formula (VII), and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "pharmaceutical composition" refers to a mixture of a compound of any of Formula (I), Formula (II), Formula (III), Formula (IV), Formula (V), Formula (VI) or Formula (VII), with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: intravenous, oral, aerosol, parenteral, ophthalmic, pulmonary and topical administration.

The term "respiratory disease," as used herein, refers to diseases affecting the organs that are involved in breathing, such as the nose, throat, larynx, eustachian tubes, trachea, bronchi, lungs, related muscles (e.g., diaphram and intercostals) and nerves. Respiratory diseases include, but are not limited to, asthma, adult respiratory distress syndrome and allergic (extrinsic) asthma, non-allergic (intrinsic) asthma, acute severe asthma, chronic asthma, clinical asthma, nocturnal asthma, neutrophilic asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

The term "subject" or "patient" encompasses mammals Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically. In yet other embodiments, the compound described herein is adminstered as a controlled-release formulation, including a sustained release formulation or a pulsatile formulation. That is, specifically, any of the compounds described herein is optionally adminstered in the form of a pulsatile-release formulation.

Pharmaceutical Composition/Formulation

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and* Drug Delivery Systems, Seventh Ed. (Lippincott Williams & Wilkins 1999).

Provided herein are pharmaceutical compositions comprising a compound of any of Formula (I), Formula (II), Formula (III), Formula (IV), Formula (V), Formula (VI) or Formula (VII), and a pharmaceutically acceptable diluent(s), excipient(s), or carrier(s). In certain embodiments, the compounds described are administered as pharmaceutical compositions in which compounds of any of Formula (I), Formula (II), Formula (III), Formula (IV), Formula (V), Formula (VI) or Formula (VII), are mixed with other active ingredients, as in combination therapy. Encompassed herein are all combinations of actives set forth in the combination therapies section below and throughout this disclosure. In specific embodiments, the pharmaceutical compositions include one or more compounds of any of Formula (I), Formula (II), Formula (III), Formula (IV), Formula (V), Formula (VI) or Formula (VII).

A pharmaceutical composition, as used herein, refers to a mixture of a compound of any of Formula (I), Formula (II), Formula (III), Formula (IV), Formula (V), Formula (VI) or Formula (VII), with other chemical components, such as carriers, stabilizers, diluents, dispersing agents, suspending agents, thickening agents, and/or excipients. In certain embodiments, the pharmaceutical composition facilitates administration of the compound to an organism. In some embodiments, practicing the methods of treatment or use provided herein, therapeutically effective amounts of compounds of any of Formula (I), Formula (II), Formula (III), Formula (IV), Formula (V), Formula (VI) or Formula (VII), provided herein are administered in a pharmaceutical composition to a mammal having a disease or condition to be treated. In specific embodiments, the mammal is a human. In certain embodiments, therapeutically effective amounts vary depending on the severity of the disease, the age and relative health of the subject, the potency of the compound used and other factors. The compounds described herein are used singly or in combination with one or more therapeutic agents as components of mixtures.

In one embodiment, one or more compounds of any of Formula (I), Formula (II), Formula (III), Formula (IV), Formula (V), Formula (VI) or Formula (VII), is formulated in an aqueous solutions. In specific embodiments, the aqueous solution is selected from, by way of example only, a physiologically compatible buffer, such as Hank's solution, Ringer's solution, or physiological saline buffer. In other embodiments, one or more compound of any of Formula (I), Formula (II), Formula (III), Formula (IV), Formula (V), Formula (VI) or Formula (VII), is formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or non-aqueous solutions. In specific embodiments, such solutions include physiologically compatible buffers and/or excipients.

In another embodiment, compounds described herein are formulated for oral administration. Compounds described herein, including compounds of any of Formula (I), Formula (II), Formula (III), Formula (IV), Formula (V), Formula (VI) or Formula (VII), are formulated by combining the active compounds with, e.g., pharmaceutically acceptable carriers or excipients. In various embodiments, the compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients are, in particular, fillers such as sugars, including lactose, sucrose, menthol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

In one embodiment, dosage forms, such as dragee cores and tablets, are provided with one or more suitable coating. In specific embodiments, concentrated sugar solutions are used for coating the dosage form. The sugar solutions, optionally contain additional components, such as by way of example only, gum arabic, talc, polyvinylpyrrolidone, carbopol gel, polyethylene glycol, and/or titanium dioxide, lacquer solutions, and suitable organic solvents or solvent mixtures. Dyestuffs and/or pigments are also optionally added to the coatings for identification purposes. Additionally, the dyestuffs and/or pigments are optionally utilized to characterize different combinations of active compound doses.

In certain embodiments, therapeutically effective amounts of at least one of the compounds described herein are formulated into other oral dosage forms. Oral dosage forms include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules, contain one or more active compound that is dissolved or suspended in a suitable liquid. Suitable liquids include, by way of example only, one or more fatty oil, liquid paraffin, or liquid polyethylene glycol. In addition, stabilizers are optionally added.

In other embodiments, therapeutically effective amounts of at least one of the compounds described herein are formulated for buccal or sublingual administration. Formulations suitable for buccal or sublingual administration include, by way of example only, tablets, lozenges, or gels. In still other embodiments, the compounds described herein are formulated for parental injection, including formulations suitable for bolus injection or continuous infusion. In specific embodiments, formulations for injection are presented in unit dosage form (e.g., in ampoules) or in multi-dose containers. Preservatives are, optionally, added to the injection formulations. In still other embodiments, the pharmaceutical composition of any of Formula (I), Formula (II), Formula (III), Formula (IV), Formula (V), Formula (VI) or Formula (VII), are formulated in a form suitable for parenteral injection as a sterile suspensions, solutions or emulsions in oily or aqueous vehicles. Parenteral injection formulations optionally contain formulatory agents such as suspending, stabilizing and/or dispersing agents. In specific embodiments, pharmaceutical formulations for parenteral administration include aqueous solutions of the active compounds in water-soluble form. In additional embodiments, suspensions of the active compounds are prepared as appropriate oily injection suspensions. Suitable lipophilic solvents or vehicles for use in the pharmaceutical compositions described herein include, by way of example only, fatty oils such as sesame oil, or synthetic fatty acid esters, such as ethyl oleate or triglycerides, or liposomes. In certain specific embodiments, aqueous injection suspensions contain substances which increase the viscosity of the suspension, such as sodium carboxymethyl cellulose, sorbitol, or dextran. Optionally, the suspension contains suitable stabilizers or agents which increase the solubility of the compounds to allow for the preparation of highly concentrated solutions. Alternatively, in other embodiments, the active ingredient is in powder form for constitution with a suitable vehicle, e.g., sterile pyrogen-free water, before use.

In still other embodiments, the compounds of any of Formula (I), Formula (II), Formula (III), Formula (IV), Formula (V), Formula (VI) or Formula (VII), are administered topically. The compounds described herein are formulated into a variety of topically administrable compositions, such as solutions, shampoos, suspensions, lotions, gels, pastes, medicated sticks, balms, creams or ointments. Such pharmaceutical compositions optionally contain solubilizers, stabilizers, tonicity enhancing agents, buffers and preservatives.

In yet other embodiments, the compounds of any of Formula (I), Formula (II), Formula (III), Formula (IV), Formula (V), Formula (VI) or Formula (VII), are formulated for transdermal administration. In specific embodiments, transdermal formulations employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of any of Formula (I), Formula (II), Formula (III), Formula (IV), Formula (V), Formula (VI) or Formula (VII), is accomplished by means of iontophoretic patches and the like. In certain embodiments, transdermal patches provide controlled delivery of the compounds of any of Formula (I), Formula (II), Formula (III), Formula (IV), Formula (V), Formula (VI) or Formula (VII). In specific embodiments, the rate of absorption is slowed by using rate-controlling membranes or by trapping the compound within a polymer matrix or gel. In alternative embodiments, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

In other embodiments, the compounds of any of Formula (I), Formula (II), Formula (III), Formula (IV), Formula (V), Formula (VI) or Formula (VII), are formulated for administration by inhalation. Various forms suitable for administration by inhalation include, but are not limited to, aerosols, mists or powders. Pharmaceutical compositions of any of Formula (I), Formula (II), Formula (III), Formula (IV), Formula (V), Formula (VI) or Formula (VII), are conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In specific embodiments, the dosage unit of a pressurized aerosol is determined by providing a valve to deliver a metered amount. In certain embodiments, capsules and cartridges of, such as, by way of example only, gelatin for use in an inhaler or insufflator are formulated containing a powder mix of the compound and a suitable powder base such as lactose or starch.

In still other embodiments, the compounds of any of Formula (I), Formula (II), Formula (III), Formula (IV), Formula (V), Formula (VI) or Formula (VII), are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In certain embodiments, pharmaceutical compositions are formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients is optionally used as suitable and as understood in the art. Pharmaceutical compositions comprising a compound of any of Formula (I), Formula (II), Formula (III), Formula (IV), Formula (V), Formula (VI) or Formula (VII), may be manufactured in a conventional manner, such as, by way of example only, by means of conventional mixing, dissolving, granulating, dragee-making, levigating, emulsifying, encapsulating, entrapping or compression processes.

Pharmaceutical compositions include at least one pharmaceutically acceptable carrier, diluent or excipient and at least one compound of any of Formula (I), Formula (II), Formula (III), Formula (IV), Formula (V), Formula (VI) or Formula (VII), described herein as an active ingredient. The active ingredient is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

Methods for the preparation of compositions comprising the compounds described herein include formulating the compounds with one or more inert, pharmaceutically acceptable excipients or carriers to form a solid, semi-solid or liquid. Solid compositions include, but are not limited to, powders, tablets, dispersible granules, capsules, cachets, and suppositories. Liquid compositions include solutions in which a compound is dissolved, emulsions comprising a compound, or a solution containing liposomes, micelles, or nanoparticles comprising a compound as disclosed herein. Semi-solid compositions include, but are not limited to, gels, suspensions and creams. The form of the pharmaceutical compositions described herein include liquid solutions or suspensions, solid forms suitable for solution or suspension in a liquid prior to use, or as emulsions. These compositions also optionally contain minor amounts of nontoxic, auxiliary substances, such as wetting or emulsifying agents, pH buffering agents, and so forth.

In some embodiments, pharmaceutical composition comprising at least one compound of any of Formula (I), Formula (II), Formula (III), Formula (IV), Formula (V), Formula (VI) or Formula (VII), illustratively takes the form of a liquid where the agents are present in solution, in suspension or both. Typically when the composition is administered as a solution or suspension a first portion of the agent is present in solution and a second portion of the agent is present in particulate form, in suspension in a liquid matrix. In some embodiments, a liquid composition includes a gel formulation. In other embodiments, the liquid composition is aqueous.

In certain embodiments, pharmaceutical aqueous suspensions include one or more polymers as suspending agents. Polymers include water-soluble polymers such as cellulosic polymers, e.g., hydroxypropyl methylcellulose, and water-insoluble polymers such as cross-linked carboxyl-containing polymers. Certain pharmaceutical compositions described herein include a mucoadhesive polymer, selected from, for example, carboxymethylcellulose, carbomer (acrylic acid polymer), poly(methylmethacrylate), polyacrylamide, polycarbophil, acrylic acid/butyl acrylate copolymer, sodium alginate and dextran.

Pharmaceutical compositions also, optionally include solubilizing agents to aid in the solubility of a compound of any of Formula (I), Formula (II), Formula (III), Formula (IV), Formula (V), Formula (VI) or Formula (VII). The term "solubilizing agent" generally includes agents that result in formation of a micellar solution or a true solution of the agent. Certain acceptable nonionic surfactants, for example polysorbate 80, are useful as solubilizing agents, as can ophthalmically acceptable glycols, polyglycols, e.g., polyethylene glycol 400, and glycol ethers.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Still other pharmaceutical compositions include one or more surfactants to enhance physical stability or for other purposes. Suitable nonionic surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

Still other pharmaceutical compositions may include one or more antioxidants to enhance chemical stability where required. Suitable antioxidants include, by way of example only, ascorbic acid and sodium metabisulfite.

In certain embodiments, pharmaceutical aqueous suspension compositions are packaged in single-dose non-reclosable containers. Alternatively, multiple-dose reclosable containers are used, in which case it is typical to include a preservative in the composition.

In alternative embodiments, other delivery systems for hydrophobic pharmaceutical compounds are employed. Liposomes and emulsions are examples of delivery vehicles or carriers herein. In certain embodiments, organic solvents such as N-methylpyrrolidone are also employed. In additional embodiments, the compounds described herein are delivered using a sustained-release system, such as semipermeable matrices of solid hydrophobic polymers containing the therapeutic agent. Various sustained-release materials are useful herein. In some embodiments, sustained-release capsules release the compounds for a few hours up to over 24 hours. Depending on the chemical nature and the biological stability of the therapeutic reagent, additional strategies for protein stabilization may be employed.

In certain embodiments, the formulations described herein include one or more antioxidants, metal chelating agents, thiol containing compounds and/or other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Methods of Dosing and Treatment Regimens

In one embodiment, the compound of any of Formula (I), Formula (II), Formula (III), Formula (IV), Formula (V), Formula (VI) or Formula (VII), are used in the preparation of medicaments for the treatment of $PGD_2$-dependent or $PGD_2$-mediated diseases or conditions. In addition, a method for treating any of the diseases or conditions described herein in a subject in need of such treatment, involves administration of pharmaceutical compositions containing at least one compound of any of Formula (I), Formula (II), Formula (III), Formula (IV), Formula (V), Formula (VI) or Formula (VII), or a pharmaceutically acceptable salt, pharmaceutically active metabolite, pharmaceutically acceptable prodrug, or pharmaceutically acceptable solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.02 mg-5000 mg per day, preferably 1-1500 mg per day. In one embodiment, the desired dose is conveniently presented in a single dose or in divided doses administered simultaneously (or over a short period of time) or at appropriate intervals, for example as two, three, four or more sub-doses per day.

In certain embodiments, the dosing interval is a regular period of time (e.g., every 6 hours, every 12 hours, once a day); in other embodiments, the dosing interval is regular, but not at a precise interval of time (e.g., before meal time); in other embodiments, the dosing interval is intermittent (e.g., twice a day for the first two days of the week, followed by once a day for the next two days, followed by 1 day without the drug, followed by once a day for the next two days); in other embodiments, the dosing only occurs as needed by the patient.

In certain embodiments, the pharmaceutical composition described herein is in unit dosage forms suitable for single administration of precise dosages. In unit dosage form, the formulation is divided into unit doses containing appropriate quantities of one or more compound. In specific embodiments, the unit dosage is in the form of a package containing discrete quantities of the formulation. Non-limiting examples are packaged tablets or capsules, and powders in vials or ampoules. Aqueous suspension compositions are optionally packaged in single-dose non-re-closeable containers. Alternatively, multiple-dose re-closeable containers are used, in which case it is typical to include a preservative in the composition. By way of example only, formulations for parenteral injection are, in some embodiments, presented in unit dosage form, which include, but are not limited to ampoules, or in multi-dose containers, with an added preservative.

In one embodiment, the daily dosages appropriate for the compound of any of Formula (I), Formula (II), Formula (III), Formula (IV), Formula (V), Formula (VI) or Formula (VII), described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Use of $DP_2$ Antagonists to Prevent and/or Treat $PGD_2$-Dependent or $PGD_2$ Mediated Diseases or Conditions The therapy of $PGD_2$-dependent or $PGD_2$-mediated diseases or conditions is designed to modulate the activity of $DP_2$, $DP_1$ and/or TP. Such modulation includes, in some embodiments, antagonizing $DP_2$ activity. In other embodiments, such modulation includes antagonizing $DP_2$ and $DP_1$.

For example, in one embodiment, a $DP_2$ antagonist is administered in order to decrease signal transduction initiated by $PGD_2$ within the individual.

In accordance with one aspect, compositions and methods described herein include compositions and methods for treating, preventing, reversing, halting or slowing the progression of $PGD_2$-dependent or $PGD_2$ mediated diseases or conditions once it becomes clinically evident, or treating the symptoms associated with or related to $PGD_2$-dependent or $PGD_2$ mediated diseases or conditions, by administering to the subject a compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). In certain embodiments, the subject already has a $PGD_2$-dependent or $PGD_2$ mediated disease or condition at the time of administration, or is at risk of developing a $PGD_2$-dependent or $PGD_2$ mediated disease or condition.

In certain aspects, the activity of $DP_2$ in a mammal is directly or indirectly modulated by the administration of (at least once) an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII), to a mammal. Such modulation includes, but is not limited to, reducing and/or inhibiting the activity of $DP_2$. In additional aspects, the activity of $PGD_2$ in a mammal is directly or indirectly modulated, including reducing and/or inhibiting, by the administration of (at least once) an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII), to a mammal. Such modulation includes, but is not limited to, reducing and/or inhibiting the activity of $DP_2$.

In one embodiment, prevention and/or treatment of $PGD_2$-dependent or $PGD_2$ mediated diseases or conditions comprises administering to a mammal at least once a therapeutically effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). In specific embodiments, the compound administered to the mammal is a compound of any of Formula (I), Formula (II), Formula (III), Formula (IV), Formula (V), Formula (VI) or Formula (VII). In some embodiments, there is provided a method of treating $PGD_2$-dependent or $PGD_2$ mediated diseases or conditions that include, but are not limited to, bone diseases and disorders, cardiovascular diseases and disorders, inflammatory diseases and disorders, immunological diseases or disorders, dermatological diseases and disorders, ocular diseases and disorders, cancer and other proliferative diseases and disorders, respiratory diseases and disorder, and non-cancerous disorders.

By way of example only, included in the prevention/treatment methods described herein are methods for treating respiratory diseases comprising administering to the mammal at least once an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). By way of example, in some embodiments, the respiratory disease is asthma. Other respiratory diseases include, but are not limited to, adult respiratory distress syndrome and allergic (extrinsic) asthma, non-allergic (intrinsic) asthma, acute severe asthma, chronic asthma, clinical asthma, nocturnal asthma, neutrophilic asthma, allergen-induced asthma, aspirin-sensitive asthma, exercise-induced asthma, isocapnic hyperventilation, child-onset asthma, adult-onset asthma, cough-variant asthma, occupational asthma, steroid-resistant asthma, seasonal asthma, allergic rhinitis, vascular responses, endotoxin shock, fibrogenesis, pulmonary fibrosis, allergic diseases, chronic inflammation, and adult respiratory distress syndrome.

By way of example only, included in such treatment methods are methods for preventing chronic obstructive pulmonary disease comprising administering to the mammal at least once an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). In addition, chronic obstructive pulmonary disease includes, but is not limited to, chronic bronchitis or emphysema, pulmonary hypertension, interstitial lung fibrosis and/or airway inflammation and cystic fibrosis.

By way of example only, included in such treatment methods are methods for preventing increased mucosal secretion and/or edema in a disease or condition comprising administering to the mammal at least once an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (II), Formula (IV), Formula (V), Formula (VI) or Formula (VII).

By way of example only, included in the prevention/treatment methods described herein are methods for preventing or treating vasoconstriction, atherosclerosis and its sequelae myocardial ischemia, myocardial infarction, aortic aneurysm, vasculitis and stroke comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for reducing cardiac reperfusion injury following myocardial ischemia and/or endotoxic shock comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for reducing the constriction of blood vessels in a mammal comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for lowering or preventing an increase in blood pressure of a mammal comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for preventing or treating eosinophil and/or basophil and/or dendritic cell and/or neutrophil and/or monocyte and/or T-cell recruitment comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for the prevention or treatment of abnormal bone remodeling, loss or gain, including diseases or conditions as, by way of example, osteopenia, osteoporosis, Paget's disease, cancer and other diseases comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for preventing ocular inflammation and allergic conjunctivitis, vernal keratoconjunctivitis, and papillary conjunctivitis comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for preventing otitis, otitis media comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for preventing CNS disorders comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). CNS disorders include, but are not limited to, multiple sclerosis, Parkinson's disease, Alzheimer's disease, stroke, cerebral ischemia, retinal ischemia, post-surgical cognitive dysfunction, migraine, peripheral neuropathy/neuropathic pain, spinal cord injury, cerebral edema and head injury.

By way of example only, included in the prevention/treatment methods described herein are methods for the treatment of cancer comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). The type of cancer may include, but is not limited to, pancreatic cancer and other solid or hematological tumors.

By way of example only, included in the prevention/treatment methods described herein are methods for preventing or reducing the chances of endotoxic shock and septic shock comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein methods for preventing, treating or alleviating rheumatoid arthritis and osteoarthritis comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for preventing increased, reducing the incidences of or treating gastrointestinal diseases comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). Such gastrointestinal diseases include, by way of example only, inflammatory bowel disease (IBD), colitis and Crohn's disease.

By way of example only, included in the prevention/treatment methods described herein are methods for the reduction or treatment of inflammation and/or preventing, reducing the incidences of or treating acute or chronic transplant rejection (including any vascular abnormality associated with acute or chronic rejection) or preventing or treating tumors or accelerating the healing of wounds comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for the prevention or treatment of rejection or dysfunction in a transplanted organ or tissue comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for treating inflammatory responses of the skin comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII). Such inflammatory responses of the skin include, by way of example, psoriasis, dermatitis, contact dermatitis, eczema, urticaria, rosacea, wound healing and scarring. In another aspect are methods for reducing psoriatic lesions in the skin, joints, or other tissues or organs, comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for the treatment of cystitis, including, e.g., interstitial cystitis, comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

By way of example only, included in the prevention/treatment methods described herein are methods for the treatment of metabolic syndromes such as Familial Mediterranean Fever comprising administering at least once to the mammal an effective amount of at least one compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII).

Combination Treatments

In certain instances, it is appropriate to administer at least one compound of any of Formula (I), Formula (II), Formula (III), Formula (IV), Formula (V), Formula (VI) or Formula (VII), in combination with another therapeutic agent. By way of example only, if one of the side effects experienced by a patient upon receiving one of the compounds herein is inflammation, then it may be appropriate to administer an anti-inflammatory agent in combination with the initial therapeutic agent. Or, in one embodiment, the therapeutic effectiveness of one of the compounds described herein is enhanced by administration of an adjuvant (i.e., by itself the adjuvant may have minimal therapeutic benefit, but in combination with another therapeutic agent, the overall therapeutic benefit to the patient is enhanced). Or, in some embodiments, the benefit of experienced by a patient is increased by administering one of the compounds described herein with another therapeutic agent (which also includes a therapeutic regimen) that also has therapeutic benefit. In one specific embodiment, the therapeutic benefit of treating asthma by administering at least one of the compounds described herein is increased by also providing the patient with other therapeutic agents or therapies for asthma. In any case, regardless of the disease, disorder or condition being treated, the overall benefit experienced by the patient may simply be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens can be determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a $DP_2$ antagonist described herein is initiated prior to, during, or after treatment with a second agent described above, and continues until any time during treatment with the second agent or after termination of treatment with the second agent. It also includes treatments in which a $DP_2$ antagonist described herein and the second agent being used in combination are administered simultaneously or at different times and/or at decreasing or increasing intervals during the treatment period. Combination treatment further includes periodic treatments that start and stop at various times to assist with the clinical management of the patient. For example, in one embodiment, a $DP_2$ antagonist described herein in the combination treatment is administered weekly at the onset of treatment, decreasing to biweekly, and decreasing further as appropriate.

Compositions and methods for combination therapy are provided herein. In accordance with one aspect, the pharmaceutical compositions disclosed herein are used to treat $PGD_2$-dependent or $PGD_2$ mediated conditions. In accordance with another aspect, the pharmaceutical compositions disclosed herein are used to treat respiratory diseases (e.g., asthma), where treatment with a $DP_2$ antagonist is indicated and to induce bronchodilation in a subject. In one embodiment, the pharmaceutical compositions disclosed herein are used to treat airways or nasal inflammation diseases such as asthma and rhinitis.

In one embodiment, pharmaceutical compositions disclosed herein are used to treat a subject suffering from a vascular inflammation-driven disorder. In one embodiment, the pharmaceutical compositions disclosed herein are used to treat skin inflammation diseases such as atopic dermatitis.

In certain embodiments, combination therapies described herein are used as part of a specific treatment regimen intended to provide a beneficial effect from the co-action of a $DP_2$ described herein and a concurrent treatment. It is understood that the dosage regimen to treat, prevent, or ameliorate the condition(s) for which relief is sought, is modified in accordance with a variety of factors. These factors include the type of respiratory disorder and the type of bronchoconstriction or inflammation from which the subject suffers, as well as the age, weight, sex, diet, and medical condition of the subject. Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more biologically active agents, the compound provided herein is administered either simultaneously with the biologically active agent(s), or sequentially. If administered sequentially, the attending physician decides on the appropriate sequence of administering protein in combination with the biologically active agent(s).

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills). In one embodiment, one of the therapeutic agents is given in multiple doses, and in another, two (or more if present) are given as multiple doses. In some embodiments of non-simultaneous administration, the timing between the multiple doses vary from more than zero weeks to less than four weeks. In addition, the combination methods, compositions and formulations are not to be limited to the use of only two agents; the use of multiple therapeutic combinations is also envisioned.

In additional embodiments, the compounds of any of Formula (I), Formula (II), Formula (III), Formula (IV), Formula (V), Formula (VI) or Formula (VII), are used in combination with procedures that provide additional or synergistic benefit to the patient. By way of example only, patients are expected to find therapeutic and/or prophylactic benefit in the methods described herein, wherein pharmaceutical composition of any of Formula (I), Formula (II), Formula (III), Formula (IV), Formula (V), Formula (VI) or Formula (VII), and/or combinations with other therapeutics are combined with genetic testing to determine whether that individual is a carrier of a mutant gene that is known to be correlated with certain diseases or conditions.

The compounds of any of Formula (I), Formula (II), Formula (III), Formula (IV), Formula (V), Formula (VI) or Formula (VII), and combination therapies are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. The administration of the compounds are initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration is accomplished via any practical route, such as, for example, by intravenous injection, a bolus injection, infusion over 5 minutes to about 5 hours, a pill, a capsule, transdermal patch, buccal delivery, and the like, or combination thereof. In specific embodiments, a compound described herein is administered as soon as is practicable after the onset of a disease or condition is detected or suspected, and for a length of time necessary for the treatment of the disease, such as, for example, from about 1 month to about 3 months. In some embodiments, the length required for effective treatment varies, and the treatment length is adjusted to suit the specific needs of each subject. For example, in specific embodiments, a compound described herein or a formulation containing the compound is administered for at least 2 weeks, about 1 month to about 5 years, or from about 1 month to about 3 years.

By way of example, therapies which combine compounds of any of Formula (I), Formula (II), Formula (III), Formula (IV), Formula (V), Formula (VI) or Formula (VII), with inhibitors of $PGD_2$ synthesis or $PGD_2$ receptor antagonists, either acting at the same or other points in the $PGD_2$ synthesis pathway, are encompassed herein for treating $PGD_2$-dependent or $PGD_2$ mediated diseases or conditions. In addition, by way of example, encompassed herein are therapies that combine compounds of any of Formula (I), Formula (II), Formula (III), Formula (IV), Formula (V), Formula (VI) or Formula (VII), with inhibitors of inflammation for treating $PGD_2$-dependent or $PGD_2$ mediated diseases or conditions.

Anti-Inflammatory Agents

In another embodiment described herein, methods for treatment of $PGD_2$-dependent or $PGD_2$ mediated conditions or diseases include administration to a patient compounds, pharmaceutical compositions, or medicaments described herein in combination with an anti-inflammatory agent including, but not limited to, non-steroidal anti-inflammatory drugs (NSAIDs) and corticosteroids (glucocorticoids). Anti-inflammatory agents include, but are not limited to: arthrotec, mesalamine, auralglan, sulfasalazine, daypro, etodolac, ponstan, and solumedrol; non-steroidal anti-inflammatory agents; corticosteroids; and leukotriene pathway modulators (e.g. montelukast, zilueton).

By way of example only, asthma is a chronic inflammatory disease characterized by pulmonary eosinophilia and airway hyperresponsiveness. In patients with asthma, $PGD_2$ is released from mast cells, eosinophils, and basophils. $PGD_2$ is involved in contraction of airway smooth muscle, an increase in vascular permeability and mucus secretions, and has been reported to attract and activate inflammatory cells in the airways of asthmatics. Thus, in another embodiment described herein, the methods for treatment of respiratory diseases include administration to a patient compounds, pharmaceutical compositions, or medicaments described herein in combination with an anti-inflammatory agent.

NSAIDs include, but are not limited to: aspirin, salicylic acid, gentisic acid, choline magnesium salicylate, choline salicylate, choline magnesium salicylate, choline salicylate, magnesium salicylate, sodium salicylate, diflunisal, carprofen, fenoprofen, fenoprofen calcium, fluorobiprofen, ibuprofen, ketoprofen, nabutone, ketolorac, ketorolac tromethamine, naproxen, oxaprozin, diclofenac, etodolac, indomethacin, sulindac, tolmetin, meclofenamate, meclofenamate sodium, mefenamic acid, piroxicam, meloxicam, COX-2 specific inhibitors (such as, but not limited to, celecoxib, rofecoxib, valdecoxib, parecoxib, etoricoxib, lumiracoxib, CS-502, JTE-522, L-745,337 and NS398).

Corticosteroids, include, but are not limited to: betamethasone (Celestone), prednisone (Deltasone), alclometasone, aldosterone, amcinonide, beclometasone, betamethasone, budesonide, ciclesonide, clobetasol, clobetasone, clocortolone, cloprednol, cortisone, cortivazol, deflazacort, deoxycorticosterone, desonide, desoximetasone, desoxycortone, dexamethasone, diflorasone, diflucortolone, difluprednate, fluclorolone, fludrocortisone, fludroxycortide, flumetasone, flunisolide, fluocinolone acetonide, fluocinonide, fluocortin, fluocortolone, fluorometholone, fluperolone, fluprednidene, fluticasone, formocortal, halcinonide, halometasone, hydrocortisone/cortisol, hydrocortisone aceponate, hydrocortisone buteprate, hydrocortisone butyrate, loteprednol, medrysone, meprednisone, methylprednisolone, methylprednisolone aceponate, mometasone furoate, paramethasone, prednicarbate, prednisone/prednisolone, rimexolone, tixocortol, triamcinolone, and ulobetasol.

In another embodiment described herein, methods for treatment of $PGD_2$-dependent or $PGD_2$ mediated conditions or diseases include administration to a patient compounds, pharmaceutical compositions, or medicaments described herein in combination in combination with NSAIDs and NO-donors or NSAIDs and proton-pump inhibitors.

$PGD_2$ Receptor Antagonists

In another embodiment described herein, methods for treatment of $PGD_2$-dependent or $PGD_2$ mediated conditions or diseases includes administering to a patient compounds, pharmaceutical compositions, or medicaments described herein in combination with other $PGD_2$ receptor antagonists including, but are not limited to, $DP_1$ receptor antagonists and TP receptor antagonists. In another embodiment described herein, methods for treatment of $PGD_2$-dependent or $PGD_2$ mediated conditions or diseases includes administered to a patient compounds, pharmaceutical compositions, or medicaments described herein in combination with a $DP_1$ receptor antagonist. $DP_1$ receptor antagonists include, but are not limited to, BWA868C (Sharif et al., *Br. J. Pharmacol.*, 2000 November; 131(6):1025-38), MK-0524 (Sturino et al, *J. Med. Chem.*, 2007, 50, 794-806 and Cheng et al, PNAS, 2006 Apr. 25; 103(17):6682-7.) and S-5751 (Arimura et al., *J. Pharmacol. Exp. Ther.*, 2001 August; 298(2):411-9). For some patients, the most appropriate formulation or method of use of such combination treatments depends on the type of $PGD_2$-dependent or $PGD_2$ mediated disorder, the time period in which the $DP_2$ antagonist acts to treat the disorder and/or the time period in which the $DP_1$ receptor antagonist acts to prevent $DP_1$ receptor activity. By way of example only, some embodiments described herein provide for such combination treatments that are used for treating a patient suffering from respiratory disorders such as asthma and rhinitis.

In another embodiment described herein, methods for treatment of $PGD_2$-dependent or $PGD_2$ mediated conditions or diseases includes administering to a patient compounds, pharmaceutical compositions, or medicaments described herein in combination with a TP receptor antagonist. TP receptor antagonists include, but are not limited to, Ramatroban ("Bayer™"), GR32191 (Beasley et al., *J. Appl. Physiol.*, 1989 April; 66(4):1685-93), ICI1192605 (Boersma et al., *Br. J. Pharmacol*, 1999 December; 128(7):1505-12) and derivatives or analogs thereof. Such combinations may be used to treat $PGD_2$-dependent or $PGD_2$ mediated disorders, including respiratory disorders.

In one embodiment, the co-administration of a $DP_2$ receptor antagonist with a $DP_1$ receptor antagonist or a TP receptor antagonist has therapeutic benefit over and above the benefit derived from the administration of a either a $DP_2$ antagonist, $DP_1$ antagonist or a TP antagonist alone. In the case that substantial inhibition of $PGD_2$ activity has undesired effects, partial inhibition of this pathway through the amelioration of the effects of the proinflammatory agonists combined with the block of the $DP_1$ receptor, TP receptor and/or $DP_2$ receptor may afford substantial therapeutic benefits, particularly for respiratory diseases.

Other Combination Therapies

In another embodiment described herein, methods for treatment of $PGD_2$-dependent or $PGD_2$ mediated conditions or diseases, such as proliferative disorders, including cancer, comprises administration to a patient compounds, pharmaceutical compositions, or medicaments described herein in combination with at least one additional agent selected, by way of example only, alemtuzumab, arsenic trioxide, asparaginase (pegylated or non-), bevacizumab, cetuximab, platinum-based compounds such as cisplatin, cladribine, daunorubicin/doxorubicin/idarubicin, irinotecan, fludarabine, 5-fluorouracil, gemtuzumab, methotrexate, Paclitaxel™, taxol, temozolomide, thioguanine, or classes of drugs including hormones (an antiestrogen, an antiandrogen, or gonadotropin releasing hormone analogues, interferons such as alpha interferon, nitrogen mustards such as busulfan or melphalan or mechlorethamine, retinoids such as tretinoin, topoisomerase inhibitors such as irinotecan or topotecan, tyrosine kinase inhibitors such as gefinitinib or imatinib, or agents to treat signs or symptoms induced by such therapy including allopurinol, filgrastim, granisetron/ondansetron/palonosetron, dronabinol.

In another embodiment described herein, methods for treatment of $PGD_2$-dependent or $PGD_2$ mediated conditions or diseases, such as the therapy of transplanted organs or tissues or cells, comprises administration to a patient compounds, pharmaceutical compositions, or medicaments described herein in combination with at least one additional agent selected from, by way of example only, azathioprine, a corticosteroid, cyclophosphamide, cyclosporin, dacluzimab, mycophenolate mofetil, OKT3, rapamycin, tacrolimus, thymoglobulin.

In another embodiment described herein, methods for treatment of $PGD_2$-dependent or $PGD_2$ mediated conditions or diseases, such as atherosclerosis, comprises administration to a patient compounds, pharmaceutical compositions, or medicaments described herein in combination with at least one additional agent selected, by way of example only, BMG-CoA reductase inhibitors (e.g., statins in their lactonized or dihydroxy open acid forms and pharmaceutically acceptable salts and esters thereof, including but not limited to lovastatin; simvastatin; dihydroxy open-acid simvastatin, particularly the ammonium or calcium salts thereof; pravastatin, particularly the sodium salt thereof; fluvastatin, particularly the sodium salt thereof; atorvastatin, particularly the calcium salt thereof; nisvastatin, also referred to as NK-104; rosuvastatin); agents that have both lipid-altering effects and other pharmaceutical activities; HMG-CoA synthase inhibitors; cholesterol absorption inhibitors such as ezetimibe; cholesterol ester transfer protein (CETP) inhibitors, for example JTT-705 and CP529, 414; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIc fibrinogen receptor antagonists and aspirin; human peroxisome proliferator activated receptor gamma (PPARγ) agonists, including the compounds commonly referred to as glitazones, for example troglitazone, pioglitazone and rosiglitazone and including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists such as 5-[(2,4-dioxo-5-thiazolidinyl)methyl]-2-methoxy-N-[[4-(trifluoromethyl)phenyl]methyl]-benzamide, known as KRP-297; vitamin B6 (also known as pyridoxine) and the pharmaceutically acceptable salts thereof such as the HCl salt; vitamin B12 (also known as cyanocobalamin); folic acid or a pharmaceutically acceptable salt or ester thereof such as the sodium salt and the methylglucamine salt; antioxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib and celecoxib.

In another embodiment described herein, methods for treatment of $PGD_2$-dependent or $PGD_2$ mediated conditions or diseases, such as the therapy of stroke, comprises administration to a patient compounds, pharmaceutical compositions, or medicaments described herein in combination with at least one additional agent selected from, by way of example only, COX-2 inhibitors; nitric oxide synthase inhibitors, such as N-(3-(aminomethyl)benzyl)acetamidine; Rho kinase inhibitors, such as fasudil; angiotension II type-1 receptor antagonists, including candesartan, losartan, irbesartan, eprosartan, telmisartan and valsartan; glycogen synthase kinase 3 inhibitors; sodium or calcium channel blockers, including crobenetine; p38 MAP kinase inhibitors, including SKB 239063; thromboxane AX-synthetase inhibitors, including isbogrel, ozagrel, ridogrel and dazoxiben; statins (HMG CoA reductase inhibitors), including lovastatin, simvastatin, dihydroxy open-acid simvastatin, pravastatin, fluvastatin, atorvastatin, nisvastatin, and rosuvastatin; neuroprotectants, including free radical scavengers, calcium channel blockers, excitatory amino acid antagonists, growth factors, antioxidants, such as edaravone, vitamin C, TROLOX™, citicoline and minicycline, and reactive astrocyte inhibitors, such as (2R)-2-propyloctanoic acid; beta andrenergic blockers, such as propranolol, nadolol, timolol, pindolol, labetalol, metoprolol, atenolol, esmolol and acebutolol; NMDA receptor antagonists, including memantine; NR2B antagonists, such as traxoprodil; 5-HTIA agonists; receptor platelet fibrinogen receptor antagonists, including tirofiban and lamifiban; thrombin inhibitors; antithrombotics, such as argatroban; antihypertensive agents, such as enalapril; vasodilators, such as cyclandelate; nociceptin antagonists; DPIV antagonists; CETP inhibitors; GABA 5 inverse agonists; and selective androgen receptor modulators.

In another embodiment described herein, methods for treatment of $PGD_2$-dependent or $PGD_2$ mediated conditions or diseases, such as the therapy of pulmonary fibrosis, comprises administration to a patient compounds, pharmaceutical compositions, or medicaments described herein in combination with at least one additional agent selected from, by way of example only, anti-inflammatory agents, such as corticosteroids, azathioprine or cyclophosphamide.

In another embodiment described herein, methods for treatment of $PGD_2$-dependent or $PGD_2$ mediated conditions or diseases, such as the therapy of interstitial cystitis, comprises administration to a patient compounds, pharmaceutical compositions, or medicaments described herein in combination with at least one additional agent selected from, by way of example only, dimethylsulfoxide, omalizumab, and pentosan polysulfate.

In another embodiment described herein, methods for treatment of $PGD_2$-dependent or $PGD_2$ mediated conditions or diseases, such as the therapy of disorders of bone, comprises administration to a patient compounds, pharmaceutical compositions, or medicaments described herein in combination with at least one additional agent selected from the, by way of example only, minerals, vitamins, bisphosphonates, anabolic steroids, parathyroid hormone or analogs, and cathepsin K inhibitors.

In yet another embodiment described herein, methods for treating $PGD_2$-dependent or $PGD_2$ mediated conditions or diseases, such as the therapy of respiratory disorders (e.g., asthma, COPD and rhinitis), comprises administration to a patient compounds, pharmaceutical compositions, or medicaments described herein in combination with at least one respiratory agent. Respiratory agents include, but are not limited to, bronchodilators (e.g., sympathomimetic agents and xanthine derivatives), leukotriene receptor antagonists, leukotriene formation inhibitors, leukotriene modulators, nasal decongestants, respiratory enzymes, lung surfactants, antihistamines (e.g., Mepyramine (pyrilamine), Antazoline, Diphenhydramine, Carbinoxamine, Doxylamine, Clemastine, Dimenhydrinate, Pheniramine, Chlorphenamine (chlorpheniramine), Dexchlorpheniramine, Brompheniramine, Triprolidine, cetirizine, Cyclizine, Chlorcyclizine, Hydroxyzine, Meclizine, loratadine, desloratidine, Promethazine, Alimemazine (trimeprazine), Cyproheptadine, Azatadine, Ketotifen, Acrivastine, Astemizole, Cetirizine, Mizolastine, Terfenadine, Azelastine, Levocabastine, Olopatadine, Levocetirizine, Fexofenadine), mucolytics, corticosteroids, glucocorticoids, anticholinergics, antitussives, analgesics, expectorants, albuterol, ephedrine, epinephrine, fomoterol, metaproterenol, terbutaline, budesonide, ciclesonide, dexamethasone, flunisolide, fluticasone propionate, triamcinolone acetonide, ipratropium bromide, pseudoephedrine, theophylline, montelukast, zafirlukast, pranlukast, tomelukast, ambrisentan, bosentan, enrasentan, sitaxsentan, tezosentan, iloprost, treprostinil, pirfenidone, FLAP inhibitors, FLAP modulators, 5-LO inhibitors, BLT1 receptor antagonists and BLT2 receptor antagonists.

In a specific embodiment described herein, methods for treating $PGD_2$-dependent or $PGD_2$ mediated conditions or diseases, such as the therapy of asthma and/or COPD, comprises administration to a patient anti-inflammatory agents. In certain embodiments, methods for treating $PGD_2$-dependent or $PGD_2$ mediated conditions or diseases, such as the therapy of asthma and/or COPD, comprise administration to a patient compounds, pharmaceutical compositions, or medicaments described herein in combination with at least one additional agent selected from, but not limited to, epinephrine, isoproterenol, orciprenaline, bronchodilators, glucocorticoids, leukotriene modifiers, mast-cell stabilizers, xanthines, anticholinergics, β-2 agonists, FLAP inhibitors, FLAP modulators or 5-LO inhibitors. β-2 agonists include, but are not limited to, short-acting β-2 agonists (e.g., salbutamol (albuterol), levalbuterol, terbutaline, pirbuterol, procaterol, metaproterenol, fenoterol and bitolterol mesylate) and long-acting β-2 agonists (e.g., salmeterol, formoterol, bambuterol and clenbuterol). FLAP inhibitors and/or FLAP modulators include, but are not limited to, 3-[3-tert-butylsulfanyl-1-[4-(6-methoxy-pyridin-3-yl)-benzyl]-5-(pyridin-2-ylmethoxy)-1H-indol-2-yl]-2,2-dimethyl-propionic acid, 3-[3-tert-butylsulfanyl-1-[4-(6-ethoxy-pyridin-3-yl)-benzyl]-5-(5-methyl-pyridin-2-ylmethoxy)-1H-indol-2-yl]-2,2-dimethyl-propionic acid, MK-886, MK-0591, DG-031 (BAY-x1005) and compounds found in US 2007/0225285, US 2007/0219206, US 2007/0173508, US 2007/0123522 and US 2007/0105866 (each of which are hereby incorporated by reference). Glucocorticoids include, but are not limited to, beclometasone, budesonide, ciclesonide, fluticasone and mometasone. Anticholinergics include, but are not limited to, ipratropium and tiotropium. Mast cell stabilizers include, but are not limited to, cromoglicate and nedocromil. Xanthines include, but are not limited to, amminophylline, theobromine and theophylline. Leukotriene antagonists include, but are not limited to, montelukast, tomelukast, pranlukast and zafirlukast. 5-LO inhibitors include, but are not limited to, zileuton, VIA-2291 (ABT761), MK-0633, CJ-13,610 (PF-4191834), AZ-4407 and ZD-2138 and compounds found in US 2007/0149579, WO2007/016784.

In another specific embodiment described herein, methods for treating $PGD_2$-dependent or $PGD_2$ mediated conditions or diseases, such as the therapy of rhinitis, comprises administration to a patient compounds, pharmaceutical compositions, or medicaments described herein in combination with at least one additional agent selected from, by way of example only, antihistamines, leukotriene antagonists, corticosteroids and decongestants. Leukotriene antagonists include, but are not limited to, montelukast, tomelukast, pranlukast and zafirlukast.

In another aspect, methods for treating $PGD_2$-dependent or $PGD_2$ mediated conditions or diseases, include administering a $DP_2$ antagonist described herein in combination with other agents to treat respiratory diseases or conditions. Therapeutic agents used in the treatment of respiratory conditions and disorders, such as, but not limited to asthma, include: glucocorticoids, such as, ciclesonide, beclomethasone, budesonide, flunisolide, fluticasone, mometasone, and triamcinolone; leukotriene modifiers, such as, montelukast, zafirlukast, pranlukast, and zileuton; mast cell stabilizers, such as, cromoglicate (cromolyn), and nedocromil; antimuscarinics/anticholinergics, such as, ipratropium, oxitropium, and tiotropium; methylxanthines, such as, theophylline and aminophylline; antihistamine, such as, mepyramine (pyrilamine), antazoline, diphenhydramine, carbinoxamine, doxylamine, clemastine, dimenhydrinate, pheniramine, chlorphenamine (chlorpheniramine), dexchlorphenamine, brompheniramine, triprolidine, cyclizine, chlorcyclizine, hydroxyzine, meclizine, promethazine, alimemazine (trimeprazine), cyproheptadine, azatadine, ketotifen, acrivastine, astemizole, cetirizine, loratadine, mizolastine, terfenadine, fexofenadine, levocetirizine, desloratadine, fexofenadine; omalizumab, an IgE blocker; beta2-adrenergic receptor agonists, such as: short acting beta2-adrenergic receptor agonists, such as, salbutamol (albuterol), levalbuterol, terbutaline, pirbuterol, procaterol, metaproterenol, fenoterol, bitolterol mesylate; and long-acting beta2-adrenergic receptor agonists, such as, salmeterol, formoterol, bambuterol.

In one aspect, $DP_2$ antagonists described herein are administered in combination with one or more agents used to treat used to treat asthma, including, but not limited to: combination inhalers (fluticasone and salmeterol oral inhalation (e.g. Advair)); inhaled Beta-2 agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled corticosteroids (beclomethasone oral inhalation; budesonide inhalation solution; budesonide inhaler; flunisolide oral inhalation; fluticasone inhalation aerosol; fluticasone powder for oral inhalation; mometasone inhalation powder; triamcinolone oral inhalation); leukotriene modifiers (montelukast; zafirlukast; pranlukast; tomelukast; zileuton); mast cell stabilizers (cromolyn inhaler; nedocromil oral inhalation); monoclonal antibodies (omalizumab); oral Beta-2 agonists (albuterol oral syrup; albuterol oral tablets; metaproterenol; terbutaline); bronchodilator (aminophylline; oxtriphylline; theophylline).

In one aspect, $DP_2$ antagonists described herein are administered in combination with one or more agents used to treat allergy, including, but not limited to: antihistamine and decongestant combinations (cetirizine and pseudoephedrine; desloratadine and pseudoephedrine ER; fexofenadine and pseudoephedrine; loratadine and pseudoephedrine); antihistamines (azelastine nasal spray; brompheniramine; brompheniramine oral suspension; carbinoxamine; cetirizine; chlorpheniramine; clemastine; desloratadine; dexchlorpheniramine ER; dexchlorpheniramine oral syrup; diphenhydramine oral; fexofenadine; loratadine; promethazine); decongestants (pseudoephedrine); leukotriene modifiers (montelukast; montelukast granules); nasal anticholinergics (ipratropium); nasal corticosteroids (beclomethasone nasal inhalation; budesonide nasal inhaler; flunisolide nasal inhalation; fluticasone nasal inhalation; mometasone nasal spray; triamcinolone nasal inhalation; triamcinolone nasal spray); nasal decongestants (phenylephrine); nasal mast cell stabilizers (cromolyn nasal spray).

In one aspect, $DP_2$ antagonists described herein are administered in combination with one or more agents used to treat chronic obstructive pulmonary disease (COPD), including, but not limited to: anticholinergics-ipratropium bromide oral inhalation); combination Inhalers (albuterol and ipratropium (e.g. Combivent, DuoNeb); fluticasone and salmeterol oral inhalation (e.g. Advair)); corticosteroids (dexamethasone tablets; fludrocortisone acetate; hydrocortisone tablets; methylprednisolone; prednisolone liquid; prednisone oral; triamcinolone oral); inhaled Beta-2 Agonists (albuterol inhaler; albuterol nebulizer solution; formoterol; isoproterenol oral inhalation; levalbuterol; metaproterenol inhalation; pirbuterol acetate oral inhalation; salmeterol aerosol inhalation; salmeterol powder inhalation; terbutaline inhaler); inhaled Corticosteroids (beclomethasone oral inhalation; budesonide inhalation solution; budesonide inhaler; flunisolide oral inhalation; fluticasone inhalation aerosol; fluticasone powder for oral inhalation; triamcinolone oral inhalation); mukolytics (guaifenesin); oral Beta-2 agonists (albuterol oral syrup; albuterol oral tablets; metaproterenol; terbutaline); bronchodilator (aminophylline; oxtriphylline; theophylline).

In one embodiment, $DP_2$ antagonists described herein are administered to a patient in combination with inhaled corticosteroids.

In one embodiment, $DP_2$ antagonists described herein are administered to a patient in combination with beta2-adrenergic receptor agonists. In one embodiment, $DP_2$ antagonists described herein are administered to a patient in combination with short acting beta2-adrenergic receptor agonists. In one embodiment, $DP_2$ antagonists described herein are administered to a patient in combination with long-acting beta2-adrenergic receptor agonists.

As discussed herein, the administration of compounds of any of Formula (I), Formula (II), Formula (III), Formula (IV), Formula (V), Formula (VI), or Formula (VII) is designed to antagonize the activity of $DP_2$. For example, in specific embodiments, the administration of a $DP_2$ inhibitor decreases signal transduction initiated by $PGD_2$ within the individual Thus, in accordance with one aspect, methods described herein include the diagnosis or determination of whether or not a patient is suffering from a $PGD_2$-dependent or $PGD_2$ mediated disease or condition by administering to the subject a compound of any of Formula (I), Formula (II), Formula (III), Formula (IV), Formula (V), Formula (VI) or Formula (VII), or pharmaceutical composition or medicament which includes a compound of any of Formula (I), Formula (II), Formula (III), Formula (IV), Formula (V), Formula (VI) or Formula (VII), and determining whether or not the patient responds to the treatment.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

EXAMPLES

These examples are provided for illustrative purposes only and not to limit the scope of the claims provided herein. In the following representative examples, M+H refers to mass spectrometric data that was obtained, where M represents the molecular ion peak.

Example 1

Synthesis of (3-{2-[(Acetyl-phenethyl-amino)-methyl]-4-bromo-phenoxy}-phenyl)-acetic acid (Compound 1-1)

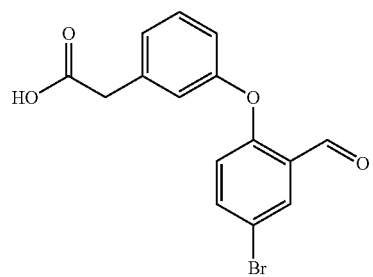 [SMILES: O=Cc1cc(Br)ccc1Oc1cccc(CC(=O)O)c1]

Step 1: [3-(4-Bromo-2-formyl-phenoxy)-phenyl]-acetic acid

3-Hydroxyphenylacetic acid (1.34 g, 8.8 mmol) and 5-bromo-2-fluorobenzaldehyde (1.78 g, 8.8 mmol) were combined in DMF (30 mL) at room temperature. Sodium hydride (60% in mineral oil; 0.72 g, 18.0 mmol) was added, and the reaction was stirred at 70° C. for 2 hours. Aqueous work-up yielded the title compound.

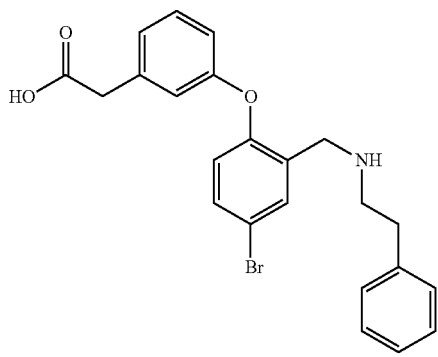 [SMILES: O=C(O)Cc1cccc(Oc2ccc(Br)cc2CNCCc2ccccc2)c1]

Step 2: {3-[4-Bromo-2-(phenethylamino-methyl)-phenoxy]-phenyl}-acetic acid

[3-(4-Bromo-2-formyl-phenoxy)-phenyl]-acetic acid (0.4 g, 1.23 mmol), 2-phenylethylamine (0.16 mL, 1.23 mmol), sodium cyanoborohydride (0.189 g, 3.0 mmol), and acetic acid (2 drops) were combined in $CH_2Cl_2$ and stirred at room temperature for 10 minutes. Aqueous work-up yielded the title compound.

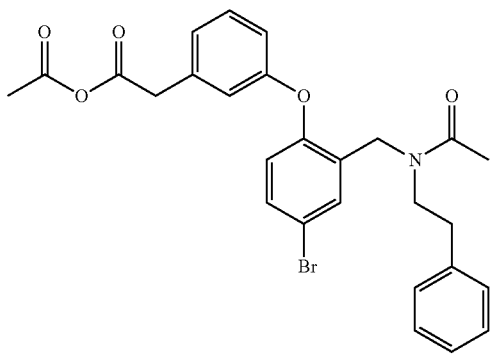 [SMILES: CC(=O)OC(=O)Cc1cccc(Oc2ccc(Br)cc2CN(CCc2ccccc2)C(C)=O)c1]

Step 3: (3-{2-[(Acetyl-phenethyl-amino)-methyl]-4-bromo-phenoxy}-phenyl)-acetic acid acetyl anhydride To {3-[4-bromo-2-(phenethylamino-methyl)-phenoxy]-phenyl}-acetic acid (1.23 mmol) in $CH_2Cl_2$ was added triethylamine (0.51 mL, 3.65 mmol) and acetyl chloride (0.13 mL, 1.84 mmol). Once the reaction was complete, the mixture was concentrated to give the title compound.

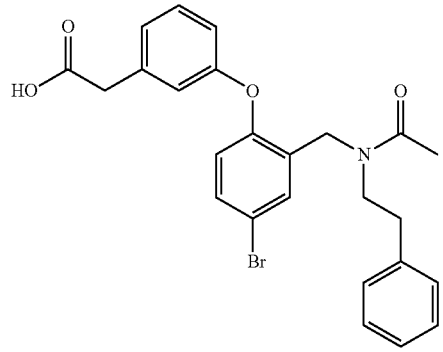 [SMILES: CC(=O)N(CCc1ccccc1)Cc1cc(Br)ccc1Oc1cccc(CC(=O)O)c1]

Step 4: (3-{2-[(Acetyl-phenethyl-amino)-methyl]-4-bromo-phenoxy}-phenyl)-acetic acid (3-{2-[(Acetyl-phenethyl-amino)-methyl]-4-bromo-phenoxy}-phenyl)-acetic acid acetyl anhydride (1.23 mmol) was treated with lithium hydroxide (6 mmol) in 1:1 THF:MeOH. Once the reaction was complete, the mixture was acidified to pH 7 and extracted. The residue was purified by silica gel chromatography to give the title compound. M+H=482.

Example 2

Synthesis of {3-[2-({Acetyl-[2-(4-fluoro-phenyl)-1,1-dimethyl-ethyl]-amino}-methyl)-4-bromo-phenoxy]-phenyl}-acetic acid (Compound 1-2)

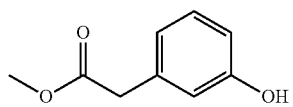

Step 1: (3-Hydroxy-phenyl)-acetic acid methyl ester

To 3-hydroxyphenylacetic acid (5.07 g, 33.32 mmol) in MeOH (50 mL) was added thionyl chloride (4.85 mL, 66.65 mmol) dropwise over 30 minutes by addition funnel. Once no starting material was seen by analytical LCMS, the mixture was concentrated, and the residue was partitioned between EtOAc and 1N aqueous NaOH. The aqueous layer was extracted twice with EtOAc, and the combined organic layers were dried and concentrated to give the title compound.

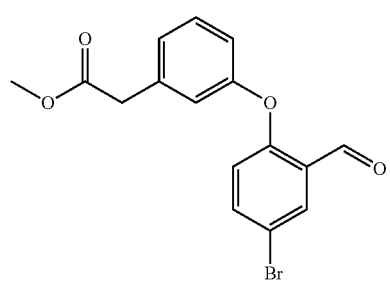 [SMILES: COC(=O)Cc1cccc(Oc2ccc(Br)cc2C=O)c1]

Step 2: [3-(4-Bromo-2-formyl-phenoxy)-phenyl]-acetic acid methyl ester (3-Hydroxy-phenyl)-acetic acid methyl ester (1.44 g, 8.66 mmol), 5-bromo-2-fluorobenzaldehyde (1.76 g, 8.66 mmol), and potassium carbonate (2.39 g, 17.32 mmol) were combined in 1,4-dioxane (18 mL) and heated to 100° C. overnight. Some starting material was still observed by analytical LCMS, so additional potassium carbonate (0.6 g, 4.3 mmol) was added, and the reaction was stirred at 100° C. for 4 hours. The mixture was cooled to room temperature and partitioned between EtOAc and H₂O. Brine was added to facilitate separation, and the aqueous layer was extracted twice with EtOAc. The combined organic layers were dried and concentrated, and the residue was purified by silica gel chromatography (10-30% EtOAc in hexanes) to give the title compound.

Step 3: [3-(4-Bromo-2-{[2-(4-fluoro-phenyl)-1,1-dimethyl-ethylamino]-methyl}-phenoxy)-phenyl]-acetic acid methyl ester

[3-(4-Bromo-2-formyl-phenoxy)-phenyl]-acetic acid methyl ester (0.150 g, 0.43 mmol), 1-(4-fluorophenyl)-2-methyl-2-propylamine (0.079 g, 0.47 mmol), and sodium cyanoborohydride (0.041 g, 0.65 mmol) were combined in MeOH (2 mL). Acetic acid (2 drops) was added, and the reaction was stirred for 5 hours at room temperature. The mixture was worked-up with EtOAc and saturated aqueous NaHCO₃, and the organic layer was dried and concentrated to give the title compound.

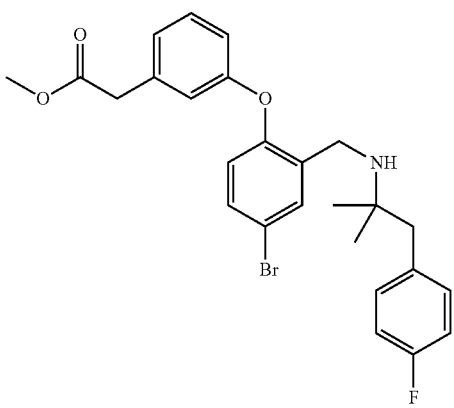 [SMILES: COC(=O)Cc1cccc(Oc2ccc(Br)cc2CNC(C)(C)Cc2ccc(F)cc2)c1]

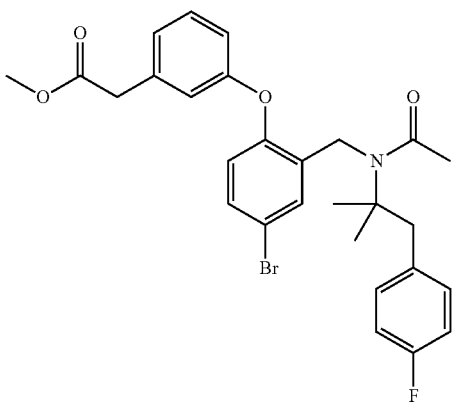 [SMILES: COC(=O)Cc1cccc(Oc2ccc(Br)cc2CN(C(C)=O)C(C)(C)Cc2ccc(F)cc2)c1]

Step 4: {3-[2-({Acetyl-[2-(4-fluoro-phenyl)-1,1-dimethyl-ethyl]-amino}-methyl)-4-bromo-phenoxy]-phenyl}-acetic acid methyl ester To [3-(4-bromo-2-{([2-(4-fluoro-phenyl)-1,1-dimethyl-ethylamino]-methyl}-phenoxy)-phenyl]-acetic acid methyl ester (0.43 mmol) in CH₂Cl₂ (2 mL) was added triethylamine (0.09 mL, 0.65 mmol) and acetyl chloride (0.03 mL, 0.47 mmol), and the reaction was stirred overnight at mom temperature. The mixture was concentrated, and the residue was purified by silica gel chromatography (10-30% EtOAc in hexanes) to give the title compound.

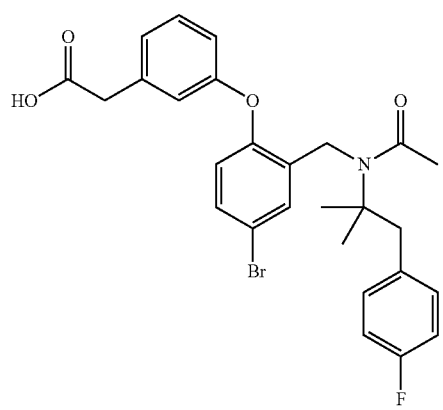 [SMILES: CC(=O)N(Cc1cc(Br)ccc1Oc1cccc(CC(=O)O)c1)C(C)(C)Cc1ccc(F)cc1]

Step 5: {3-[2-({Acetyl-[2-(4-fluoro-phenyl)-1,1-dimethyl-ethyl]-amino}-methyl)-4-bromo-phenoxy]-phenyl}-acetic acid To {3-[2-({acetyl-[2-(4-fluoro-phenyl)-1,1-dimethyl-ethyl]-amino}-methyl)-4-bromo-phenoxy]-phenyl}-acetic acid methyl ester (0.094 g, 0.17 mmol) in THF (2 mL) was added 1N aqueous lithium hydroxide (2 mL), and the reaction was stirred at room temperature until no starting material was seen by analytical LCMS. The mixture was acidified with 1N aqueous HCl and extracted three times with EtOAc. The combined organic layers were dried and concentrated, and the residue was purified by preparative HPLC to give the title compound. M+H=529.

Example 3

Synthesis of (3-{2-[(Benzyl-methoxycarbonyl-amino)-methyl]-4-bromo-phenoxy}-phenyl)-acetic acid (Compound 1-3)

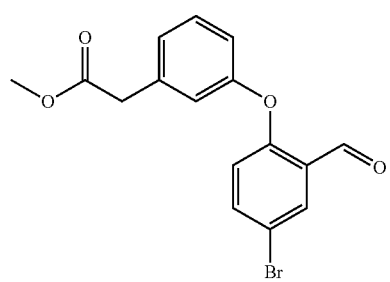 [SMILES: COC(=O)Cc1cccc(Oc2ccc(Br)cc2C=O)c1]

Step 1: [3-(4-Bromo-2-formyl-phenoxy)-phenyl]-acetic acid methyl ester

To [3-(4-bromo-2-formyl-phenoxy)-phenyl]-acetic acid (1 g, 2.98 mmol) in MeOH (10 mL) was added thionyl chloride (0.43 mL, 5.97 mmol), and the reaction was heated to 65° C. for 2 hours, and then stirred overnight at room temperature. The mixture was neutralized with 1N aqueous NaOH and extracted three times with EtOAc. The combined organic layer was washed with H2O, dried, and concentrated, and the residue was purified by silica gel chromatography (20-40% EtOAc in hexanes) to give the title compound, as well as the corresponding acetal.

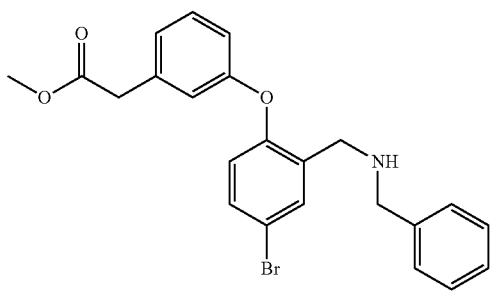 [SMILES: COC(=O)Cc1cccc(Oc2ccc(Br)cc2CNCc2ccccc2)c1]

Step 2: {3-[2-(Benzylamino-methyl)-4-bromo-phenoxy]-phenyl}-acetic acid methyl ester

[3-(4-Bromo-2-formyl-phenoxy)-phenyl]-acetic acid methyl ester (0.151 g, 0.43 mmol), benzylamine (0.05 mL, 0.48 mmol), and sodium cyanoborohydride (0.041 g, 0.65 mmol) were combined in $CH_2Cl_2$ (3 mL). Acetic acid (2 drops) was added, and the reaction was stirred overnight at room temperature. The mixture was partitioned between $CH_2Cl_2$ and saturated aqueous $NaHCO_3$, and the aqueous layer was separated and extracted twice with $CH_2Cl_2$. The combined organic layers were dried over $MgSO_4$ and concentrated, and the residue was purified by silica gel chromatography (10-30% EtOAc in hexanes) to give the title compound.

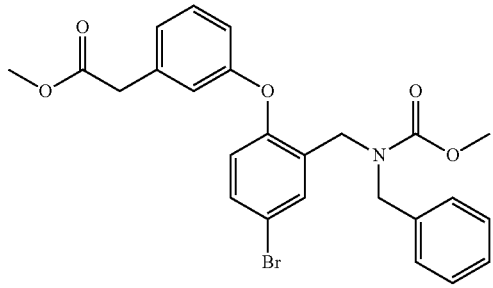

Step 3: (3-{2-[(Benzyl-methoxycarbonyl-amino)-methyl]-4-bromo-phenoxy}-phenyl)-acetic acid methyl ester To {3-[2-(benzylamino-methyl)-4-bromo-phenoxy]-phenyl}-acetic acid methyl ester (0.076, 0.17 mmol) and methyl chloroformate (0.01 mL, 0.18 mmol) in CH2Cl2 (2 mL) was added triethylamine (0.02 mL, 0.18 mmol), and the reaction was stirred at room temperature for 3 hours. Some starting material was still observed by analytical LCMS, so additional methyl chloroformate (0.02 mL) and triethylamine (0.03 mL) was added, and the reaction was stirred overnight. The mixture was concentrated and purified by silica gel chromatography (10-30% EtOAc in hexanes) to give the title compound.

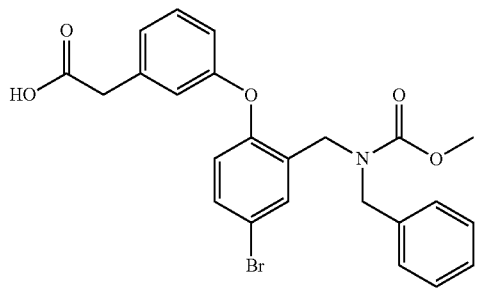 [SMILES: COC(=O)N(Cc1ccccc1)Cc1cc(Br)ccc1Oc1cccc(CC(=O)O)c1]

Step 4: (3-{2-[(Benzyl-methoxycarbonyl-amino)-methyl]-4-bromo-phenoxy}-phenyl)-acetic acid To (3-{2-[(benzyl-methoxycarbonyl-amino)-methyl]-4-bromo-phenoxy}-phenyl)-acetic acid methyl ester (0.07 g) in THF (2 mL) was added 1N aqueous lithium hydroxide (2 mL), and the reaction was stirred at room temperature until no starting material was seen by analytical LCMS. The mixture was acidified with 1N aqueous HCl to pH 3-4, and extracted three times with EtOAc. The combined organic layers were washed with $H_2O$, dried, and concentrated to give the title compound. M+H=485.

Example 4

Synthesis of (3-{4-Bromo-2-[(methoxycarbonyl-phenethyl-amino)-methyl]-phenoxy}-phenyl)-acetic acid (Compound 1-4)

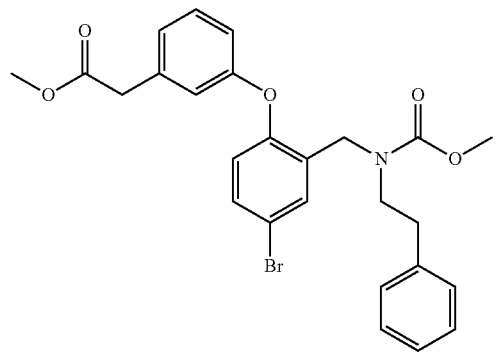

Step 1: (3-{4-Bromo-2-[(methoxycarbonyl-phenethyl-amino)-methyl]-phenoxy}-phenyl)-acetic acid methyl ester Prepared according to the procedure described in Example 1, Step 3, using the following starting materials: {3-[4-Bromo-2-(phenethylamino-methyl)-phenoxy]-phenyl}-acetic acid and methyl chloroformate.

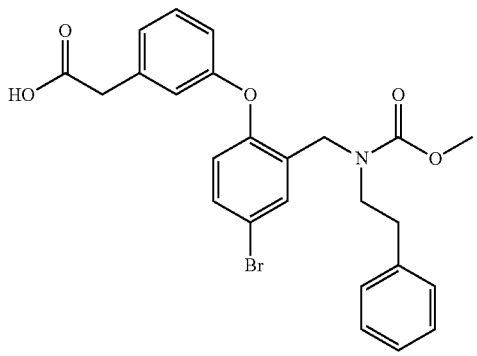 [SMILES: COC(=O)N(CCc1ccccc1)Cc1cc(Br)ccc1Oc1cccc(CC(=O)O)c1]

Step 2: (3-{4-Bromo-2-[(methoxycarbonyl-phenethyl-amino)-methyl]-phenoxy}-phenyl)-acetic acid To (3-{4-bromo-2-[(methoxycarbonyl-phenethyl-amino)-methyl]-phenoxy}-phenyl)-acetic acid methyl ester in THF and MeOH was added lithium hydroxide, and the reaction was stirred overnight at room temperature. The mixture was acidified with 1N aqueous HCl and extracted with EtOAc, and the combined organic layers were concentrated and purified by preparative HPLC to give the title compound. M+H=498.

Example 5

Synthesis of [3-(4-Bromo-2-{[methoxycarbonyl-((S)-1-methyl-2-phenyl-ethyl)-amino]-methyl}-phenoxy)-phenyl]-acetic acid (Compound 1-5)

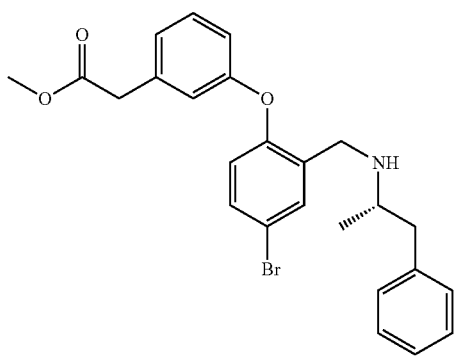 [SMILES: COC(=O)Cc1cccc(Oc2ccc(Br)cc2CN[C@@H](C)Cc2ccccc2)c1]

Step 1: (3-{4-Bromo-2-[((S)-1-methyl-2-phenyl-ethylamino)-methyl]-phenoxy}-phenyl)-acetic acid methyl ester Prepared according to the procedure described in Example 2, Step 3, using the following starting materials: [3-(4-bromo-2-formyl-phenoxy)-phenyl]-acetic acid methyl ester and D-amphetamine sulfate.

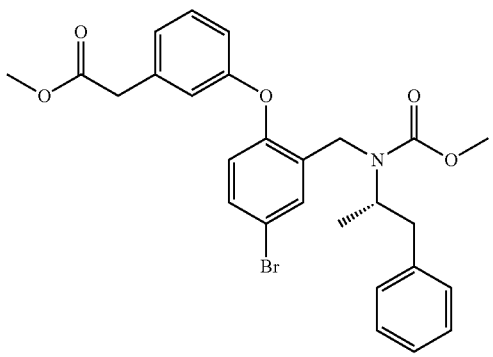

Step 2: [3-(4-Bromo-2-{[methoxycarbonyl-((S)-1-methyl-2-phenyl-ethyl)-amino]-methyl}-phenoxy)-phenyl]-acetic acid methyl ester Prepared according to the procedure described in Example 2, Step 4, using the following starting materials: (3-{4-bromo-2-[((S)-1-methyl-2-phenyl-ethylamino)-methyl]-phenoxy}-phenyl)-acetic acid methyl ester and methyl chloroformate.

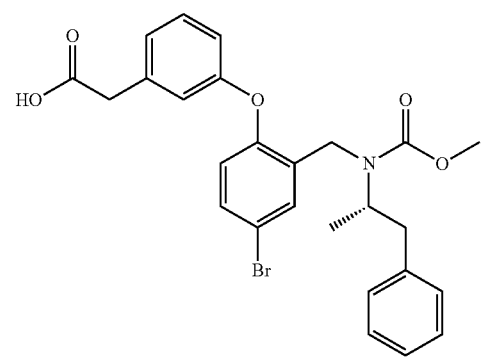 [SMILES: COC(=O)N(Cc1cc(Br)ccc1Oc1cccc(CC(=O)O)c1)[C@@H](C)Cc1ccccc1]

Step 3: [3-(4-Bromo-2-{[methoxycarbonyl-((S)-1-methyl-2-phenyl-ethyl)-amino]-methyl}-phenoxy)-phenyl]-acetic acid Prepared according to the procedure described in Example 2, Step 5, using the following starting material: [3-(4-bromo-2-{[methoxycarbonyl-((S)-1-methyl-2-phenyl-ethyl)-amino]-methyl}-phenoxy)-phenyl]-acetic acid methyl ester. M+H=513.

Example 6

Synthesis of (3-{2-[(((R)-Benzyloxycarbonyl-indan-1-yl-amino)-methyl]-4-bromo-phenoxy}-phenyl)-acetic acid (Compound 1-6)

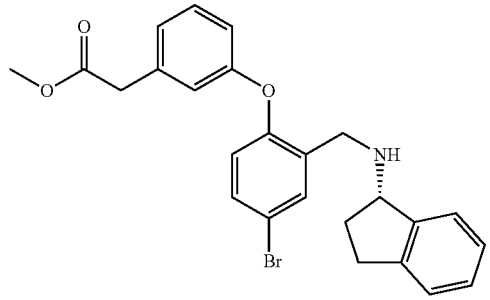 [SMILES: COC(=O)Cc1cccc(Oc2ccc(Br)cc2CN[C@H]2CCc3ccccc32)c1]

Step 1: {3-[4-Bromo-2-((S)-indan-1-ylaminomethyl)-phenoxy]-phenyl}-acetic acid methyl ester Prepared according to the procedure described in Example 3, Step 2, using the following starting materials: [3-(4-bromo-2-formyl-phenoxy)-phenyl]-acetic acid methyl ester and (S)-(+)-1-aminoindan.

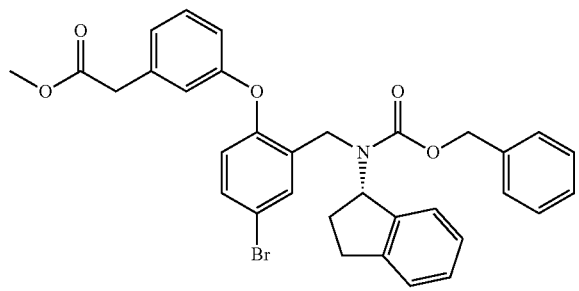 [SMILES: COC(=O)Cc1cccc(Oc2ccc(Br)cc2CN(C(=O)OCc2ccccc2)[C@H]2CCc3ccccc32)c1]

Step 2: (3-{2-[((S)-Benzyloxycarbonyl-indan-1-yl-amino)-methyl]-4-bromo-phenoxy}-phenyl)-acetic acid methyl ester Prepared according to the procedure described in Example 3, Step 3, using the following starting materials: {3-[4-bromo-2-((S)-indan-1-ylaminomethyl)-phenoxy]-phenyl}-acetic acid methyl ester and benzyl chloroformate.

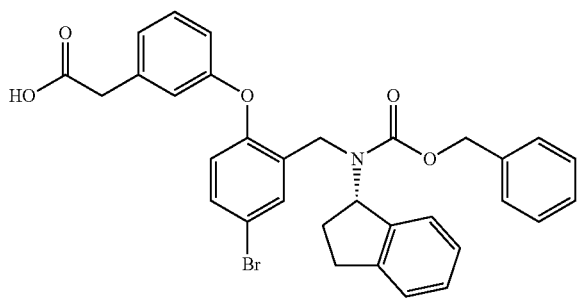 [SMILES: O=C(O)Cc1cccc(Oc2ccc(Br)cc2CN(C(=O)OCc2ccccc2)[C@H]2CCc3ccccc32)c1]

Step 3: (3-{2-[((S)-Benzyloxycarbonyl-indan-1-yl-amino)-methyl]-4-bromo-phenoxy}-phenyl)-acetic acid Prepared according to the procedure described in Example 3, Step 4, using the following starting material: (3-{2-[((S)-benzyloxycarbonyl-indan-1-yl-amino)-methyl]-4-bromo-phenoxy}-phenyl)-acetic acid methyl ester. M+H=587.

Example 7

Synthesis of (3-{4-Bromo-2-[((1S,2R)-2-hydroxy-indan-1-ylamino)-methyl]-phenoxy}-4-methoxy-phenyl)-acetic acid (Compound 1-7)

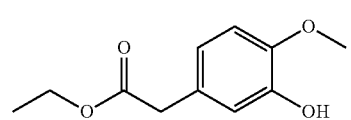

Step 1: (3-Hydroxy-4-methoxy-phenyl)-acetic acid ethyl ester

To 3-hydroxy-4-methoxyphenylacetic acid (5.0 g, 23.8 mmol) in EtOH (100 mL) was added sulfuric acid (1 mL), and the reaction was stirred overnight at room temperature. Once no starting material was seen by analytical TLC, the mixture was concentrated to give the title compound.

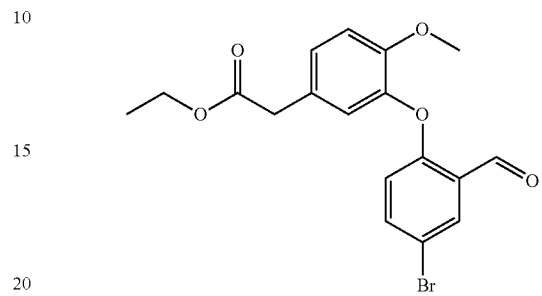

Step 2: [3-(4-Bromo-2-formyl-phenoxy)-4-methoxy-phenyl]-acetic acid ethyl ester (3-Hydroxy-4-methoxy-phenyl)-acetic acid ethyl ester (2.0 g, 9.5 mmol), 5-bromo-2-fluorobenzaldehyde (2.0 g, 9.5 mmol), and potassium carbonate (2.0 g, 14.3 mmol) were combined in 1,4-dioxane and heated to 90° C. overnight. After work-up, the crude material was purified by silica gel chromatography (0-25% EtOAc in hexanes) to give the title compound.

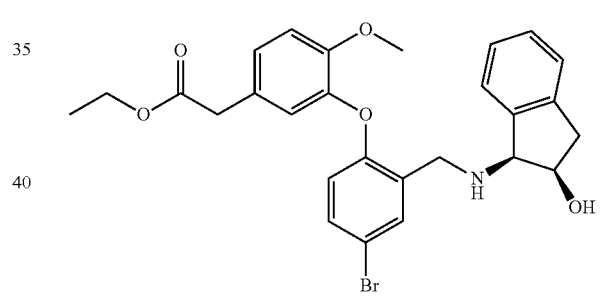

Step 3: (3-{4-Bromo-2-[((1S,2R)-2-hydroxy-indan-1-ylamino)-methyl]-phenoxy}-4-methoxy-phenyl)-acetic acid ethyl ester Prepared according to the procedure described in Example 3, Step 2, using the following starting materials: [3-(4-bromo-2-formyl-phenoxy)-4-methoxy-phenyl]acetic acid ethyl ester and (1S,2R)-(−)-cis-1-amino-2-indanol.

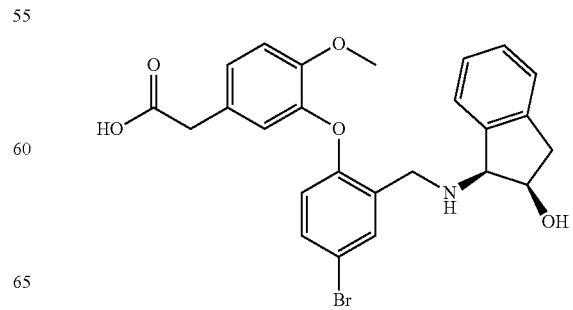

Step 4: (3-{4-Bromo-2-[((1S,2R)-2-hydroxy-indan-1-ylamino)-methyl]-phenoxy}-4-methoxy-phenyl)-acetic acid Prepared according to the procedure described in Example 3, Step 4, using the following starting material: (3-{4-bromo-2-[((1S,2R)-2-hydroxy-indan-1-ylamino)-methyl]-phenoxy}-4-methoxy-phenyl)-acetic acid ethyl ester. M+H=499.

Example 8

Synthesis of (3-{2-[(Acetyl-ethyl-amino)-methyl]-4-bromo-phenoxy}-4-methoxy-phenyl)-acetic acid (Compound 1-8)

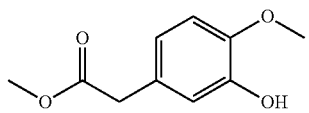

Step 1: (3-Hydroxy-4-methoxy-phenyl)-acetic acid methyl ester

Prepared according to the procedure described in Example 7, Step 1, using the following starting material: 3-hydroxy-4-methoxyphenylacetic acid.

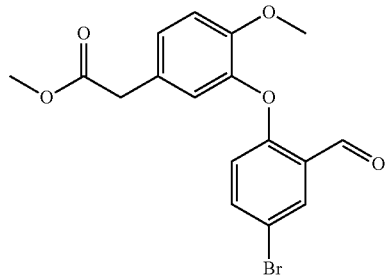 [SMILES: COC(=O)Cc1ccc(OC)c(Oc2ccc(Br)cc2C=O)c1]

Step 2: [3-(4-Bromo-2-formyl-phenoxy)-4-methoxy-phenyl]-acetic acid methyl ester Prepared according to the procedure described in Example 7, Step 2, using the following starting materials: (3-hydroxy-4-methoxy-phenyl)-acetic acid methyl ester and 5-bromo-2-fluorobenzaldehyde.

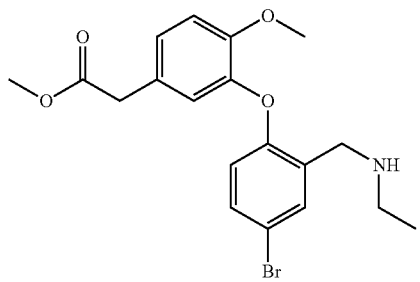 [SMILES: CCNCc1cc(Br)ccc1Oc1cc(CC(=O)OC)ccc1OC]

Step 3: [3-(4-Bromo-2-ethylaminomethyl-phenoxy)-4-methoxy-phenyl]-acetic acid methyl ester Prepared according to the procedure described in Example 3, Step 2, using the following starting materials: [3-(4-bromo-2-formyl-phenoxy)-4-methoxy-phenyl]-acetic acid methyl ester and ethylamine (2M in THF).

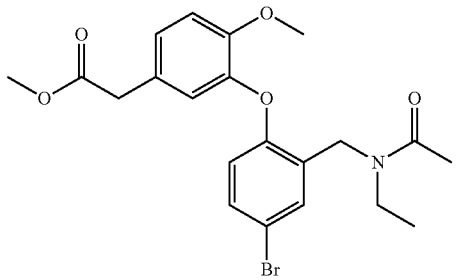 [SMILES: CCN(Cc1cc(Br)ccc1Oc1cc(CC(=O)OC)ccc1OC)C(C)=O]

Step 4: (3-{2-[(Acetyl-ethyl-amino)-methyl]-4-bromo-phenoxy}-4-methoxy-phenyl)-acetic acid methyl ester Prepared according to the procedure described in Example 3, Step 3, using the following starting materials: [3-(4-bromo-2-ethylaminomethyl-phenoxy)-4-methoxy-phenyl]-acetic acid methyl ester and acetyl chloride.

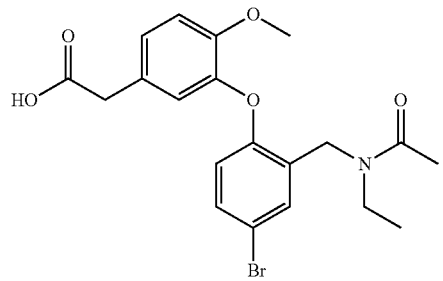 [SMILES: CCN(Cc1cc(Br)ccc1Oc1cc(CC(=O)O)ccc1OC)C(C)=O]

Step 5: (3-{2-[(Acetyl-ethyl-amino)-methyl]-4-bromo-phenoxy}-4-methoxy-phenyl)-acetic acid Prepared according to the procedure described in Example 3, Step 4, using the following starting material: (3-{2-[(acetyl-ethyl-amino)-methyl]-4-bromo-phenoxy}-4-methoxy-phenyl)-acetic acid methyl ester. M+H=437.

Example 9

Synthesis of (3-{2-[(Acetyl-benzyl-amino)-methyl]-4-bromo-phenoxy}-4-methoxy-phenyl)-acetic acid (Compound 1-9)

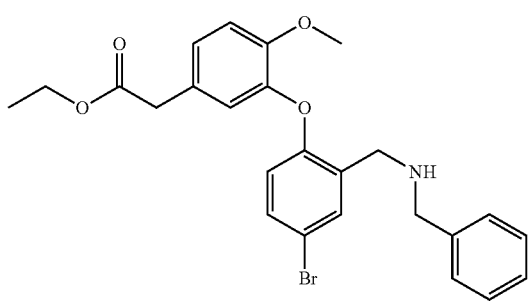 [SMILES: CCOC(=O)Cc1ccc(OC)c(Oc2ccc(Br)cc2CNCc2ccccc2)c1]

Step 1: {3-[2-(Benzylamino-methyl)-4-bromo-phenoxy]-4-methoxy-phenyl}-acetic acid ethyl ester Prepared according to the procedure described in Example 3, Step 2, using the following starting materials: [3-(4-bromo-2-formyl-phenoxy)-4-methoxy-phenyl]-acetic acid ethyl ester and benzylamine.

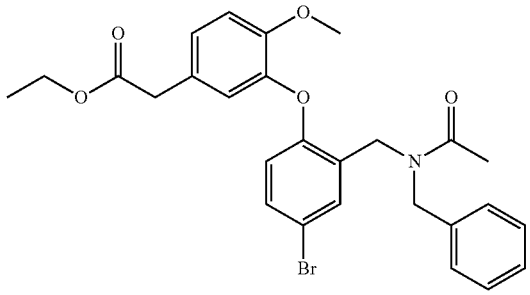 [SMILES: CCOC(=O)Cc1ccc(OC)c(Oc2ccc(Br)cc2CN(Cc2ccccc2)C(C)=O)c1]

Step 2: (3-{2-[(Acetyl-benzyl-amino)-methyl]-4-bromo-phenoxy}-4-methoxy-phenyl)-acetic acid ethyl ester Prepared according to the procedure described in Example 3, Step 3, using the following starting materials: {3-[2-(benzylamino-methyl)-4-bromo-phenoxy]-4-methoxy-phenyl}-acetic acid ethyl ester and acetyl chloride.

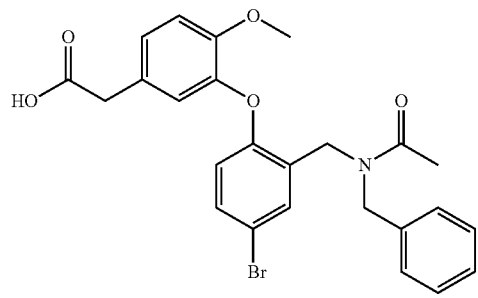

Step 3: (3-{2-[(Acetyl-benzyl-amino)-methyl]-4-bromo-phenoxy}-4-methoxy-phenyl)-acetic acid Prepared according to the procedure described in Example 3, Step 4, using the following starting material: (3-{2-[(acetyl-benzyl-amino)-methyl]-4-bromo-phenoxy}-4-methoxy-phenyl)-acetic acid ethyl ester. M+H=499.

Example 10

Synthesis of (3-{4-Bromo-2-[(ethyl-methoxycarbonyl-amino)-methyl]-phenoxy}-4-methoxy-phenyl)-acetic acid (Compound 1-10)

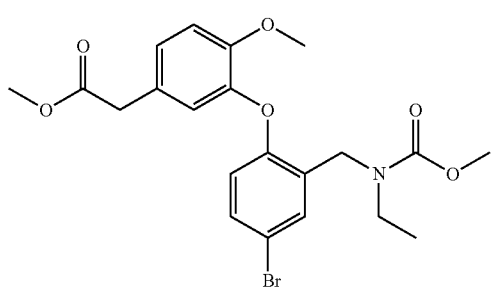

Step 1: (3-{4-Bromo-2-[(ethyl-methoxycarbonyl-amino)-methyl]-phenoxy}-4-methoxy-phenyl)-acetic acid methyl ester Prepared according to the procedure described in Example 3 Step 3, using the following starting materials: [3-(4-bromo-2-ethylaminomethyl-phenoxy)-4-methoxy-phenyl]-acetic acid methyl ester and methyl chloroformate.

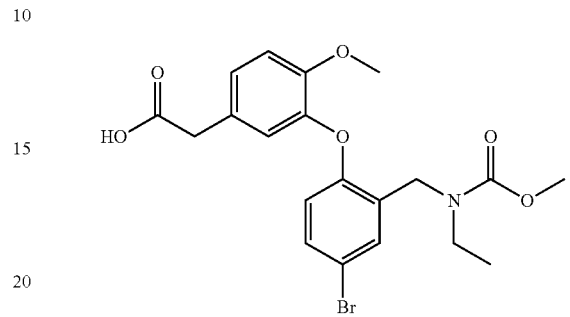

Step 2: (3-{4-Bromo-2-[(ethyl-methoxycarbonyl-amino)-methyl]-phenoxy}-4-methoxy-phenyl)-acetic acid Prepared according to the procedure described in Example 3, Step 4, using the following starting material: (3-{4-bromo-2-[(ethyl-methoxycarbonyl-amino)-methyl]-phenoxy}-4-methoxy-phenyl)-acetic acid methyl ester. M+H=453.

Example 11

Synthesis of (3-{2-[(Benzyl-methoxycarbonyl-amino)-methyl]-4-bromo-phenoxy}-4-methoxy-phenyl)-acetic acid (Compound 1-11)

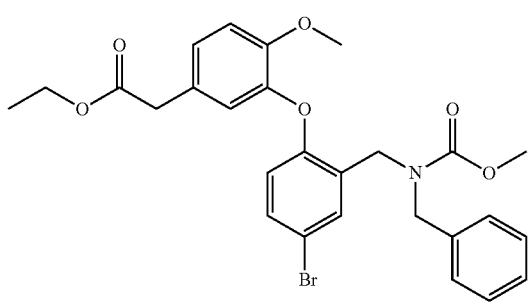 [SMILES: CCOC(=O)Cc1ccc(OC)c(Oc2ccc(Br)cc2CN(Cc2ccccc2)C(=O)OC)c1]

Step 1: (3-{2-[(Benzyl-methoxycarbonyl-amino)-methyl]-4-bromo-phenoxy}-4-methoxy-phenyl)-acetic acid ethyl ester Prepared according to the procedure described in Example 3, Step 3, using the following starting materials: {3-[2-(benzylamino-methyl)-4-bromo-phenoxy]-4-methoxy-phenyl}-acetic acid ethyl ester and methyl chloroformate.

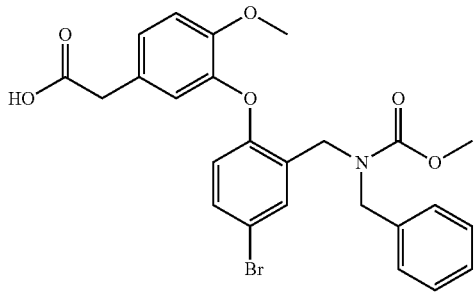 [SMILES: COC(=O)N(Cc1ccccc1)Cc1cc(Br)ccc1Oc1cc(CC(=O)O)ccc1OC]

Step 2: (3-{2-[(Benzyl-methoxycarbonyl-amino)-methyl]-4-bromo-phenoxy}-4-methoxy-phenyl)-acetic acid Prepared according to the procedure described in Example 3, Step 4, using the following starting material: (3-{2-[(benzyl-methoxycarbonyl-amino)-methyl]-4-bromo-phenoxy}-4-methoxy-phenyl)-acetic acid ethyl ester. M+H=515.

Example 12

Synthesis of (3-{2-[((1S,2R)-2-Hydroxy-1-methyl-2-phenyl-ethylamino)-methyl]-4-trifluoromethyl-phenoxy}-phenyl)-acetic acid (Compound 1-12)

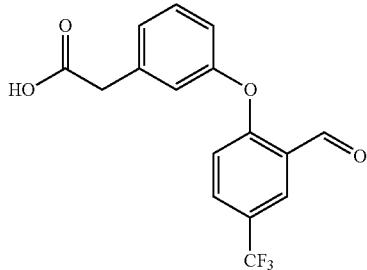

Step 1: [3-(2-Formyl-4-trifluoromethyl-phenoxy)-phenyl]-acetic acid

3-Hydroxyphenylacetic acid (1 g, 5.2 mmol), 2-fluoro-5-(trifluoromethyl)benzaldehyde (1 g, 6.6 mmol), and potassium carbonate (2.2 g, 15.6 mmol) were combined in THF (20 mL) and MeCN (20 mL), and the reaction was stirred at 70° C. for 3 days. After acidic workup, the crude material was purified by silica gel chromatography (20-100% EtOAc in hexanes) to give the title compound.

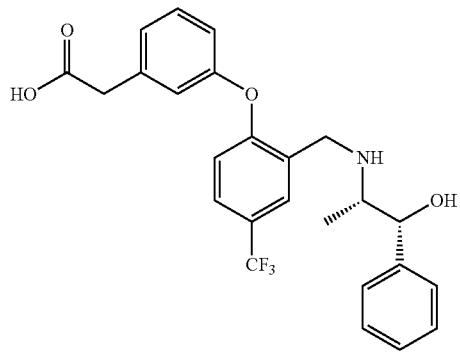 [SMILES: C[C@H](NCc1cc(C(F)(F)F)ccc1Oc1cccc(CC(=O)O)c1)[C@H](O)c1ccccc1]

Step 2: (3-{2-[((1S,2R)-2-Hydroxy-1-methyl-2-phenyl-ethylamino)-methyl]-4-trifluoromethyl-phenoxy}-phenyl)-acetic acid

[3-(2-Formyl-4-trifluoromethyl-phenoxy)-phenyl]-acetic acid (0.12 g, 0.37 mmol), (1R,2S)-(−)-norephedrine (0.056 g, 0.37 mmol), and sodium triacetoxyborohydride (0.12 g, 0.56 mmol) were combined in $CH_2Cl_2$ (10 mL), and the reaction was stirred at room temperature for 2 hours. The mixture was worked-up to give the title compound. M+H=460.

Example 13

Synthesis of (3-{2-[((R)-Acetyl-indan-1-yl-amino)-methyl]-4-trifluoromethyl-phenoxy}-phenyl)-acetic acid (Compound 1-13)

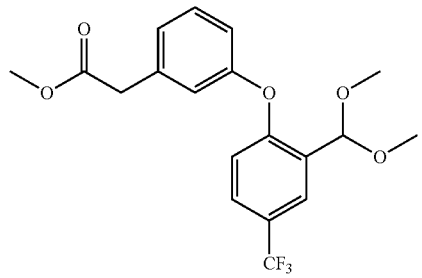

Step 1: [3-(2-Dimethoxymethyl-4-trifluoromethyl-phenoxy)-phenyl]-acetic acid methyl ester To [3-(2-formyl-4-trifluoromethyl-phenoxy)-phenyl]-acetic acid (2.67 g, 8.23 mmol) in MeOH (27 mL) at 0° C. was added thionyl chloride (1.2 mL, 16.47 mmol), and the reaction was stirred at 0° C. for 30 minutes. Analytical TLC showed some starting material was still present, so additional thionyl chloride (0.4 mL) was added, and the reaction was stirred at room temperature for 2 hours. The mixture was partitioned between EtOAc and 1N aqueous NaOH, and the aqueous layer was separated and extracted twice with EtOAc. The combined organic layers were dried and concentrated to give the title compound.

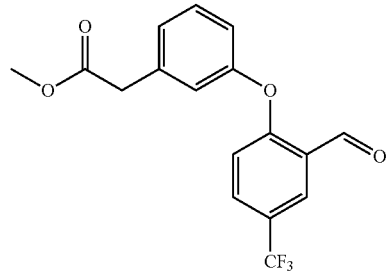 [SMILES: COC(=O)Cc1cccc(Oc2ccc(C(F)(F)F)cc2C=O)c1]

Step 2: [3-(2-Formyl-4-trifluoromethyl-phenoxy)-phenyl]-acetic acid methyl ester

[3-(2-Dimethoxymethyl-4-trifluoromethyl-phenoxy)-phenyl]-acetic acid methyl ester (0.479 g, 1.42 mmol) and hydrogen chloride (4N in 1,4-dioxane; 1.5 mL, 6.0 mmol) were combined in THF (4 mL) and stirred at 70° C. for 1 hour. Some starting material was still seen by analytical LCMS, so additional hydrogen chloride (4N in 1,4-dioxane; 0.5 mL) was added, and the reaction was stirred for another hour at 70° C. After cooling to room temperature, the mixture was worked up with EtOAc and $H_2O$, and the combined organic layers were dried and concentrated to give the title compound.

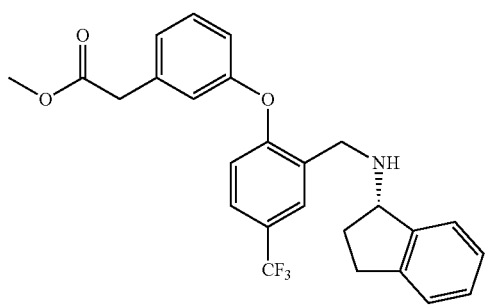 [SMILES: COC(=O)Cc1cccc(Oc2ccc(C(F)(F)F)cc2CN[C@H]2CCc3ccccc32)c1]

Step 3: {3-[2-((S)-Indan-1-ylaminomethyl)-4-trifluoromethyl-phenoxy]-phenyl}-acetic acid methyl ester Prepared according to the procedure described in Example 3, Step 2, using the following starting materials: [3-(2-formyl-4-trifluoromethyl-phenoxy)-phenyl]-acetic acid methyl ester and (S)-(+)-1-aminoindan.

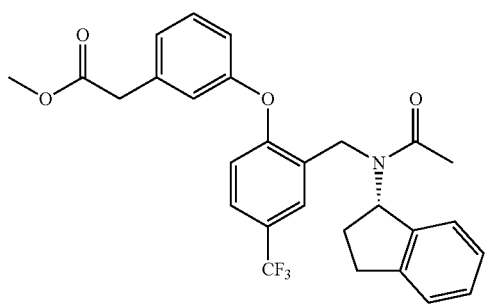 [SMILES: COC(=O)Cc1cccc(Oc2ccc(C(F)(F)F)cc2CN(C(C)=O)[C@H]2CCc3ccccc32)c1]

Step 4: (3-{2-[((S)-Acetyl-indan-1-yl-amino)-methyl]-4-trifluoromethyl-phenoxy}-phenyl)-acetic acid methyl ester Prepared according to the procedure described in Example 3, Step 3, using the following starting materials: {3-[2-((S)-indan-1-ylaminomethyl)-4-trifluoromethyl-phenoxy]-phenyl}-acetic acid methyl ester and acetyl chloride.

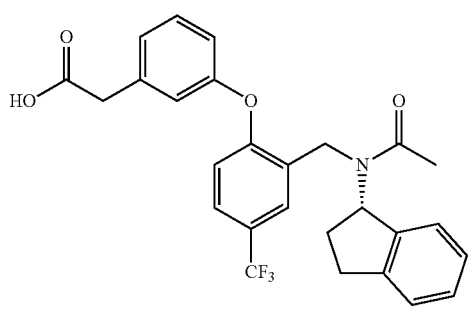 [SMILES: CC(=O)N(Cc1cc(C(F)(F)F)ccc1Oc1cccc(CC(=O)O)c1)[C@H]1CCc2ccccc21]

Step 5: (3-{2-[((S)-Acetyl-indan-1-yl-amino)-methyl]-4-trifluoromethyl-phenoxy}-phenyl)-acetic acid Prepared according to the procedure described in Example 3, Step 4, using the following starting material: (3-{2-[((S)-acetyl-indan-1-yl-amino)-methyl]-4-trifluoromethyl-phenoxy}-phenyl)-acetic acid methyl ester. M+H=484.

Example 14

Synthesis of (3-{2-[((S)-Acetyl-indan-1-yl-amino)-methyl]-4-trifluoromethyl-phenoxy}-phenyl)-acetic acid (Compound 1-14)

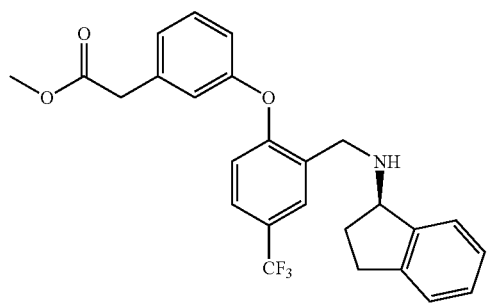 [SMILES: COC(=O)Cc1cccc(Oc2ccc(C(F)(F)F)cc2CN[C@@H]2CCc3ccccc32)c1]

Step 1: {3-[2-((R)-Indan-1-ylaminomethyl)-4-trifluoromethyl-phenoxy]-phenyl}-acetic acid methyl ester Prepared according to the procedure described in Example 3, Step 2, using the following starting materials: [3-(2-formyl-4-trifluoromethyl-phenoxy)-phenyl]-acetic acid methyl ester and (R)-(−)-1-amino indan.

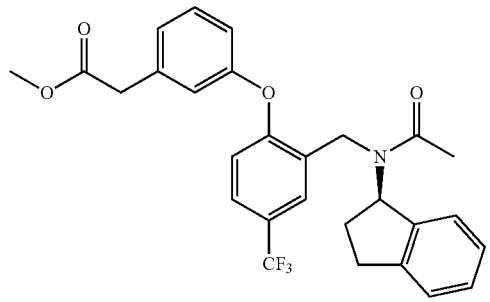 [SMILES: COC(=O)Cc1cccc(Oc2ccc(C(F)(F)F)cc2CN(C(C)=O)[C@@H]2CCc3ccccc32)c1]

Step 2: (3-{2-[((R)-Acetyl-indan-1-yl-amino)-methyl]-4-trifluoromethyl-phenoxy}-phenyl)-acetic acid methyl ester Prepared according to the procedure described in Example 3, Step 3, using the following starting materials: {3-[2-((R)-indan-1-ylaminomethyl)-4-trifluoromethyl-phenoxy]-phenyl}-acetic acid methyl ester and acetyl chloride.

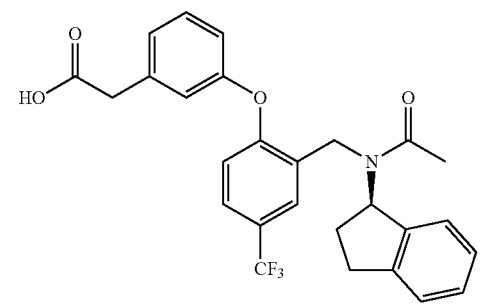 [SMILES: CC(=O)N(Cc1cc(C(F)(F)F)ccc1Oc1cccc(CC(=O)O)c1)[C@@H]1CCc2ccccc21]

101

Step 3: (3-{2-[((R)-Acetyl-indan-1-yl-amino)-methyl]-4-trifluoromethyl-phenoxy}-phenyl)-acetic acid Prepared according to the procedure described in Example 3, Step 4, using the following starting material: (3-{2-[((R)-acetyl-indan-1-yl-amino)-methyl]-4-trifluoromethyl-phenoxy}-phenyl)-acetic acid methyl ester. M+H=484.

Example 15

Synthesis of (3-{2-[(4-Chloro-benzoylamino)-methyl]-4-trifluoromethyl-phenoxy}-phenyl)-acetic acid (Compound 1-15)

Step 1: (3-Hydroxy-phenyl)-acetic acid ethyl ester

3-Hydroxyphenylacetic acid (5 g, 32.9 mmol) and sulfuric acid (1 mL) were stirred in EtOH (100 mL) at 70° C. for 1 hour. The mixture was worked-up to give the title compound.

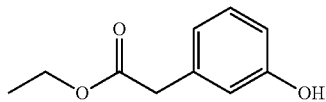

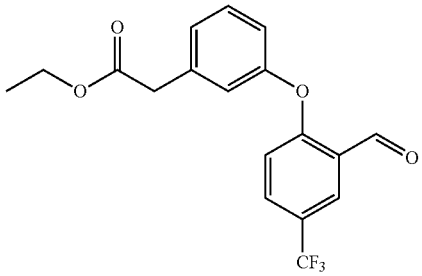

Step 2: [3-(2-Formyl-4-trifluoromethyl-phenoxy)-phenyl]-acetic acid ethyl ester (3-Hydroxy-phenyl)-acetic acid ethyl ester (1.0 g, 5.2 mmol) 2-fluoro-5-(trifluoromethyl)benzaldehyde (0.72 g, 5.2 mmol), and potassium carbonate (1.44 g, 10.4 mmol) were combined in 1,4-dioxane (30 mL), and the reaction was stirred at 120° C. for 3 days. After work-up, the crude material was purified by silica gel chromatography (0-20% EtOAc in hexanes) to give the title compound.

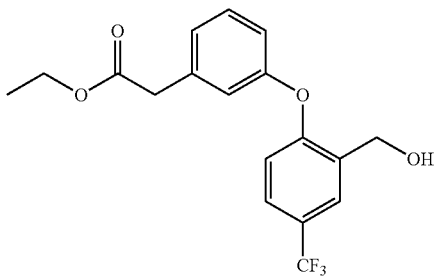 [SMILES: CCOC(=O)Cc1cccc(Oc2ccc(C(F)(F)F)cc2CO)c1]

102

Step 3: [3-(2-Hydroxymethyl-4-trifluoromethyl-phenoxy)-phenyl]-acetic acid ethyl ester To [3-(2-formyl-4-trifluoromethyl-phenoxy)-phenyl]-acetic acid ethyl ester (0.411 g, 1.17 mmol) in MeOH (15 mL) was added sodium borohydride (0.045 g, 1.17 mmol), and the reaction was stirred for 15 minutes at room temperature. The mixture was concentrated, and the residue was partitioned between EtOAc and $H_2O$. The aqueous layer was separated and extracted twice with EtOAc, and the combined organic layers were dried and concentrated to give the title compound.

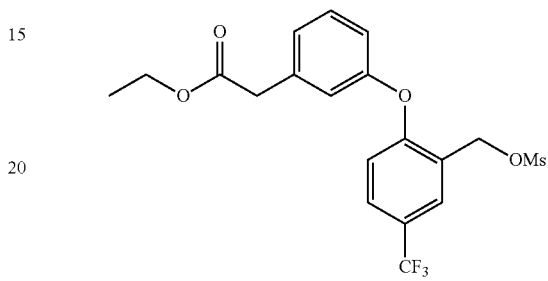

Step 4: [3-(2-Methanesulfonyloxymethyl-4-trifluoromethyl-phenoxy)-phenyl]-acetic acid ethyl ester

[3-(2-Hydroxymethyl-4-trifluoromethyl-phenoxy)-phenyl]-acetic acid ethyl ester (0.355 g, 1.0 mmol) and triethylamine (0.21 mL, 1.5 mmol) were combined in $CH_2Cl_2$ (7.2 mL) and cooled to 0° C. Methanesulfonyl chloride (0.09 mL, 1.1 mmol) was added, and the reaction was stirred for 3 hours. Some starting material was still seen by analytical LCMS, so additional methanesulfonyl chloride (0.04 mL) and triethylamine (0.07 mL) was added at 0° C., and the reaction was stirred for another 2 hours. The mixture was partitioned between $CH_2Cl_2$ and $H_2O$, and the aqueous layer was separated and extracted twice with $CH_2Cl_2$. The combined organic layers were dried and concentrated to give the title compound.

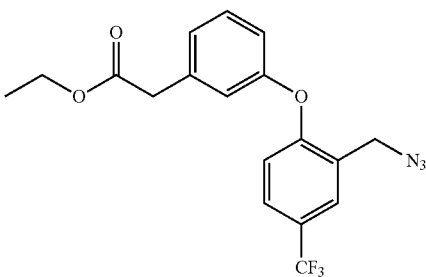 [SMILES: CCOC(=O)Cc1cccc(Oc2ccc(C(F)(F)F)cc2CN=[N+]=[N-])c1]

Step 5: [3-(2-Azidomethyl-4-trifluoromethyl-phenoxy)-phenyl]-acetic acid ethyl ester

[3-(2-Methanesulfonyloxymethyl-4-trifluoromethyl-phenoxy)-phenyl]-acetic acid ethyl ester (1.0 mmol) and sodium azide (0.195 g, 3.0 mmol) were combined in DMF (10 mL) and stirred at 80° C. for 1 hour. Once no starting material was seen by analytical LCMS, the mixture was cooled to room temperature and partitioned between EtOAc and $H_2O$. The aqueous layer was separated and extracted twice with EtOAc, and the combined organic layers were washed three times with H₂O, and then dried and concentrated. The residue was purified by silica gel chromatography (0-10% EtOAc in hexanes) to give the title compound.

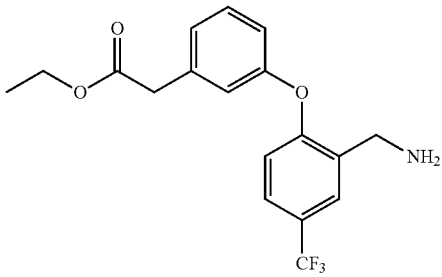 [SMILES: CCOC(=O)Cc1cccc(Oc2ccc(C(F)(F)F)cc2CN)c1]

Step 6: [3-(2-Aminomethyl-4-trifluoromethyl-phenoxy)-phenyl]-acetic acid ethyl ester

[3-(2-Azidomethyl-4-trifluoromethyl-phenoxy)-phenyl]-acetic acid ethyl ester (0.187 g, 0.49 mmol) was dissolved in EtOH (6 mL), and the solution was purged with H₂ under an H₂ balloon. Palladium on carbon (10%; 0.038 mg) was added, and the mixture was purged again with H₂. The reaction was sealed and stirred at room temperature overnight. Analytical LCMS indicated that starting material was still present, so additional palladium on carbon (10%; 0.038 g) was added, and the mixture was stirred under 65 psi of H₂ using a Parr apparatus. After 6 hours, no starting material was seen by analytical LCMS, so the mixture was filtered through a pad of Celite, and the filter cake was washed with EtOH. The filtrate was concentrated to give the title compound.

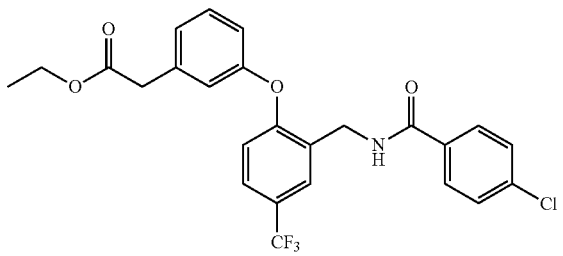 [SMILES: CCOC(=O)Cc1cccc(Oc2ccc(C(F)(F)F)cc2CNC(=O)c2ccc(Cl)cc2)c1]

Step 7: (3-{2-[(4-Chloro-benzoylamino)-methyl]-4-trifluoromethyl-phenoxy}-phenyl)-acetic acid ethyl ester To [3-(2-aminomethyl-4-trifluoromethyl-phenoxy)-phenyl]-acetic acid ethyl ester (0.084 g, 0.24 mmol) and pyridine (2.0 mL) in CH₂Cl₂ (2.5 mL) was added 4-chlorobenzoyl chloride (0.04 mL, 0.29 mmol), and the reaction was stirred for 30 minutes at room temperature. The mixture was partitioned between CH₂Cl₂ and 1N aqueous HCl, and the organic layer was separated and washed twice with 1N aqueous HCl. The organic layer was dried and concentrated, resulting in the formation of a white precipitate. The precipitate was filtered off, and the filtrate was concentrated to give the title compound.

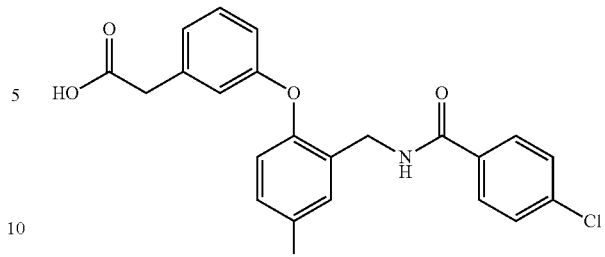

Step 8: (3-{2-[(4-Chloro-benzoylamino)-methyl]-4-trifluoromethyl-phenoxy}-phenyl)-acetic acid Prepared according to the procedure described in Example 2, Step 5, using the following starting material: (3-{2-[(4-chloro-benzoylamino)-methyl]-4-trifluoromethyl-phenoxy}-phenyl)-acetic acid ethyl ester. M+H=464.

Example 16

Synthesis of (3-{2-[(Methyl-phenylacetyl-amino)-methyl]-4-trifluoromethyl-phenoxy}-phenyl)-acetic acid (Compound 1-16)

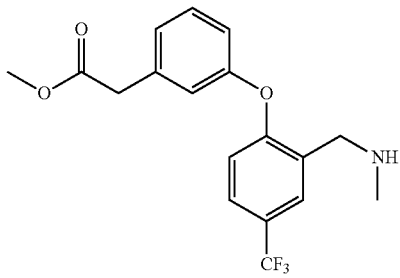

Step 1: [3-(2-Methylaminomethyl-4-trifluoromethyl-phenoxy)-phenyl]-acetic acid methyl ester Prepared according to the procedure described in Example 3, Step 2, using the following starting materials: [3-(2-formyl-4-trifluoromethyl-phenoxy)-phenyl]-acetic acid methyl ester and methylamine (2M in THF).

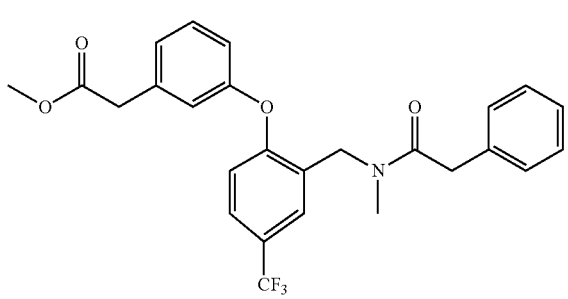 [SMILES: COC(=O)Cc1cccc(Oc2ccc(C(F)(F)F)cc2CN(C)C(=O)Cc2ccccc2)c1]

Step 2: (3-{2-[(Methyl-phenylacetyl-amino)-methyl]-4-trifluoromethyl-phenoxy}-phenyl)-acetic acid methyl ester Prepared according to the procedure described in Example 15, Step 7, using the following starting materials: [3-(2-methylaminomethyl-4-trifluoromethyl-phenoxy)-phenyl]-acetic acid methyl ester and phenylacetyl chloride.

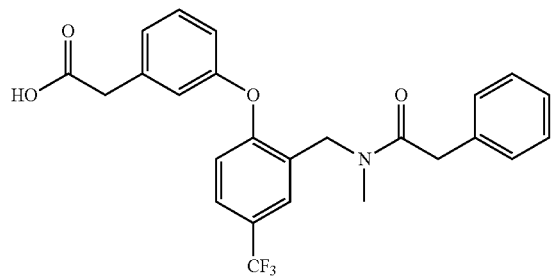 [SMILES: CN(Cc1cc(C(F)(F)F)ccc1Oc1cccc(CC(=O)O)c1)C(=O)Cc1ccccc1]

Step 3: (3-{2-[(Methyl-phenylacetyl-amino)-methyl]-4-trifluoromethyl-phenoxy}-phenyl)-acetic acid Prepared according to the procedure described in Example 3, Step 4, using the following starting material: (3-{2-[(methyl-phenylacetyl-amino)-methyl]-4-trifluoromethyl-phenoxy}-phenyl)-acetic acid methyl ester. M+H=458.

Example 17

Synthesis of (3-{2-[(Benzoyl-ethyl-amino)-methyl]-4-trifluoromethyl-phenoxy}-phenyl)-acetic acid (Compound 1-17)

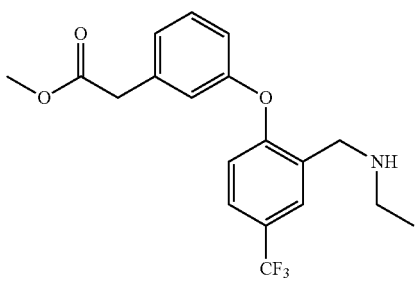 [SMILES: CCNCc1cc(C(F)(F)F)ccc1Oc1cccc(CC(=O)OC)c1]

Step 1: [3-(2-Ethylaminomethyl-4-trifluoromethyl-phenoxy)-phenyl]-acetic acid methyl ester Prepared according to the procedure described in Example 3, Step 2, using the following starting materials: [3-(2-formyl-4-trifluoromethyl-phenoxy)-phenyl]-acetic acid methyl ester and ethylamine (2M in THF).

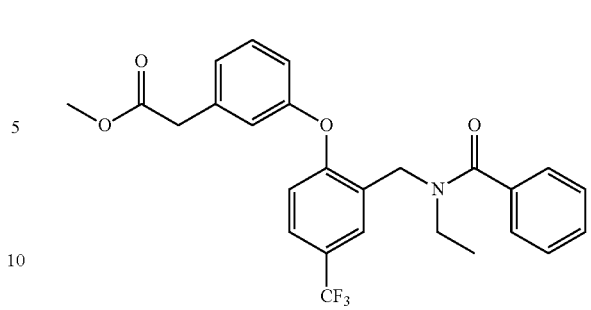

Step 2: (3-{2-[(Benzoyl-ethyl-amino)-methyl]-4-trifluoromethyl-phenoxy}-phenyl)-acetic acid methyl ester Prepared according to the procedure described in Example 15, Step 7, using the following starting materials: [3-(2-ethylaminomethyl-4-trifluoromethyl-phenoxy)-phenyl]-acetic acid methyl ester and benzoyl chloride.

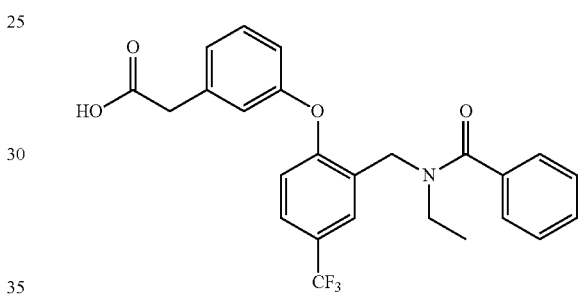

Step 3: (3-{2-[(Benzoyl-ethyl-amino)-methyl]-4-trifluoromethyl-phenoxy}-phenyl)-acetic acid Prepared according to the procedure described in Example 3, Step 4, using the following starting material: (3-{2-[(benzoyl-ethyl-amino)-methyl]-4-trifluoromethyl-phenoxy}-phenyl)-acetic acid methyl ester. M+H=458.

Example 18

Synthesis of (3-{2-[(Ethyl-phenylacetyl-amino)-methyl]-4-trifluoromethyl-phenoxy}-phenyl)-acetic acid (Compound 1-18)

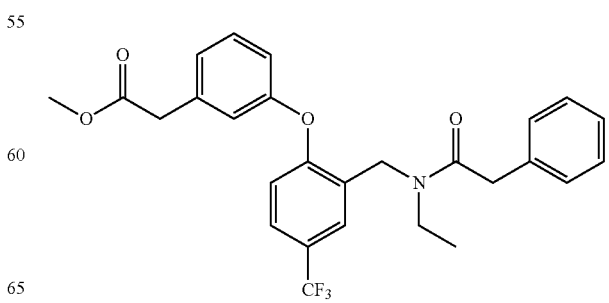

Step 1: (3-{2-[(Ethyl-phenylacetyl-amino)-methyl]-4-trifluoromethyl-phenoxy}-phenyl)-acetic acid methyl ester Prepared according to the procedure described in Example 15, Step 7, using the following starting materials: [3-(2-ethylaminomethyl-4-trifluoromethyl-phenoxy)-phenyl]-acetic acid methyl ester and phenylacetyl chloride.

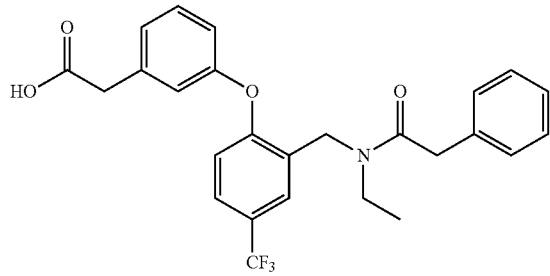 [SMILES: CCN(Cc1cc(C(F)(F)F)ccc1Oc1cccc(CC(=O)O)c1)C(=O)Cc1ccccc1]

Step 2: (3-{2-[(Ethyl-phenylacetyl-amino)-methyl]-4-trifluoromethyl-phenoxy}-phenyl)-acetic acid Prepared according to the procedure described in Example 3, Step 4, using the following starting material: (3-{2-[(ethyl-phenylacetyl-amino)-methyl]-4-trifluoromethyl-phenoxy}-phenyl)-acetic acid methyl ester. M+H=472.

Example 19

Synthesis of (3-{2-[((R)-Indan-1-yl-methoxycarbonyl-amino)-methyl]-4-trifluoromethyl-phenoxy}-phenyl)-acetic acid (Compound 1-19)

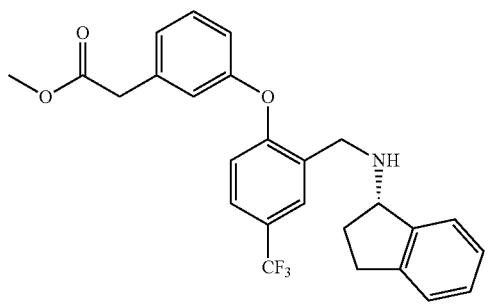 [SMILES: COC(=O)Cc1cccc(Oc2ccc(C(F)(F)F)cc2CN[C@H]2CCc3ccccc32)c1]

Step 1: {3-[2-((S)-Indan-1-ylaminomethyl)-4-trifluoromethyl-phenoxy]-phenyl}-acetic acid methyl ester Prepared according to the procedure described in Example 3, Step 2, using the following starting materials: [3-(2-formyl-4-trifluoromethyl-phenoxy)-phenyl]-acetic acid methyl ester and (S)-(+)-1-aminoindan.

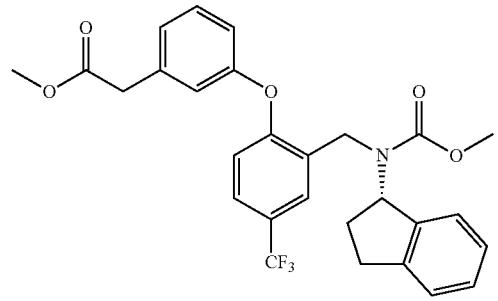

Step 2: (3-{2-[((S)-Indan-1-yl-methoxycarbonyl-amino)-methyl]-4-trifluoromethyl-phenoxy}-phenyl)-acetic acid methyl ester Prepared according to the procedure described in Example 3, Step 3, using the following starting materials: {3-[2-((S)-indan-1-ylaminomethyl)-4-trifluoromethyl-phenoxy]-phenyl}-acetic acid methyl ester and methyl chloroformate.

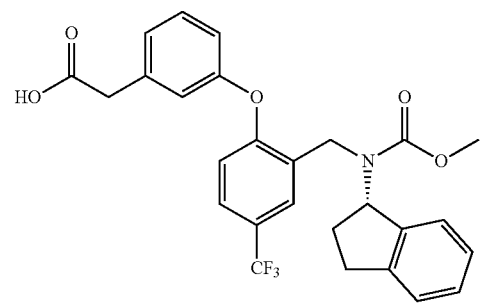 [SMILES: COC(=O)N(Cc1cc(C(F)(F)F)ccc1Oc1cccc(CC(=O)O)c1)[C@H]1CCc2ccccc21]

Step 3: (3-{2-[((S)-Indan-1-yl-methoxycarbonyl-amino)-methyl]-4-trifluoromethyl-phenoxy}-phenyl)-acetic acid Prepared according to the procedure described in Example 3, Step 4, using the following starting material: (3-{2-[((S)-indan-1-yl-methoxycarbonyl-amino)-methyl]-4-trifluoromethyl-phenoxy}-phenyl)-acetic acid methyl ester. M+H=500.

Example 20

Synthesis of (3-{2-[(Indan-2-yl-methoxycarbonyl-amino)-methyl]-4-trifluoromethyl-phenoxy}-phenyl)-acetic acid (Compound 1-20)

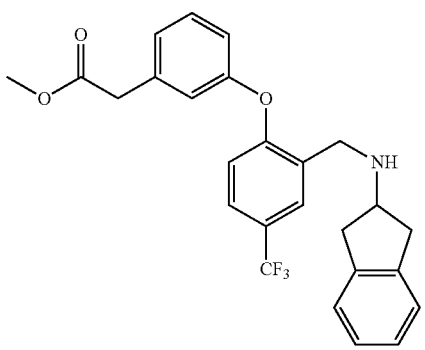 [SMILES: COC(=O)Cc1cccc(Oc2ccc(C(F)(F)F)cc2CNC2Cc3ccccc3C2)c1]

Step 1: {3-[2-(Indan-2-ylaminomethyl)-4-trifluoromethyl-phenoxy]-phenyl}-acetic acid methyl ester To 2-aminoindan hydrochloride (0.253 g, 1.49 mmol) in MeOH (2 mL) was added sodium acetate (0.122 g, 1.49 mmol), and the mixture was heated with a heating gun for 2 minutes. [3-(2-Formyl-4-trifluoromethyl-phenoxy)-phenyl]-acetic acid methyl ester (0.420 g, 1.24 mmol) in MeOH was added, followed by sodium cyanoborohydride (0.140 g, 2.23 mmol), and the reaction was stirred at room temperature for 2 hours and at 50° C. for 2 hours. After cooling to room temperature, the mixture was partitioned between EtOAc and saturated aqueous NaHCO$_3$, and the aqueous layer was separated and extracted twice with EtOAc. The combined organic layers were dried and concentrated to give the title compound.

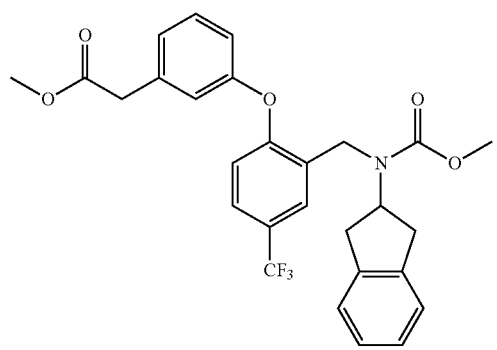

Step 2: (3-{2-[(Indan-2-yl-methoxycarbonyl-amino)-methyl]-4-trifluoromethyl-phenoxy}-phenyl)-acetic acid methyl ester Prepared according to the procedure described in Example 3, Step 3, using the following starting materials: {3-[2-(indan-2-ylaminomethyl)-4-trifluoromethyl-phenoxy]-phenyl}-acetic acid methyl ester and methyl chloroformate.

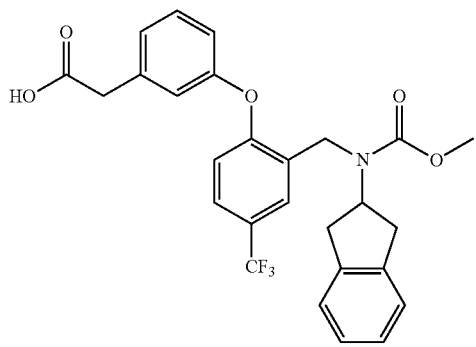 [SMILES: COC(=O)N(Cc1cc(C(F)(F)F)ccc1Oc1cccc(CC(=O)O)c1)C1Cc2ccccc2C1]

Step 3: (3-{2-[(Indan-2-yl-methoxycarbonyl-amino)-methyl]-4-trifluoromethyl-phenoxy}-phenyl)-acetic acid Prepared according to the procedure described in Example 2, Step 5, using the following starting material: (3-{2-[(indan-2-yl-methoxycarbonyl-amino)-methyl]-4-trifluoromethyl-phenoxy}-phenyl)-acetic acid methyl ester. M+H=500.

Example 21

Synthesis of (3-{2-[(Benzyloxycarbonyl-methyl-amino)-methyl]-4-trifluoromethyl-phenoxy}-phenyl)-acetic acid (Compound 1-21)

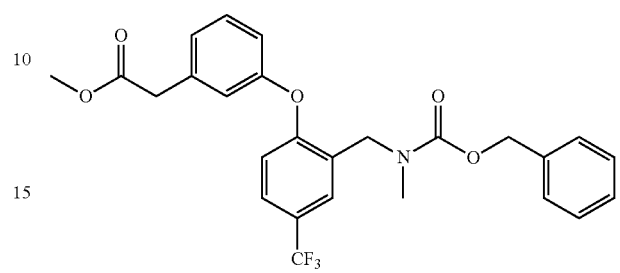

Step 1: (3-{2-[(Benzyloxycarbonyl-methyl-amino)-methyl]-4-trifluoromethyl-phenoxy}-phenyl)-acetic acid methyl ester Prepared according to the procedure described in Example 3, Step 3, using the following starting materials: [3-(2-methylaminomethyl-4-trifluoromethyl-phenoxy)-phenyl]-acetic acid methyl ester and benzyl chloroformate.

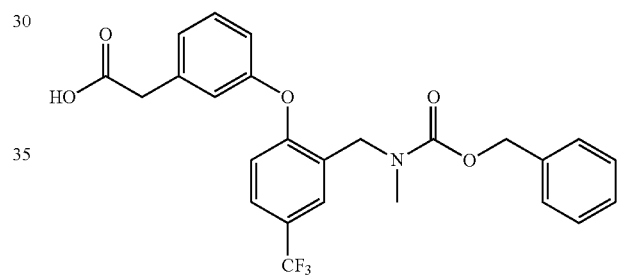

Step 2: (3-{2-[(Benzyloxycarbonyl-methyl-amino)-methyl]-4-trifluoromethyl-phenoxy}-phenyl)-acetic acid Prepared according to the procedure described in Example 3, Step 4, using the following starting material: (3-{2-[(benzyloxycarbonyl-methyl-amino)-methyl]-4-trifluoromethyl-phenoxy}-phenyl)-acetic acid methyl ester. M+H=474.

Example 22

Synthesis of (3-{2-[(4-Chloro-benzenesulfonylamino)-methyl]-4-trifluoromethyl-phenoxy}-phenyl)-acetic acid (Compound 1-22)

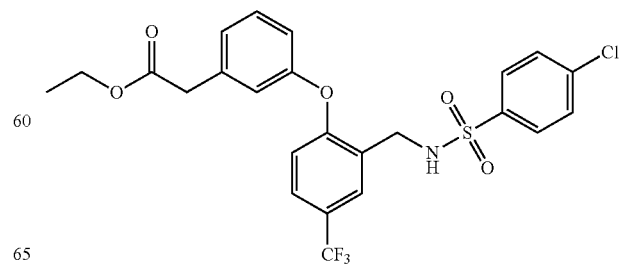

Step 1: (3-{2-[(4-Chloro-benzenesulfonylamino)-methyl]-4-trifluoromethyl-phenoxy}-phenyl)-acetic acid ethyl ester

[3-(2-Aminomethyl-4-trifluoromethyl-phenoxy)-phenyl]acetic acid ethyl ester (0.084 g, 0.24 mmol) and 4-chlorobenzenesulfonyl chloride (0.060 g, 0.29 mmol) were combined in CH$_2$Cl$_2$ (3 mL). Triethylamine (0.05 mL, 0.36 mmol) was added, and the reaction was stirred at room temperature for 1 hour. The mixture was concentrated, and the residue was purified by silica gel chromatography (10-20% EtOAc in hexanes) to give the title compound.

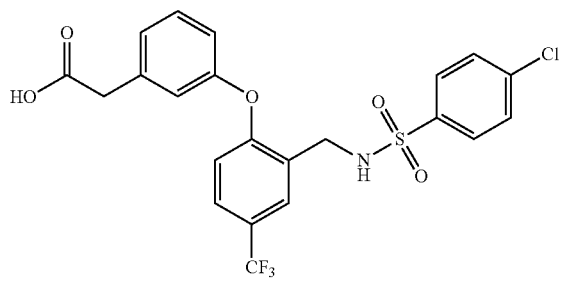 [SMILES: O=C(O)Cc1cccc(Oc2ccc(C(F)(F)F)cc2CNS(=O)(=O)c2ccc(Cl)cc2)c1]

Step 2: (3-{2-[(4-Chloro-benzenesulfonylamino)-methyl]-4-trifluoromethyl-phenoxy}-phenyl)-acetic acid Prepared according to the procedure described in Example 3, Step 4, using the following starting material: (3-{2-[(4-chloro-benzenesulfonylamino)-methyl]-4-trifluoromethyl-phenoxy}-phenyl)-acetic acid ethyl ester. M+H=500.

Example 23

Synthesis of [3-(2-{[(4-Chloro-benzenesulfonyl)-methyl-amino]-methyl}-4-trifluoromethyl-phenoxy)-phenyl]-acetic acid (Compound 1-23)

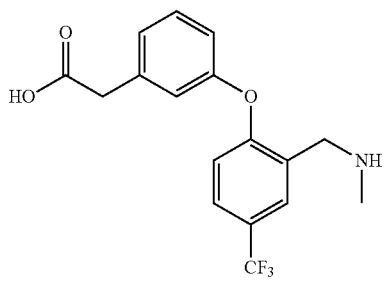 [SMILES: CNCc1cc(C(F)(F)F)ccc1Oc1cccc(CC(=O)O)c1]

Step 1: [3-(2-Methylaminomethyl-4-trifluoromethyl-phenoxy)-phenyl]-acetic acid Prepared according to the procedure described in Example 3, Step 2, using the following starting materials: [3-(2-formyl-4-trifluoromethyl-phenoxy)-phenyl]-acetic acid and methylamine (2M in THF)

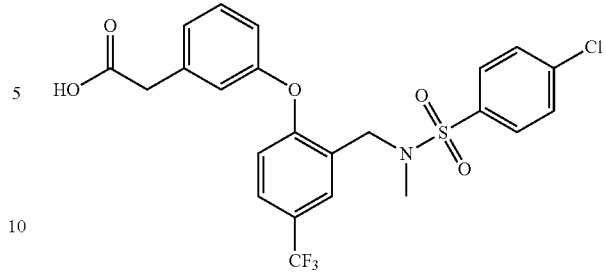

Step 2: [3-(2-{[(4-Chloro-benzenesulfonyl)-methylamino]-methyl}-4-trifluoromethyl-phenoxy)-phenyl]-acetic acid Prepared according to the procedure described in Example 22, Step 1, using the following starting materials: [3-(2-methylaminomethyl-4-trifluoromethyl-phenoxy)-phenyl]-acetic acid and 4-chlorobenzenesulfonyl chloride. M+H=514.

Example 24

Synthesis of [3-(2-{[Methyl-(2-trifluoromethyl-benzenesulfonyl)-amino]-methyl}-4-trifluoromethyl-phenoxy)-phenyl]-acetic acid (Compound 1-24)

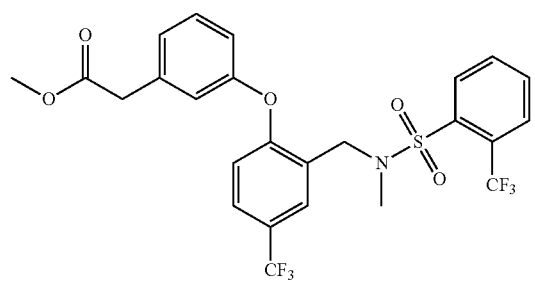 [SMILES: COC(=O)Cc1cccc(Oc2ccc(C(F)(F)F)cc2CN(C)S(=O)(=O)c2ccccc2C(F)(F)F)c1]

Step 1: [3-(2-{[Methyl-(2-trifluoromethyl-benzenesulfonyl)-amino]-methyl}-4-trifluoromethyl-phenoxy)-phenyl]-acetic acid methyl ester Prepared according to the procedure described in Example 22, Step 1, using the following starting materials: [3-(2-methylaminomethyl-4-trifluoromethyl-phenoxy)-phenyl]-acetic acid methyl ester and 2-(trifluoromethyl)benzenesulfonyl chloride.

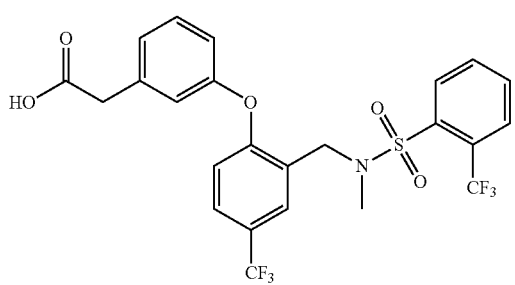 [SMILES: CN(Cc1cc(C(F)(F)F)ccc1Oc1cccc(CC(=O)O)c1)S(=O)(=O)c1ccccc1C(F)(F)F]

Step 2: [3-(2-{[Methyl-(2-trifluoromethyl-benzenesulfonyl)-amino]-methyl}-4-trifluoromethyl-phenoxy)-phenyl]-acetic acid Prepared according to the procedure described in Example 3, Step 4, using the following starting material: [3-(2-{[methyl-(2-trifluoromethyl-benzenesulfonyl)-amino]-methyl}-4-trifluoromethyl-phenoxy)-phenyl]-acetic acid methyl ester. M+H=548.

Example 25

Synthesis of [3-(2-{[(4-Methoxy-benzenesulfonyl)-methyl-amino]-methyl}-4-trifluoromethyl-phenoxy)-phenyl]-acetic acid (Compound 1-25)

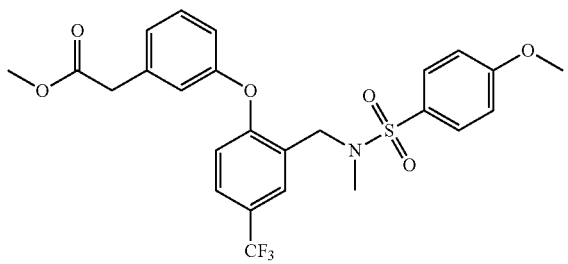

Step 1: [3-(2-{[(4-Methoxy-benzenesulfonyl)-methyl-amino]-methyl}-4-trifluoromethyl-phenoxy)-phenyl]-acetic acid methyl ester Prepared according to the procedure described in Example 22, Step 1, using the following starting materials: [3-(2-methylaminomethyl-4-trifluoromethyl-phenoxy)-phenyl]-acetic acid methyl ester and 4-methoxybenzenesulfonyl chloride.

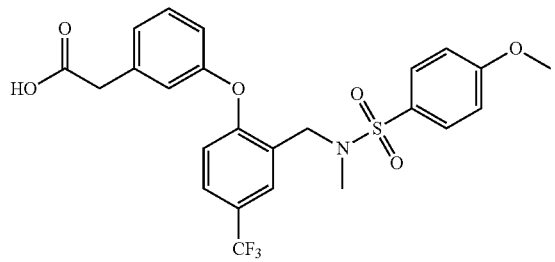 [SMILES: COc1ccc(S(=O)(=O)N(C)Cc2cc(C(F)(F)F)ccc2Oc2cccc(CC(=O)O)c2)cc1]

Step 2: [3-(2-{[(4-Methoxy-benzenesulfonyl)-methyl-amino]-methyl}-4-trifluoromethyl-phenoxy)-phenyl]-acetic acid Prepared according to the procedure described in Example 3, Step 4, using the following starting material: [3-(2-{[(4-methoxy-benzenesulfonyl)-methyl-amino]-methyl}-4-trifluoromethyl-phenoxy)-phenyl]-acetic acid methyl ester. M+H=510.

Example 26

Synthesis of [3-(2-{[Ethyl-(4-methoxy-benzenesulfonyl)-amino]-methyl}-4-trifluoromethyl-phenoxy)-phenyl]-acetic acid (Compound 1-26)

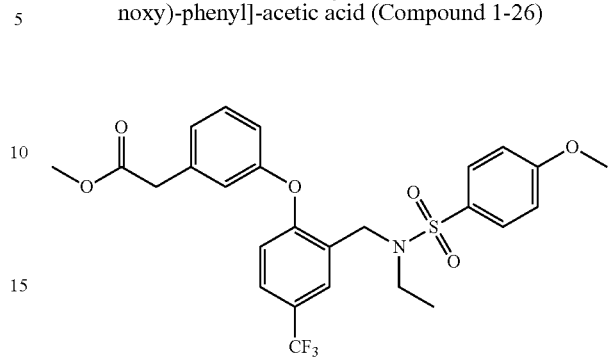

Step 1: [3-(2-{[Ethyl-(4-methoxy-benzenesulfonyl)-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and 4-methoxybenzenesulfonyl chloride.

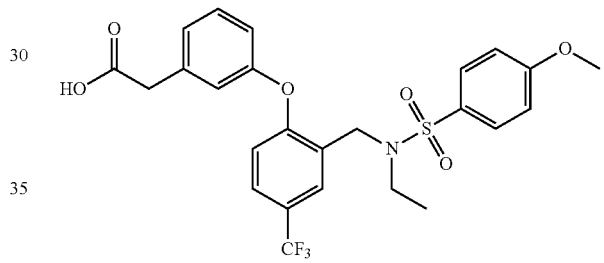

Step 2: [3-(2-{[Ethyl-(4-methoxy-benzenesulfonyl)-amino]-methyl}-4-trifluoromethyl-phenoxy)-phenyl]-acetic acid Prepared according to the procedure described in Example 3, Step 4, using the following starting material: [3-(2-{[ethyl-(4-methoxy-benzenesulfonyl)-amino]-methyl}-4-trifluoromethyl-phenoxy)-phenyl]acetic acid methyl ester. M+H=524.

Example 27

Synthesis of [3-(2-{[Ethyl-(toluene-4-sulfonyl)-amino]-methyl}-4-trifluoromethyl-phenoxy)-phenyl]-acetic acid (Compound 1-27)

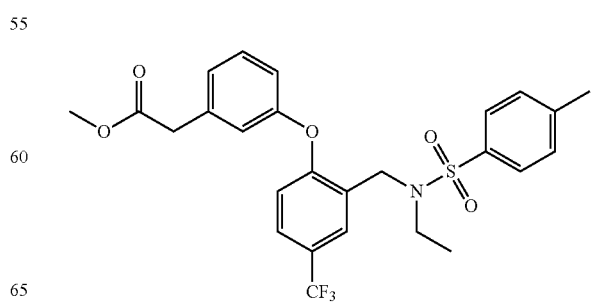

Step 1: [3-(2-{[Ethyl-(toluene-4-sulfonyl)-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and p-toluenesulfonyl chloride.

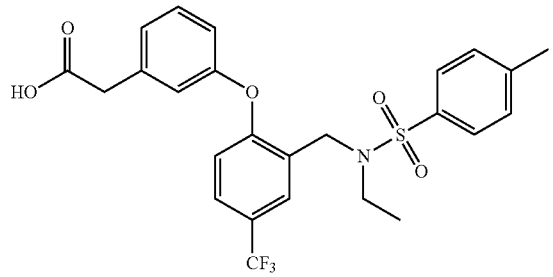 [SMILES: CCN(Cc1cc(C(F)(F)F)ccc1Oc1cccc(CC(=O)O)c1)S(=O)(=O)c1ccc(C)cc1]

Step 2: [3-(2-{[Ethyl-(toluene-4-sulfonyl)-amino]-methyl}-4-trifluoromethyl-phenoxy)-phenyl]-acetic acid Prepared according to the procedure described in Example 3, Step 4, using the following starting material: [3-(2-{[ethyl-(toluene-4-sulfonyl)-amino]-methyl}-4-trifluoromethyl-phenoxy)-phenyl]-acetic acid methyl ester. M+H=508.

Example 28

Synthesis of [3-(2-{[Ethyl-(4-methanesulfonyl-benzenesulfonyl)-amino]-methyl}-4-trifluoromethyl-phenoxy)-phenyl]-acetic acid (Compound 1-28)

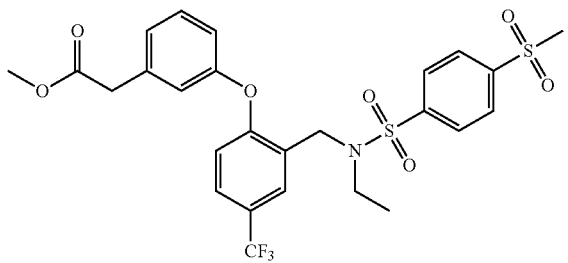

Step 1: [3-(2-{[Ethyl-(4-methanesulfonyl-benzenesulfonyl)-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and 4-methylsulfonylbenzenesulfonyl chloride.

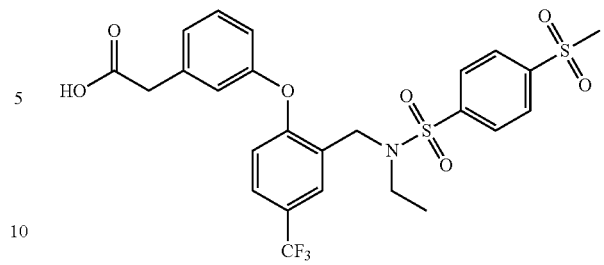

Step 2: [3-(2-{[Ethyl-(4-methanesulfonyl-benzenesulfonyl)-amino]-methyl}-4-trifluoromethyl-phenoxy)-phenyl]-acetic acid Prepared according to the procedure described in Example 3, Step 4, using the following starting material: [3-(2-{[ethyl-(4-methanesulfonyl-benzenesulfonyl)-amino]-methyl}-4-trifluoromethyl-phenoxy)-phenyl]-acetic acid methyl ester. M+H=572.

Example 29

Synthesis of [3-(2-{[(4-Acetyl-benzenesulfonyl)-ethyl-amino]-methyl}-4-trifluoromethyl-phenoxy)-phenyl]-acetic acid (Compound 1-29)

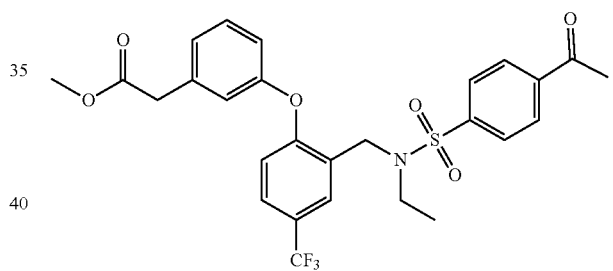

Step 1: [3-(2-{[(4-Acetyl-benzenesulfonyl)-ethyl-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and 4-acetylbenzenesulfonyl chloride.

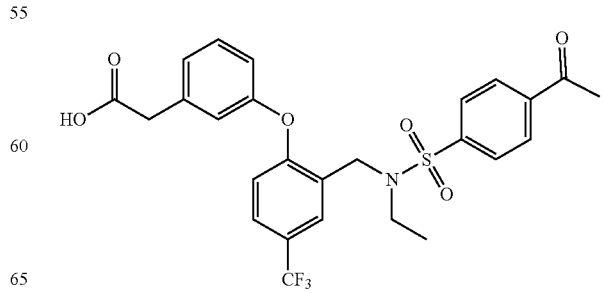

Step 2: [3-(2-{[(4-Acetyl-benzenesulfonyl)-ethyl-amino]-methyl}-4-trifluoromethyl-phenoxy)-phenyl]-acetic acid Prepared according to the procedure described in Example 3, Step 4, using the following starting material: [3-(2-{[(4-acetyl-benzenesulfonyl)-ethyl-amino]-methyl}-4-trifluoromethyl-phenoxy)-phenyl]-acetic acid methyl ester. M+H=536.

Example 30

Synthesis of [3-(2-{[Ethyl-(naphthalene-2-sulfonyl)-amino]-methyl}-4-trifluoromethyl-phenoxy)-phenyl]-acetic acid (Compound 1-30)

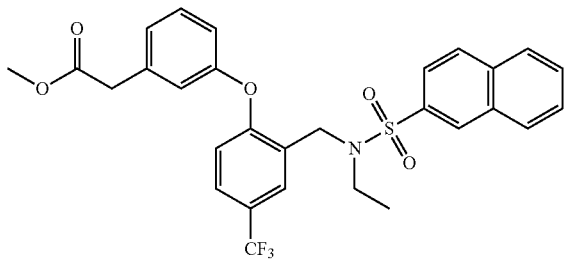 [SMILES: CCN(Cc1cc(C(F)(F)F)ccc1Oc1cccc(CC(=O)OC)c1)S(=O)(=O)c1ccc2ccccc2c1]

Step 1: [3-(2-{[Ethyl-(naphthalene-2-sulfonyl)-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and 2-naphthalenesulfonyl chloride.

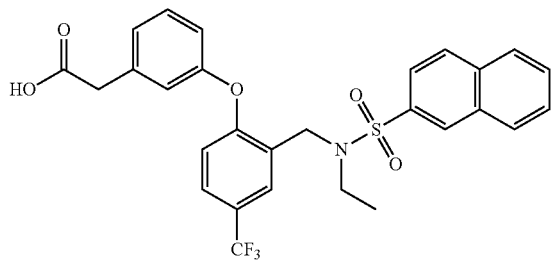 [SMILES: CCN(Cc1cc(C(F)(F)F)ccc1Oc1cccc(CC(=O)O)c1)S(=O)(=O)c1ccc2ccccc2c1]

Step 2: [3-(2-{[Ethyl-(naphthalene-2-sulfonyl)-amino]-methyl}-4-trifluoromethyl-phenoxy)-phenyl]-acetic acid Prepared according to the procedure described in Example 3, Step 4, using the following starting material: [3-(2-{[ethyl-(naphthalene-2-sulfonyl)-amino]-methyl}-4-trifluoromethyl-phenoxy)-phenyl]-acetic acid methyl ester. M+H=544.

Example 31

Synthesis of [3-(2-{[(4-Bromo-benzenesulfonyl)-ethyl-amino]-methyl}-4-trifluoromethyl-phenoxy)-phenyl]-acetic acid (Compound 1-31)

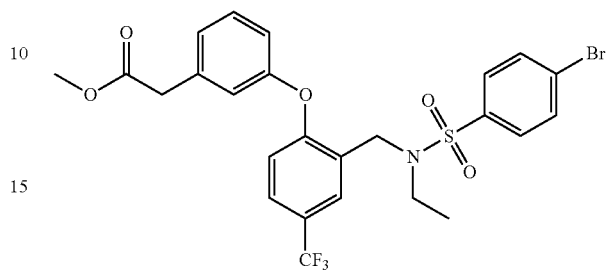

Step 1: [3-(2-{[(4-Bromo-benzenesulfonyl)-ethyl-amino]-methyl}-4-trifluoromethyl-phenoxy)-phenyl]-acetic acid methyl ester Prepared according to the procedure described in Example 22, Step 1, using the following starting materials: [3-(2-ethylaminomethyl-4-trifluoromethyl-phenoxy)-phenyl]-acetic acid methyl ester and 4-bromobenzenesulfonyl chloride.

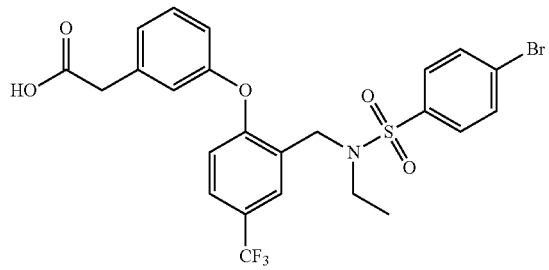 [SMILES: CCN(Cc1cc(C(F)(F)F)ccc1Oc1cccc(CC(=O)O)c1)S(=O)(=O)c1ccc(Br)cc1]

Step 2: [3-(2-{[(4-Bromo-benzenesulfonyl)-ethyl-amino]-methyl}-4-trifluoromethyl-phenoxy)-phenyl]-acetic acid Prepared according to the procedure described in Example 3, Step 4, using the following starting material: [3-(2-{[(4-bromo-benzenesulfonyl)-ethyl-amino]-methyl}-4-trifluoromethyl-phenoxy)-phenyl]-acetic acid methyl ester. M+H=573.

Example 32

Synthesis of [3-(2-{[Ethyl-(4-m-tolylamino-benzenesulfonyl)-amino]-methyl}-4-trifluoromethyl-phenoxy)-phenyl]-acetic acid (Compound 1-32)

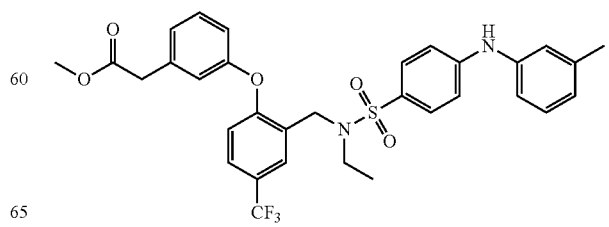

Step 1: [3-(2-{[Ethyl-(4-m-tolylamino-benzenesulfonyl)-amino]-methyl}-4-trifluoromethyl-phenoxy)-phenyl]-acetic acid methyl ester

[3-(2-{[(4-Bromo-benzenesulfonyl)-ethyl-amino]-methyl}-4-trifluoromethyl-phenoxy)-phenyl]-acetic acid methyl ester (0.183 g, 0.31 mmol), m-toluidine (0.04 mL, 0.38 mmol), and 4,5-bis(diphenylphosphino)-9,9-dimethylxanthene (0.009 g, 0.02 mmol) were combined in 1,4-dioxane (3.6 mL). Cesium carbonate (0.505 g, 1.55 mmol) and tris(dibenzylideneacetone)dipalladium (0) (0.028 g, 0.03 mmol) were added, and the mixture was purged with N₂ for 15 minutes and then stirred at 70° C. overnight under N₂. Once no starting material was seen by analytical LCMS, the mixture was filtered through Celite. The filter cake was washed with EtOAc, and the filtrate was concentrated and purified by silica gel chromatography (10-30% EtOAc in hexanes) to give the title compound.

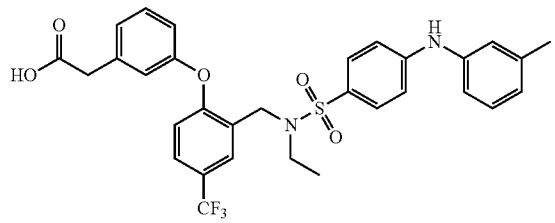

Step 2: [3-(2-{[Ethyl-(4-m-tolylamino-benzenesulfonyl)-amino]-methyl}-4-trifluoromethyl-phenoxy)-phenyl]-acetic acid Prepared according to the procedure described in Example 2, Step 5, using the following starting material: [3-(2-{[ethyl-(4-m-tolylamino-benzenesulfonyl)-amino]-methyl}-4-trifluoromethyl-phenoxy)-phenyl]-acetic acid methyl ester. M+H=599.

Example 33

Synthesis of {3-[2-({Ethyl-[4-(methyl-m-tolyl-amino)-benzenesulfonyl]-amino}-methyl)-4-trifluoromethyl-phenoxy]-phenyl}-acetic acid (Compound 1-33)

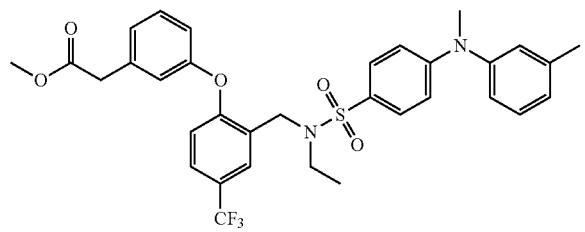

Step 1: {3-[2-({Ethyl-[4-(methyl-m-tolyl-amino)-benzenesulfonyl]-amino}-methyl)-4-trifluoromethyl-phenoxy]-phenyl}-acetic acid methyl ester To [3-(2-{[ethyl-(4-m-tolylamino-benzenesulfonyl)-amino]-methyl}-4-trifluoromethyl-phenoxy)-phenyl]-acetic acid methyl ester (0.080 g, 0.13 mmol) in THF (2 mL) under N₂ was added sodium hydride (60% in mineral oil; 0.016 g, 0.39 mmol), and the mixture was stirred for 30 minutes at room temperature. Iodomethane (0.02 mL, 0.39 mmol) was added, and the reaction was stirred at room temperature for 4 hours. Analytical LCMS indicated that some starting material remained, so additional sodium hydride (60% in mineral oil; 0.008 g, 0.20 mmol)) and iodomethane (0.01 mL, 0.20=01) was added, and the reaction was stirred for 30 minutes and then taken directly to the hydrolysis step as a solution in THF.

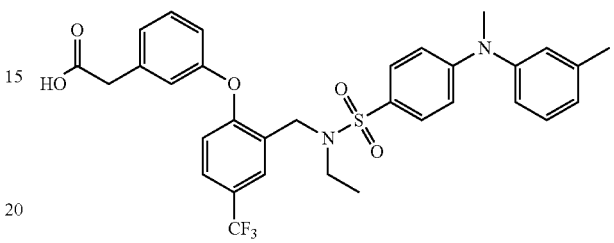

Step 2: {3-[2-({Ethyl-[4-(methyl-m-tolyl-amino)-benzenesulfonyl]-amino}-methyl)-4-trifluoromethyl-phenoxy]-phenyl}-acetic acid To a solution of crude {3-[2-({ethyl-[4-(methyl-m-tolyl-amino)-benzenesulfonyl]-amino}-methyl)-4-trifluoromethyl-phenoxy]-phenyl}-acetic acid methyl ester (0.013 mmol) in THF was added aqueous lithium hydroxide (3 mL), and the reaction was stirred overnight at room temperature. The mixture was acidified with 1N aqueous HCl and extracted with EtOAc, and the combined organic layers were dried and concentrated. The residue was purified by preparative HPLC to give the title compound. M+H=613.

Example 34

Synthesis of (3-{2-[(Acetyl-ethyl-amino)-methyl]-4-trifluoromethyl-phenoxy}-4-methoxy-phenyl)-acetic acid (Compound 1-34)

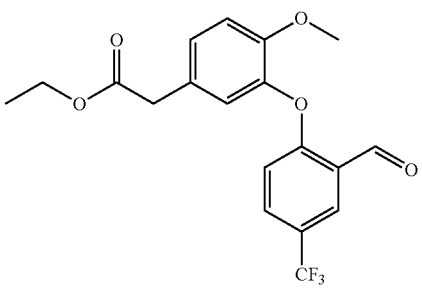 [SMILES: CCOC(=O)Cc1ccc(OC)c(Oc2ccc(C(F)(F)F)cc2C=O)c1]

Step 1: [3-(2-Formyl-4-trifluoromethyl-phenoxy)-4-methoxy-phenyl]-acetic acid ethyl ester Prepared according to the procedure described in Example 2, Step 2, using the following starting materials: (3-hydroxy-4-methoxy-phenyl)-acetic acid ethyl ester and 2-fluoro-5-(trifluoromethyl)benzaldehyde.

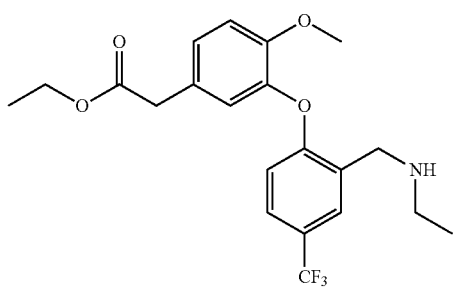 [SMILES: CCNCc1cc(C(F)(F)F)ccc1Oc1cc(CC(=O)OCC)ccc1OC]

Step 2: [3-(2-Ethylaminomethyl-4-trifluoromethyl-phenoxy)-4-methoxy-phenyl]-acetic acid ethyl ester Prepared according to the procedure described in Example 3, Step 2, using the following starting materials: [3-(2-formyl-4-trifluoromethyl-phenoxy)-4-methoxy-phenyl]-acetic acid ethyl ester and ethylamine (2M in THF).

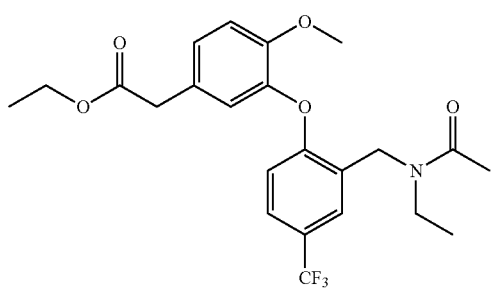 [SMILES: CCOC(=O)Cc1ccc(OC)c(Oc2ccc(C(F)(F)F)cc2CN(CC)C(C)=O)c1]

Step 3: (3-{2-[(Acetyl-ethyl-amino)-methyl]-4-trifluoromethyl-phenoxy}-4-methoxy-phenyl)-acetic acid ethyl ester Prepared according to the procedure described in Example 3, Step 3, using the following starting materials: [3-(2-ethylaminomethyl-4-trifluoromethyl-phenoxy)-4-methoxy-phenyl]-acetic acid ethyl ester and acetyl chloride.

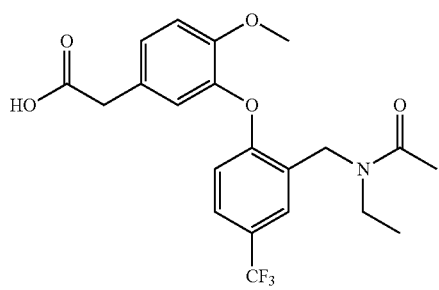 [SMILES: CCN(Cc1cc(C(F)(F)F)ccc1Oc1cc(CC(=O)O)ccc1OC)C(C)=O]

Step 4: (3-{2-[(Acetyl-ethyl-amino)-methyl]-4-trifluoromethyl-phenoxy}-4-methoxy-Phenyl)-acetic acid Prepared according to the procedure described in Example 3, Step 4, using the following starting material: (3-{2-[(acetyl-ethyl-amino)-methyl]-4-trifluoromethyl-phenoxy}-4-methoxy-phenyl)-acetic acid ethyl ester. M+H=526.

Example 35

Synthesis of (3-{2-[(Acetyl-benzyl-amino)-methyl]-4-trifluoromethyl-phenoxy}-4-methoxy-phenyl)-acetic acid (Compound 1-35)

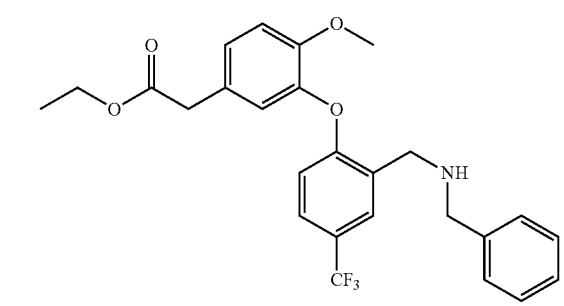 [SMILES: CCOC(=O)Cc1ccc(OC)c(Oc2ccc(C(F)(F)F)cc2CNCc2ccccc2)c1]

Step 1: {3-[2-(Benzylamino-methyl)-4-trifluoromethyl-phenoxy]-4-methoxy-phenyl}-acetic acid ethyl ester Prepared according to the procedure described in Example 3, Step 3, using the following starting materials: [3-(2-formyl-4-trifluoromethyl-phenoxy)-4-methoxy-phenyl]-acetic acid ethyl ester and benzylamine.

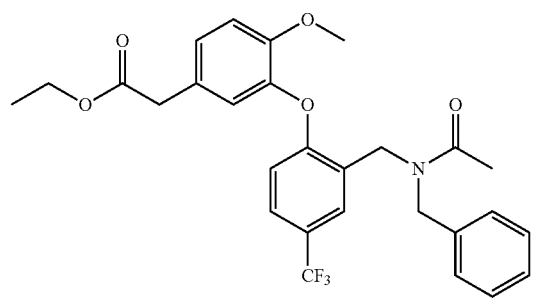 [SMILES: CCOC(=O)Cc1ccc(OC)c(Oc2ccc(C(F)(F)F)cc2CN(Cc2ccccc2)C(C)=O)c1]

Step 2: (3-{2-[(Acetyl-benzyl-amino)-methyl]-4-trifluoromethyl-phenoxy}-4-methoxy-phenyl)-acetic acid ethyl ester Prepared according to the procedure described in Example 3, Step 3, using the following starting materials: {3-[2-(benzylamino-methyl)-4-trifluoromethyl-phenoxy]-4-methoxy-phenyl}-acetic acid ethyl ester and acetyl chloride.

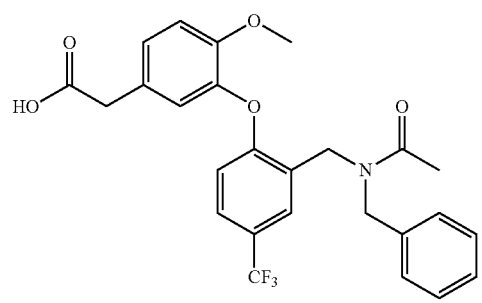 [SMILES: COc1ccc(CC(=O)O)cc1Oc1ccc(C(F)(F)F)cc1CN(Cc1ccccc1)C(C)=O]

Step 3: (3-{2-[(Acetyl-benzyl-amino)-methyl]-4-trifluoromethyl-phenoxy}-4-methoxy-phenyl)-acetic acid Prepared according to the procedure described in Example 3, Step 4, using the following starting material: (3-{2-[(acetyl-benzyl-amino)-methyl]-4-trifluoromethyl-phenoxy}-4-methoxy-phenyl)-acetic acid ethyl ester. M+H=488.

Example 36

Synthesis of (3-{2-[(Ethyl-methoxycarbonyl-amino)-methyl]-4-trifluoromethyl-phenoxy}-4-methoxy-phenyl)-acetic acid (Compound 1-36)

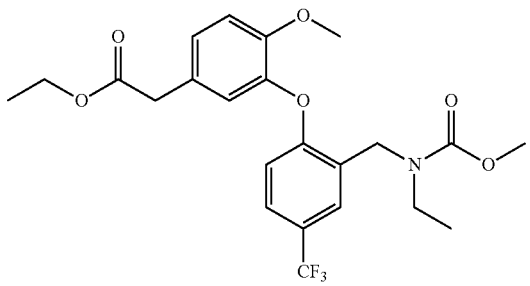 [SMILES: CCOC(=O)Cc1ccc(OC)c(Oc2ccc(C(F)(F)F)cc2CN(CC)C(=O)OC)c1]

Step 1: (3-{2-[(Ethyl-methoxycarbonyl-amino)-methyl]-4-trifluoromethyl-phenoxy}-4-methoxy-phenyl)-acetic acid ethyl ester Prepared according to the procedure described in Example 3, Step 3, using the following starting materials: [3-(2-ethylaminomethyl-4-trifluoromethyl-phenoxy)-4-methoxy-phenyl]-acetic acid ethyl ester and methyl chloroformate.

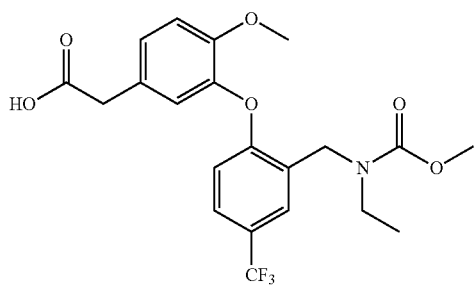 [SMILES: CCN(Cc1cc(C(F)(F)F)ccc1Oc1cc(CC(=O)O)ccc1OC)C(=O)OC]

Step 2: (3-{2-[(Ethyl-methoxycarbonyl-amino)-methyl]-4-trifluoromethyl-phenoxy}-4-methoxy-phenyl)-acetic acid Prepared according to the procedure described in Example 3, Step 4, using the following starting material: (3-{2-[(ethyl-methoxycarbonyl-amino)-methyl]-4-trifluoromethyl-phenoxy}-4-methoxy-phenyl)-acetic acid ethyl ester. M+H=442.

Example 37

Synthesis of (3-{2-[(Benzyl-methoxycarbonyl-amino)-methyl]-4-trifluoromethyl-phenoxy}-4-methoxy-phenyl)-acetic acid (Compound 1-37)

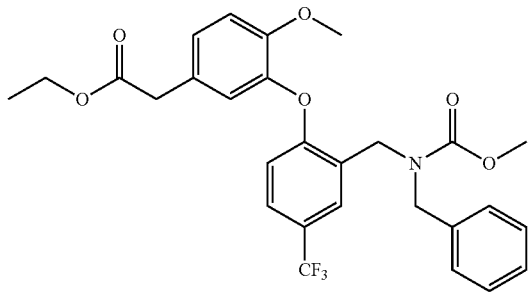

Step 1: (3-{2-[(Benzyl-methoxycarbonyl-amino)-methyl]-4-trifluoromethyl-phenoxy}-4-methoxy-phenyl)-acetic acid ethyl ester Prepared according to the procedure described in Example 3, Step 3, using the following starting materials: {3-[2-(benzylamino-methyl)-4-trifluoromethyl-phenoxy]-4-methoxy-phenyl}-acetic acid ethyl ester and methyl chloroformate.

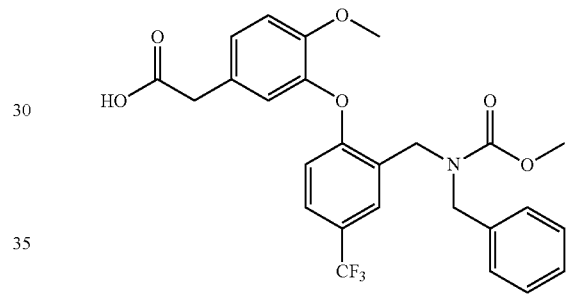

Step 2: (3-{2-[(Benzyl-methoxycarbonyl-amino)-methyl]-4-trifluoromethyl-phenoxy}-4-methoxy-phenyl)-acetic acid Prepared according to the procedure described in Example 3, Step 4, using the following starting material: (3-{2-[(benzyl-methoxycarbonyl-amino)-methyl]-4-trifluoromethyl-phenoxy}-4-methoxy-phenyl)-acetic acid ethyl ester. M+H=504.

Example 38

Synthesis of [3-(4-Acetylamino-2-{[methoxycarbonyl-((S)-1-methyl-2-phenyl-ethyl)-amino]-methyl}-phenoxy)-phenyl]-acetic acid (Compound 1-38)

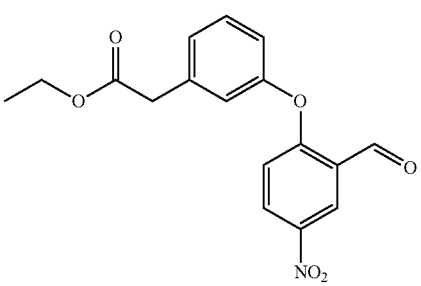 [SMILES: CCOC(=O)Cc1cccc(Oc2ccc([N+](=O)[O-])cc2C=O)c1]

Step 1: [3-(2-Formyl-4-nitro-phenoxy)-phenyl]-acetic acid ethyl ester

Prepared according to the procedure described in Example 2, Step 2, using the following starting materials: (3-hydroxyphenyl)-acetic acid ethyl ester and 2-fluoro-5-nitrobenzaldehyde.

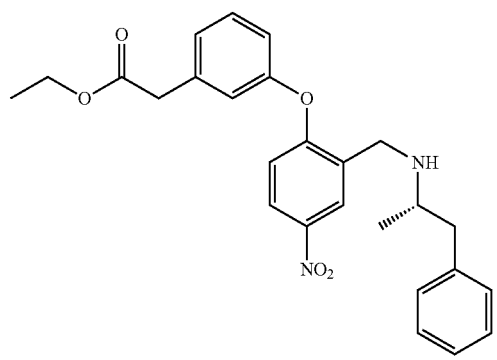 [SMILES: CCOC(=O)Cc1cccc(Oc2ccc([N+](=O)[O-])cc2CN[C@@H](C)Cc2ccccc2)c1]

Step 2: (3-{2-[((S)-1-Methyl-2-phenyl-ethylamino)-methyl]-4-nitro-phenoxy}-phenyl)-acetic acid ethyl ester Prepared according to the procedure described in Example 2, Step 3, using the following starting materials: [3-(2-formyl-4-nitro-phenoxy)-phenyl]-acetic acid ethyl ester and D-amphetamine sulfate.

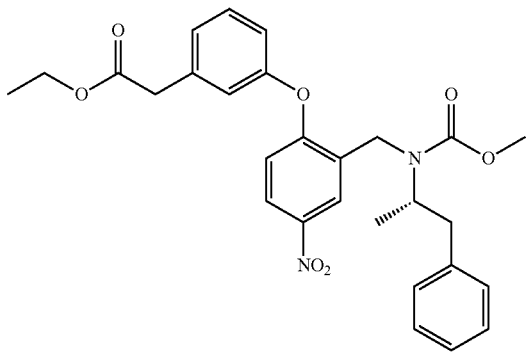 [SMILES: CCOC(=O)Cc1cccc(Oc2ccc([N+](=O)[O-])cc2CN(C(=O)OC)[C@@H](C)Cc2ccccc2)c1]

Step 3: [3-(2-{[Methoxycarbonyl-((S)-1-methyl-2-phenyl-ethyl)-amino]-methyl}-4-nitro-phenoxy)-phenyl]-acetic acid ethyl ester Prepared according to the procedure described in Example 3, Step 3, using the following starting materials: (3-{2-[((S)-1-methyl-2-phenyl-ethylamino)-methyl]-4-nitro-phenoxy}-phenyl)-acetic acid ethyl ester and methyl chloroformate.

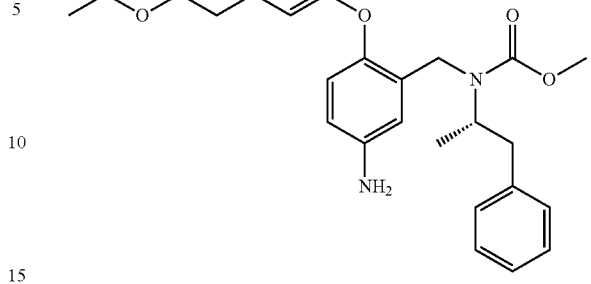

Step 4: [3-(4-Amino-2-{[methoxycarbonyl-((S)-1-methyl-2-phenyl-ethyl)-amino]-methyl}-phenoxy)-phenyl]-acetic acid ethyl ester

[3-(2-{[Methoxycarbonyl-((S)-1-methyl-2-phenyl-ethyl)-amino]-methyl}-4-nitro-phenoxy)-phenyl]-acetic acid ethyl ester (0.174 g, 0.34 mmol) and palladium on carbon (10%; 0.060 g) were combined in EtOH (20 mL) and stirred under H$_2$ in a Parr apparatus overnight at room temperature. Once no starting material was seen by analytical LCMS, the mixture was filtered through Celite, and the filter cake was washed with EtOH. The filtrate was concentrated to give the title compound.

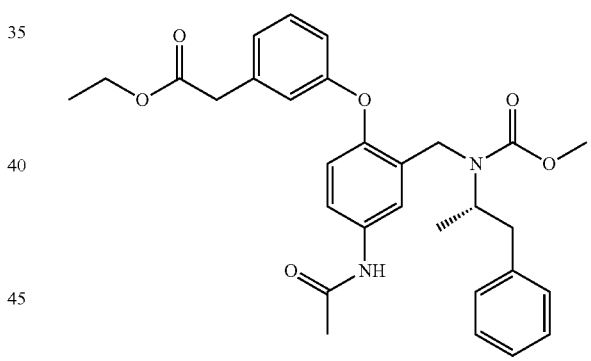

Step 5: [3-(4-Acetylamino-2-{[methoxycarbonyl-((S)-1-methyl-2-phenyl-ethyl)-amino]-methyl}-phenoxy)-phenyl]-acetic acid ethyl ester To [3-(4-amino-2-{[methoxycarbonyl-((S)-1-methyl-2-phenyl-ethyl)-amino]-methyl}-phenoxy)-phenyl]-acetic acid ethyl ester (0.156 g, 0.33 mmol) and triethylamine (0.07 mL, 0.49 mmol) in CH$_2$Cl$_2$ (2 mL) was added acetyl chloride (0.02 mL, 0.33 mmol), and the reaction was stirred at room temperature for 2 minutes. LCMS analysis showed some starting material remained, so additional acetyl chloride (0.01 mL) was added, and the reaction was stirred for 30 minutes, until no starting material was seen by analytical LCMS. The mixture was worked-up with CH$_2$Cl$_2$ and H$_2$O, and the organic layer was dried and concentrated to give the title compound.

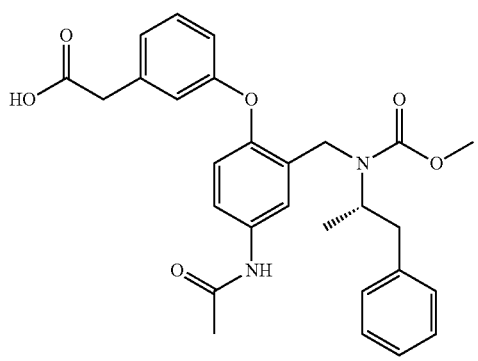 [SMILES: COC(=O)N(Cc1cc(NC(C)=O)ccc1Oc1cccc(CC(=O)O)c1)[C@@H](C)Cc1ccccc1]

Step 6: [3-(4-Acetylamino-2-{[methoxycarbonyl-((S)-1-methyl-2-phenyl-ethyl)-amino]-methyl}-phenoxy)-phenyl]-acetic acid To [3-(4-acetylamino-2-{[methoxycarbonyl-((S)-1-methyl-2-phenyl-ethyl)-amino]-methyl}-phenoxy)-phenyl]-acetic acid ethyl ester (0.048 g, 0.09 mmol) in THF (2 mL) was added 1N aqueous lithium hydroxide (2 mL), and the reaction was stirred over the weekend at room temperature. Once no starting material was seen by analytical LCMS, the mixture was acidified with 1N aqueous HCl and extracted with EtOAc. The combined organic layers were dried and concentrated, and the residue was purified by preparative HPLC and converted to the free base with saturated aqueous NaHCO$_3$ to give the title compound. M+H=491.

Example 39

Synthesis of [3-(4-(Acetyl-methyl-amino)-2-{[methoxycarbonyl-((S)-1-methyl-2-phenyl-ethyl)-amino]-methyl}-phenoxy)-phenyl]-acetic acid (Compound 1-39) and 2-[3-(4-(Acetyl-methyl-amino)-2-{[methoxycarbonyl-((S)-1-methyl-2-phenyl-ethyl)-amino]-methyl}-phenoxy)-phenyl]-propionic acid (Compound 1-40)

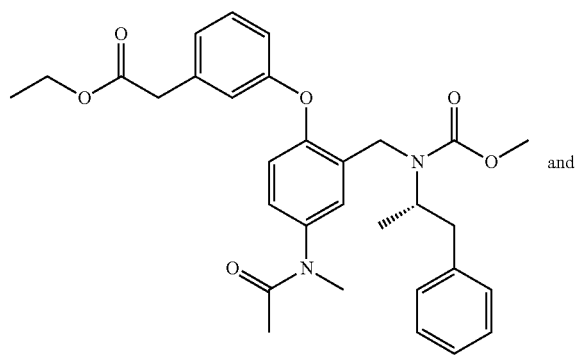

and

-continued

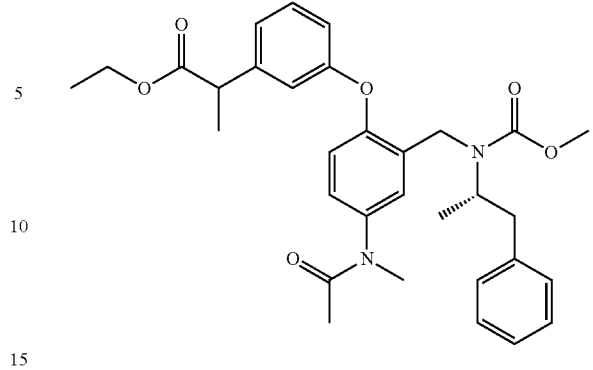

Step 1: [3-(4-(Acetyl-methyl-amino)-2-{[methoxycarbonyl-((S)-1-methyl-2-phenyl-ethyl)-amino]-methyl}-phenoxy)-phenyl]-acetic acid ethyl ester and 2-[3-(4-(Acetyl-methyl-amino)-2-{[methoxycarbonyl-((S)-1-methyl-2-phenyl-ethyl)-amino]-methyl}-phenoxy)-phenyl]-propionic acid ethyl ester To [3-(4-acetylamino-2-{[methoxycarbonyl-((S)-1-methyl-2-phenyl-ethyl)-amino]-methyl}-phenoxy)-phenyl]-acetic acid ethyl ester (0.096 g, 0.19 mmol) in THF (2 mL) at 0° C. was added sodium hydride (60% in mineral oil; 0.011 g, 0.28 mmol), and the mixture was stirred for 20 minutes. Iodomethane (0.02 mL, 0.28 mmol) was added at 0° C., and the reaction was stirred for 1 hour. Analytical LCMS indicated that the starting material and methylated product had been hydrolyzed to the corresponding acid, and so additional sodium hydride (60% in mineral oil; 0.011 g, 0.28 mmol) and iodomethane (0.02 mL, 0.28 mmol) were added to push the reaction to completion. Once only methylated products were seen by analytical LCMS, the mixture was worked-up with saturated aqueous NH$_4$Cl and EtOAc, and the organic layer was dried and concentrated to give a mixture of the title compounds.

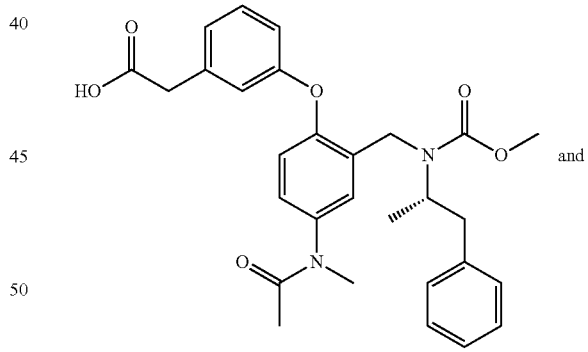

and

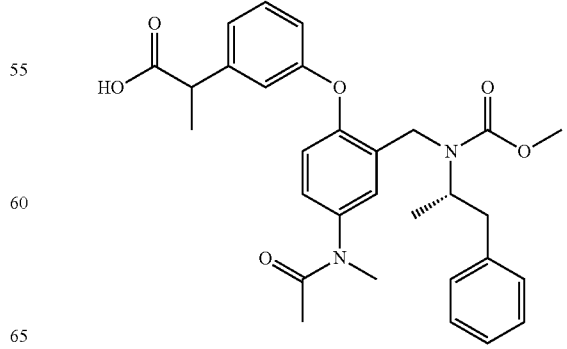

Step 2: [3-(4-(Acetyl-methyl-amino)-2-{[methoxy-carbonyl-((S)-1-methyl-2-phenyl-ethyl)-amino]-methyl}-phenoxy)-phenyl]-acetic acid and 2-[3-(4-(Acetyl-methyl-amino)-2-{[methoxycarbonyl-((S)-1-methyl-2-phenyl-ethyl)-amino]-methyl}-phenoxy)-phenyl]-propionic acid A mixture of [3-(4-(acetyl-methyl-amino)-2-{[methoxy-carbonyl-((S)-1-methyl-2-phenyl-ethyl)-amino]-methyl}-phenoxy)-phenyl]-acetic acid ethyl ester and 2-[3-(4-(acetyl-methyl-amino)-2-{[methoxycarbonyl-((S)-1-methyl-2-phenyl-ethyl)-amino]-methyl}-phenoxy)-phenyl]-propionic acid ethyl ester in THF (2 mL) were treated with 1N aqueous lithium hydroxide (2 mL) at room temperature over the weekend. Once no starting material was seen by analytical LCMS, the mixture was acidified with 1N aqueous HCl and extracted with EtOAc. The combined organic layers were dried and concentrated, and the residue was purified by preparative HPLC to give the title compounds. M+H for Compound 1-39=505. M+H for Compound 1-40=519.

Example 40

Synthesis of [3-(4-Methanesulfonylamino-2-{[methoxycarbonyl-((S)-1-methyl-2-phenyl-ethyl)amino]-methyl}-phenoxy)-phenyl]-acetic acid (Compound 1-41)

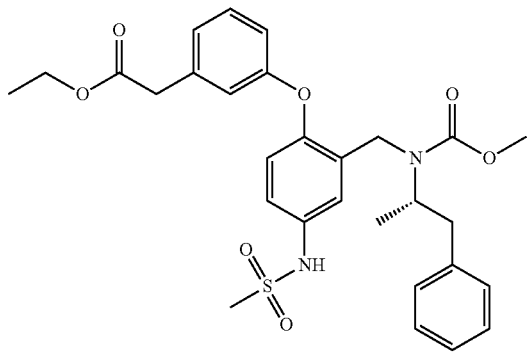 [SMILES: CCOC(=O)Cc1cccc(Oc2ccc(NS(C)(=O)=O)cc2CN(C(=O)OC)[C@@H](C)Cc2ccccc2)c1]

Step 1: [3-(4-Methanesulfonylamino-2-{[methoxy-carbonyl-((S)-1-methyl-2-phenyl-ethyl)-amino]-methyl}-phenoxy)-phenyl]-acetic acid ethyl ester To [3-(4-amino-2-{[methoxycarbonyl-((S)-1-methyl-2-phenyl-ethyl)-amino]-methyl}-phenoxy)-phenyl]-acetic acid ethyl ester (0.144 g, 0.3 mmol) and methanesulfonyl chloride (0.02 mL, 0.3 mmol) in CH$_2$Cl$_2$ (2 mL) was added triethylamine (0.08 mL, 0.6 mmol), and the reaction was stirred at room temperature for 1 hour. The mixture was worked-up with CH$_2$Cl$_2$ and H$_2$O, and the organic layer was dried and concentrated. The residue was purified by silica gel chromatography (20-40% EtOAc in hexanes) to give the title compound.

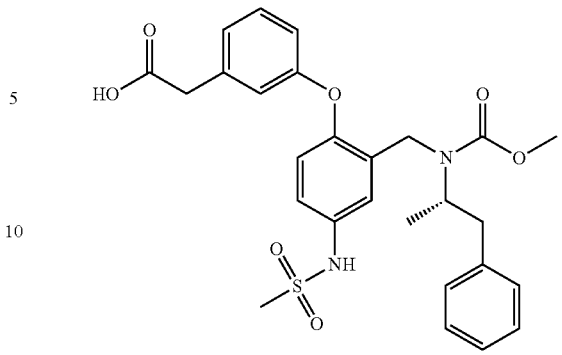

Step 2: [3-(4-Methanesulfonylamino-2-{[methoxy-carbonyl-((S)-1-methyl-2-phenyl-ethyl)-amino]-methyl}-phenoxy)-phenyl]-acetic acid Prepared according to the procedure described in Example 2, Step 5, using the following starting material: [3-(4-methanesulfonylamino-2-{[methoxycarbonyl-((S)-1-methyl-2-phenyl-ethyl)-amino]-methyl}-phenoxy)-phenyl]-acetic acid ethyl ester. M+H=527.

Example 41

Synthesis of [3-(4-(Methanesulfonyl-methyl-amino)-2-{[methoxycarbonyl-((S)-1-methyl-2-phenyl-ethyl)-amino]-methyl}-phenoxy)-phenyl]-acetic acid (Compound 1-42) and 2-[3-(4-(Methanesulfonyl-methyl-amino)-2-{[methoxycarbonyl-((S)-1-methyl-2-phenyl-ethyl)-amino]-methyl}-phenoxy)-phenyl]-propionic acid (Compound 1-43)

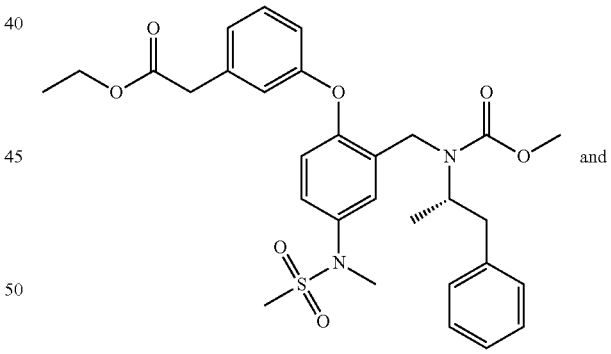

and

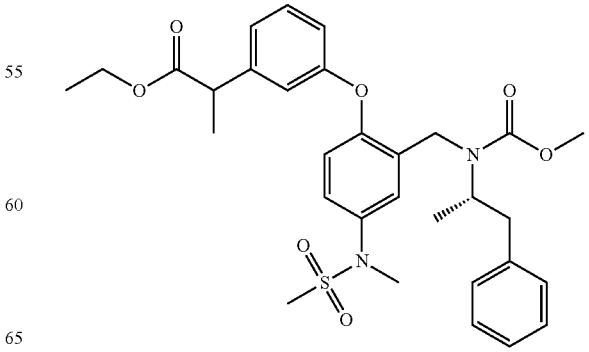

Step 1: [3-(4-(Methanesulfonyl-methyl-amino)-2-{[methoxycarbonyl-((S)-1-methyl-2-phenyl-ethyl)-amino]-methyl}-phenoxy)-phenyl]-acetic acid ethyl ester and 2-[3-(4-(Methanesulfonyl-methyl-amino)-2-{[methoxycarbonyl-((S)-1-methyl-2-phenyl-ethyl)-amino]-methyl}-phenoxy)-phenyl]-propionic acid ethyl ester Prepared according to the procedure described in Example 39, Step 1, using the following starting materials: [3-(4-Methanesulfonylamino-2-{[methoxycarbonyl-((S)-1-methyl-2-phenyl-ethyl)-amino]-methyl}-phenoxy)-phenyl]-acetic acid ethyl ester and iodomethane.

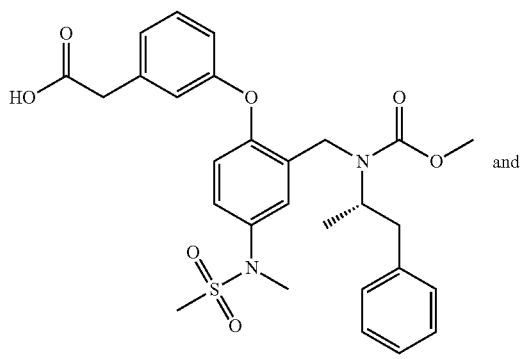

and

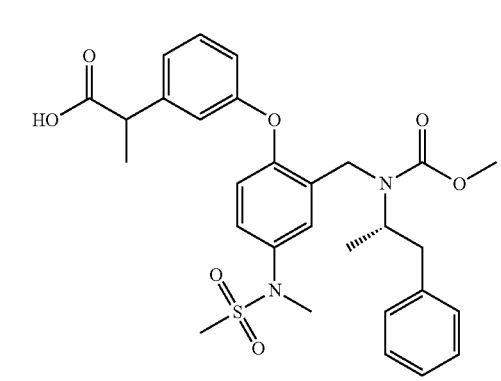 [SMILES: COC(=O)N(Cc1cc(NS(C)(=O)=O)ccc1Oc1cccc(CC(=O)O)c1)[C@@H](C)Cc1ccccc1]

Step 2: [3-(4-(Methanesulfonyl-methyl-amino)-2-{[methoxycarbonyl-((S)-1-methyl-2-phenyl-ethyl)-amino]-methyl}-phenoxy)-phenyl]-acetic acid and 2-[3-(4-(Methanesulfonyl-methyl-amino)-2-{[methoxycarbonyl-((S)-1-methyl-2-phenyl-ethyl)-amino]-methyl}-phenoxy)-phenyl]-propionic acid Prepared according to the procedure described in Example 39, Step 2, using the following starting materials: a mixture of [3-(4-(methanesulfonyl-methyl-amino)-2-{[methoxycarbonyl-((S)-1-methyl-2-phenyl-ethyl)-amino]-methyl}-phenoxy)-phenyl]-acetic acid ethyl ester and 2-[3-(4-(methanesulfonyl-methyl-amino)-2-{[methoxycarbonyl-((S)-1-methyl-2-phenyl-ethyl)-amino]-methyl}-phenoxy)-phenyl]-propionic acid ethyl ester. M+H for Compound 1-42=541. M+H for Compound 1-43=555.

Example 42

Synthesis of {3-[2-[(Benzyloxycarbonyl-ethyl-amino)-methyl]-4-(4-chloro-benzoylamino)-phenoxy]-4-methoxy-phenyl}-acetic acid (Compound 1-44)

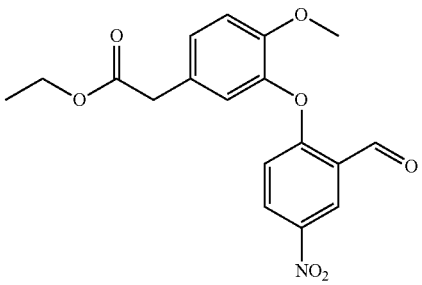

Step 1: [3-(2-Formyl-4-nitro-phenoxy)-4-methoxy-phenyl]-acetic acid ethyl ester 2-Fluoro-5-nitrobenzaldehyde (8.8 g, 52 mmol), (3-hydroxy-4-methoxy-phenyl)-acetic acid ethyl ester (10.0 g, 48 mmol), and potassium carbonate (10.0 g, 69 mmol) were combined in 1,4-dioxane (150 mL), and the reaction was stirred at 100° C. for 24 hours. The mixture was worked up to give the title compound.

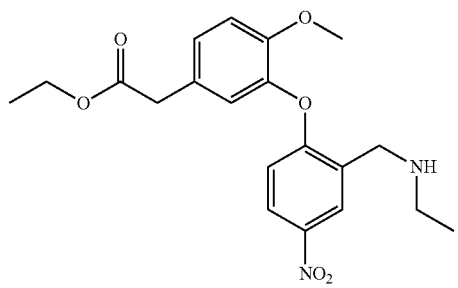 [SMILES: CCNCc1cc([N+](=O)[O-])ccc1Oc1cc(CC(=O)OCC)ccc1OC]

Step 2: [3-(2-Ethylaminomethyl-4-nitro-phenoxy)-4-methoxy-phenyl]-acetic acid ethyl ester

[3-(2-Formyl-4-nitro-phenoxy)-4-methoxy-phenyl]-acetic acid ethyl ester (1.0 g, 2.79 mmol), ethylamine (2M in THF; 2.8 mL, 5.6 mmol), and sodium cyanoborohydride (0.26 g, 4.2 mmol) were combined in CH$_2$Cl$_2$ (30 mL), and the reaction was stirred at room temperature for 3 hours. After work-up, the mixture was concentrated to give the title compound.

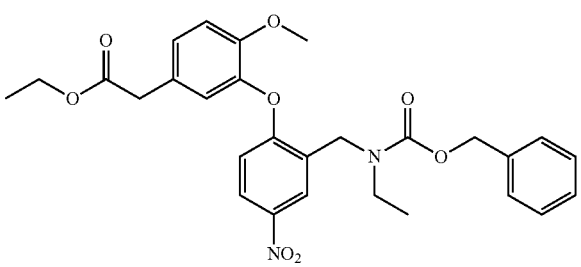 [SMILES: CCOC(=O)Cc1ccc(OC)c(Oc2ccc([N+](=O)[O-])cc2CN(CC)C(=O)OCc2ccccc2)c1]

Step 3: (3-{2-[(Benzyloxycarbonyl-ethyl-amino)-methyl]-4-nitro-phenoxy}-4-methoxy-phenyl)-acetic acid ethyl ester To [3-(2-ethylaminomethyl-4-nitro-phenoxy)-4-methoxy-phenyl]-acetic acid ethyl ester (0.5 g, 1.29 mmol) in CH$_2$Cl$_2$ (20 mL) was added triethylamine (1 mL, 7.17 mmol), followed by benzyl chloroformate (0.25 g, 1.5 mmol), and the reaction was stirred at room temperature for 30 minutes. After work-up, the crude material was purified by silica gel chromatography (0-40% EtOAc in hexanes) to give the title compound.

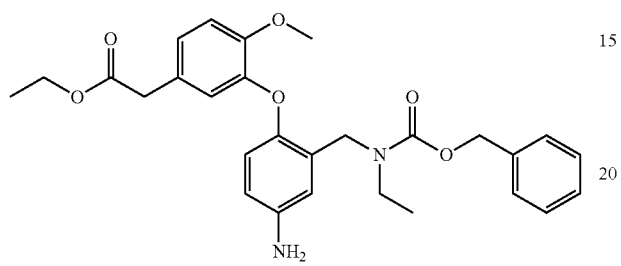

Step 4: (3-{4-Amino-2-[(benzyloxycarbonyl-ethyl-amino)-methyl]-phenoxy}-4-methoxy-phenyl)-acetic acid ethyl ester (3-{2-[(Benzyloxycarbonyl-ethyl-amino)-methyl]-4-nitro-phenoxy}-4-methoxy-phenyl)-acetic acid ethyl ester (0.1 g, 0.19 mmol), 1,1-dimethylhydrazine (0.1 g, 1.3 mmol), ferric chloride (0.01 g), and DARCO (0.05 g) were combined in EtOH (5 mL), and the reaction was stirred at 65° C. until complete. The mixture was worked up to give the title compound.

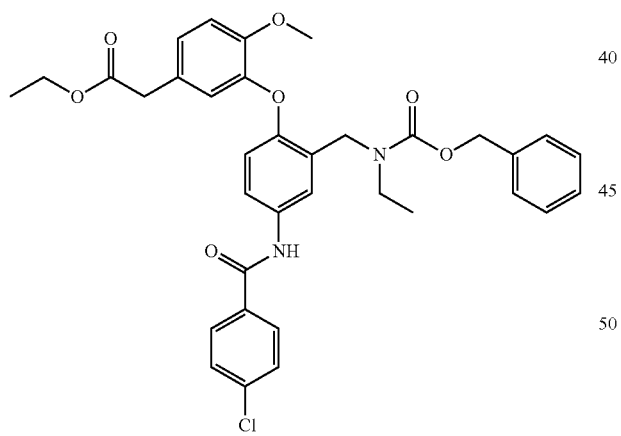

Step 5: {3-[2-[(Benzyloxycarbonyl-ethyl-amino)-methyl]-4-(4-chloro-benzoylamino)-phenoxy]-4-methoxy-phenyl}-acetic acid ethyl ester (3-{4-Amino-2-[(benzyloxycarbonyl-ethyl-amino)-methyl]-phenoxy}-4-methoxy-phenyl)-acetic acid ethyl ester (0.1 g, 0.19 mmol), 4-chlorobenzoyl chloride (0.1 g, 0.57 mmol), and triethylamine (0.5 mL, 3.6 mmol) were combined in CH$_2$Cl$_2$ (10 mL) and stirred at room temperature for 20 minutes. The mixture was concentrated to give the title compound.

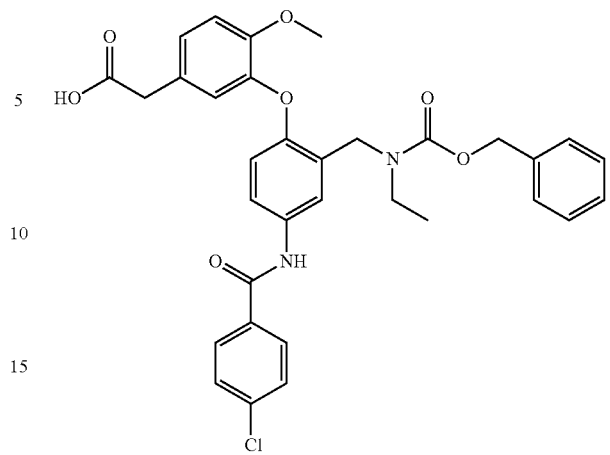

Step 6: {3-[2-[(Benzyloxycarbonyl-ethyl-amino)-methyl]-4-(4-chloro-benzoylamino)-phenoxy]-4-methoxy-phenyl}-acetic acid To a solution of {3-[2-[(benzyloxycarbonyl-ethyl-amino)-methyl]-4-(4-chloro-benzoylamino)-phenoxy]-4-methoxy-phenyl}-acetic acid ethyl ester (0.18 mmol) in MeOH and H$_2$O was added lithium hydroxide (0.100 g, 2.4 mmol), and the reaction was stirred at 60° C. for 20 minutes. After work-up, the crude material was purified by preparative HPLC to give the title compound. M+H=603.

Example 43

Synthesis of {3-[2-[(Acetyl-ethyl-amino)-methyl]-4-(2,2-dimethyl-propionylamino)-phenoxy]-4-methoxy-phenyl}-acetic acid (Compound 1-45)

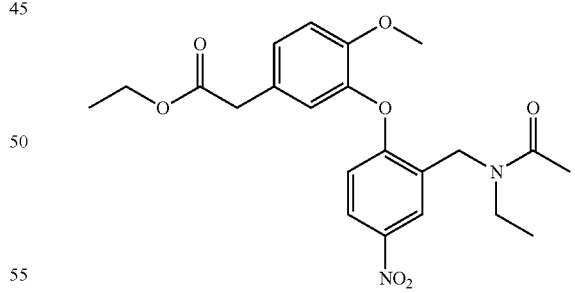

Step 1: (3-{2-[(Acetyl-ethyl-amino)-methyl]-4-nitro-phenoxy}-4-methoxy-phenyl)-acetic acid ethyl ester Prepared according to the procedure described in Example 42, Step 3, using the following starting materials: [3-(2-ethylaminomethyl-4-nitro-phenoxy)-4-methoxy-phenyl]-acetic acid ethyl ester and acetyl chloride.

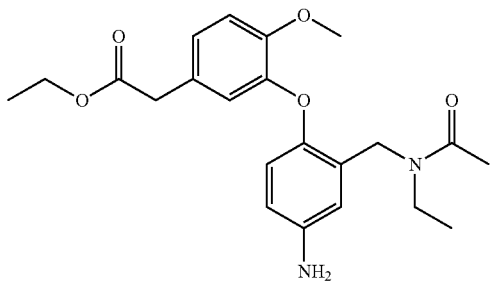 [SMILES: CCOC(=O)Cc1ccc(OC)c(Oc2ccc([N+](=O)[O-])cc2CN(CC)C(C)=O)c1]

Step 2: (3-{2-[(Acetyl-ethyl-amino)-methyl]-4-amino-phenoxy}-4-methoxy-phenyl)-acetic acid ethyl ester Prepared according to the procedure described in Example 42, Step 4, using the following starting materials: (3-{2-[(acetyl-ethyl-amino)-methyl]-4-nitro-phenoxy}-4-methoxy-phenyl)-acetic acid ethyl ester, 1,1-dimethylhydrazine, ferric chloride, and DARCO.

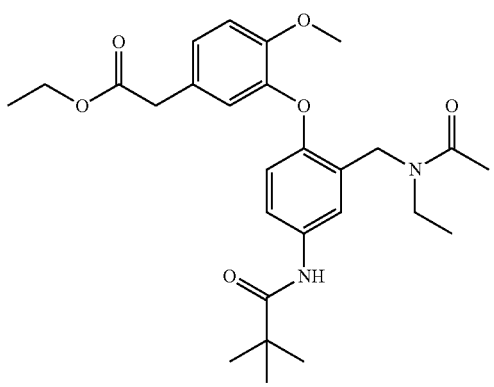 [SMILES: CCOC(=O)Cc1ccc(OC)c(Oc2ccc(NC(=O)C(C)(C)C)cc2CN(CC)C(C)=O)c1]

Step 3: {3-[2-[(Acetyl-ethyl-amino)-methyl]-4-(2,2-dimethyl-propionylamino)-phenoxy]-4-methoxy-phenyl}-acetic acid ethyl ester Prepared according to the procedure described in Example 42, Step 5, using the following starting materials: (3-{2-[(acetyl-ethyl-amino)-methyl]-4-amino-phenoxy}-4-methoxy-phenyl)-acetic acid ethyl ester and trimethylacetyl chloride.

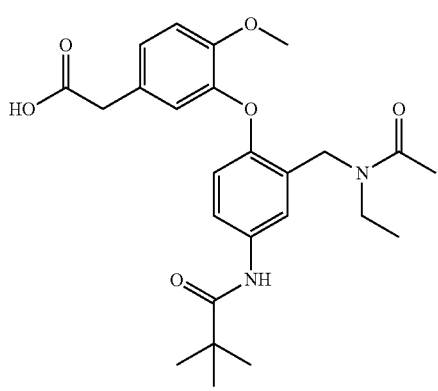 [SMILES: CCN(Cc1cc(NC(=O)C(C)(C)C)ccc1Oc1cc(CC(=O)O)ccc1OC)C(C)=O]

Step 4: {3-[2-[(Acetyl-ethyl-amino)-methyl]-4-(2,2-dimethyl-propionylamino)-phenoxy]-4-methoxy-phenyl}-acetic acid Prepared according to the procedure described in Example 42, Step 6, using the following starting material: {3-[2-[(acetyl-ethyl-amino)-methyl]-4-(2,2-dimethyl-propionylamino)-phenoxy]-4-methoxy-phenyl}-acetic acid ethyl ester. M+H=457.

Example 44

Synthesis of {3-[2-[(Acetyl-ethyl-amino)-methyl]-4-(4-chloro-benzoylamino)-phenoxy]-4-methoxy-phenyl}-acetic acid (Compound 1-46)

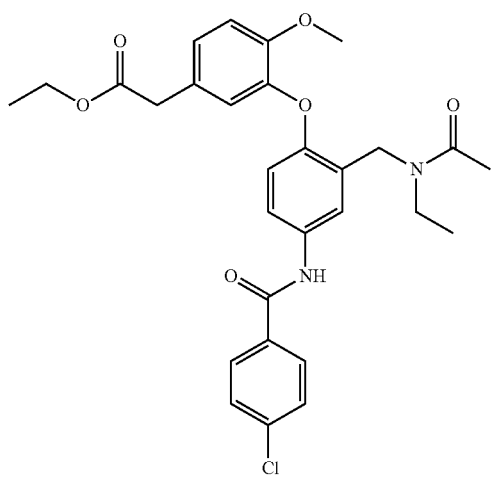 [SMILES: CCOC(=O)Cc1ccc(OC)c(Oc2ccc(NC(=O)c3ccc(Cl)cc3)cc2CN(CC)C(C)=O)c1]

Step 1: {3-[2-[(Acetyl-ethyl-amino)-methyl]-4-(4-chloro-benzoylamino)-phenoxy]-4-methoxy-phenyl}-acetic acid ethyl ester Prepared according to the procedure described in Example 42, Step 5, using the following starting materials: (3-{2-[(acetyl-ethyl-amino)-methyl]-4-amino-phenoxy}-4-methoxy-phenyl)-acetic acid ethyl ester and 4-chlorobenzoyl chloride.

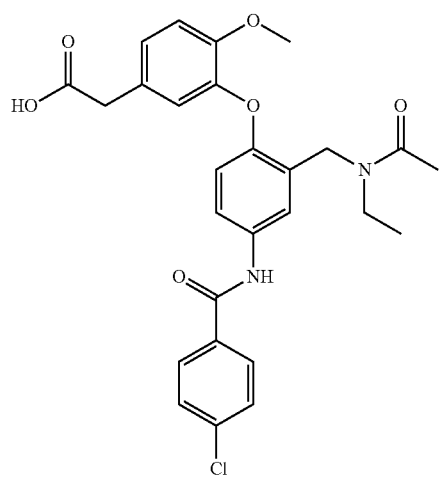 [SMILES: CCN(Cc1cc(NC(=O)c2ccc(Cl)cc2)ccc1Oc1cc(CC(=O)O)ccc1OC)C(C)=O]

Step 2: {3-[2-[(Acetyl-ethyl-amino)-methyl]-4-(4-chloro-benzoylamino)-phenoxy]-4-methoxy-phenyl}-acetic acid Prepared according to the procedure described in Example 42, Step 6, using the following starting material: {3-[2-[(acetyl-ethyl-amino)-methyl]-4-(4-chloro-benzoylamino)-phenoxy]-4-methoxy-phenyl}-acetic acid ethyl ester. M+H=511.

Example 45

Synthesis of {3-[2-[(Cyclopropanecarbonyl-ethyl-amino)-methyl]-4-(2,2-dimethyl-propionylamino)-phenoxy]-4-methoxy-phenyl}-acetic acid (Compound 1-47)

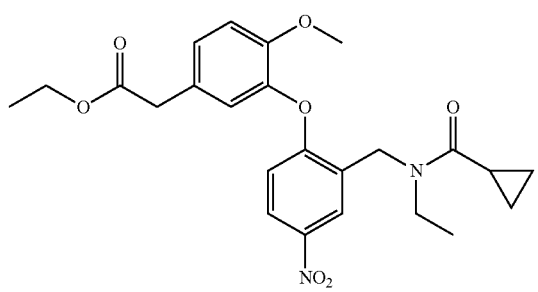

Step 1: (3-{2-[(Cyclopropanecarbonyl-ethyl-amino)-methyl]-4-nitro-phenoxy}-4-methoxy-phenyl)-acetic acid ethyl ester Prepared according to the procedure described in Example 42, Step 3, using the following starting materials: [3-(2-ethylaminomethyl-4-nitro-phenoxy)-4-methoxy-phenyl]-acetic acid ethyl ester and cyclopropanecarbonyl chloride.

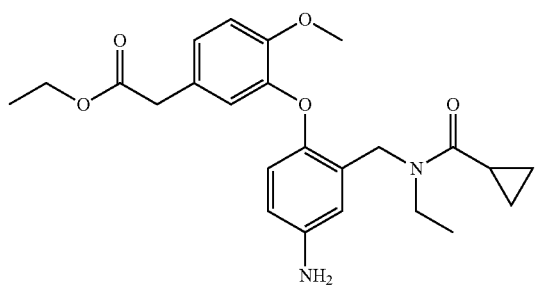 [SMILES: CCOC(=O)Cc1ccc(OC)c(Oc2ccc(N)cc2CN(CC)C(=O)C2CC2)c1]

Step 2: (3-{4-Amino-2-[(cyclopropanecarbonyl-ethyl-amino)-methyl]-phenoxy}-4-methoxy-phenyl)-acetic acid ethyl ester Prepared according to the procedure described in Example 42, Step 4, using the following starting materials: (3-{2-[(cyclopropanecarbonyl-ethyl-amino)-methyl]-4-nitro-phenoxy}-4-methoxy-phenyl)-acetic acid ethyl ester, 1,1-dimethylhydrazine, ferric chloride, and DARCO.

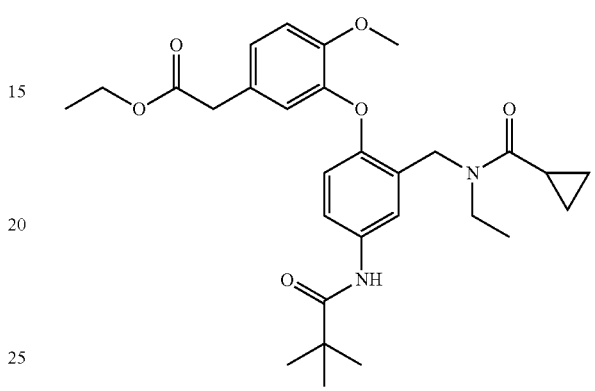

Step 3: {3-[2-[(Cyclopropanecarbonyl-ethyl-amino)-methyl]-4-(2,2-dimethyl-propionylamino)-phenoxy]-4-methoxy-phenyl}-acetic acid ethyl ester Prepared according to the procedure described in Example 42, Step 5, using the following starting materials: (3-{4-amino-2-[(cyclopropanecarbonyl-ethyl-amino)-methyl]-phenoxy}-4-methoxy-phenyl)-acetic acid ethyl ester and trimethylacetyl chloride.

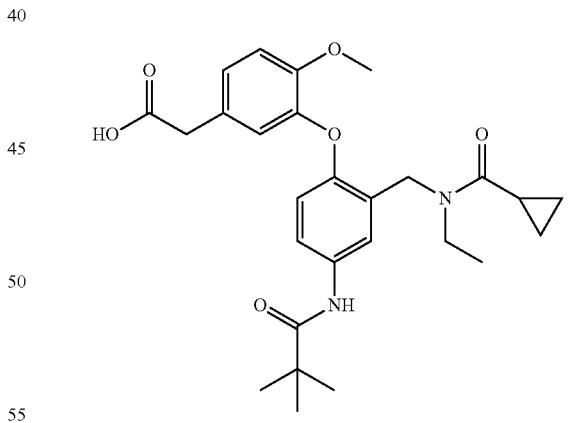

Step 4: {3-[2-[(Cyclopropanecarbonyl-ethyl-amino)-methyl]-4-(2,2-dimethyl-propionylamino)-phenoxy]-4-methoxy-phenyl}-acetic acid Prepared according to the procedure described in Example 42, Step 6, using the following starting material: {3-[2-[(cyclopropanecarbonyl-ethyl-amino)-methyl]-4-(2,2-dimethyl-propionylamino)-phenoxy]-4-methoxy-phenyl}-acetic acid ethyl ester. M+H=483.

Example 46

Synthesis of (3-{4-(4-Chloro-benzoylamino)-2-[(cyclopropanecarbonyl-ethyl-amino)-methyl]-phenoxy}-4-methoxy-phenyl)-acetic acid (Compound 1-48)

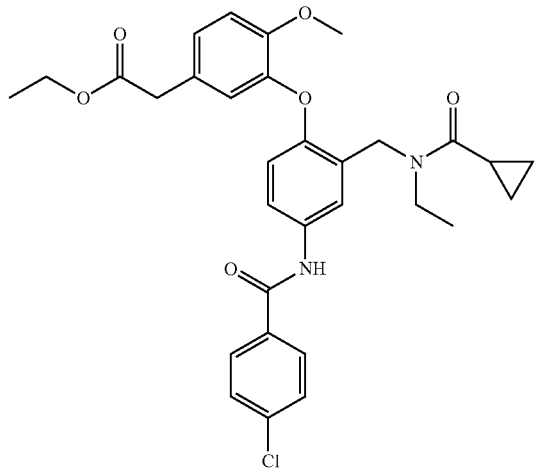 [SMILES: CCOC(=O)Cc1ccc(OC)c(Oc2ccc(NC(=O)c3ccc(Cl)cc3)cc2CN(CC)C(=O)C2CC2)c1]

Step 1: (3-{4-(4-Chloro-benzoylamino)-2-[(cyclopropanecarbonyl-ethyl-amino)-methyl]-phenoxy}-4-methoxy-phenyl)-acetic acid ethyl ester Prepared according to the procedure described in Example 42, Step 5, using the following starting materials: (3-{4-amino-2-[(cyclopropanecarbonyl-ethyl-amino)-methyl]-phenoxy}-4-methoxy-phenyl)-acetic acid ethyl ester and 4-chlorobenzoyl chloride.

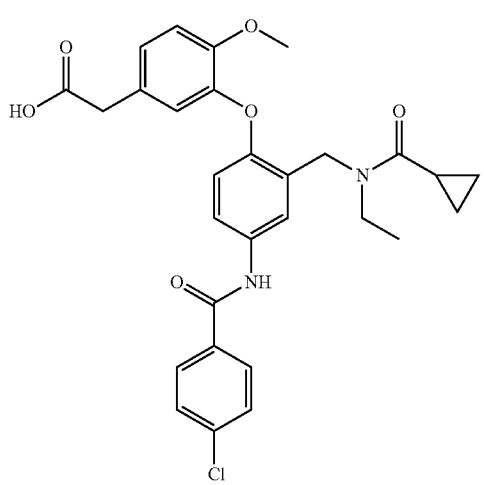 [SMILES: CCN(Cc1cc(NC(=O)c2ccc(Cl)cc2)ccc1Oc1cc(CC(=O)O)ccc1OC)C(=O)C1CC1]

Step 2: (3-{4-(4-Chloro-benzoylamino)-2-[(cyclopropanecarbonyl-ethyl-amino)-methyl]-phenoxy}-4-methoxy-phenyl)-acetic acid Prepared according to the procedure described in Example 42, Step 6, using the following starting material: (3-{4-(4-chloro-benzoylamino)-2-[(cyclopropanecarbonyl-ethylamino)-methyl]-phenoxy}-4-methoxy-phenyl)-acetic acid ethyl ester. M+H=538.

Example 47

CRTH2 Assays

Example 47a

DP$_2$/CRTH2 Binding Assay

The ability of a compound to bind to the human DP$_2$ receptor is assessed via a radioligand binding assay using [$^3$H]PGD$_2$. HEK293 cells stably expressing recombinant human DP$_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM [$^3$H] PGD$_2$ and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polyethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM PGD$_2$. IC$_{50}$s were determined using GraphPad prism analysis of drug titration curves. Compounds tested had an IC$_{50}$ of less than 100 micromolar in this assay.

Example 47b

GTPγS Binding Assay

The ability of a compound to inhibit binding of GTP to DP$_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 μg per well) are incubated in 96-well plates with 0.05 nM [$^{35}$S]-GTPγS, 80 nM PGD$_2$, 5 μM GDP, and test compound in Assay Buffer (50 mM Hepes, pH 7.4, 100 mM NaCl, 5 mM MgCl$_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD$_2$). IC$_{50}$s were determined using Graphpad prism analysis of drug titration curves.

Example 47c

Eosinophil Shape Change Assay

The ability of a compound to inhibit PGD$_2$-induced eosinophil shape change is assessed via a flow cytometric assay.

Blood was drawn from consenting human volunteers into citrate containing vacutainer tubes and red blood cells sedimented by the addition of ⅓ volume 3% Dextran T-500. The dextran-sedimented plasma was layered over an equal volume of Histopaque-1077 (Sigma) and centrifuged at 400×g for 30 minutes at room temperature. The cell pellet containing granulocytes and red blood cells was washed once in phosphate buffered saline (PBS) and then the red blood cells lysed by incubating in water for 30 seconds. The granulocytes (neutrophils and eosinophils) were washed twice in GAFS/BSA buffer (PBS containing 0.9 mM $CaCl_2$, 0.5 mM $MgCl_2$, 10 mM Hepes, 7.4, 10 mM glucose and 0.1% BSA) and then resuspended in GAFS buffer to $5 \times 10^6$ cells/ml and incubated at 37° C. for 30 minutes. The cells were then washed in GAFS/BSA buffer and resuspended in GAFS/HSA buffer (PBS containing 0.9 mM $CaCl_2$, 0.5 mM $MgCl_2$, 10 mM Hepes, 7.4, 10 mM glucose and 0.2% human serum albumin) to $5 \times 10^6$ cells/ml. A 40 µl aliquot of cells was mixed with 40 µl test compound in GAFS/HSA buffer and incubated at room temperature for 10 minutes. 20 µl of $PGD_2$ in GAFS/HSA buffer was added for a final concentration of 50 nM $PGD_2$ and the reaction incubated at 37° C. for 5 minutes before termination of the reaction by the addition of ice-cold 1:4 diluted Cytofix (Becton Dickinson). The reactions were kept on ice and analyzed on a FACSCalibur (Becton Dickinson) within 2 hours. Eosinophils were gated on the basis of autofluorescence in the FL2 channel and shape change on 500 eosinophils was assayed by forward scatter and side scatter analysis. The specific change in shape induced by $PGD_2$ was calculated as the difference between the percentage of high forward scatter eosinophils in the presence and absence of $PGD_2$. $IC_{50}$s were determined using Graphpad prism analysis of drug titration curves.

Example 47d $DP_1$ Binding Assay

The ability of a compound to bind to the human DP1 receptor was evaluated via a radioligand membrane binding assay using the $DP_1$ selective synthetic ligand [$^3$H]BW A868C. Packed human platelets (Biological Specialty Corporation), were resuspended in 6 volumes of Hepes/HBSS buffer (10 mM Hepes, 1 mM DTT in Hanks Balanced Salt Solution (HBSS)), lysed and centrifuged at 75,000×g to pellet the membranes. Membranes were resuspended in Hepes/HBSS buffer to approximately 12 mg protein/ml. Membranes (20 µg protein/well) are incubated in 96-well plates with 2 nM [$^3$H]BWA868C and test compound in Assay Buffer (50 mM Hepes, 10 mM $MnCl_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polyethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 µM BW A868C. $IC_{50}$s were determined using GraphPad prism analysis of drug titration curves.

Example 48

Mouse Allergic Rhinitis Model

The compounds ability to inhibit allergen-induced sneezing and nasal rubbing is assessed using a mouse model of allergic rhinitis. Methods were adapted from those detailed in Nakaya, M., et al., 2006. Noninvasive system for evaluating allergen-induced nasal hypersensitivity in murine allergic rhinitis. *Laboratory Investigation*, 86:917-926. Female BALB/c mice (20-25 g) are immunized by an intraperitoneal injection (i.p.) of 2 µg ovalbumin (OVA) complexed with alum in a volume 0.2 ml on days 0 and 14. Seven days later (day 21) mice are challenged intranasally with 20 µl of a 10 mg/ml solution of OVA. The challenge period occurs daily from days 21 to day 28. Mice (5/group) are randomly assigned to receive either compound or vehicle and are treated by oral gavage one hour prior to each OVA challenge. The number of sneezes and nasal rubs are counted by an independent blind observe during a period of 8 minutes immediately following OVA challenge on days 21, 25 and 28. A significant increase in allergen-induced sneezing and nasal rubbing occurs over the 8-day challenge period. Inhibition of this effect by select compounds is determined statistically using Graphpad prism.

Example 49

Guinea Pig IV-DKPGD2-Induced Peripheral Blood Leukocyte Influx

The compounds ability to inhibit leukocyte migration in vivo was assessed using intravenous injection of 13,14-dihydro-15-keto-prostaglandin D2 (DK-PGD2). Methods were adapted from those detailed Shichijo et al., 2003, Chemoattractant receptor-homologous molecule expressed on Th2 cells activation in vivo increases blood leukocyte counts and its blockade abrogates 13,14-dihydro-15-keto-prostaglandin D2-induced eosinophilia in rats. *Journal of Pharmacology and Experimental Therapeutics*, 307:518-525. Male Hartley guinea pigs were immunized with ovalbumin (OVA) on day 0 by intraperitoneal (IP) injection of 1 ml of a 100 µg/ml solution in Imject Alum. They were then used in the DK-PGD2 procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD2 (1 mg/kg, IV). Thirty minutes after IV administration, blood was collected via the marginal ear vein into EDTA tubes for cell analysis. 10 µl blood was lysed in 190 µl water followed by a further 20-fold dilution in PBS. A 10 µl fraction was mixed with equal parts trypan blue and loaded on a hemocytometer. Cells were visualized at a magnification of 40× using a LabPro light microscope and totals counted and recorded. Cells are expressed as total cells×$10^8$ per ml of blood. Inhibition of this effect by select compounds is determined statistically using Graphpad prism.

The compounds that were tested in Table 1 and Table 2 had $IC_{50}$ below 30 µM in the hDP2 (CRTH2) binding assay.

TABLE 4

Representative Biological Data

| Compound | hDP2 |
|---|---|
| Compound 1-1 | A |
| Compound 1-2 | A |
| Compound 1-3 | A |
| Compound 1-4 | A |

TABLE 4-continued

Representative Biological Data

| Compound | hDP2 |
| --- | --- |
| Compound 1-5 | A |
| Compound 1-6 | A |
| Compound 1-7 | C |
| Compound 1-8 | A |
| Compound 1-9 | A |
| Compound 1-10 | A |
| Compound 1-11 | A |
| Compound 1-12 | C |
| Compound 1-13 | A |
| Compound 1-14 | A |
| Compound 1-15 | B |
| Compound 1-16 | A |
| Compound 1-17 | A |
| Compound 1-18 | B |
| Compound 1-19 | A |
| Compound 1-20 | A |
| Compound 1-21 | A |
| Compound 1-22 | A |
| Compound 1-23 | A |
| Compound 1-24 | B |
| Compound 1-25 | B |
| Compound 1-26 | A |
| Compound 1-27 | A |
| Compound 1-28 | B |
| Compound 1-29 | A |
| Compound 1-30 | A |
| Compound 1-31 | A |
| Compound 1-32 | A |
| Compound 1-33 | A |
| Compound 1-34 | B |
| Compound 1-35 | A |
| Compound 1-36 | B |
| Compound 1-37 | A |
| Compound 1-38 | A |
| Compound 1-39 | B |
| Compound 1-40 | B |
| Compound 1-41 | A |
| Compound 1-42 | B |
| Compound 1-43 | C |
| Compound 1-44 | A |
| Compound 1-45 | A |
| Compound 1-46 | A |
| Compound 1-47 | A |
| Compound 1-48 | A |
| Ramatroban | B |

A = $IC_{50}$ less than 0.3 µM; B = $IC_{50}$ greater than 0.3 µM; C = $IC_{50}$ greater than 1 µM.

Example 50

Clinical Trials in Humans

Study 1: Clinical Trial Evaluating Effect of Compound on Ex Vivo PGD2-Induced Blood Eosinophil Shape Change In this double-blind, randomized, placebo-controlled, single ascending dose study of Compound of any one of Formula (I), Formula (II), Formula (III), Formula (IV), Formula (V), Formula (VI) or Formula (VII), in healthy volunteers the inhibition of ex vivo PGD2-induced blood eosinophil shape change is determined to show proof of biochemical mechanism of DP2 receptor antagonism. Eight subjects (6 active, 2 placebo) per dose level are used. Pre dose blood is drawn and challenged with PGD2 to determine baseline shape change as described above in Example 47. At varying times after dosing blood is drawn for both pharmacokinetic analyses of drug concentration in blood, and also for PGD2 challenge and eosinophil shape change determination. The extent of receptor blockage is determined from the relationship between drug blood concentration and percentage inhibition of eosinophil shape change.

Study 2: Clinical Trial Evaluating Effect of Compound on Allergen-Induced Nasal Symptoms and Inflammatory and Allergic Biomarkers In this double-blind, randomized, placebo-controlled study of Compound of any one of Formula (I), Formula (II), Formula (III), Formula (IV), Formula (V), Formula (VI) or Formula (VII), in individuals with allergic rhinitis the inhibition of nasal symptoms and allergic biomarkers is determined following nasal challenge with appropriate allergen. Fifteen subjects (10 active, 5 placebo) are used. Subjects are dosed for 7 days with either placebo or an amount of compound of any one of Formula (I), Formula (II), Formula (III), Formula (IV), Formula (V), Formula (VI) or Formula (VII), that results in complete DP2 receptor block in an ex vivo PGD2-induced blood eosinophil shape change pharmacodynamic study as described above. On day 7 subjects undergo nasal allergen challenge (2 hours post-dose) and early allergic response (0.25-1.0 hr) and late allergic response (4-24 hr) are evaluated as an increase from baseline for treated vs placebo. In addition changes in inflammatory cell differentials, TH2 cytokines and other inflammatory markers are determined as increase from baseline for treated vs placebo.

Compound Assay

The plasma concentrations of compound of any one of Formula (I), Formula (II), Formula (III), Formula (IV), Formula (V), Formula (VI) or Formula (VII), are determined by gas chromatography, giving a detection limit of 1 ng·ml-1 (Ritter W. Determination of BAY u 3405, a novel thromboxane antagonist, in plasma and urine by HPLC and GC. In: Reid E, Wilson I D, eds. Bioanalytical Approaches for Drugs, Including Anti-asthmatics and Metabolites. Methodological Surveys in Biochemistry and Analysis, 1992; 22: 211-216).

Example 51a

Parenteral Composition

To prepare a parenteral pharmaceutical composition suitable for administration by injection, 100 mg of a water-soluble salt of a compound of any one of Formula (I), Formula (II), Formula (III), Formula (IV), Formula (V), Formula (VI) or Formula (VII), is dissolved in DMSO and then mixed with 10 mL of 0.9% sterile saline. The mixture is incorporated into a dosage unit form suitable for administration by injection.

Example 51b

Oral Composition

To prepare a pharmaceutical composition for oral delivery, 100 mg of a compound of any one of Formula (I), Formula (II), Formula (III), Formula (IV), Formula (V), Formula (VI) or Formula (VII), is mixed with 750 mg of starch. The mixture is incorporated into an oral dosage unit for, such as a hard gelatin capsule, which is suitable for oral administration.

Example 51c

Sublingual (Hard Lozenge) Composition

To prepare a pharmaceutical composition for buccal delivery, such as a hard lozenge, mix 100 mg of a compound of any one of Formula (I), Formula (II), Formula (III), Formula (IV), Formula (V), Formula (VI) or Formula (VII), with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 51d

Fast-Disintegrating Sublingual Tablet

A fast-disintegrating sublingual tablet is prepared by mixing 48.5% by weight of a compound of any one of Formula (I), Formula (II), Formula (III), Formula (IV), Formula (V), Formula (VI) or Formula (VII), 44.5% by weight of microcrystalline cellulose (KG-802), 5% by weight of low-substituted hydroxypropyl cellulose (50 µm), and 2% by weight of magnesium stearate. Tablets are prepared by direct compression (*AAPS PharmSciTech*. 2006; 7(2):E41). The total weight of the compressed tablets is maintained at 150 mg. The formulation is prepared by mixing the amount of compound of any one of Formula (I), Formula (II), Formula (III), Formula (IV), Formula (V), Formula (VI) or Formula (VII), with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 51e

Inhalation Composition

To prepare a pharmaceutical composition for inhalation delivery, 20 mg of a compound of any one of Formula (I), Formula (II), Formula (III), Formula (IV), Formula (V), Formula (VI) or Formula (VII), is mixed with 50 mg of anhydrous citric acid and 100 mL of 0.9% sodium chloride solution. The mixture is incorporated into an inhalation delivery unit, such as a nebulizer, which is suitable for inhalation administration.

Example 51f

Rectal Gel Composition

To prepare a pharmaceutical composition for rectal delivery, 100 mg of a compound of any one of Formula (I), Formula (II), Formula (III), Formula (IV), Formula (V), Formula (VI) or Formula (VII), is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 51g

Topical Gel Composition

To prepare a pharmaceutical topical gel composition, 100 mg of a compound of any one of Formula (I), Formula (II), Formula (III), Formula (IV), Formula (V), Formula (VI) or Formula (VII), is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 51h

Ophthalmic Solution Composition

To prepare a pharmaceutical ophthalmic solution composition, 100 mg of a compound of any one of Formula (I), Formula (II), Formula (III), Formula (IV), Formula (V), Formula (VI) or Formula (VII), is mixed with 0.9 g of NaCl in 100 ml of purified water and filtered using a 0.2 micron filter. The resulting isotonic solution is then incorporated into ophthalmic delivery units, such as eye drop containers, which are suitable for ophthalmic administration.

Example 51i

Nasal Spray Solution

To prepare a pharmaceutical nasal spray solution, 10 g of a compound of any one of Formula (I), Formula (II), Formula (III), Formula (IV), Formula (V), Formula (VI) or Formula (VII), is mixed with 30 mL of a 0.05M phosphate buffer solution (pH 4.4). The solution is placed in a nasal administrator designed to deliver 100 µl of spray for each application.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), or a pharmaceutically acceptable salt thereof:

Formula (I)

wherein,
Q is tetrazolyl or —C(=O)-$Q^1$;
$Q^1$ is —OH, or —O($C_1$-$C_6$alkyl);
X is —O—, —S—, —S(=O)—, —S(=O)$_2$—, —$NR^{13}$—, —$CH_2$—, or —C(=O)—;
each $R^1$ is independently selected from H, F, and $C_1$-$C_4$alkyl;
each of $R^2$, $R^3$, $R^4$, $R^5$, $R^6$, and $R^7$ is independently H, halogen, —CN, —$NO_2$, —OH, —$OR^{13}$, —$SR^{12}$, —S(=O)$R^{12}$, —S(=O)$_2R^{12}$, —C(=O)$R^{12}$, —OC(=O)$R^{12}$, —$CO_2R^{13}$, —$OCO_2R^{13}$, —CH($R^{13}$)$_2$, —N($R^{13}$)$_2$, —$NHCH_2CO_2R^{13}$, —$OCH_2CO_2R^{13}$, —$SCH_2CO_2R^{13}$, —C(=O)N($R^{13}$)$_2$, —OC(=O)N($R^{13}$)$_2$, —$NR^{13}$C(=O)N($R^{13}$)$_2$, —$NR^{13}$C(=O)$R^{12}$, —$NR^{13}$C(=O)$OR^{12}$, —$NR^{13}$S(=O)$_2R^{12}$, —C(OH)($R^{13}$)$_2$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted $C_2$-$C_{10}$heterocycloalkyl, optionally substituted phenyl, or optionally substituted monocyclic heteroaryl;
each $R^8$ is H;

$R^{10}$ is —C(=O)$R^{14}$, —C(=O)O$R^{15}$, —C(=O)N($R^{16}$)$_2$, —S(=O)$_2$N($R^{16}$)$_2$ or —S(=O)$_2R^{14}$;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl), —$C_1$-$C_4$alkyl-(optionally substituted heteroaryl), or -$L^3$-$X^3$-$Q^3$;

$L^3$ is a $C_1$-$C_4$alkylene, or arylene;

$X^3$ is a bond, —O—, —S—, —S(=O)—, —S(=O)$_2$—, —C(=O)—, —$NR^{13}$S(=O)$_2$—, or —$NR^{13}$—;

$Q^3$ is $C_1$-$C_6$alkyl, $C_1$-$C_6$fluoroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl), or —$C_1$-$C_4$alkyl-(optionally substituted heteroaryl);

$R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl) or —$C_1$-$C_4$alkyl-(optionally substituted heteroaryl);

each $R^{16}$ is independently H, —CN, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl) or —$C_1$-$C_4$alkyl-(optionally substituted heteroaryl); or two $R^{16}$ groups attached to the same N atom are taken together with the N atom to which they are attached to form an optionally substituted $C_2$-$C_{10}$heterocycloalkyl;

$R^{11}$ is H, $C_1$-$C_6$alkyl, $C_1$-$C_6$heteroalkyl, $C_1$-$C_6$haloalkyl, an optionally substituted monocyclic or bicyclic $C_3$-$C_{10}$cycloalkyl, an optionally substituted monocyclic or bicyclic $C_2$-$C_{10}$heterocycloalkyl, an optionally substituted aryl, an optionally substituted heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted aryl), —$C_1$-$C_4$alkyl-(optionally substituted heteroaryl), —$C_1$-$C_6$alkylene-O—$R^{17}$, —$C_1$-$C_6$alkylene-S—$R^{17}$, —$C_1$-$C_6$alkylene-S(=O)—$R^{17}$, —$C_1$-$C_6$alkylene-S(=O)$_2$—$R^{17}$, —$C_1$-$C_6$alkylene-$NR^{13}R^{17}$, —$C_1$-$C_6$alkylene-C(=O)—$R^{17}$, —$C_1$-$C_6$alkylene-C(=O)O—$R^{17}$, —$C_1$-$C_6$alkylene-OC(=O)—$R^{17}$, —$C_1$-$C_6$alkylene-$NR^{13}$C(=O)—$R^{17}$ or —$C_1$-$C_6$alkylene-C(=O)$NR^{13}$—$R^{17}$;

$R^{17}$ is H, $C_1$-$C_4$heteroalkyl, $C_1$-$C_4$haloalkyl, an optionally substituted $C_3$-$C_{10}$cycloalkyl, an optionally substituted $C_2$-$C_{10}$heterocycloalkyl, an optionally substituted aryl, an optionally substituted benzyl, or an optionally substituted heteroaryl;

$R^{12}$ is $C_1$-$C_6$alkyl, $C_1$-$C_6$heteroalkyl, $C_1$-$C_6$fluoroalkyl, optionally substituted $C_3$-$C_{10}$cycloalkyl, optionally substituted $C_2$-$C_{10}$heterocycloalkyl, optionally substituted aryl, —$C_1$-$C_4$alkyl-(optionally substituted aryl) or optionally substituted heteroaryl; and each $R^{13}$ is independently selected from H, $C_1$-$C_6$alkyl, $C_1$-$C_6$heteroalkyl, $C_1$-$C_6$fluoroalkyl, an optionally substituted $C_3$-$C_{10}$cycloalkyl, an optionally substituted $C_2$-$C_{10}$heterocycloalkyl, an optionally substituted aryl, —$C_1$-$C_4$alkyl-(optionally substituted aryl), and an optionally substituted heteroaryl; or two $R^{13}$ groups attached to the same N atom are taken together with the N atom to which they are attached to form an optionally substituted $C_2$-$C_{10}$heterocycloalkyl;

m is 0, 1, or 2; and n is 1.

2. The compound of claim 1, or a pharmaceutically acceptable salt thereof, wherein:

Q is —C(=O)-$Q^1$;

$Q^1$ is —OH, or —O($C_1$-$C_4$alkyl);

each $R^1$ is independently selected from H, F, and —$CH_3$;

X is —O—, —S—, —S(=O)—, —S(=O)$_2$—, or —$CH_2$—; and m is 0 or 1.

3. The compound of claim 2, or a pharmaceutically acceptable salt thereof, wherein:

each $R^1$ is H;

X is —O—;

each of $R^2$, $R^3$, $R^6$ and $R^7$ is independently H, halogen, —OH, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl;

$R^4$ is H, halogen, —OH, —$OR^{13}$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl; and $R^5$ is H, halogen, —CN, —$NO_2$, —OH, —$OR^{13}$, —$SR^{12}$, —S(=O)$R^{12}$, —S(=O)$_2R^{12}$, —C(=O)$R^{12}$, —OC(=O)$R^{12}$, —$CO_2R^{13}$, —$OCO_2R^{13}$, —N($R^{13}$)$_2$, —$NHCH_2CO_2R^{13}$, —$OCH_2CO_2R^{13}$, —$SCH_2CO_2R^{13}$, —C(=O)N($R^{13}$)$_2$, —OC(=O)N($R^{13}$)$_2$, —$NR^{13}$C(=O)N($R^{13}$)$_2$, —$NR^{13}$C(=O)$R^{12}$, —$NR^{13}$C(=O)$OR^{12}$, —$NR^{13}$S(=O)$_2R^{12}$, $C_1$-$C_6$alkyl, $C_1$-$C_6$fluoroalkyl, $C_1$-$C_6$fluoroalkoxy, $C_1$-$C_6$alkoxy, $C_1$-$C_6$heteroalkyl, an optionally substituted $C_3$-$C_{10}$cycloalkyl, an optionally substituted $C_2$-$C_{10}$heterocycloalkyl, optionally substituted phenyl, or an optionally substituted monocyclic heteroaryl.

4. The compound of claim 3, or a pharmaceutically acceptable salt thereof, wherein:

$R^{10}$ is —C(=O)$R^{14}$, —C(=O)O$R^{15}$, —C(=O)N($R^{16}$)$_2$, or —S(=O)$_2R^{14}$;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, —$C_1$-$C_4$alkyl-(an optionally substituted cycloalkyl), —$C_1$-$C_4$alkyl-(an optionally substituted aryl) or —$C_1$-$C_4$alkyl-(an optionally substituted heteroaryl); or $R^{14}$ is $L^3$-$X^3$-$Q^3$;

$L^3$ is a $C_1$-$C_4$alkylene or arylene;

$X^3$ is a bond, —O—, —S—, —S(=O)—, —S(=O)$_2$—, —C(=O)—, —$NR^{13}$S(=O)$_2$—, or —$NR^{13}$—;

$Q^3$ is $C_1$-$C_6$alkyl, $C_1$-$C_6$fluoroalkyl an optionally substituted $C_3$-$C_{10}$cycloalkyl, an optionally substituted aryl, an optionally substituted heteroaryl, —$C_1$-$C_4$alkyl-(an optionally substituted $C_3$-$C_{10}$cycloalkyl), —$C_1$-$C_4$alkyl-(an optionally substituted aryl), or —$C_1$-$C_4$alkyl-(an optionally substituted heteroaryl);

$R^{15}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, —$C_1$-$C_4$alkyl-(an optionally substituted $C_3$-$C_6$cycloalkyl), —$C_1$-$C_4$alkyl-(an optionally substituted aryl) or —$C_1$-$C_4$alkyl-(an optionally substituted heteroaryl);

each $R^{16}$ is independently H, —CN, $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted aryl, an optionally substituted heteroaryl, —$C_1$-$C_4$alkyl-(an optionally substituted $C_3$-$C_6$cycloalkyl), —$C_1$-$C_4$alkyl-(an optionally substituted aryl) or —$C_1$-$C_4$alkyl-(an optionally substituted heteroaryl); or two $R^{16}$ groups attached to the same N atom are taken together with the N atom to which they are attached to form an optionally substituted $C_2$-$C_{10}$heterocycloalkyl; and $R^{11}$ is H, —$CH_3$, —$CH_2CH_3$, —$CH_2CH_2CH_3$, —CH($CH_3$)$_2$, —$CH_2CH_2CH_2CH_3$, —$CH_2C(CH_3)_3$, —$CH_2CF_3$, —$CH_2CH_2OH$, —$CH_2CH_2OCH_3$, —$CH_2CH_2N(CH_3)_2$, —$CH_2COOH$, —$CH_2C(O)NH_2$, —$CH_2$-(optionally substituted phenyl), —$CH_2CH_2$-(optionally substituted phenyl), —$CH(CH_3)CH_2$-(optionally substituted phenyl), —$C(CH_3)_2CH_2$-(optionally substituted phenyl), optionally substituted phenyl, o-tolyl, cyclopropyl, cyclobutyl, cyclopentyl, cyclohexyl, indan-1-yl, indan-2-yl, 2-hydroxy-indan-1-yl, or 2-methoxy-indan-1-yl.

5. The compound of claim 4, or a pharmaceutically acceptable salt thereof, wherein:

$R^{10}$ is —C(=O)$R^{14}$;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted naphthyl, an optionally substituted monocyclic heteroaryl, an optionally substituted bicyclic heteroaryl, —$C_1$-$C_4$alkyl-(an optionally substituted $C_3$-$C_{10}$cycloalkyl), —$C_1$-$C_4$alkyl-(an optionally substituted phenyl) or —$C_1$-$C_4$alkyl-(an optionally substituted monocyclic heteroaryl); or $R^{14}$ is $L^3$-$X^3$-$Q^3$;

$L^3$ is a $C_1$-$C_4$alkylene or phenylene;

$X^3$ is a bond, —O—, —S—, —S(=O)—, —S(=O)$_2$—, —C(=O)—, —$NR^{13}$S(=O)$_2$—, or —$NR^{13}$—; and $Q^3$ is $C_1$-$C_4$alkyl, $C_3$-$C_6$cycloalkyl, an optionally substituted phenyl, —$C_1$-$C_4$alkyl-($C_3$-$C_6$cycloalkyl), or —$C_1$-$C_4$alkyl-(an optionally substituted phenyl).

6. The compound of claim 5, or a pharmaceutically acceptable salt thereof, wherein:

$R^{14}$ is $C_1$-$C_4$alkyl, $C_1$-$C_4$fluoroalkyl, $C_3$-$C_6$cycloalkyl, an optionally substituted phenyl, an optionally substituted naphthyl, or an optionally substituted monocyclic heteroaryl.

7. The compound of claim 4, or a pharmaceutically acceptable salt thereof, wherein:

$R^{10}$ is —S(=O)$_2$$R^{14}$; and $R^{14}$ is $C_1$-$C_4$alkyl, $C_1$-$C_4$fluoroalkyl, $C_3$-$C_6$cycloalkyl, an optionally substituted phenyl, an optionally substituted naphthyl, or an optionally substituted monocyclic heteroaryl.

8. The compound of claim 4, or a pharmaceutically acceptable salt thereof, wherein:

$R^{10}$ is —C(=O)$OR^{15}$; and $R^{15}$ is $C_1$-$C_4$alkyl, $C_3$-$C_6$cycloalkyl, an optionally substituted phenyl, an optionally substituted monocyclic heteroaryl, —$C_1$-$C_2$alkyl-($C_3$-$C_6$cycloalkyl), —$C_1$-$C_2$alkyl-(an optionally substituted phenyl) or —$C_1$-$C_2$alkyl-(an optionally substituted monocyclic heteroaryl).

9. The compound of claim 4, or a pharmaceutically acceptable salt thereof, wherein:

$R^{10}$ is —C(=O)N($R^{16}$)$_2$; and one $R^{16}$ is H or $C_1$-$C_4$alkyl and the other $R^{16}$ is H, $C_1$-$C_4$alkyl, $C_3$-$C_6$cycloalkyl, an optionally substituted phenyl, an optionally substituted monocyclic heteroaryl, —$C_1$-$C_2$alkyl-($C_3$-$C_6$cycloalkyl), —$C_1$-$C_2$alkyl-(an optionally substituted phenyl) or —$C_1$-$C_2$alkyl-(an optionally substituted monocyclic heteroaryl).

10. The compound of claim 4, or a pharmaceutically acceptable salt thereof, wherein:

$R^4$ is H, F, Cl, Br, —$OCH_3$, —$CH_3$, —$CF_3$, or —$OCF_3$;

$R^5$ is H, F, Cl, Br, —OH—$CH_3$, —$CH_2CH_3$, —$CH_2CH_2CH_3$, —CH($CH_3$)$_2$, —C($CH_3$)$_3$, —$CF_3$, —$CH_2CF_3$, —$OCH_3$, —$OCH_2CH_3$, —$OCF_3$, —S(=O)$_2$$CH_3$, —NHC(=O)($C_1$-$C_6$alkyl), —NHC(=O) (optionally substituted phenyl), —N($CH_3$)C(=O)($C_1$-$C_6$alkyl), —N($CH_3$)C(=O) (optionally substituted phenyl), —NHS(=O)$_2$($C_1$-$C_6$alkyl), —NHS(=O)$_2$ (optionally substituted phenyl), —N($CH_3$)S(=O)$_2$($C_1$-$C_6$alkyl), or —N($CH_3$)S(=O)$_2$ (optionally substituted phenyl); and $R^{11}$ is H, —$CH_3$, —$CH_2CH_3$, —$CH_2CH_2CH_3$, —CH($CH_3$)$_2$, —$CH_2CH_2CH_2CH_3$, —$CH_2C(CH_3)_3$, —$CH_2CF_3$, —$CH_2$-(optionally substituted phenyl), —$CH_2CH_2$-(optionally substituted phenyl), —$CH(CH_3)CH_2$-(optionally substituted phenyl), —$C(CH_3)_2CH_2$-(optionally substituted phenyl), optionally substituted phenyl, o-tolyl, cyclopropyl, cyclobutyl, cyclopentyl, or cyclohexyl.

11. The compound of claim 1, wherein the compound has the structure of Formula (VII), or a pharmaceutically acceptable salt thereof:

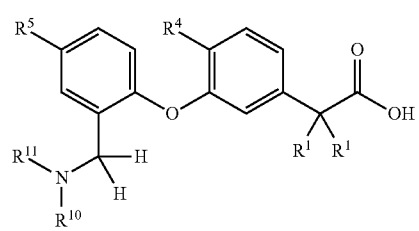

Formula (VII)

wherein, each $R^1$ is H;

$R^4$ is H, halogen, —OH, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, or $C_3$-$C_6$cycloalkyl;

$R^5$ is H, halogen, —CN, —$NO_2$, —OH, —$OR^{13}$, —$SR^{12}$, —S(=O)$R^{12}$, —S(=O)$_2$$R^{12}$, —C(=O)$R^{12}$, —OC(=O)$R^{12}$, —$CO_2R^{13}$, —$OCO_2R^{13}$, —N($R^{13}$)$_2$, —C(=O)N($R^{13}$)$_2$, —OC(=O)N($R^{13}$)$_2$, —$NR^{13}$C(=O)N($R^{13}$)$_2$, —$NR^{13}$C(=O)$R^{12}$, —$NR^{13}$C(=O)$OR^{12}$, —$NR^{13}$S(=O)$_2R^{12}$, —C(OH)($R^{13}$)$_2$, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, $C_3$-$C_6$cycloalkyl, an optionally substituted $C_2$-$C_{10}$heterocycloalkyl, optionally substituted phenyl, or optionally substituted monocyclic heteroaryl;

$R^{10}$ is —C(=O)$R^{14}$, —C(=O)O$R^{15}$, —C(=O)N($R^{16}$)$_2$, or —S(=O)$_2$$R^{14}$;

$R^{14}$ is $C_1$-$C_6$alkyl, $C_1$-$C_6$fluoroalkyl, $C_1$-$C_6$heteroalkyl, an optionally substituted $C_3$-$C_{10}$cycloalkyl, an optionally substituted phenyl, an optionally substituted napthyl, an optionally substituted monocyclic or bicyclic heteroaryl, —$C_1$-$C_4$alkyl-(optionally substituted $C_3$-$C_{10}$cycloalkyl), —$C_1$-$C_4$alkyl-(optionally substituted $C_2$-$C_{10}$heterocycloalkyl), —$C_1$-$C_4$alkyl-(optionally substituted phenyl), —$C_1$-$C_4$alkyl-(optionally substituted napthyl), —$C_1$-$C_4$alkyl-(optionally substituted monocyclic or bicyclic heteroaryl), or $L^3$-$X^3$-$Q^3$;

$L^3$ is a $C_1$-$C_4$alkylene or phenylene;

$X^3$ is a bond, —O—, —S—, —S(=O)—, —S(=O)$_2$—, —C(=O)—, —N$R^{13}$S(=O)$_2$—, or —N$R^{13}$—;

$Q^3$ is $C_1$-$C_4$alkyl, $C_1$-$C_4$fluoroalkyl, $C_3$-$C_6$cycloalkyl, an optionally substituted phenyl, an optionally substituted monocyclic heteroaryl, —$C_1$-$C_4$alkyl-(optionally substituted phenyl), or —$C_1$-$C_4$alkyl-(optionally substituted monocyclic heteroaryl);

$R^{15}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, —$C_1$-$C_4$alkyl-($C_3$-$C_6$cycloalkyl), —$C_1$-$C_4$alkyl-(optionally substituted phenyl) or —$C_1$-$C_4$alkyl-(optionally substituted monocyclic heteroaryl);

each $R^{16}$ is independently H, —CN, $C_1$-$C_6$alkyl, $C_1$-$C_6$fluoroalkyl, $C_1$-$C_6$heteroalkyl, $C_3$-$C_6$cycloalkyl, an optionally substituted $C_2$-$C_8$heterocycloalkyl, an optionally substituted phenyl, an optionally substituted monocyclic heteroaryl, —$C_1$-$C_4$alkyl-($C_3$-$C_6$cycloalkyl), —$C_1$-$C_4$alkyl-(optionally substituted $C_2$-$C_8$heterocycloalkyl), —$C_1$-$C_4$alkyl-(optionally substituted phenyl) or —$C_1$-$C_4$alkyl-(optionally substituted monocyclic heteroaryl); or two $R^{16}$ groups attached to the same N atom are taken together with the N atom to which they are attached to form an optionally substituted $C_2$-$C_8$heterocycloalkyl;

$R^{11}$ is H, $C_1$-$C_6$alkyl, $C_1$-$C_6$heteroalkyl, $C_1$-$C_6$haloalkyl, an optionally substituted monocyclic or bicyclic $C_3$-$C_{10}$cycloalkyl, an optionally substituted phenyl, an optionally substituted monocyclic heteroaryl, —$C_1$-$C_4$alkyl-($C_3$-$C_6$cycloalkyl), —$C_1$-$C_4$alkyl-(optionally substituted phenyl), or —$C_1$-$C_4$alkyl-(optionally substituted monocyclic heteroaryl);

$R^{12}$ is $C_1$-$C_6$alkyl, $C_1$-$C_6$heteroalkyl, $C_1$-$C_6$fluoroalkyl, optionally substituted $C_3$-$C_{10}$cycloalkyl, optionally substituted $C_2$-$C_{10}$heterocycloalkyl, optionally substituted aryl, —$C_1$-$C_4$alkyl-(optionally substituted aryl) or optionally substituted heteroaryl; and each $R^{13}$ is independently selected from H, $C_1$-$C_6$alkyl, $C_1$-$C_6$heteroalkyl, $C_1$-$C_6$fluoroalkyl, an optionally substituted $C_3$-$C_{10}$cycloalkyl, an optionally substituted $C_2$-$C_{10}$heterocycloalkyl, an optionally substituted aryl, —$C_1$-$C_4$alkyl-(optionally substituted aryl), and an optionally substituted heteroaryl; or two $R^{13}$ groups attached to the same N atom are taken together with the N atom to which they are attached to form an optionally substituted $C_2$-$C_{10}$heterocycloalkyl.

12. The compound of claim 11, or a pharmaceutically acceptable salt thereof, wherein:

$R^4$ is H, halogen, —OH, $C_1$-$C_4$alkyl, $C_1$-$C_4$fluoroalkyl, $C_1$-$C_4$fluoroalkoxy, or $C_1$-$C_4$alkoxy;

$R^5$ is H, halogen, —OH, —O$R^{13}$, —S(=O)$_2$($C_1$-$C_4$alkyl), —NHC(=O)($C_1$-$C_6$alkyl), —NHC(=O) (optionally substituted phenyl), —N(CH$_3$)C(=O)($C_1$-$C_6$alkyl), —N(CH$_3$)C(=O) (optionally substituted phenyl), —NHS(=O)$_2$($C_1$-$C_6$alkyl), —NHS(=O)$_2$ (optionally substituted phenyl), —N(CH$_3$)S(=O)$_2$($C_1$-$C_6$alkyl), —N(CH$_3$)S(=O)$_2$ (optionally substituted phenyl), —C(OH)($C_1$-$C_4$alkyl)$_2$, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, $C_3$-$C_6$cycloalkyl, an optionally substituted $C_2$-$C_{10}$heterocycloalkyl, optionally substituted phenyl, or optionally substituted monocyclic heteroaryl; and $R^{11}$ is H, $C_1$-$C_6$alkyl, $C_1$-$C_6$heteroalkyl, $C_1$-$C_6$haloalkyl, —$C_1$-$C_4$alkyl-($C_3$-$C_6$cycloalkyl), —$C_1$-$C_4$alkyl-(optionally substituted phenyl), or —$C_1$-$C_4$alkyl-(optionally substituted monocyclic heteroaryl).

13. The compound of claim 12, or a pharmaceutically acceptable salt thereof, wherein:

$R^{14}$ is $C_1$-$C_6$alkyl, $C_1$-$C_6$fluoroalkyl, $C_1$-$C_6$heteroalkyl, $C_3$-$C_6$cycloalkyl, an optionally substituted phenyl, an optionally substituted naphthyl, or an optionally substituted monocyclic or bicyclic heteroaryl;

$R^{15}$ is $C_1$-$C_6$alkyl, $C_1$-$C_6$fluoroalkyl, $C_3$-$C_6$cycloalkyl, —$C_1$-$C_2$alkyl-($C_3$-$C_6$cycloalkyl), or —$C_1$-$C_2$alkyl-(optionally substituted phenyl); and one $R^{16}$ is H or $C_1$-$C_4$alkyl and the other $R^{16}$ is H, $C_1$-$C_6$alkyl, $C_1$-$C_6$fluoroalkyl, $C_1$-$C_6$heteroalkyl, $C_3$-$C_6$cycloalkyl, an optionally substituted phenyl, an optionally substituted monocyclic heteroaryl, —$C_1$-$C_2$alkyl-($C_3$-$C_6$cycloalkyl), —$C_1$-$C_2$alkyl-(optionally substituted phenyl) or —$C_1$-$C_4$alkyl-(optionally substituted monocyclic heteroaryl).

14. The compound of claim 1, wherein the compound is:
(3-{2-[(Acetyl-phenethyl-amino)-methyl]-4-bromo-phenoxy}-phenyl)-acetic acid; {3-[2-({Acetyl-[2-(4-fluoro-phenyl)-1,1-dimethyl-ethyl]-amino}-methyl)-4-bromo-phenoxy]-phenyl}-acetic acid; (3-{2-[(Benzyl-methoxycarbonyl-amino)-methyl]-4-bromo-phenoxy}-phenyl)-acetic acid; (3-{4-Bromo-2-[(methoxycarbonyl-phenethyl-amino)-methyl]-phenoxy}-phenyl)-acetic acid; [3-(4-Bromo-2-{[methoxycarbonyl-((S)-1-methyl-2-phenyl-ethyl)-amino]methyl}-phenoxy)-phenyl]-acetic acid; (3-{2-[((R)-Benzyloxycarbonyl-indan-1-yl-amino)-methyl]-4-bromo-phenoxy}-phenyl)-acetic acid (Compound 1-6); (3-{2-[(Acetyl-ethyl-amino)-methyl]-4-bromo-phenoxy}-4-methoxy-phenyl)-acetic acid; (3-{2-[(Acetyl-benzyl-amino)-methyl]-4-bromo-phenoxy}-4-methoxy-phenyl)-acetic acid; (3-{4-Bromo-2-[ethyl-methoxycarbonyl-amino)-methyl]-phenoxy}-4-methoxy-phenyl)-acetic acid; (3-{2-[(Benzyl-methoxycarbonyl-amino)-methyl]-4-bromo-phenoxy}-4-methoxy-phenyl)-acetic acid; 3-{2-[((R)-Acetyl-indan-1-yl-amino)-methyl]-4-trifluoromethyl-phenoxy}-phenyl)-acetic acid; (3-{2-[((S)-Acetyl-indan-1-yl-amino)-methyl]-4-trifluoromethyl-phenoxy}-phenyl)-acetic acid; (3-{2-[(4-Chloro-benzoylamino)-methyl]-4-trifluoromethyl-phenoxy}-phenyl)-acetic acid; (3-{2-[(Methyl-phenylacetyl-amino)-methyl]-4-trifluoromethyl-phenoxy}-phenyl)-acetic acid; (3-{2-[(Benzoyl-ethyl-amino)-methyl]-4-trifluoromethyl-phenoxy}-phenyl)-acetic acid; (3-{2-[(Ethyl-phenylacetyl-amino)-methyl]-4-trifluoromethyl-phenoxy}-phenyl)-acetic acid; (3-{2-

[((R)-Indan-1-yl-methoxycarbonyl-amino)-methyl]-4-trifluoromethyl-phenoxy}-phenyl)-acetic acid; (3-{2-[(Indan-2-yl-methoxycarbonyl-amino)-methyl]-4-trifluoromethyl-phenoxy}-phenyl)-acetic acid; (3-{2-[(Benzyloxycarbonyl-methyl-amino)-methyl]-4-trifluoromethyl-phenoxy}-phenyl)-acetic acid; (3-{2-[(4-Chloro-benzenesulfonylamino)-methyl]-4-trifluoromethyl-phenoxy}-phenyl)-acetic acid; [3-(2-{[(4-Chloro-benzenesulfonyl)-methyl-amino]-methyl}-4-trifluoromethyl-phenoxy)-phenyl]-acetic acid; [3-(2-{[Methyl-(2-trifluoromethyl-benzenesulfonyl)-amino]-methyl}-4-trifluoromethyl-phenoxy)-phenyl]-acetic acid; [3-(2-{[(4-Methoxy-benzenesulfonyl)-methyl-amino]-methyl}-4-trifluoromethyl-phenoxy)-phenyl]-acetic acid; [3-(2-{[Ethyl-(4-methoxy-benzenesulfonyl)-amino]-methyl}-4-trifluoromethyl-phenoxy)-phenyl]-acetic acid; [3-(2-{[Ethyl-(toluene-4-sulfonyl)-amino]-methyl}-4-trifluoromethyl-phenoxy)-phenyl]-acetic acid; [3-(2-{[Ethyl-(4-methanesulfonyl-benzenesulfonyl)-amino]-methyl}-4-trifluoromethyl-phenoxy)-phenyl]-acetic acid; [3-(2-{[(4-Acetyl-benzenesulfonyl)-ethyl-amino]-methyl}-4-trifluoromethyl-phenoxy)-phenyl]-acetic acid; [3-(2-{[Ethyl-(naphthalene-2-sulfonyl)-amino]-methyl}-4-trifluoromethyl-phenoxy)-phenyl]-acetic acid; [3-(2-{[(4-Bromo-benzenesulfonyl)-ethyl-amino]-methyl}-4-trifluoromethyl-phenoxy)-phenyl]-acetic acid; [3-(2-{[Ethyl-(4-m-tolylamino-benzenesulfonyl)-amino]-methyl}-4-trifluoromethyl-phenoxy)-phenyl]-acetic acid; {3-[2-({Ethyl-[4-(methyl-m-tolyl-amino)-benzenesulfonyl]-amino}-methyl)-4-trifluoromethyl-phenoxy]-phenyl}-acetic acid; (3-{2-[(Acetyl-ethyl-amino)-methyl]-4-trifluoromethyl-phenoxy}-4-methoxy-phenyl)-acetic acid; (3-{2-[(Acetyl-benzyl-amino)-methyl]-4-trifluoromethyl-phenoxy}-4-methoxy-phenyl)-acetic acid; (3-{2-[(Ethyl-methoxycarbonyl-amino)-methyl]-4-trifluoromethyl-phenoxy}-4-methoxy-phenyl)-acetic acid; (3-{2-[(Benzyl-methoxycarbonyl-amino)-methyl]-4-trifluoromethyl-phenoxy}-4-methoxy-phenyl)-acetic acid; [3-(4-Acetylamino-2-{[methoxycarbonyl-((S)-1-methyl-2-phenyl-ethyl)-amino]-methyl}-phenoxy)-phenyl]-acetic acid; [3-(4-(Acetyl-methyl-amino)-2-{[methoxycarbonyl-((S)-1-methyl-2-phenyl-ethyl)-amino]-methyl}-phenoxy)-phenyl]-acetic acid; 2-[3-(4-(Acetyl-methyl-amino)-2-{[methoxycarbonyl-((S)-1-methyl-2-phenyl-ethyl)-amino]-methyl}-phenoxy)-phenyl]-propionic acid; [3-(4-Methanesulfonylamino-2-{[methoxycarbonyl-((S)-1-methyl-2-phenyl-ethyl)-amino]-methyl}-phenoxy)-phenyl]-acetic acid; [3-(4-(Methanesulfonyl-methyl-amino)-2-{[methoxycarbonyl-((S)-1-methyl-2-phenyl-ethyl)-amino]-methyl}-phenoxy)-phenyl]-acetic acid; 2-[3-(4-(Methanesulfonyl-methyl-amino)-2-{[methoxycarbonyl-((S)-1-methyl-2-phenyl-ethyl)-amino]-methyl}-phenoxy)-phenyl]-propionic acid; {3-[2-[(Benzyloxycarbonyl-ethyl-amino)-methyl]-4-(4-chloro-benzoylamino)-phenoxy]-4-methoxy-phenyl}-acetic acid; {3-[2-[(Acetyl-ethyl-amino)-methyl]-4-(2,2-dimethyl-propionylamino)-phenoxy]-4-methoxy-phenyl}-acetic acid; {3-[2-[(Acetyl-ethyl-amino)-methyl]-4-(4-chloro-benzoylamino)-phenoxy]-4-methoxy-phenyl}-acetic acid; {3-[2-[(Cyclopropanecarbonyl-ethyl-amino)-methyl]-4-(2,2-dimethyl-propionylamino)-phenoxy]-4-methoxy-phenyl}-acetic acid; or (3-{4-(4-Chloro-benzoylamino)-2-[(cyclopropanecarbonyl-ethyl-amino)-methyl]-phenoxy}-4-methoxy-phenyl)-acetic acid; or a pharmaceutically acceptable salt thereof.

15. A pharmaceutical composition comprising a therapeutically effective amount of a compound of claim 1, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers.

16. The pharmaceutical composition of claim 15, wherein the pharmaceutical composition is formulated for intravenous injection, oral administration, inhalation, nasal administration, topical administration, ophthalmic administration or otic administration.

17. The pharmaceutical composition of claim 15, wherein the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

* * * * *